US012766190B2

(12) United States Patent
Chene et al.

(10) Patent No.: US 12,766,190 B2
(45) **Date of Patent: *Oct. 20, 2026**

(54) ANTIGENIC PEPTIDES FOR PREVENTION AND TREATMENT OF CANCER

(71) Applicant: ENTEROME S.A., Paris (FR)

(72) Inventors: Laurent Chene, Neuville aux Bois (FR); Christophe Bonny, Paris (FR); Francesco Strozzi, Paris (FR)

(73) Assignee: ENTEROME S.A., Paris (FR)

( * ) Notice: Subject to any disclaimer, the term of this patent is extended or adjusted under 35 U.S.C. 154(b) by 71 days.

This patent is subject to a terminal disclaimer.

(21) Appl. No.: 18/654,304

(22) Filed: May 3, 2024

(65) Prior Publication Data

US 2024/0293520 A1 Sep. 5, 2024

Related U.S. Application Data

(63) Continuation of application No. 17/043,192, filed as application No. PCT/EP2019/059329 on Apr. 11, 2019, now Pat. No. 12,016,910.

(30) Foreign Application Priority Data

Apr. 11, 2018 (EP) .................................... 18305444
Oct. 9, 2018 (WO) ................ PCT/EP2018/077512

(51) Int. Cl.
*A61K 39/00* (2006.01)
*A61P 35/00* (2006.01)

(52) U.S. Cl.
CPC .. *A61K 39/001152* (2018.08); *A61K 39/0011* (2013.01); *A61K 39/001119* (2018.08); *A61K 39/00115* (2018.08); *A61K 39/001154* (2018.08); *A61P 35/00* (2018.01); *A61K 2039/55566* (2013.01)

(58) Field of Classification Search
CPC .. A61K 39/0011; A61P 35/00; C07K 14/4748
See application file for complete search history.

(56) References Cited

U.S. PATENT DOCUMENTS

| | | | |
|---|---|---|---|
| 2007/0087411 | A1 | 4/2007 | Sharma et al. |
| 2008/0166374 | A1 | 7/2008 | Debinski et al. |
| 2011/0110955 | A1 | 5/2011 | Debinski et al. |
| 2012/0052080 | A1 | 3/2012 | Okada |
| 2014/0141044 | A1 | 5/2014 | Bhatt et al. |
| 2018/0078627 | A1 | 3/2018 | Zeng et al. |
| 2018/0133339 | A1 | 5/2018 | Derouazi et al. |
| 2019/0388532 | A1 | 12/2019 | Chene et al. |
| 2020/0025774 | A1 | 1/2020 | Chene et al. |
| 2020/0113983 | A1 | 4/2020 | Chene et al. |
| 2020/0256877 | A1 | 8/2020 | Chene et al. |
| 2021/0106652 | A1 | 4/2021 | Chene et al. |
| 2021/0113678 | A1 | 4/2021 | Chene et al. |
| 2022/0323561 | A1 | 10/2022 | Chene et al. |

FOREIGN PATENT DOCUMENTS

| | | | |
|---|---|---|---|
| CN | 1954217 | A | 4/2007 |
| CN | 104774261 | A | 7/2015 |
| EP | 1587532 | A2 | 10/2005 |
| EP | 2189471 | A1 | 5/2010 |
| EP | 3536334 | A1 | 9/2019 |
| JP | 2003524016 | A | 8/2003 |
| JP | 2006517529 | A | 7/2006 |
| JP | 2015518835 | A | 7/2015 |
| WO | 1995021862 | A1 | 8/1995 |
| WO | 2001000225 | A1 | 1/2001 |
| WO | 2001/058479 | A1 | 8/2001 |
| WO | 2001062776 | A1 | 8/2001 |
| WO | 2003/092717 | A1 | 11/2003 |
| WO | 2004031211 | A2 | 4/2004 |
| WO | 2004067023 | A2 | 8/2004 |
| WO | 2006034334 | A2 | 3/2006 |
| WO | 2008073463 | A2 | 6/2008 |
| WO | 2010/018136 | A1 | 2/2010 |
| WO | 2010/129033 | A3 | 3/2011 |
| WO | 2011140284 | A2 | 11/2011 |
| WO | 2012027379 | A2 | 3/2012 |
| WO | 2013142477 | A1 | 9/2013 |
| WO | WO2013/135553 | A1 * | 9/2013 |
| WO | 2013148147 | A1 | 10/2013 |
| WO | 2013173411 | A1 | 11/2013 |
| WO | 2014088432 | A1 | 6/2014 |
| WO | 2014089375 | A1 | 6/2014 |

(Continued)

OTHER PUBLICATIONS

Office action issued in corresponding U.S. Appl. No. 16/338,954 dated Mar. 3, 2022.
Restriction requirement issued in corresponding U.S. Appl. No. 16/338,954 dated Jun. 24, 2022.
Notice of Allowance issued in corresponding U.S. Appl. No. 16/338,954 dated Dec. 1, 2022.
Restriction Requirement issued in corresponding U.S. Appl. No. 16/338,953 dated Apr. 5, 2021.
Notice of Allowance issued in corresponding U.S. Appl. No. 16/338,953 dated Mar. 2, 2022.
Notice of Allowance issued in corresponding U.S. Appl. No. 16/338,953 dated Apr. 5, 2022.
Notice of Allowance issued in corresponding U.S. Appl. No. 16/338,953 dated Jun. 15, 2022.

(Continued)

*Primary Examiner* — Bao Q Li
(74) *Attorney, Agent, or Firm* — Harness Dickey & Pierce P.L.C.

(57) ABSTRACT

The present invention relates to antigen-based immunotherapy, in particular cancer immunotherapy. In particular, the present invention provides antigenic peptides, which are distinct from, but have amino acid similarity to, fragments of human tumor antigens. The present invention further provides immunogenic compounds, nanoparticles, cells and pharmaceutical compositions comprising such antigenic peptides and nucleic acids encoding such antigenic peptides.

12 Claims, 11 Drawing Sheets

Specification includes a Sequence Listing.

(56) References Cited

FOREIGN PATENT DOCUMENTS

| | | | |
|---|---|---|---|
| WO | 2017203526 | A1 | 11/2017 |
| WO | 2019072871 | A2 | 4/2019 |
| WO | 2021074389 | A1 | 4/2021 |
| WO | 2021094562 | A2 | 5/2021 |

OTHER PUBLICATIONS

Restriction Requirement issued in corresponding U.S. Appl. No. 16/338,955 dated Mar. 9, 2021.
Notice of Allowance issued in corresponding U.S. Appl. No. 16/338,955 dated Aug. 8, 2022.
Notice of Allowance issued in corresponding U.S. Appl. No. 16/338,955 dated Aug. 31, 2022.
Office Action issued in corresponding RU Appln. No. 2020135927 dated Nov. 3, 2022.
Baryšnikov A. Û, "The Interation of Tumor and Immune System of the Organism," Prakti?eskaâ Onkologiâ [Practical Oncology] 4(3), p. 127-130 (2003).
Dhanik, et al. "In-silico discovery of cancer-specific peptide-HLA complexes for targeted therapy," BCM Bioinformatics 17:286 (2016), 14 pages.
Xiao et al., "Peptide-Based Treatment: A Promising Cancer Therapy," Journal of Immunology Research, Vo. 2015, Article ID 761820, 13 pages.
Office Action from corresponding U.S. Appl. No. 16/338,954 dated Mar. 3, 2022.
Restriction Requirement from corresponding U.S. Appl. No. 16/338,954 dated Jun. 24, 2022.
Baylot, V., et al., "Chapter 13: TCTP Has a Crucial Role in the Different Stages of Prostate Cancer Malignant Progression," Springer International Publishing AG, 2017, p. 255-261.
Badri, H., et al., "Optimization of radiation dosing schedules for proneural glioblastoma," J. Math. Biol., 72: 1301-1336 (2016).
Office Action from corresponding Russian Application No. 2020135927 dated Jun. 16, 2023.
Fichtner-Feigl et al., "IL-13 signaling through the IL-13alpha2 receptor is involved in induction of TGF-beta1 production and fibrosis," Nature Medicine, 12(1): 99-106 (2006).
Hirsova et al., "Emerging Roles of T Cells in the Pathogenesis of Nonalcoholic Steatohepatitis and Hepatocellular Carcinoma," Front. Endocrinol. 12(760860): 1-14 (2021).
Office action issued in U.S. Appl. No. 17/043,197 dated Jun. 1, 2023.
Dosset et al. (2012). Universal cancer peptide-based therapeutic vaccine breaks tolerance against telomerase and eradicates established tumor. Clinical Cancer Res., 18(22):6284-95.
Flugel and Fischer (2014). Simian Virus Tumor Antigen: A virus-specific and preexisting cell protein. Journal of the National Cancer Institute, 55:4.
Restriction Requirement issued in U.S. Appl. No. 16/753,657 dated Aug. 9, 2023.
Office Action issued in U.S. Appl. No. 17/929,063 dated Nov. 9, 2023.
Office Action issued in Chinese Application No. CN201880065726.X dated Jan. 20, 2023.
Search Report issued in Chinese Application No. 201880065726.X dated Jan. 17, 2023.
Office Action from U.S. Appl. No. 17/043,197 dated Jan. 16, 2024.
Attallah et al. (2016) Interferon-gamma is associated with hepatic dysfunction in fibrosis, cirrhosis, and hepatocellular carcinoma. J Immunoassay Immunochem, 37(6): 597-610.
Tian et al. (2020). Small and mighty: adaptation of superphylum Patescibacteria to groundwater environment drives their genome simplicity. Microbiome, 8:51.
Cania et al. (2019). A long-term field experiment demonstrates the influence of tillage on the bacterial potential to produce soil structure-stabilizing agents such as exopolysaccharides and lipopolysaccharides. Environmental Microbiome, 14:1.
Dill et al. (2011). Physical limits of cells and proteomes. PNAS, 108(44):17876.
Aglietta et al. (2009). Reduced-intensity allogeneic hematopoietic stem cell transplantation in metastatic colorectal cancer as a novel adoptive cell therapy approach. The European group for blood and marrow transplantation experience. Biol Blood Marrow Transplant, 15:326.
Non-Final Office Action from U.S. Appl. No. 17/823,117 dated Feb. 28, 2024.
International Search Report from PCT Application No. PCT/EP2018/077515 dated May 6, 2019.
Written Opinion from PCT Application No. PCT/EP2018/077515 dated May 6, 2019.
Eguchi, J., et al., "Identification of Interleukin-13 Receptor a2 Peptide Analogues Capable of Inducing Improved Antiglioma CTL Responses," Cancer Res. 66(11): 5883-5891 (2006).
Fikes, John, "The Rational Design of T-Cell Epitopes With Enhanced Immunogenicity," Handbook of Cancer Vaccines, Humana Press, pp. 11-17 (2004).
Noedominguez-Romero, A., et al., "Variable epitope library carrying heavily mutated survivin-derived CTL epitope variants as a new class of efficient vaccine immunogen tested in a mouse model of breat cancer," Human Vaccines & Immunotherapeutics, 10(11): 3201-3213 (2014).
Scardino, A., et al., "HER-2/neu and hTERT Cryptic Epitopes as Novel Targets for Broad Spectrum Tumor Immunotherapy," The Journal of Immunology, 168(11): 5900-5906 (2000).
Buhrman, J.D., and Slansky, J.E., "Improving T cell responses to modified peptides in tumor vaccines," Immunol Res 55: 34-47 (2013).
Database UniParc XP-002777567 (2017).
Database UniParc XP-002777566 (2016).
Database UniParc XP-002777565 (2016).
Database UniParc XP-002777564 (2016).
Database UniParc XP-002790579 (2013).
Parkhurst et al., "Improved Induction of Melanoma-Reactive CTL with Peptides from the Melanoma Antigen gp100 Modified at HLA-A*0201-Binding Residues," The American Association of Immunologists, 1996, 157(6): 2539-2548.
Rodeberg, David et al., "Recognition of Six-Transmembrane Epithelial Antigen of the Prostate-Expressing Tumor Cells by Peptide Antigen-Induced Cytotoxic T Lymphocytes," Clinical Cancer Research, 2005, 11(12): 4545-4552.
Tourdot, Sophie et al., "A general strategy to enhance immunogenicity of low-affinity HLA-A2.1-associated peptides: implication in the identification of cryptic tumor epitopes," European Journal of Immunology, 2000, 30(1): 3411-3421.
Vertuani, Simona et al., "Improved Immunogenicity of an Immunodominant Epitope of the Her-2/neu Protooncogene by Alterations of MHC Contact Residues," Journal of Immunology, 2004, 172(6): 3501-3508.
Database UniParc (Online) Apr. 6, 2016 (Apr. 6, 2016), XP002777564, Database accession No. UPI0008B57C7B abstract.
Database UniParc [Online] Jun. 4, 2016 (Jun. 4, 2016), XP002777565, Database accession No. UPI000ADDED27 abstract.
Database UniParc [Online] Nov. 6, 2017 (Nov. 6, 2017), XP002777567, Database accession No. UPI000B513427 abstract.
Database UniParc [Online] Apr. 6, 2016 (Apr. 6, 2016), XP002777566, Database accession No. UPI000AFC0494 abstract.
International Search Report and Written Opinion issued in PCT/EP2017/075683, Apr. 4, 2018, 20 pages.
Nakashima, Hideyuki et al., "IL-13 receptor-directed cancer vaccines and immunotherapy," Immunotherapy, 2012, 4(4): 443-451.
Nakashima, Hideyuki et al., "A Novel Combination Immunotherapy for Cancer by IL-13R a2-Targeted DNA Vaccine and Immunotoxin in Murine Tumor Models," The Journal of Immunology, 2011, 187(10): 4935-4946.
Intemational Search Report and Written Opinion issued in PCT/EP2017/075673, Apr. 30, 2018, 17 pgs.
Intemational Search Report and Written Opinion issued in PCT/EP2017/075676, Jun. 15, 2018, 18 pgs.

(56) References Cited

OTHER PUBLICATIONS

Cuzick, J., et al., "Tamoxifen for prevention of breast cancer: extended long-term follow-up of the IBIS-I breast cancer prevention trial," Lancet Oncol, 16(1): 67-75 (2015).
Carter, J., "Conjugation of Peptides to Carrier Proteins via Glutaraldehyde," The Protein Protocols Handbook, 117: 679-687 (1996).
Shah, R., et al., "Pathogenesis, prevention, diagnosis and treatment of breast cancer," World J Clin Oncol, 5(3): 283-298 (2014).
Ma, W., et al., "PLGA nanoparticle-mediated delivery of tumor antigenic peptides elicits effective immune responses," International Journal of Nanomedicine, 7: 1475-1487 (2012).
Office Action from corresonding U.S. Appl. No. 16/338,955 dated May 14, 2021.
Office Action from corresponding U.S. Appl. No. 16/338,953 dated Jul. 20, 2021.
Huarte, E., et al., "Enhancing Immunogenicity of a CTL Epitope from Carcinoembryonic Antigen by Selective Amino Acid Replacements", Clinical Cancer Research, 8: 2336-2344 (2002).
Accession No. C2MB65, version 17, Heavy metal efflux pump, CzcA family, Database Uniprot [online], (2016).
Accession No. F4KLC2, version 28, Acriflavin resistance protein, Database Uniprot [online] (2016).
International Search Report from PCT Application No. PCT/EP2019/059319 dated Dec. 17, 2019.
Written Opinion from PCT Application No. PCT/EP2019/059319 dated Dec. 17, 2019.
Andrews, A., et al., "IL-13 receptor alpha 2: A regulator of IL-13 and IL-4 signal transduction in primary human fibroblasts," Journal of Allergy and Clinical Immuno., 118(4): 858-865, (2006).
International Search Report from PCT Application No. PCT/EP2019/059329 dated Oct. 28, 2019.
Written Opinion from PCT Application No. PCT/EP2019/059329 dated Oct. 28, 2019.
Database UniParc XP-002794914 (2017).
Yokomine, K., et al., "The forkhead box M1 transcription factor as a candidate of target for anti-cancer immunotherapy," Int. J. Cancer, 126: 2153-2163 (2010).
International Search Report from corresponding PCT Application No. PCT/EP2020/079226 dated Mar. 19, 2021.
Written Opinion from corresponding PCT Application No. PCT/EP2020/079226 dated Mar. 19, 2021.
Papewalis, C., et al., "Chromogranin A as potential target for immunotherapy of malignant pheochromocytoma," Molecular and Cellular Endocrinology, 335: 569-77 (2011).
Office Action from corresponding U.S. Appl. No. 16/338,953 dated Nov. 23, 2021.
Office Action from corresponding U.S. Appl. No. 16/338,955 dated May 14, 2021.
Office Action from corresponding U.S. Appl. No. 16/338,955 dated Oct. 8, 2021.
Office Action from corresponding U.S. Appl. No. 16/338,955 dated May 20, 2022.
Office Action issued in corresponding CN Appln. No. 201780074779.3 dated Oct. 14, 2022.
Search Report issued in corresponding CN Appln. No. 201780074779.3 dated Oct. 8, 2022.
Office Action from Japanese Application No. 2023-191203 dated Nov. 26, 2024.

* cited by examiner

A

B

A

B

ANTIGENIC PEPTIDES FOR PREVENTION AND TREATMENT OF CANCER

CROSS REFERENCE TO RELATED PATENT APPLICATIONS

The present application is a continuation of U.S. patent application Ser. No. 17/043,192 filed on 29 Sep. 2020, which is a U.S. national stage application of International Patent Application No. PCT/EP2019/059329 filed on 11 Apr. 2019, which claims foreign priority to International Patent Application No. PCT/EP2018/077512 filed on 9 Oct. 2018 and European Patent Application No. 18305444.4 filed on 11 Apr. 2018. The entire content of each patent application recited above is hereby incorporated by reference.

REFERENCE TO AN ELECTRONIC SEQUENCE LISTING

This application contains references to nucleic acid sequences and/or amino acid sequences which have been submitted concurrently herewith as the sequence listing .xml file entitled "15095L-000041-US-COA_2_May_2024_ST26", file size 978 KB, created on 2 May 2024. The aforementioned sequence listing is hereby incorporated by reference in its entirety.

FIELD

The present invention relates to the field of cancer therapy, more particularly by immunotherapeutic methods. In particular, the present invention provides various peptides, which are useful in cancer immunotherapy.

BACKGROUND

Cancer is one of the leading causes of death across the world. According to the World Health Organization (WHO), in 2012 only, 14 million new cases and 8.2 million cancer-related deaths were reported worldwide, and it is expected that the number of new cancer cases will rise by about 70% within the next two decades. So far, more than 60% of world's total new annual cases occur in Africa, Asia and Central and South America. These regions also account for 70% of the world's cancer deaths. Among men, the five most common sites of cancer are lung, prostate, colorectum, stomach and liver; while in women, those are breast, colorectum, lung, cervix, and stomach.

Cancer has long been managed with surgery, radiation therapy, cytotoxic chemotherapy, and endocrine manipulation, which are typically combined in sequential order so as to best control the disease. However, major limitations to the true efficacy of these standard therapies are their imprecise specificity which leads to the collateral damage of normal tissues incurred with treatment, a low cure rate, and intrinsic drug resistance.

In the last years, there has been a tremendous increase in the development of cancer therapies due notably to great advances in the expression profiling of tumors and normal cells, and recent researches and first clinical results in immunotherapy, or molecular targeted therapy, have started to change our perception of this disease.

Promising anticancer immunotherapies have now become a reality and evidences that the host immune system can recognize tumor antigens have led to the development of anticancer drugs which are now approved by regulatory agencies as the US Food and Drug Administration (FDA)

and European Medicines Agency (EMA). Various therapeutic approaches include, among others, adoptive transfer of ex vivo expanded tumor-infiltrating lymphocytes (TIL), cancer cell vaccines, immunostimulatory cytokines and variants thereof, Pattern recognition receptor (PRR) agonists, and immunomodulatory monoclonal antibodies targeting tumor antigens or immune checkpoints (Galuzzi et al., Classification of current anticancer immunotherapies. Oncotarget. 2014 Dec. 30; 5(24):12472-508).

Unfortunately, a significant percentage of patients can still present an intrinsic resistance to some of these immunotherapies or even acquire resistance during the course of treatment. For example, the three-year survival rate has been reported to be around 20% with the anti-CTLA-4 antibody Ipilumumab in unresectable or metastatic melanoma (Snyder et al., Genetic basis for clinical response to CTLA-4 blockade in melanoma. N Engl J Med. 2014 Dec. 4; 371 (23):2189-2199; Schadendorf et al., Pooled Analysis of Long-Term Survival Data From Phase II and Phase III Trials of Ipilimumab in Unresectable or Metastatic Melanoma. J Clin Oncol. 2015 Jun. 10; 33(17):1889-94), while the three-year survival rate with another checkpoint inhibitor, Nivolumab targeting PD-1, has been reported to be of 44% in renal cell carcinoma (RCC) and 18% in non-small-cell lung carcinoma (NSCLC) (Mc Dermott et al., Survival, Durable Response, and Long-Term Safety in Patients With Previously Treated Advanced Renal Cell Carcinoma Receiving Nivolumab. J Clin Oncol. 2015 Jun. 20; 33(18):2013-20; Gettinger et al., Overall Survival and Long-Term Safety of Nivolumab (Anti-Programmed Death 1 Antibody, BMS-936558, ONO-4538) in Patients With Previously Treated Advanced Non-Small-Cell Lung Cancer. J Clin Oncol. 2015 Jun. 20; 33(18):2004-12). Fundamental drug resistance thus represents a fixed barrier to the efficacy of these immunotherapies. It is thus clear that a different approach to cancer treatment is needed to break this barrier.

Absence of response in a large number of subjects treated with these immunotherapies might be associated with a deficient anti-tumor immune response (as defect in antigen presentation by antigen-presenting cells (APC) or antigen recognition by T cells). In other words, positive response to immunotherapy correlates with the ability of the immune system to develop specific lymphocytes subsets able to recognize MHC class I-restricted antigens that are expressed by human cancer cells (Kvistborg et al., Human cancer regression antigens. Curr Opin Immunol. 2013 April; 25(2): 284-90). This hypothesis is strongly supported by data demonstrating that response to adoptive transfer of tumor-infiltrating lymphocytes (TIL), is directly correlated with the numbers of CD8 T-cells transfused to the patient (Besser et al., Adoptive transfer of tumor-infiltrating lymphocytes in patients with metastatic melanoma: intent-to-treat analysis and efficacy after failure to prior immunotherapies. Clin Cancer Res. 2013 Sep. 1; 19(17):4792-800). A potent anti-tumoral response will thus depend on the presentation of immunoreactive peptides and the presence of a sufficient number of reactive cells "trained" to recognize these antigens.

Tumor antigen-based vaccination represent a unique approach to cancer therapy that has gained considerable interest as it can enlist the patient's own immune system to recognize, attack and destroy tumors, in a specific and durable manner. Tumor cells are indeed known to express a large number of peptide antigens susceptible to be recognized by the immune system. Vaccines based on such antigens thus provide great opportunities not only to improve patient's overall survival but also for the monitoring of immune responses and the preparation of GMP-grade product thanks to the low toxicity and low molecular weight of tumor antigens. Examples of tumor antigens include, among others, by-products of proteins transcribed from normally silent genes or overexpressed genes and from proteins expressed by oncovirus (Kvistborg et al., Human cancer regression antigens. Curr Opin Immunol. 2013 April; 25(2):284-90), and neo-antigens, resulting from point mutations of cellular proteins. The later are of particular interest as they have been shown to be directly associated with increased overall survival in patient treated with CTLA-4 inhibitors (Snyder et al., Genetic basis for clinical response to CTLA-4 blockade in melanoma. N Engl J Med. 2014 Dec. 4; 371(23):2189-2199; Brown et al., Neo-antigens predicted by tumor genome meta-analysis correlate with increased patient survival. Genome Res. 2014 May: 24(5):743-50).

Nevertheless, the number of human tumor antigens on which cancer vaccines can be developed is limited. In particular, antigens derived from mutated or modified self-proteins may induce immune tolerance and/or undesired autoimmunity side effects.

There is thus a need in the art to identify alternative cancer therapeutics, which can overcome the limitations encountered in this field.

The invention has for objective to meet the aforementioned needs. This object is achieved by means of the subject-matter set out below, in particular in the items provided by the present invention and in the appended claims.

SUMMARY

The present invention provides in particular the following items:

1. An antigenic peptide comprising or consisting of an amino acid sequence as set forth in any one of SEQ ID NOs 1-580 and 861-887.
2. The antigenic peptide according to item 1 comprising or consisting of an amino acid sequence as set forth in any one of SEQ ID NOs 1-580.
3. The antigenic peptide according to item 1 comprising or consisting of an amino acid sequence as set forth in any one of SEQ ID NOs 861-887.
4. The antigenic peptide according to item 1 or 2 comprising or consisting of an amino acid sequence as set forth in any one of SEQ ID NOs 1-160, 162-253 and 255-580.
5. The antigenic peptide according to item 2 or 4, wherein the antigenic peptide comprises or consists of an amino acid sequence as set forth in any one of SEQ ID NOs 30, 31, 32, 87, 97, 145, 193, 194, 220, 221, 255, 521 and 524.
6. The antigenic peptide according to any one of items 1-5, wherein the antigenic peptide comprises or consists of an amino acid sequence as set forth in any one of SEQ ID NOs 30, 31, 32, 87, 97, 193, 194, 220, 255, 521 and 524.
7. The antigenic peptide according to any one of items 1-6, wherein the antigenic peptide comprises or consists of an amino acid sequence as set forth in any one of SEQ ID NOs 30, 31, 32, 87, 97, 194, 220, 255, 521 and 524.
8. The antigenic peptide according to any one of items 1-7, wherein the antigenic peptide comprises or consists of an amino acid sequence as set forth in any one of SEQ ID NOs 30, 32, 87, 97, and 194.
9. The antigenic peptide according to item 1 or 2, wherein the antigenic peptide comprises or consists of an amino acid sequence as set forth in any one of SEQ ID NOs 30, 32, 194, 220, 254 or 255.
10. An immunogenic compound comprising the antigenic peptide according to any one of items 1-9.
11. The immunogenic compound according to item 10, wherein the antigenic peptide is linked to a carrier molecule.
12. The immunogenic compound according to item 11, wherein the carrier molecule is a carrier protein or a carrier peptide.
13. The immunogenic compound according to any one of items 10-12, comprising or consisting of a polypeptide of formula (I)

PepNt-CORE-PepCt (I)

wherein:

"PepNt" consists of a polypeptide having a length varying from 0 to 500 amino acid residues and is located at the N-terminal end of the polypeptide of formula (I);

CORE consists of an antigenic peptide as defined in any one of items 1-6; and

"PepCt" consists of a polypeptide having a length varying from 0 to 500 amino acid residues and is located at the C-terminal end of the polypeptide of formula (I).

14. A nanoparticle loaded with at least one of the antigenic peptides according to any one of items 1-9, or at least one of the immunogenic compounds according to any one of items 10-13;

and, optionally, with an adjuvant.

15. A cell loaded with the antigenic peptide according to any one of items 1-9 or with the immunogenic compound according to any one of items 10-13.
16. The cell according to item 15, wherein said cell is an antigen presenting cell (APC), preferably a dendritic cell.
17. A nucleic acid encoding the antigenic peptide according to any one of items 1-9, the polypeptide of formula (I) as defined in item 13, or the immunogenic compound according to any one of items 10-13, wherein the immunogenic compound is a peptide or a protein.
18. The nucleic acid according to item 17, wherein the nucleic acid is a DNA molecule or an RNA molecule; preferably selected from genomic DNA; cDNA; siRNA; rRNA; mRNA; antisense DNA; antisense RNA; ribozyme; complementary RNA and/or DNA sequences; RNA and/or DNA sequences with or without expression elements, regulatory elements, and/or promoters; a vector; and combinations thereof.
19. A host cell comprising the nucleic acid according to item 17 or 18.
20. The host cell according to item 19, wherein the nucleic acid is a vector.
21. The host cell according to item 19 or 20, wherein the host cell is a bacterial cell, preferably a gut bacterial cell.
22. A pharmaceutical composition comprising the antigenic peptide according to any one of items 1-9, the immunogenic compound according to any one of items 10-13, the nanoparticle according to item 14, the cell according to item 15 or 16, the nucleic acid according to item 17 or 18, and/or the host cell according to any one of items 19-21, and, optionally, one or more pharmaceutically acceptable excipients or carriers.

23. The pharmaceutical composition according to item 22, further comprising one or more immunostimulatory agents.
24. The pharmaceutical composition according to item 23, wherein the immunostimulatory agent is selected from the group consisting of immuno-adjuvants and antigen-presenting cells.
25. The pharmaceutical composition according to item 24, wherein the antigen-presenting cell is a dendritic cell.
26. The pharmaceutical composition according to any one of items 22-25, wherein the composition comprises
    (i) at least two distinct antigenic peptides according to any one of items 1-9;
    (ii) at least two distinct immunogenic compounds according to any one of items 10-13;
    (iii) at least two distinct nanoparticles according to item 14, and/or
    (iv) at least two distinct nucleic acids according to item 17 or 18.
27. A kit comprising
    the antigenic peptide according to any one of items 1-9,
    the immunogenic compound according to any one of items 10-13,
    the nanoparticle according to item 14,
    the cell according to item 15 or 16,
    the nucleic acid according to item 17 or 18,
    the host cell according to any one of items 19-21, and/or
    the pharmaceutical composition according to any one of items 22-26.
28. The kit according to item 27 further comprising a package insert or instruction leaflet with directions to prevent or to treat a cancer by using the antigenic peptide, the immunogenic compound, the nanoparticle, the cell, the nucleic acid, the host cell, and/or the pharmaceutical composition.
29. The kit according to item 27 or 28, wherein the kit comprises at least two distinct antigenic peptides according to any one of items 1-9.
30. The kit according to item 27 or 28, wherein the kit comprises at least two distinct immunogenic compounds according to any one of items 10-13.
31. The kit according to item 27 or 28, wherein the kit comprises at least two distinct nanoparticles according to item 14.
32. The kit according to item 27 or 28, wherein the kit comprises at least two distinct nucleic acids according to item 15 or 16.
33. The antigenic peptide according to any one of items 1-9,
    the immunogenic compound according to any one of items 10-13,
    the nanoparticle according to item 14,
    the cell according to item 15 or 16,
    the nucleic acid according to item 17 or 18,
    the host cell according to any one of items 19-21,
    the pharmaceutical composition according to any one of items 22-26, or
    the kit according to any one of items 27-32
    for use in the prevention and/or treatment of a cancer.
34. The antigenic peptide, the immunogenic compound, the nanoparticle, the cell, the nucleic acid, the host cell, the pharmaceutical composition or the kit for use according to item 33, wherein the cancer is selected from glioma, kidney cancer, skin cancer, in particular melanoma, lung cancer, ovarian cancer, breast cancer, colorectal cancer, liver cancer, pancreatic cancer, head and neck cancer, urothelial cancer and prostate cancer.
35. A combination of at least two distinct antigenic peptides according to any one of items 1-9 for use in the prevention and/or treatment of a cancer.
36. A combination of at least two distinct immunogenic compounds according to any one of items 10-13 for use in the prevention and/or treatment of a cancer.
37. A combination of at least two distinct nanoparticles according to item 14 for use in the prevention and/or treatment of a cancer.
38. A combination of at least two distinct nucleic acids according to item 17 or 18 for use in the prevention and/or treatment of a cancer.
39. The combination for use according to any one of items 35-38, wherein the at least two distinct components are comprised in distinct compositions.
40. The combination for use according to any one of items 35-38, wherein the at least two distinct components are comprised in the same composition.
41. The combination for use according to any one of items 35-39, wherein the at least two distinct components are administered via distinct routes of administration.
42. The combination for use according to any one of items 35-40, wherein the at least two distinct components are administered via the same route of administration.
43. The combination for use according to any one of items 35-39, 41 and 42 wherein the at least two distinct components are administered consecutively.
44. The combination for use according to any one of items 35-42 wherein the at least two distinct components are administered at about the same time.
45. A method for preventing and/or treating a cancer or initiating, enhancing or prolonging an anti-tumor-response in a subject in need thereof comprising administering to the subject
    the antigenic peptide according to any one of items 1-9,
    the immunogenic compound according to any one of items 10-13,
    the nanoparticle according to item 14,
    the cell according to item 15 or 16,
    the nucleic acid according to item 17 or 18,
    the host cell according to any one of items 19-21,
    the pharmaceutical composition according to any one of items 22-26, and/or
    the combination as defined in any one of items 35-44.
46. The method according to item 45, wherein the cancer is selected from glioma, kidney cancer, skin cancer, in particular melanoma, lung cancer, ovarian cancer, breast cancer, colorectal cancer, liver cancer, pancreatic cancer, head and neck cancer, urothelial cancer and prostate cancer.
47. A peptide-MHC (pMHC) multimer comprising the antigenic peptide according to any one of items 1-9.

The invention, and in particular the items outlined above, are described in more detail below.

BRIEF DESCRIPTION OF THE FIGURES

In the following a brief description of the appended figures will be given. The figures are intended to illustrate the present invention in more detail. However, they are not intended to limit the subject matter of the invention in any way.

DEFINITIONS

Figure 1:
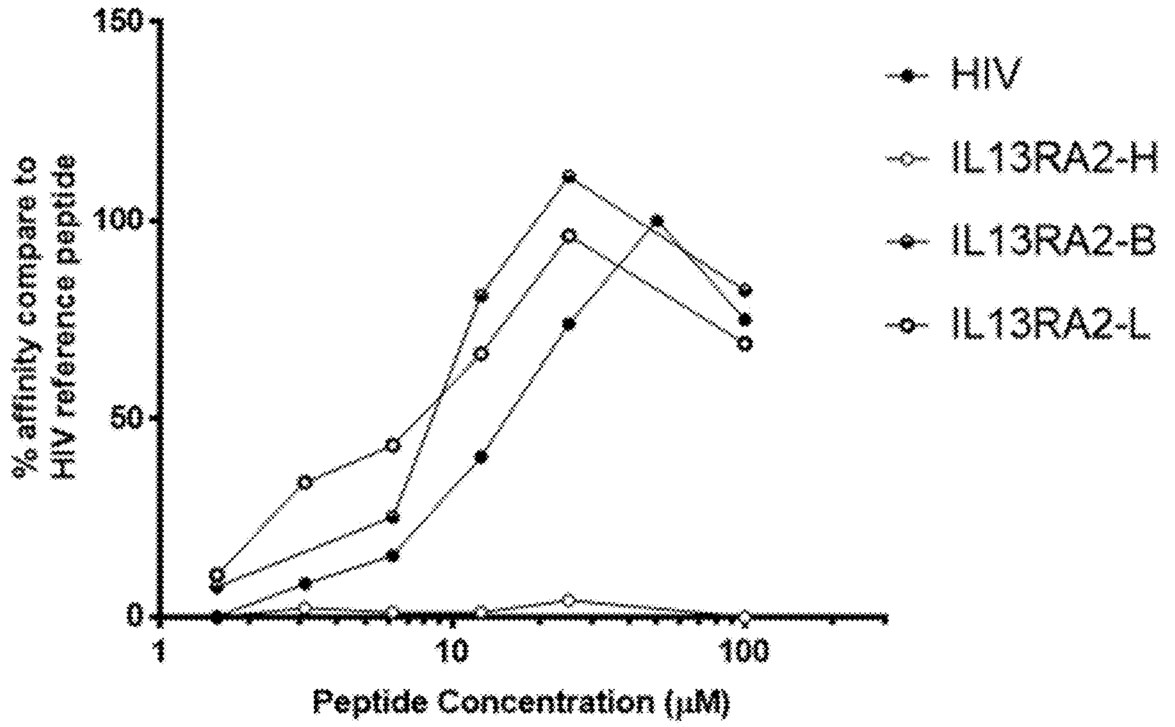
FIG. 1: shows for Example 2 in vitro affinity for antigenic peptides IL13RA2-B and IL13RA2-L in comparison to the corresponding human IL13RA2 epitope IL13RA2-H.
Figure 2:
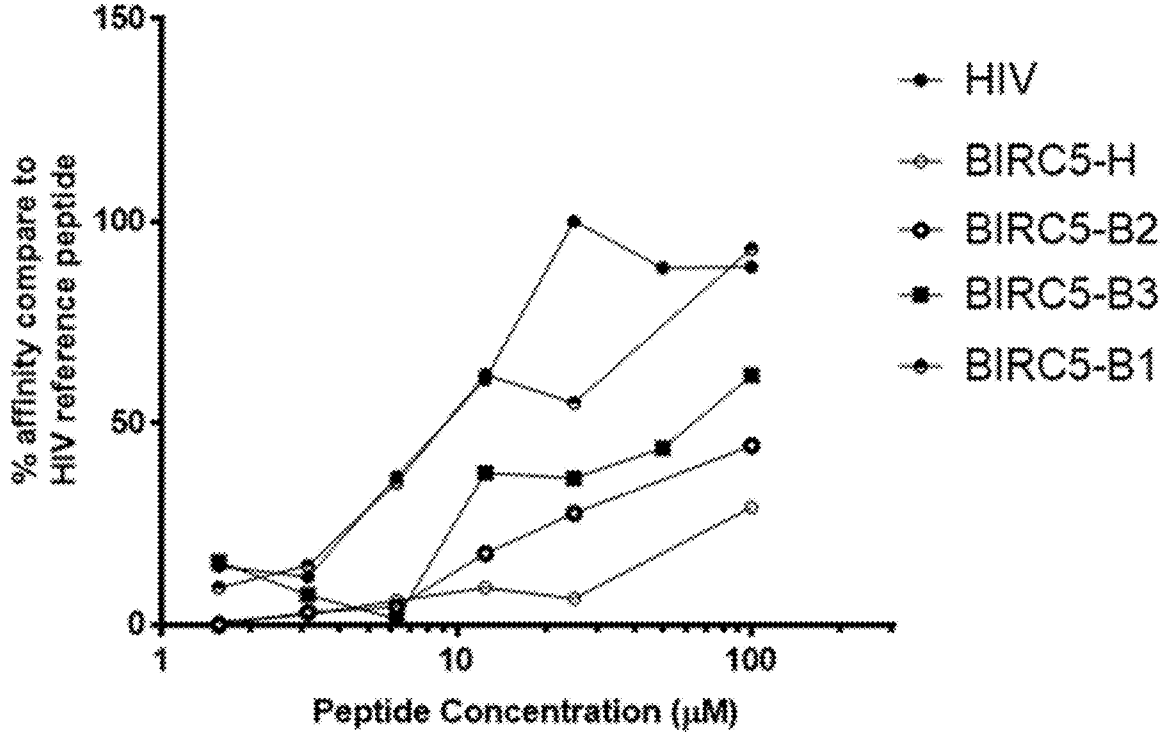
FIG. 2: shows for Example 2 in vitro affinity for antigenic peptides BIRC5-B1, BIRC5-B2 and BIRC5-B3 in comparison to the corresponding human BIRC5 epitope BIRC5-H.
Figure 3:
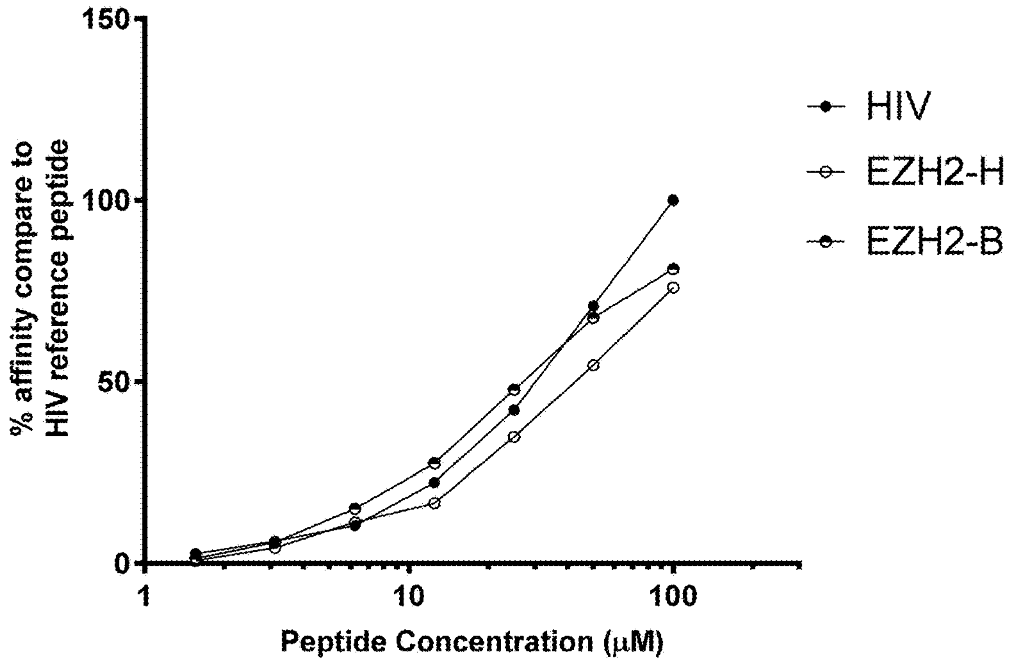
FIG. 3: shows for Example 2 in vitro affinity for (A) antigenic peptide EZH2-B in comparison to the corresponding human EZH2 epitope EZH2-H and (B) antigenic peptide EZH2-B2 in comparison to the corresponding human EZH2 epitope EZH2-H2.
Figure 3:
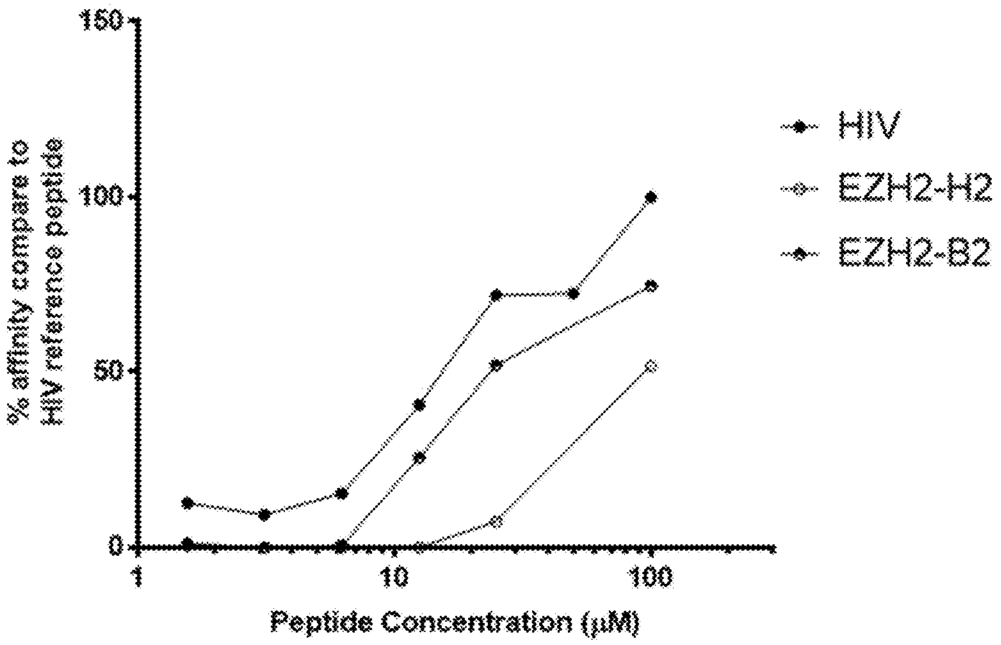
Figure 4:
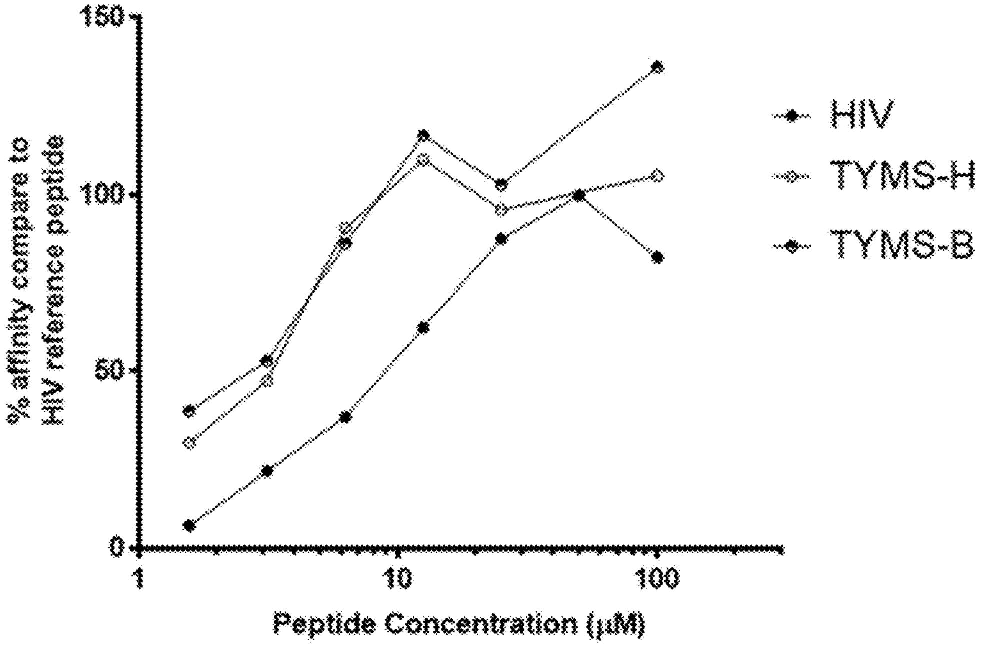
FIG. 4: shows for Example 2 in vitro affinity for (A) antigenic peptide TYMS-B in comparison to the corresponding human TYMS epitope TYMS-H and (B) antigenic peptide TYMS-B2 in comparison to the corresponding human TYMS epitope TYMS-H2.
Figure 4:
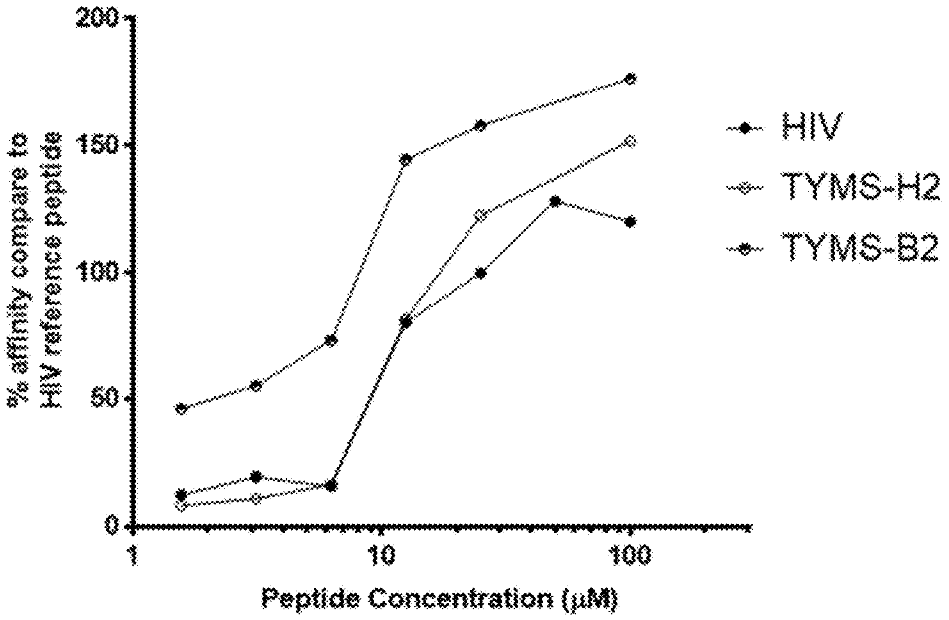
Figure 5:
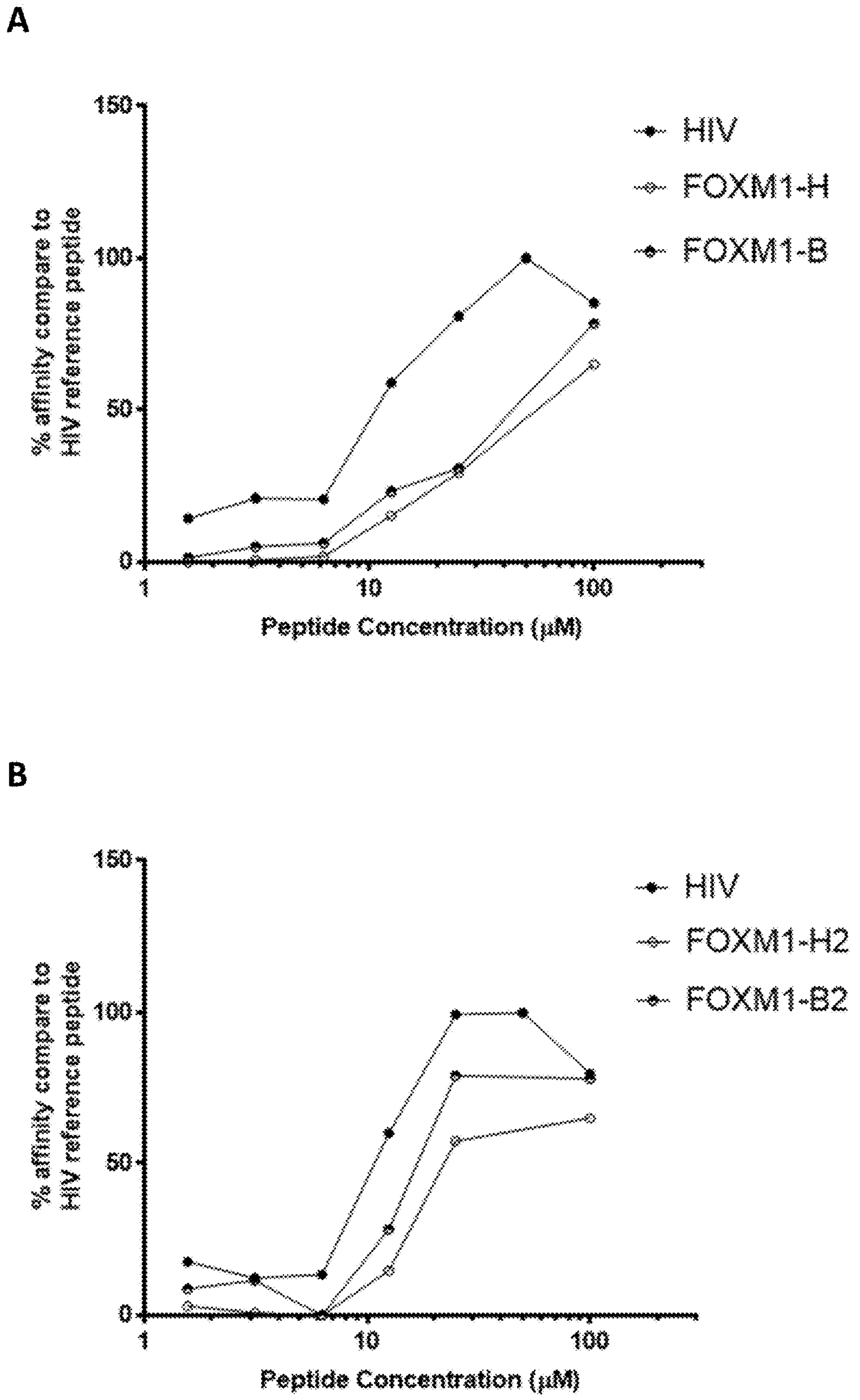
FIG. 5: shows for Example 2 in vitro affinity for (A) antigenic peptide FOXM1-B in comparison to the corresponding human FOXM1 epitope FOXM1-H and (B) antigenic peptide FOXM1-B2 in comparison to the corresponding human FOXM1 epitope FOXM1-H2.

Unless otherwise defined herein, scientific and technical terms used in the present application shall have the meanings that are commonly understood by those of ordinary skill in the art. Further, unless otherwise required by context, nomenclatures used herein, and techniques of cell and tissue culture are those well-known and commonly used in the art.

Such techniques are fully explained in the literature, such as Owen et al. (Kuby Immunology, 7', edition, 2013—W. H. Freeman) and Sambrook et al. (Molecular cloning: A laboratory manual 4th edition, Cold Spring Harbor Laboratory Press—Cold Spring Harbor, NY, USA, 2012).

Nevertheless, with respect to the use of different terms throughout the current specification, the following definitions more particularly apply.

The terms "peptide", "polypeptide", "protein" and variations of these terms refer to peptides, oligopeptides, polypeptides, or proteins comprising at least two amino acids joined to each other preferably by a normal peptide bond, or, alternatively, by a modified peptide bond, such as for example in the cases of isosteric peptides. The term "(poly) peptide" refers to a peptide and/or to a polypeptide. In particular, the terms "peptide", "polypeptide" and "protein" refer to a sequential chain of amino acids of any length linked together via peptide bonds (—NHCO—). Peptides, polypeptides and proteins can play a structural and/or functional role in a cell in vitro and/or in vivo. The terms "peptide", "polypeptide", "protein" preferably encompass amino acids chains in size ranging from 2 to at least about 1000 amino acid residues. The term "peptide" preferably encompasses herein amino acid chains in size of less than about 30 amino acids, while the terms "polypeptide" and "protein" preferably encompass amino acid chains in size of at least 30 amino acids. The terms "polypeptide" and "protein" are used herein interchangeably. In a preferred embodiment, the terms "peptide", "polypeptide", "protein" also include "peptidomimetics" which are defined as peptide analogs containing non-peptidic structural elements, which peptides are capable of mimicking or antagonizing the biological action(s) of a natural parent peptide. A peptidomimetic lacks classical peptide characteristics such as enzymatically scissile peptide bonds.

In particular, a peptide, polypeptide or protein can comprise amino acids other than the 20 amino acids defined by the genetic code in addition to these amino acids, or it can be composed of amino acids other than the 20 amino acids defined by the genetic code. In particular, a peptide, polypeptide or protein in the context of the present invention can equally be composed of amino acids modified by natural processes, such as post-translational maturation processes or by chemical processes, which are well known to a person skilled in the art. Such modifications are fully detailed in the literature. These modifications can appear anywhere in the polypeptide: in the peptide skeleton, in the amino acid chain or even at the carboxy- or amino-terminal ends. In particular, a peptide or polypeptide can be branched following an ubiquitination or be cyclic with or without branching. This type of modification can be the result of natural or synthetic post-translational processes that are well known to a person skilled in the art. The terms "peptide", "polypeptide", "protein" in the context of the present invention in particular also include modified peptides, polypeptides and proteins. For example, peptide, polypeptide or protein modifications can include acetylation, acylation, ADP-ribosylation, amidation, covalent fixation of a nucleotide or of a nucleotide derivative, covalent fixation of a lipid or of a lipidic derivative, the covalent fixation of a phosphatidylinositol, covalent or non-covalent cross-linking, cyclization, disulfide bond formation, demethylation, glycosylation including pegylation, hydroxylation, iodization, methylation, myristoylation, oxidation, proteolytic processes, phosphorylation, prenylation, racemization, seneloylation, sulfatation, amino acid addition such as arginylation or ubiquitination. Such modifications are fully detailed in the literature (Proteins Structure and Molecular Properties (1993) 2nd Ed., T. E. Creighton, New York; Post-translational Covalent Modifications of Proteins (1983) B. C. Johnson, Ed., Academic Press, New York; Seifter et al. (1990) Analysis for protein modifications and nonprotein cofactors, Meth. Enzymol. 182: 626-646 and Rattan et al., (1992) Protein Synthesis: Post-translational Modifications and Aging, Ann NY Acad Sci, 663: 48-62). Accordingly, the terms "peptide", "polypeptide", "protein" preferably include for example lipopeptides, lipoproteins, glycopeptides, glycoproteins and the like.

In a preferred embodiment, a (poly)peptide or protein is a "classical" (poly)peptide or protein, whereby a "classical" (poly)peptide or protein is typically composed of amino acids selected from the 20 amino acids defined by the genetic code, linked to each other by a normal peptide bond.

As well-known in the art, peptides, polypeptides and proteins can be encoded by nucleic acids. The terms "nucleic acid", "nucleic acid molecule", "nucleic acid sequence", "polynucleotide", "nucleotide sequence" are used herein interchangeable and refer to a precise succession of natural nucleotides (e.g., A, T, G, C and U), or synthetic nucleotides, i.e. to a chain of at least two nucleotides. In particular, the terms "nucleic acid", "nucleic acid molecule", "nucleic acid sequence", "polynucleotide", "nucleotide sequence" refer to DNA or RNA. Nucleic acids preferably comprise single stranded, double stranded or partially double stranded DNA or RNA, preferably selected from genomic DNA (gDNA). complementary DNA (cDNA), ribosomal DNA (rDNA), and the transcription product of said DNA, such as RNA. Preferred examples of nucleic acids include ribosomal RNA (rRNA), messenger RNA (mRNA); antisense DNA, antisense RNA; complementary RNA and/or DNA sequences, ribozyme, (complementary) RNA/DNA sequences with or without expression elements, a vector; a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a transfer RNA (tRNA), or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof. It is within the skill of the person in the art to determine nucleotide sequences which can encode a specific amino acid sequence.

The (poly)peptides and/or nucleic acids according to the invention may be prepared by any known method in the art including, but not limited to, any synthetic method, any recombinant method, any ex vivo generation method and the like, and any combination thereof. Such techniques are fully explained in the literature as mentioned above.

The term "antigenic peptide" as used herein refers to a peptide, which is prone to induce/elicit, increase, prolong or maintain an immune response in a subject to whom it is administered. In particular, the antigenic peptide is a sequence variant of (a fragment/epitope of) a (human) tumor antigen. In other words, the antigenic peptide is preferably distinct from (a fragment/epitope of) a (human) tumor antigen, but it has preferably amino acid similarity with (a fragment/epitope of) the (human) tumor antigen. Preferably, the immune response induced/elicited, increased, prolonged or maintained by the antigenic peptide (also) targets the respective (fragment/epitope of) a (human) tumor antigen.

As used herein, the term "tumor antigen" comprises tumor-specific antigens and tumor-associated antigens. In general, the term "tumor antigen" or "tumor protein" designates herein an antigenic substance produced in tumor cells, and sometimes also in normal cells, and which can trigger an immune response upon administration in a subject. In humans, those have been classified according to their expression pattern, function or genetic origin, and include without limitation, overexpressed self-antigens (such as HER2/neu and its variant dHER2, p53, Wilm's Tumor 1, Ephrin receptor, Proteinase-3, Mucin-1, Mesothelin, EGFR, CD20); cancer-testis (CT) antigens (such as MAGE-1, BAGE, GAGE, NY-ESO-1); mutational antigens, also known as neo-antigens (such as mutants from MUM-1, bcr-abl, ras, b-raf, p53, CDK-4, CDC27, beta-catenin, alpha-actenin-4); tissue-specific differentiation antigens (such as the melanoma antigens Melan A/MART-1, tyrosinase, TRP1/pg75, TRP2, gp100 and gangliosides GM3, GM2, GD2 and GD3; the prostate cancer antigens PSMA, PSA and PAP); viral antigens which are expressed by oncoviruses (such as HPV, EBV); oncofetal antigens (such as alpha-fetoprotein AFP and carcinoembryonic antigen CEA); and universal antigens (telomerase, hTERT, survivin, mdm-2, CYP-1B1) (Srinivasan and Wolchok, Tumor antigens for cancer immunotherapy: therapeutic potential of xenogeneic DNA vaccines. J Transl Med. 2004 Apr. 16; 2(1):12). Accordingly, human tumor antigens are well-known in the art. For instance, the Interleukin-13 receptor subunit alpha-2 (IL-13Rα2 or IL13RA2) is a membrane bound protein that in humans is encoded by the IL13RA2 gene. In a non-exhaustive manner, IL13RA2 has been reported as a potential immunotherapy target (see Beard et al.; Clin Cancer Res; 72(11); 2012). The high expression of IL13RA2 has further been associated with invasion, liver metastasis and poor prognosis in colorectal cancer (Barderas et al.; Cancer Res; 72(11); 2012). In particular, the antigenic peptides according to the present invention are preferably sequence variants of (an epitope/fragment of) the tumor antigens shown in Table 1B and may be used in particular in the disease outlined for the respective tumor antigen in Table 1B.

The term "microbiota", as used herein, refers to commensal microorganisms found in and on all multicellular organisms studied to date from plants to animals. In particular, microbiota have been found to be crucial for immunologic, hormonal and metabolic homeostasis of their host. Microbiota include bacteria, archaea, protists, fungi and viruses. Accordingly, a "microbiota sequence variant" is a sequence variant of a reference sequence (in particular an epitope/a fragment of a human tumor antigen), which occurs in microbiota (e.g., it may be contained in a microbiota protein). A "sequence variant" typically shares, in particular over the whole length of the sequence, at least 50% sequence identity with a reference sequence, namely, a fragment/epitope of a (reference) tumor antigen. Preferably, the sequence variant shares at least 60%, preferably at least 70%, preferably at least 75%, more preferably at least 80%, even more preferably at least 85%, still more preferably at least 90%, particularly preferably at least 95%, and most preferably at least 99% sequence identity with the reference sequence, namely, a fragment/epitope of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. The microbiota sequence variant is preferably selected from the group consisting of bacterial sequence variants, archaca sequence variants, protist sequence variants, fungi sequence variants and viral sequence variants. More preferably, the microbiota sequence variant is a bacterial sequence variant.

Anatomically, microbiota reside on or within any of a number of tissues and biofluids, including the skin, conjunctiva, mammary glands, vagina, placenta, seminal fluid, uterus, ovarian follicles, lung, saliva, oral cavity (in particular oral mucosa), and the gastrointestinal tract, in particular the gut. In the context of the present invention the microbiota sequence variant is preferably a sequence variant of microbiota of the gastrointestinal tract (microorganisms residing in the gastrointestinal tract), more preferably a sequence variant of microbiota of the gut (microorganisms residing in the gut). Accordingly, it is most preferred that the microbiota sequence variant is a (human) gut bacterial sequence variant (i.e. a sequence variant of bacteria residing in the (human) gut).

While microbiota can be found in and on many multicellular organisms (all multicellular organisms studied to date from plants to animals), microbiota found in and on human are preferred. Such microbiota are referred to herein as "human microbiota" (wherein the term human refers specifically to the localization/residence of the microbiota). Within the context of the present invention, the microbiota sequence variant is a human microbiota sequence variant.

The term "immunogenic compound" refers to a compound comprising an antigenic peptide according to the present invention. An "immunogenic compound" is able to induce/elicit, increase, prolong or maintain an immune response against said antigenic peptide in a subject to whom it is administered. In some embodiments, immunogenic compounds comprise at least one antigenic peptide, or alternatively at least one compound comprising such an antigenic peptide, linked to a protein, such as a carrier protein.

A "carrier protein" is usually a protein, which is able to transport a cargo, such as the antigenic peptide according to the present invention. For example, the carrier protein may transport its cargo across a membrane. In the context of the present invention, a carrier protein in particular (also) encompasses a peptide or a polypeptide that is able to elicit an immune response against the antigenic peptide that is linked thereto. Carrier proteins are known in the art.

Alternatively such carrier peptide or polypeptide may be co-administered in the form of immune adjuvant.

Preferably, the antigenic peptide as described herein may be co-administrated or linked, for example by covalent or non-covalent bond, to a protein/peptide having immuno-adjuvant properties, such as providing stimulation of CD4+ Th1 cells. While the antigenic peptide as described herein preferably binds to MHC class 1, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be distinct from the antigenic peptide according to the present invention. Preferably, the adjuvant peptide/protein is capable of recalling immune memory or provides a non-specific help or could be a specific helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination?Cancer J. 2011 September-October; 17(5):343-50). Accordingly, tetanus helper peptide, keyhole limpet hemocyanin peptide and PADRE peptide are preferred examples of such adjuvant peptide/proteins. In particular, the antigenic peptide as described herein, or a polypeptide comprising the said antigenic peptide, may be linked, for example by covalent or non-covalent bond, to the HHD-DR3 peptide of sequence MAKTIAYDEEARRGLERGLN (SEQ ID NO: 856). This peptide represents another example of a helper peptide (having immuno-adjuvant properties), which is preferred in the context of the present invention. Another preferred example is h-pAg T13L (sequence: TPPAYRPPNAPIL; SEQ ID NO: 860; Bhasin M, Singh H, Raghava G P (2003) MHCBN: a comprehensive database of MHC binding and non-binding peptides. Bioinformatics 19: 665-666).

Further examples of preferred helper peptides include the UCP2 peptide (for example as described in WO 2013/135553 A1 or in Dosset M, Godet Y, Vauchy C, Beziaud L, Lone Y C, Sedlik C, Liard C, Levionnois E, Clerc B, Sandoval F, Daguindau E, Wain-Hobson S, Tartour E, Langlade-Demoven P, Borg C, Adotévi O: Universal cancer peptide-based therapeutic vaccine breaks tolerance against telomerase and eradicates established tumor. Clin Cancer Res. 2012 Nov. 15; 18(22):6284-95. doi: 10.1158/1078-0432.CCR-12-0896. Epub 2012 Oct. 2) and the BIRC5 peptide (for example as described in EP2119726 A1 or in Widenmeyer M, Gricsemann H, Stevanović S, Feyerabend S, Klein R, Attig S, Hennenlotter J, Wernet D, Kuprash D V, Sazykin A Y, Pascolo S, Stenzl A, Gouttefangeas C, Rammensee H G: Promiscuous survivin peptide induces robust CD4+ T-cell responses in the majority of vaccinated cancer patients. Int J Cancer. 2012 Jul. 1; 131(1):140-9. doi: 10.1002/ijc.26365. Epub 2011 Sep. 14). The most preferred helper peptide is the UCP2 peptide (amino acid sequence: KSVWSKLQSIGIRQH; SEQ ID NO: 859, for example as described in WO 2013/135553 A1 or in Dosset et al., Clin Cancer Res. 2012 Nov. 15; 18(22):6284-95.

As used herein, the term "immunogenic composition" refers to a composition that is able to elicit, induce, increase, prolong or maintain an immune response, in particular which elicits, induces, increases, prolongs or maintains an immune response, when it is administered to a mammal, and especially when it is administered to a human individual. Preferably, an immunogenic composition further comprises one or more immuno-adjuvant substances.

By "pharmaceutically acceptable excipient or carrier", it is meant herein a compound of pharmaceutical grade which improves the delivery, stability or bioavailability of an active agent, and can be metabolized by, and is non-toxic to, a subject to whom it is administered. Preferred excipients and carriers according to the invention include any of the excipients or carriers commonly used in pharmaceutical products, such as, for example, water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable excipients or carriers may further comprise minor amounts of auxiliary substances such as wetting or emulsifying agents, or preservatives.

By "vaccine", it is meant herein a composition capable of stimulating the immune system of a living organism so that protection against a harmful antigen is provided, either through prophylaxis or through therapy. Prophylactic vaccines are preferred. Preferably, a vaccine or a vaccine composition further comprises one or more immuno-adjuvant substances.

According to the different aspects and embodiments of the invention described herein, a "subject" or "host" preferably refers to a mammal, and most preferably to a human being. Said subject may have, been suspected of having, or be at risk of developing cancer.

The term "cancer", as used herein, refers to a malignant neoplasm. In particular, the term "cancer" refers herein to any member of a class of diseases or disorders that are characterized by uncontrolled division of cells and the ability of these cells to invade other tissues, either by direct growth into adjacent tissue through invasion or by implantation into distant sites by metastasis. Metastasis is defined as the stage in which cancer cells are transported through the bloodstream or lymphatic system. It encompasses, among others, esophageal cancer, gastric cancer, duodenal cancer, small intestinal cancer, appendiceal cancer, large bowel cancer, colon cancer, rectum cancer, colorectal cancer, anal cancer, pancreatic cancer, liver cancer, gallbladder cancer, spleen cancer, renal cancer, bladder cancer, prostatic cancer, testicular cancer, uterine cancer, endometrial cancer, ovarian cancer, vaginal cancer, vulvar cancer, breast cancer, pulmonary cancer, thyroid cancer, thymus cancer, brain cancer, nervous system cancer, gliomas, oral cavity cancer, skin cancer, blood cancer, lymphomas, eye cancer, bone cancer, bone marrow cancer, muscle cancer, etc. . . . . In the context of the present invention, melanoma, head and neck, breast, colorectal or renal cancer (such as clear cell renal cell carcinoma) are preferred.

As used herein, the term "preventing", "prevention", "prophylaxis" or "prevent" generally means to avoid or minimize the onset or development of a disease or condition before its onset, while the term "treating, "treatment" or "treat" encompasses reducing, ameliorating or curing a disease or condition (or symptoms of a disease or condition) after its onset. The term "preventing" encompasses "reducing the likelihood of occurrence of" or "reducing the likelihood of reoccurrence".

An "effective amount" or "effective dose" as used herein is an amount which provides the desired effect. For therapeutic purposes, an effective amount is an amount sufficient to provide a beneficial or desired clinical result. The preferred effective amount for a given application can be easily determined by the skilled person taking into consideration, for example, the size, age, weight of the subject, the type of disease/disorder to be prevented or treated, and the amount of time since the disease/disorder began. In the context of the present invention, in terms of prevention or treatment, an effective amount of the composition is an amount that is sufficient to induce a humoral and/or cell-mediated immune response directed against the disease/disorder.

Throughout this specification and the claims which follow, unless the context requires otherwise, the term "comprise", and variations such as "comprises" and "comprising", will be understood to imply the inclusion of a stated member, integer or step but not the exclusion of any other non-stated member, integer or step. The term "consist of" is a particular embodiment of the term "comprise", wherein any other non-stated member, integer or step is excluded. In the context of the present invention, the term "comprise" encompasses the term "consist of". The term "comprising" thus encompasses "including" as well as "consisting" e.g., a composition "comprising" X may consist exclusively of X or may include something additional e.g., X+Y.

The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. No language in the specification should be construed as indicating any non-claimed element essential to the practice of the invention.

The word "substantially" does not exclude "completely" e.g., a composition which is "substantially free" from Y may be completely free from Y. Where necessary, the word "substantially" may be omitted from the definition of the invention.

The term "about" in relation to a numerical value x means x±10%.

Additional definitions are provided throughout the specification.

The present invention may be understood more readily by reference to the following detailed description, including preferred embodiments of the invention, and examples included herein.

DETAILED DESCRIPTION

Although the present invention is described in detail below, it is to be understood that this invention is not limited to the particular methodologies, protocols and reagents described herein as these may vary. It is also to be understood that the terminology used herein is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

The present inventors have identified a set of antigenic peptides that can be used to induce a specific immune response against tumor cells. Those antigenic peptides are distinct from, but have amino acid similarity to, (fragments of) human tumor antigens, as shown in Table 1A and Table 11B.

In particular, the antigenic peptides according to the present invention are comprised in polypeptides and proteins produced by commensal bacteria from the human gut. Accordingly, the antigenic peptides according to the present invention are not human sequences, but bacterial sequences. Without wishing to be bound by any particular theory, the inventors believe that the human immune repertoire contains T-cell clones that are reactive against bacterial peptides (comprised in proteins produced by commensal bacteria from the gut), which have amino acid similarity to fragments of human tumor antigens. In particular, the antigenic peptides according to the present invention can elicit a stronger immune response than the corresponding human peptides, since T cells able to recognize strictly human peptides have been depleted as recognizing self-antigens during maturation, which is not the case for the antigenic peptides according to the present invention. This may explain why the antigenic peptides described herein are able to induce an immune response, and especially a T-cell response, when these peptides are administered to a (human) individual.

Accordingly, the inventors believe that proteins produced by commensal bacteria from the gut are able to "mimic" tumor antigens, and can be used for triggering a specific immune response against tumor cells. These findings provide further evidence that commensal bacteria may contribute to tumor cells eradication.

The antigenic peptides disclosed herein can be prepared using well known techniques. For example, the peptides can be prepared synthetically, by recombinant DNA technology or chemical synthesis. Peptides disclosed herein can be synthesized individually or as longer polypeptides comprising two or more peptides (e.g., two or more peptides or a peptide and a non-peptide). The antigenic peptides can be isolated i.e., purified to be substantially free of other naturally occurring host cell proteins and fragments thereof, e.g., at least about 70%, 80% or 90% purified. Preferably, the antigenic peptides according to the present invention are isolated antigenic peptides.

Antigenic Peptides According to the Present Invention

In a first aspect the present invention provides an antigenic peptide comprising or consisting of an amino acid sequence as set forth in any one of SEQ ID NOs 1-580 and 861-887. Preferably, the antigenic peptide comprises or consists of an amino acid sequence as set forth in any one of SEQ ID NOs 1-580. It is also preferred that the antigenic peptide comprises or consists of an amino acid sequence as set forth in any one of SEQ ID NOs 861-887.

Accordingly, the invention relates to antigenic peptides having amino acid similarity with a tumor antigen. The expression "having amino acid similarity with a tumor antigen" as used herein, refers in particular to a sequence variant of fragments of a (reference) human tumor antigen, such as IL13RA2 or the other exemplified human tumor antigens described below in Tables 1A and 1B. A "sequence variant" typically shares, in particular over the whole length of the sequence, at least 50% sequence identity with a reference sequence, namely, a fragment of a (reference) tumor antigen. Preferably, the sequence variant shares at least 60%, preferably at least 70%, preferably at least 75%, more preferably at least 80%, even more preferably at least 85%, still more preferably at least 90%, particularly preferably at least 95%, and most preferably at least 99% sequence identity with the reference sequence, namely, a fragment of a (reference) tumor antigen. Sequence identity may be calculated as known in the art, in particular as described below. Preferably, a sequence variant preserves the specific function of the reference sequence, for example its function as tumor epitope and/or its ability to elicit or maintain an immune response. In particular, an amino acid sequence variant has an altered sequence in which one or more of the amino acids in the reference sequence is mutated, e.g. deleted or substituted, or one or more amino acids are inserted into the sequence of the reference amino acid sequence. For example, variant sequences which are at least 90% identical have no more than 10 alterations, i.e. any combination of deletions, insertions or substitutions, per 100 amino acids of the reference sequence.

Methods for comparing the identity (similarity) of two or more sequences are well known in the art. The percentage to which two sequences are identical can, e.g., be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al., 1990, J. Mol. Biol. 215, 403-410 or Altschul el al. (1997), Nucleic Acids Res, 25:3389-3402), accessible through the home page of the NCBI at world wide web site ncbi.nlm.nih.gov) and FASTA (Pearson (1990), Methods Enzymol. 183, 63-98; Pearson and Lipman (1988), Proc. Natl. Acad. Sci. U. S. A 85, 2444-2448). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may also be used to determine the % identity between two polynucleotides and the % identity between two (poly)peptide sequences. BESTFIT uses the "local homology" algorithm of Smith and Waterman (1981), J. Mol. Biol. 147, 195-197 and finds the best single region of similarity between two sequences.

The "fragment" of the (reference) tumor antigen, which typically serves as reference sequence, preferably comprises at least seven, more preferably at least eight and most preferably (at least) nine amino acids or ten amino acids. It is understood that the "fragment" of the (reference) tumor antigen (protein) is not the full-length tumor antigen (protein). Accordingly, the "fragment" of the (reference) tumor antigen may have a maximum length of 95%, 90%, 85%, 80%, 75%, 70%, 65%, 60%, 55%, 50%, 45%, 40%, 35%, 30%, 25%, 20%, 19%, 18%, 17%, 16%, 15%, 14%, 13%, 12%, 11%, 10%, 9%, 8%, 7%, 6%, 5%, 4%, 3%, 2% or 1% of the full-length (reference) tumor antigen.

In some embodiments, the length of the fragment of the (reference) tumor antigen does not exceed 50% of the length of the (full-length) (reference) tumor antigen. In other embodiments, the length of the fragment of the (reference) tumor antigen does not exceed 20% or 10% of the length of the (full-length) (reference) tumor antigen.

In general, the antigenic peptide according to the present invention may be of any length. Preferably, the length of the antigenic peptide according to the present invention does not exceed 350 amino acids. For example, the maximum length of the antigenic peptide according to the present invention may be 300 or 250 amino acids. More preferably, the maximum length of the antigenic peptide according to the present invention does not exceed 200 amino acids, e.g., not more than 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14 or 13 amino acids. In particular, the length of the antigenic peptides according to the present invention is preferably at most 30 or 25 amino acids, more preferably at most 20 or 15 amino acids, with smaller molecules of 10 or 9 amino acids in length being even more preferred. In particular, the antigenic peptides are not the full-length proteins produced by commensal bacteria from the gut from which the antigenic peptides are derived from.

In more general, the present invention provides an antigenic peptide, which comprises or consists of a microbiota sequence variant of a fragment of a human tumor antigen. The human tumor antigen may be selected from the group consisting of ACPP, ANKRD30A, AREG, ASCL1, ASCL2, BIRC5, CA9, CCNA1, CCND1, CDH17, CDH6, CDKN2A, CEACAM5, CHI3L1, CHI3L2, COL11A1, CT83, CTCFL, DCT, DMRTA2, EGFR, ERBB2, ERG, ESR1, EZH2, FAP, FLT1, FOXM1, FSIP1, GAL3ST1, GPR143, HES6, IL13RA2, K1SS1R, KLHDC8A, KLHL14, KLK4, KRT81, LEMD1, LRRC15, MAGEA1, MAGEA10, MAGEA11, MAGEA12, MAGEA4, MLANA, NKX2-1, NPTX2, PAGE3, PAX2, PCDHB16, PIWIL1, PMEL, PRAME, PTHLH, SEMG1, SERHL2, SLC45A3, SLC6A3, SNX31, SOX11, SPINK1, STEAP1, TBL1Y, TDRD1, TOP2A, TPTE, TRPM8, TYMS, TYR, UPK2, VCAM1, WFDC2, WT1, ZEB1, ZNF165, and ZNF280A.

In particular, the present invention provides an antigenic peptide, which is a microbiota sequence variant of a fragment of a human tumor antigen, wherein the fragment of the human tumor antigen may comprise or consist of any one of SEQ ID NOs 580-858 and 888-895.

Table 1A below provides an overview over the antigenic peptides according to the present inventions with their amino acid sequences and SEQ ID NOs and with the corresponding fragment/epitope of a human tumor antigen (also referred to herein as “human reference peptide”). Table 1A also provides information to which tumor antigen each antigenic peptide according to the present invention relates. SEQ ID NOs 1 to 580 and 861 to 887 refer to antigenic peptides according to the present invention.

TABLE 1A

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| ACPP | FLFLLFFWL | 581 | VLFLLFFPV | 1 |
| ACPP | SLSLGFLFL | 582 | SMSLGFLSV | 2 |
| ACPP | SLSLGFLFL | 582 | FLSLGFLAV | 3 |
| ACPP | LSLGFLFLL | 583 | LLLGFLFLI | 4 |
| ANKRD30A | YTSNDSYIV | 584 | YLSNDSYRV | 5 |
| ANKRD30A | ILIDSGADI | 585 | GLIDSGAFL | 6 |
| ANKRD30A | ILIDSGADI | 585 | LLIDSGALV | 7 |
| ANKRD30A | ILIDSGADI | 585 | RLIDSGATV | 8 |
| ANKRD30A | SLFESSAKI | 586 | KLFESSAAL | 9 |
| ANKRD30A | SLFESSAKI | 586 | TLFESSAFA | 10 |
| ANKRD30A | SLTPLLLSI | 587 | MLTPLLLGL | 11 |
| ANKRD30A | SLTPLLLSI | 587 | YLTPLLLIL | 12 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| ANKRD30A | SLTPLLLSI | 587 | IMTPLLLPV | 13 |
| ANKRD30A | SLTPLLLSI | 587 | FMTPLLLCL | 14 |
| ANKRD30A | SLTPLLLSI | 587 | FLTPLLLWL | 15 |
| AREG | MSAVILTAV | 588 | WMAVILTAL | 16 |
| AREG | MSAVILTAV | 588 | VLAVILTAV | 17 |
| AREG | ALAAIAAFM | 589 | VLAAIAAGV | 18 |
| AREG | ALAAIAAFM | 589 | LLAAIAAFL | 19 |
| AREG | ALAAIAAFM | 589 | KLAAIAAAV | 20 |
| AREG | ALAAIAAFM | 589 | ILAAIAAAV | 21 |
| AREG | ALAAIAAFM | 589 | GMAAIAAFL | 22 |
| AREG | ALAAIAAFM | 589 | FLAAIAAVL | 23 |
| AREG | ALAAIAAFM | 589 | ALAAIAALV | 24 |
| ASCL1 | VSAAFQAGV | 590 | ALAAFQAGL | 25 |
| ASCL2 | KLVNLGFQA | 591 | SLVNLGFSL | 26 |
| ASCL2 | KLVNLGFQA | 591 | GLVNLGFAL | 27 |
| ASCL2 | ELLDFSSWL | 592 | QLLDFSSSL | 28 |
| ASCL2 | ELLDFSSWL | 592 | ILLDFSSVV | 29 |
| BIRC5 | LTLGEFLKL | 593 | YTLGEFLYI | 30 |
| BIRC5 | LTLGEFLKL | 593 | GLLGEFLQI | 31 |
| BIRC5 | LTLGEFLKL | 593 | FMLGEFLKL | 32 |
| CA9 | AAGDILALV | 594 | VLGDILALL | 33 |
| CA9 | AAGDILALV | 594 | KVGDILALV | 34 |
| CA9 | ALVFGLLFA | 595 | NLVFGLLPV | 35 |
| CA9 | ALVFGLLFA | 595 | FLVFGLLGL | 36 |
| CA9 | ALVFGLLFA | 595 | ALVFGLLRV | 37 |
| CA9 | FQYEGSLTT | 596 | GVYEGSLTV | 38 |
| CA9 | HLSTAFARV | 597 | VLSTAFALV | 39 |
| CA9 | HLSTAFARV | 597 | GLSTAFAAV | 40 |
| CA9 | HLSTAFARV | 597 | ALSTAFAVV | 41 |
| CA9 | LSLLLLVPV | 598 | MLLLLLVPV | 42 |
| CA9 | LSLLLLVPV | 598 | LLLLLLVPV | 43 |
| CA9 | LSLLLLVPV | 598 | AILLLLVPV | 44 |
| CA9 | QLLLSLLLL | 599 | YLLLSLLRL | 45 |
| CA9 | QLLLSLLLL | 599 | FLLLSLLTL | 46 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| CA9 | QLLLSLLLL | 599 | ALLLSLLPL | 47 |
| CA9 | VQLLLSLLL | 600 | RLLLLSLLV | 48 |
| CA9 | VOLLLSLLL | 600 | KLLLLSLLL | 49 |
| CA9 | VQLLLSLLL | 600 | FLLLLSLLI | 50 |
| CCNA1 | NLAKYVAEL | 601 | RLAKYVALV | 51 |
| CCNA1 | LIAAAAFCL | 602 | LIAAAAFTV | 52 |
| CCNA1 | LIAAAAFCL | 602 | GMAAAAFCL | 53 |
| CCNA1 | LIAAAAFCL | 602 | GLAAAAFCI | 54 |
| CCNA1 | LIAAAAFCL | 602 | FLAAAAFCL | 55 |
| CCND1 | LLNDRVLRA | 603 | WLNDRVLQL | 56 |
| CDH17 | GILLTTLLV | 604 | KLLLTTLLV | 57 |
| CDH17 | ILAVVFIRI | 605 | GMAVVFINV | 58 |
| CDH17 | ILAVVFIRI | 605 | GMAVVFIEV | 59 |
| CDH17 | ILLTTLLVI | 606 | LLLTTLLAV | 60 |
| CDH17 | ILLTTLLVI | 606 | ALLTTLLLV | 61 |
| CDH17 | ILLTTLLVI | 606 | ALLTTLLGL | 62 |
| CDH17 | LVIGIILAV | 607 | KIIGIILAV | 63 |
| CDH6 | ALVAILLCI | 608 | YLVAILLLV | 64 |
| CDH6 | ALVAILLCI | 608 | TLVAILLNV | 65 |
| CDH6 | ALVAILLCI | 608 | MLVAILLAV | 66 |
| CDH6 | ALVAILLCI | 608 | LLVAILLSV | 67 |
| CDH6 | ALVAILLCI | 608 | FLVAILLNL | 68 |
| CDH6 | ALVAILLCI | 608 | AMVAILLNI | 69 |
| CDH6 | ALVAILLCI | 608 | ALVAILLAI | 70 |
| CDH6 | EMSDVGTFV | 609 | LLSDVGTLL | 71 |
| CDH6 | EMSTYLLPV | 610 | FLSTYLLPM | 72 |
| CDH6 | FLLEEYTGS | 611 | ALLEEYTGI | 73 |
| CDH6 | ILLCIVILL | 612 | SLLCIVIGL | 74 |
| CDH6 | ILLCIVILL | 612 | ILLCIVIGL | 75 |
| CDH6 | LLVTVVLFA | 613 | MLVTVVLTV | 76 |
| CDH6 | LLVTVVLFA | 613 | MLVTVVLLV | 77 |
| CDH6 | LLVTVVLFA | 613 | LLVTVVLPV | 78 |
| CDH6 | LLVTVVLFA | 613 | LLVTVVLAV | 79 |
| CDH6 | LLVTVVLFA | 613 | KLVTVVLAV | 80 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| CDH6 | LLVTVVLFA | 613 | ILVTVVLGI | 81 |
| CDKN2A | AVALVLMLL | 614 | LMALVLMLV | 82 |
| CEACAM5 | LLTFWNPPT | 615 | GLTFWNPNV | 83 |
| CHI3L1 | KQLLLSAAL | 616 | FMLLLSAAA | 84 |
| CHI3L1 | KQLLLSAAL | 616 | FLLLLSAAL | 85 |
| CHI3L1 | LLLSAALSA | 617 | YLLSAALTL | 86 |
| CHI3L1 | LLLSAALSA | 617 | YLLSAALTI | 87 |
| CHI3L1 | LLLSAALSA | 617 | VLLSAALLL | 88 |
| CHI3L1 | LLLSAALSA | 617 | VLLSAALFL | 89 |
| CHI3L1 | LLLSAALSA | 617 | SLLSAALTV | 90 |
| CHI3L1 | LLLSAALSA | 617 | RLLSAALAL | 91 |
| CHI3L1 | LLLSAALSA | 617 | LMLSAALLL | 92 |
| CHI3L1 | LLLSAALSA | 617 | LMLSAALCV | 93 |
| CHI3L1 | LLLSAALSA | 617 | LMLSAALAV | 94 |
| CHI3L1 | LLLSAALSA | 617 | LLLSAALWV | 95 |
| CHI3L1 | LLLSAALSA | 617 | LLLSAALTV | 96 |
| CHI3L1 | LLLSAALSA | 617 | LLLSAALSV | 97 |
| CHI3L1 | LLLSAALSA | 617 | LLLSAALMI | 98 |
| CHI3L1 | LLLSAALSA | 617 | LLLSAALLL | 99 |
| CHI3L1 | LLLSAALSA | 617 | LLLSAALCV | 100 |
| CHI3L1 | LLLSAALSA | 617 | LLLSAALAL | 101 |
| CHI3L1 | LLLSAALSA | 617 | KLLSAALSV | 102 |
| CHI3L1 | LLLSAALSA | 617 | ILLSAALLL | 103 |
| CHI3L1 | LLLSAALSA | 617 | ILLSAALGI | 104 |
| CHI3L1 | LLLSAALSA | 617 | FLLSAALVV | 105 |
| CHI3L1 | LLLSAALSA | 617 | FLLSAALIL | 106 |
| CHI3L1 | LLLSAALSA | 617 | ALLSAALML | 107 |
| CHI3L1 | LLLSAALSA | 617 | ALLSAALLV | 108 |
| CHI3L1 | LLLSAALSA | 617 | ALLSAALLL | 109 |
| CHI3L1 | QLAGAMVWA | 618 | YMAGAMVOL | 110 |
| CHI3L1 | QLAGAMVWA | 618 | RMAGAMVPV | 111 |
| CHI3L1 | QLAGAMVWA | 618 | RLAGAMVDV | 112 |
| CHI3L1 | SQTGFVVLV | 619 | MMTGFVVLM | 113 |
| CHI3L1 | TLASSETGV | 620 | YLASSETHV | 114 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| CHI3L2 | ILLSIGGYL | 621 | SMLSIGGYV | 115 |
| CHI3L2 | HLIYSFASI | 622 | LLIYSFARV | 116 |
| CHI3L2 | VLIHELAEA | 623 | KLIHELAEV | 117 |
| CHI3L2 | VLIHELAEA | 623 | ILIHELAHI | 118 |
| CHI3L2 | SLWAGVVVL | 624 | HLWAGVVLV | 119 |
| COL11A1 | WLWDFTVTT | 625 | RLWDFTVGV | 120 |
| CT83 | LLASSILCA | 626 | VLASSILYI | 121 |
| CT83 | LLASSILCA | 626 | SLASSILQL | 122 |
| CT83 | LLASSILCA | 626 | ALASSILQL | 123 |
| CTCFL | KLAVSLAET | 627 | FLAVSLAPL | 124 |
| DCT | ALVGLFVLL | 628 | ILVGLFVPV | 125 |
| DCT | ALVGLFVLL | 628 | ILVGLFVAV | 126 |
| DCT | GLFVLLAFL | 629 | YLFVLLAGI | 127 |
| DCT | GLFVLLAFL | 629 | SLFVLLAAV | 128 |
| DCT | GLFVLLAFL | 629 | KLFVLLALV | 129 |
| DCT | SVYDFFVWL | 630 | GIYDFFVKV | 130 |
| DCT | VVMGTLVAL | 631 | TIMGTLVSV | 131 |
| DCT | VVMGTLVAL | 631 | RVMGTLVGI | 132 |
| DMRTA2 | GTAEGLALA | 632 | TLAEGLALA | 133 |
| DMRTA2 | GLAAGLGPA | 633 | FLAAGLGQV | 134 |
| EGFR | ALESILHRI | 634 | VLESILHPV | 135 |
| EGFR | ALESILHRI | 634 | RMESILHEV | 136 |
| EGFR | ALLAALCPA | 635 | ALLAALCYV | 137 |
| EGFR | ALLALLAAL | 636 | YLLALLAWL | 138 |
| EGFR | ALLALLAAL | 636 | VLLALLAEV | 139 |
| EGFR | ALLALLAAL | 636 | SLLALLAFV | 140 |
| EGFR | ALLALLAAL | 636 | RLLALLASV | 141 |
| EGFR | ALLALLAAL | 636 | RLLALLAAV | 142 |
| EGFR | ALLALLAAL | 636 | LLLALLAPV | 143 |
| EGFR | ALLALLAAL | 636 | ALLALLASV | 144 |
| EGFR | ILDEAYVMA | 637 | ILDEAYVRV | 145 |
| EGFR | LLLLLVVAL | 638 | ALLLLVVGV | 146 |
| EGFR | MVGALLLLL | 639 | GLGALLLLV | 147 |
| EGFR | NLQEILHGA | 640 | YMQEILHRL | 148 |
| EGFR | SLAVVSLNI | 641 | TLAVVSLAV | 149 |
| EGFR | SLAVVSLNI | 641 | LLAVVSLFV | 150 |
| ERBB2 | AVVGILLVV | 642 | YLVGILLVL | 151 |
| ERBB2 | AVVGILLVV | 642 | KVVGILLPI | 152 |
| ERBB2 | AVVGILLVV | 642 | ILVGILLVV | 153 |
| ERBB2 | AVVGILLVV | 642 | FVVGILLQV | 154 |
| ERBB2 | ILDEAYVMA | 643 | ILDEAYVRV | 155 |
| ERBB2 | LLALLPPGA | 644 | LLALLPPEV | 156 |
| ERBB2 | LLALLPPGA | 644 | LLALLPPEL | 157 |
| ERBB2 | LLALLPPGA | 644 | AMALLPPEV | 158 |
| ERBB2 | LLALLPPGA | 644 | ALALLPPPV | 159 |
| ERBB2 | SIISAVVGI | 645 | ILISAVVGL | 160 |
| ERBB2 | VVLGVVFGI | 646 | IVLGVVFGV | 161 |
| ERBB2 | VVLGVVFGI | 646 | IILGVVFGL | 162 |
| ERG | FLLELLSDS | 647 | YLLELLSAL | 163 |
| ERG | QLWQFLLEL | 857 | IMWQFLLEL | 164 |
| ESR1 | ALLDAEPPI | 648 | YLLDAEPQL | 165 |
| ESR1 | KITDTLIHL | 649 | KLTDTLIPL | 166 |
| ESR1 | KITDTLIHL | 649 | KLTDTLIEL | 167 |
| ESR1 | KLLFAPNLL | 650 | YLLFAPNAV | 168 |
| ESR1 | KLLFAPNLL | 650 | FLLFAPNSA | 169 |
| ESR1 | LLDAEPPIL | 651 | YLDAEPPAV | 170 |
| ESR1 | LLNSGVYTF | 652 | TLNSGVYLI | 171 |
| ESR1 | LLNSGVYTF | 652 | KMNSGVYVI | 172 |
| ESR1 | LMIGLVWRS | 653 | LLIGLVWSL | 173 |
| ESR1 | PLYDLLLEM | 654 | YLYDLLLTV | 174 |
| ESR1 | PLYDLLLEM | 654 | VLYDLLLEV | 175 |
| ESR1 | PLYDLLLEM | 654 | TLYDLLLSL | 176 |
| ESR1 | PLYDLLLEM | 654 | QLYDLLLVA | 177 |
| ESR1 | PLYDLLLEM | 654 | QLYDLLLSL | 178 |
| ESR1 | PLYDLLLEM | 654 | GLYDLLLRI | 179 |
| ESR1 | PLYDLLLEM | 654 | AVYDLLLEV | 180 |
| ESR1 | PLYDLLLEM | 654 | ALYDLLLEV | 181 |
| ESR1 | QLLLILSHI | 655 | VLLLILSGV | 182 |

TABLE 1A-continued

| Antigenic peptides according to the invention | | | | |
|---|---|---|---|---|
| Tumor antigen | Sequence human reference peptide | SEQ ID NO. human reference peptide | Sequence antigenic peptide | SEQ ID NO. antigenic peptide |
| ESR1 | QLLLILSHI | 655 | VLLLILSEV | 183 |
| ESR1 | QLLLILSHI | 655 | SLLLILSFV | 184 |
| ESR1 | QLLLILSHI | 655 | MLLLILSYL | 185 |
| ESR1 | QLLLILSHI | 655 | ILLLILSGI | 186 |
| ESR1 | QLLLILSHI | 655 | FLLLILSLL | 187 |
| ESR1 | QLLLILSHI | 655 | FLLLILSFL | 188 |
| ESR1 | RLAQLLLIL | 656 | SLAQLLLAI | 189 |
| ESR1 | RLAQLLLIL | 656 | MLAQLLLTV | 190 |
| ESR1 | TLIHLMAKA | 657 | KLIHLMAAV | 191 |
| ESR1 | VLDKITDTL | 658 | FLDKITDLV | 192 |
| EZH2 | FMVEDETVL | 659 | FLVEDETVI | 193 |
| EZH2 | SMFRVLIGT | 660 | AVFRVLIPV | 194 |
| FAP | ATSAVLALL | 661 | LLSAVLALV | 195 |
| FAP | ATSAVLALL | 661 | LLSAVLALA | 196 |
| FAP | ATSAVLALL | 661 | GISAVLALV | 197 |
| FAP | TGWAGGFFV | 662 | NLWAGGFFL | 198 |
| FAP | VLALLVMCI | 663 | YLALLVMLL | 199 |
| FAP | VLALLVMCI | 663 | LLALLVMAV | 200 |
| FAP | VLALLVMCI | 663 | ALALLVMAV | 201 |
| FLT1 | ALLSCLLLT | 664 | TMLSCLLHL | 202 |
| FLT1 | ALLSCLLLT | 664 | MLLSCLLFM | 203 |
| FLT1 | ALLSCLLLT | 664 | LLLSCLLPL | 204 |
| FLT1 | ALLSCLLLT | 664 | LLLSCLLHL | 205 |
| FLT1 | ALLSCLLLT | 664 | ILLSCLLLL | 206 |
| FLT1 | ALLSCLLLT | 664 | FLLSCLLCL | 207 |
| FLT1 | ALLSCLLLT | 664 | ALLSCLLML | 208 |
| FLT1 | CVAATLFWL | 665 | YVAATLFAL | 209 |
| FLT1 | EMYSEIPEI | 666 | YLYSEIPDI | 210 |
| FLT1 | KMASTLVVA | 667 | YMASTLVHL | 211 |
| FLT1 | KMASTLVVA | 667 | QMASTLVYL | 212 |
| FLT1 | SIFDKIYST | 668 | YQFDKIYSI | 213 |
| FLT1 | TLFWLLLTL | 669 | MMFWLLLVV | 214 |
| FLT1 | VLLWEIFSL | 670 | GMLWEIFGV | 215 |
| FLT1 | WLKDGLPAT | 671 | AMKDGLPEV | 216 |

TABLE 1A-continued

| Antigenic peptides according to the invention | | | | |
|---|---|---|---|---|
| Tumor antigen | Sequence human reference peptide | SEQ ID NO. human reference peptide | Sequence antigenic peptide | SEQ ID NO. antigenic peptide |
| FOXM1 | ILLDISFPG | 672 | TLLDISFAA | 217 |
| FOXM1 | ILLDISFPG | 672 | NMLDISFYL | 218 |
| FOXM1 | ILLDISFPG | 672 | WLLDISFPL | 861 |
| FOXM1 | ILLDISFPG | 672 | HLLDISFPA | 862 |
| FOXM1 | ILLDISFPG | 672 | ELLDISFPA | 863 |
| FOXM1 | ILLDISFPG | 672 | VLLDISFEL | 864 |
| FOXM1 | ILLDISFPG | 672 | VLLDISFKV | 865 |
| FOXM1 | ILLDISFPG | 672 | IMLDISFLL | 866 |
| FOXM1 | LLDISFPGL | 673 | ILDISFPLV | 219 |
| FOXM1 | LLDISFPGL | 673 | LLDISFPSL | 867 |
| FOXM1 | LMDLSTTPL | 674 | LMDLSTTEV | 220 |
| FOXM1 | LMDLSTTPL | 674 | LMDLSTTNV | 868 |
| FOXM1 | RVSSYLVPI | 675 | RLSSYLVEI | 221 |
| FOXM1 | RVSSYLVPI | 675 | MVSSYLVEV | 222 |
| FOXM1 | RVSSYLVPI | 675 | KVSSYLVEV | 223 |
| FOXM1 | RVSSYLVPI | 675 | MLSSYLVPI | 869 |
| FOXM1 | RVSSYLVPI | 675 | LLSSYLVPI | 870 |
| FOXM1 | RVSSYLVPI | 675 | FVSSYLVPT | 871 |
| FOXM1 | SLSKILLDI | 676 | ILSKILLFA | 224 |
| FOXM1 | SQLSYSQEV | 677 | YQLSYSQMV | 225 |
| FOXM1 | SQLSYSQEV | 677 | KLLSYSQEL | 226 |
| FOXM1 | WAAELPFPA | 678 | KIAELPFPL | 227 |
| FOXM1 | NLSLHDMFV | 888 | SLSLHDMFL | 872 |
| FOXM1 | KMKPLLPRV | 889 | KLKPLLPWI | 873 |
| FOXM1 | KMKPLLPRV | 889 | KLKPLLPFL | 874 |
| FOXM1 | YLVPIQFPV | 890 | KVVPIQFPV | 875 |
| FOXM1 | YLVPIQFPV | 890 | KIVPIQFPI | 876 |
| FOXM1 | YMAMIQFAI | 891 | YQAMIQFLI | 877 |
| FSIP1 | LLNESETKV | 679 | YLNESETVL | 228 |
| FSIP1 | RLVELLKDL | 680 | MLVELLKKV | 229 |
| FSIP1 | RLVELLKDL | 680 | KLVELLKLL | 230 |
| FSIP1 | RLVELLKDL | 680 | ALVELLKPL | 231 |
| GAL3ST1 | GLASTTPEA | 681 | FLASTTPTA | 232 |
| GAL3ST1 | RMAREVAAL | 682 | SLAREVAAV | 233 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| GAL3ST1 | RMAREVAAL | 682 | GMAREVAAV | 234 |
| GPR143 | FLLSLAFYG | 683 | WLLSLAFLL | 235 |
| GPR143 | FLLSLAFYG | 683 | SLLSLAFSA | 236 |
| GPR143 | FLLSLAFYG | 683 | LLLSLAFIL | 237 |
| GPR143 | ILNPAQGFL | 684 | KLNPAQGYV | 238 |
| GPR143 | MAWGLATLL | 685 | KLWGLATLI | 239 |
| GPR143 | RLALGLLQL | 686 | VLALGLLAV | 240 |
| GPR143 | RLALGLLQL | 686 | SLALGLLQV | 241 |
| GPR143 | RLALGLLQL | 686 | SLALGLLLV | 242 |
| GPR143 | RLALGLLQL | 686 | MLALGLLEV | 243 |
| GPR143 | RLALGLLQL | 686 | GLALGLLFV | 244 |
| GPR143 | RLALGLLQL | 686 | GLALGLLAV | 245 |
| GPR143 | RLALGLLQL | 686 | FLALGLLFL | 246 |
| GPR143 | RLALGLLQL | 686 | ALALGLLMV | 247 |
| HES6 | RLLLAGAEV | 687 | VLLLAGAYV | 248 |
| IL13RA2 | CLYTFLIST | 688 | YLYTFLIVL | 249 |
| IL13RA2 | CLYTFLIST | 688 | GMYTFLIPM | 250 |
| IL13RA2 | CLYTFLIST | 688 | GLYTFLIPM | 251 |
| IL13RA2 | FLISTTFGC | 689 | FLISTTFAA | 252 |
| IL13RA2 | VLLDTNYNL | 690 | ILLDTNYEI | 253 |
| IL13RA2 | WLPFGFILI | 691 | FLPFGFILV | 254 |
| IL13RA2 | WLPFGFILIL | 692 | FLPFGFILPV | 255 |
| IL13RA2 | WLPFGFILIL | 692 | FMPFGFILPI | 878 |
| IL13RA2 | WLPFGFILIL | 692 | FMPFGFILGV | 879 |
| IL13RA2 | FLISTTFGCT | 892 | FLISTTFTIN | 880 |
| IL13RA2 | FLISTTFGCT | 892 | FMISTTFMRL | 881 |
| IL13RA2 | FLISTTFGCT | 892 | QMISTTFGNV | 882 |
| IL13RA2 | YLYLQWQPPL | 893 | WLYLQWQPSV | 883 |
| IL13RA2 | GVLLDTNYNL | 894 | FVLLDTNYEI | 884 |
| IL13RA2 | GVLLDTNYNL | 894 | FILLDTNYEI | 885 |
| IL13RA2 | FQLQNIVKPL | 895 | YELQNIVLPI | 886 |
| IL13RA2 | FQLQNIVKPL | 895 | FMLQNIVKNL | 887 |
| KISS1R | ALYLLPLLA | 693 | MLYLLPLSL | 256 |
| KISS1R | ALYLLPLLA | 693 | MLYLLPLAL | 257 |
| KISS1R | ALYLLPLLA | 693 | LLYLLPLFL | 258 |
| KISS1R | FALYNLLAL | 694 | SMLYNLLAL | 259 |
| KISS1R | FALYNLLAL | 694 | AMLYNLLAL | 260 |
| KISS1R | FALYNLLAL | 694 | ALLYNLLAL | 261 |
| KISS1R | QLFLVLQAL | 695 | ILFLVLQRV | 262 |
| KISS1R | RLVAAVVLL | 696 | YLVAAVVLL | 263 |
| KISS1R | VLAERAGAV | 697 | YLAERAGHV | 264 |
| KISS1R | WLVPLFFAA | 698 | ILVPLFFTL | 265 |
| KISS1R | WLVPLFFAA | 698 | GLVPLFFAL | 266 |
| KISS1R | WLVPLFFAA | 698 | FLVPLFFVV | 267 |
| KISS1R | WLVPLFFAA | 698 | FLVPLFFLL | 268 |
| KISS1R | WLVPLFFAA | 698 | ALVPLFFAL | 269 |
| KISS1R | YLLPLLATC | 699 | YMLPLLAGA | 270 |
| KISS1R | YLLPLLATC | 699 | YLLPLLALA | 271 |
| KISS1R | YLLPLLATC | 699 | WLLPLLAVV | 272 |
| KISS1R | YLLPLLATC | 699 | WLLPLLACL | 273 |
| KISS1R | YLLPLLATC | 699 | WLLPLLAAL | 274 |
| KISS1R | YLLPLLATC | 699 | TLLPLLAAV | 275 |
| KISS1R | YLLPLLATC | 699 | TLLPLLAAA | 276 |
| KISS1R | YLLPLLATC | 699 | SLLPLLAGV | 277 |
| KISS1R | YLLPLLATC | 699 | RLLPLLAVL | 278 |
| KISS1R | YLLPLLATC | 699 | RLLPLLAAI | 279 |
| KISS1R | YLLPLLATC | 699 | QLLPLLAYV | 280 |
| KISS1R | YLLPLLATC | 699 | LLLPLLAGL | 281 |
| KISS1R | YLLPLLATC | 699 | LLLPLLADL | 282 |
| KISS1R | YLLPLLATC | 699 | LLLPLLAAA | 283 |
| KISS1R | YLLPLLATC | 699 | HVLPLLATV | 284 |
| KISS1R | YLLPLLATC | 699 | HLLPLLAEV | 285 |
| KISS1R | YLLPLLATC | 699 | GLLPLLAKI | 286 |
| KISS1R | YLLPLLATC | 699 | GILPLLATV | 287 |
| KLHDC8A | GLSDAVEAL | 700 | YLSDAVEAV | 288 |
| KLHDC8A | MLREAAMGI | 701 | ILREAAMPV | 289 |
| KLHL14 | ALIPAPELV | 702 | FLIPAPESL | 290 |
| KLHL14 | NLLHGLNLL | 703 | FLLHGLNLM | 291 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| KLHL14 | YVSSLPQPL | 704 | YMSSLPQGL | 292 |
| KLK4 | YLILGVAGS | 705 | YMILGVAMI | 293 |
| KLK4 | YLILGVAGS | 705 | VLILGVAAV | 294 |
| KLK4 | YLILGVAGS | 705 | SLILGVAAV | 295 |
| KLK4 | YLILGVAGS | 705 | ILILGVAGI | 296 |
| KRT81 | NMDCIIAEI | 706 | LLDCIIAFL | 297 |
| LEMD1 | AVLGIFIIV | 707 | LILGIFISV | 298 |
| LEMD1 | KLAVLGIFI | 70 | YLAVLGISL | 299 |
| LRRC15 | AIAAIVIGI | 709 | VLAAIVIGV | 300 |
| LRRC15 | ALACSLAAC | 710 | LLACSLAML | 301 |
| LRRC15 | IVIGIVALA | 711 | FVIGIVALV | 302 |
| LRRC15 | RIVAVPTPL | 712 | YVVAVPTPV | 303 |
| LRRC15 | RIVAVPTPL | 712 | YIVAVPTPV | 304 |
| LRRC15 | RIVAVPTPL | 712 | FIVAVPTPI | 305 |
| LRRC15 | SLKELSPGI | 713 | MLKELSPEL | 306 |
| LRRC15 | SLKELSPGI | 713 | FLKELSPGL | 307 |
| MAGEA1 | KVADLVGFL | 714 | FVADLVGHV | 308 |
| MAGEA1 | LVLGTLEEV | 858 | SLLGTLEEL | 309 |
| MAGEA10 | GMLSDVQSM | 715 | VMLSDVQSV | 310 |
| MAGEA10 | GMLSDVQSM | 715 | RLLSDVQGL | 311 |
| MAGEA10 | ILILILSIV | 716 | SLILILSSV | 312 |
| MAGEA10 | ILILILSIV | 716 | KLILILSYL | 313 |
| MAGEA11 | AMDAIFGSL | 717 | ALDAIFGGV | 314 |
| MAGEA11 | GLITKAEML | 718 | FLITKAEEL | 315 |
| MAGEA11 | GTLEELPAA | 719 | SLLEELPAL | 316 |
| MAGEA11 | GTLEELPAA | 719 | MTLEELPFL | 317 |
| MAGEA11 | KVLEYIANA | 720 | IILEYIALL | 318 |
| MAGEA12 | QLVFGIEVV | 721 | YMVFGIEGI | 319 |
| MAGEA4 | AVSSSSPLV | 722 | SLSSSSPLV | 320 |
| MAGEA4 | KVDELAHFL | 723 | KLDELAHFL | 321 |
| MAGEA4 | KVLEHVVRV | 724 | FVLEHVVPL | 322 |
| MLANA | VILGVLLLI | 725 | YLLGVLLLL | 323 |
| MLANA | VILGVLLLI | 725 | YILGVLLTA | 324 |
| MLANA | VILGVLLLI | 725 | MLLGVLLLL | 325 |
| MLANA | VILGVLLLI | 725 | MILGVLLFL | 326 |
| MLANA | VILGVLLLI | 725 | LMLGVLLLA | 327 |
| MLANA | VILGVLLLI | 725 | LLLGVLLLL | 328 |
| MLANA | VILGVLLLI | 725 | KLLGVLLLV | 329 |
| MLANA | VILGVLLLI | 725 | IILGVLLAV | 330 |
| MLANA | VILGVLLLI | 725 | FILGVLLSL | 331 |
| MLANA | VILGVLLLI | 725 | ALLGVLLLL | 332 |
| MLANA | VILGVLLLI | 725 | ALLGVLLLA | 333 |
| MLANA | VILGVLLLI | 725 | AILGVLLLV | 334 |
| NKX2-1 | MTAAGVPQL | 726 | ILAAGVPEL | 335 |
| NKX2-1 | SVSDILSPL | 727 | YVSDILSYV | 336 |
| NKX2-1 | SVSDILSPL | 727 | YISDILSYV | 337 |
| NKX2-1 | SVSDILSPL | 727 | VISDILSFL | 338 |
| NKX2-1 | SVSDILSPL | 727 | SMSDILSRL | 339 |
| NKX2-1 | SVSDILSPL | 727 | FVSDILSAA | 340 |
| NPTX2 | ALLAASVAL | 728 | WLLAASVTV | 341 |
| NPTX2 | ALLAASVAL | 728 | ILLAASVLV | 342 |
| NPTX2 | ALLAASVAL | 728 | FLLAASVMM | 343 |
| NPTX2 | ALLAASVAL | 728 | ALLAASVLV | 344 |
| NPTX2 | LLAASVALA | 729 | LLAASVALL | 345 |
| NPTX2 | LLAASVALA | 729 | LLAASVAGV | 346 |
| NPTX2 | LLAASVALA | 729 | ILAASVAAV | 347 |
| NPTX2 | LLAASVALA | 729 | GLAASVAPV | 348 |
| NPTX2 | QLLRKVAEL | 730 | ALLRKVAEV | 349 |
| NPTX2 | TLPELYAFT | 731 | SLPELYAWI | 350 |
| NPTX2 | YLYGKIKKT | 732 | ILYGKIKYL | 351 |
| PAGE3 | QVLGLAAYL | 733 | MLLGLAAFL | 352 |
| PAGE3 | QVLGLAAYL | 733 | GLLGLAAFL | 353 |
| PAGE3 | QVLGLAAYL | 733 | ALLGLAAFL | 354 |
| PAX2 | GLDEVKSSL | 734 | YLDEVKSLV | 355 |
| PAX2 | GLDEVKSSL | 734 | YLDEVKSLI | 356 |
| PAX2 | GLDEVKSSL | 734 | YLDEVKSIL | 357 |
| PAX2 | GLDEVKSSL | 734 | LLDEVKSLV | 358 |
| PCDHB16 | FVLLSLSGA | 735 | FILLSLSPV | 359 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| PCDHB16 | SLFLFSVLL | 736 | RLFLFSVLV | 360 |
| PCDHB16 | SLTVYLVVA | 737 | ALTVYLVYL | 361 |
| PCDHB16 | VLLFVAVRL | 738 | RLLFVAVPI | 362 |
| PCDHB16 | VLLFVAVRL | 738 | RLLFVAVGL | 363 |
| PCDHB16 | VLLFVAVRL | 738 | FLLFVAVSV | 364 |
| PCDHB16 | VSSLFLFSV | 739 | FISLFLFSV | 365 |
| PIWIL1 | SIAGFVASI | 740 | LIAGFVALV | 366 |
| PMEL | ILLVLMAVV | 741 | YLLVLMASI | 367 |
| PMEL | LIVGILLVL | 742 | YLVGILLVL | 368 |
| PMEL | LIVGILLVL | 742 | KIVGILLGI | 369 |
| PMEL | LIVGILLVL | 742 | KIVGILLAV | 370 |
| PMEL | LIVGILLVL | 742 | ILVGILLVV | 371 |
| PMEL | LIVGILLVL | 742 | GIVGILLNV | 372 |
| PMEL | LIVGILLVL | 742 | GIVGILLAV | 373 |
| PMEL | LMAVVLASL | 743 | LLAVVLAFV | 374 |
| PMEL | LMAVVLASL | 743 | LLAVVLAAV | 375 |
| PMEL | PLLDGTATL | 744 | GVLDGTATV | 376 |
| PMEL | SLADTNSLA | 745 | ALADTNSYV | 377 |
| PMEL | SLADTNSLA | 745 | ALADTNSYL | 378 |
| PMEL | VLQAAIPLT | 746 | AMQAAIPML | 379 |
| PRAME | AVLDGLDVL | 747 | IVLDGLDLV | 380 |
| PRAME | AVLDGLDVL | 747 | AVLDGLDPV | 381 |
| PRAME | QLLALLPSL | 748 | YLLALLPLL | 382 |
| PRAME | QLLALLPSL | 748 | YLLALLPIL | 383 |
| PRAME | QLLALLPSL | 748 | QLLALLPGV | 384 |
| PRAME | QLLALLPSL | 748 | LLLALLPTV | 385 |
| PRAME | RLRELLCEL | 749 | FLRELLCQL | 386 |
| PRAME | VLYPVPLES | 750 | LLYPVPLGV | 387 |
| PTHLH | AVFLLSYAV | 751 | ALFLLSYTV | 388 |
| SEMG1 | FVLSLLLIL | 752 | YVLSLLLTL | 389 |
| SEMG1 | FVLSLLLIL | 752 | VLLSLLLIV | 390 |
| SEMG1 | FVLSLLLIL | 752 | SLLSLLLIL | 391 |
| SEMG1 | FVLSLLLIL | 752 | RLLSLLLVL | 392 |
| SEMG1 | FVLSLLLIL | 752 | LVLSLLLLV | 393 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| SEMG1 | FVLSLLLIL | 752 | KLLSLLLVL | 394 |
| SEMG1 | FVLSLLLIL | 752 | ILLSLLLVL | 395 |
| SEMG1 | FVLSLLLIL | 752 | FTLSLLLTL | 396 |
| SEMG1 | FVLSLLLIL | 752 | ALLSLLLIL | 397 |
| SEMG1 | IIFVLSLLL | 753 | VLFVLSLFL | 398 |
| SEMG1 | IIFVLSLLL | 753 | ILFVLSLQL | 399 |
| SEMG1 | LILEKQAAV | 754 | LLLEKQAEV | 400 |
| SERHL2 | LISELKLAV | 755 | VLSELKLAV | 401 |
| SERHL2 | RAIEHVLQV | 756 | RMIEHVLTV | 402 |
| SERHL2 | SSFDRLIPL | 757 | QIFDRLIPI | 403 |
| SERHL2 | SSFDRLIPL | 757 | GVFDRLIPI | 404 |
| SERHL2 | TLKEQFQFV | 758 | YLKEQFQTL | 405 |
| SLC45A3 | AILDSAFLL | 759 | SLLDSAFLL | 406 |
| SLC45A3 | AISLVFSLV | 760 | MLSLVFSLI | 407 |
| SLC45A3 | AISLVFSLV | 760 | LMSLVFSLV | 408 |
| SLC45A3 | ALQILPYTL | 761 | WMQILPYQV | 409 |
| SLC45A3 | ALTGFTFSA | 762 | MMTGFTFGV | 410 |
| SLC45A3 | AQLLLVNLL | 763 | MLLLLVNLV | 411 |
| SLC45A3 | CLFGLLTLI | 764 | VLFGLLTFL | 412 |
| SLC45A3 | CLFGLLTLI | 764 | QLFGLLTDV | 413 |
| SLC45A3 | CLFGLLTLI | 764 | FLFGLLTMI | 414 |
| SLC45A3 | CLFGLLTLI | 764 | FLFGLLTDA | 415 |
| SLC45A3 | GILLSLFLI | 765 | TLLLSLFLL | 416 |
| SLC45A3 | GILLSLFLI | 765 | FILLSLFML | 417 |
| SLC45A3 | GLLPPPPAL | 766 | ILLPPPPVV | 418 |
| SLC45A3 | GLLTLIFLT | 767 | VLLTLIFAL | 419 |
| SLC45A3 | GLLTLIFLT | 767 | RLLTLIFTL | 420 |
| SLC45A3 | GLLTLIFLT | 767 | QLLTLIFYL | 421 |
| SLC45A3 | GLLTLIFLT | 767 | LLLTLIFPI | 422 |
| SLC45A3 | GLLTLIFLT | 767 | FLLTLIFSL | 423 |
| SLC45A3 | GLVAIYFAT | 768 | VMVAIYFTL | 424 |
| SLC45A3 | NLGALLPRL | 769 | LLGALLPAV | 425 |
| SLC45A3 | NLGALLPRL | 769 | ILGALLPLL | 426 |
| SLC45A3 | SVAAFPVAA | 770 | SVAAFPVTV | 427 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| SLC6A3 | FLLSLFCVT | 771 | LLLSLFCLI | 428 |
| SLC6A3 | FLLSLFCVT | 771 | KLLSLFCTL | 429 |
| SLC6A3 | FLLSLFCVT | 771 | FLLSLFCIA | 430 |
| SLC6A3 | FSLGVGFGV | 772 | ILLGVGFGI | 431 |
| SLC6A3 | FSLGVGFGV | 772 | ALLGVGFGI | 432 |
| SLC6A3 | GLIDEFQLL | 773 | RLIDEFQSV | 433 |
| SLC6A3 | GMESVITGL | 774 | FLESVITTV | 434 |
| SLC6A3 | ILFGVLIEA | 775 | GLFGVLIGV | 435 |
| SLC6A3 | ILFGVLIEA | 775 | AMFGVLISV | 436 |
| SLC6A3 | KIDFLLSVI | 776 | FIDFLLSEV | 437 |
| SLC6A3 | LLFMVIAGM | 777 | GLFMVIAGV | 438 |
| SLC6A3 | LLFMVIAGM | 777 | FLFMVIAFA | 439 |
| SLC6A3 | LVPYLLFMV | 778 | HLPYLLFLL | 440 |
| SLC6A3 | QLTACLVLV | 779 | TLTACLVGV | 441 |
| SNX31 | MISEKMVKL | 780 | MLSEKMVQL | 442 |
| SOX11 | LMFDLSLNF | 781 | NLFDLSLVA | 443 |
| SOX11 | LMFDLSLNF | 781 | GLFDLSLRV | 444 |
| SOX11 | LMFDLSLNF | 781 | ALFDLSLPI | 445 |
| SOX17 | ALPAVMAGL | 782 | TLPAVMAEV | 446 |
| SOX17 | GLAEPQAAA | 783 | LLAEPQASL | 447 |
| SOX17 | GLAEPQAAA | 783 | ILAEPQALV | 448 |
| SOX17 | GLAEPQAAA | 783 | FIAEPQAAL | 449 |
| SPINK1 | GIFLLSALA | 784 | LLFLLSALL | 450 |
| STEAP1 | ASLTFLYTL | 785 | KMLTFLYTA | 451 |
| STEAP1 | AVLHAIYSL | 786 | AVLHAIYGV | 452 |
| STEAP1 | FFFAVLHAI | 787 | HLFAVLHAV | 453 |
| STEAP1 | GVIAAIVQL | 788 | SVIAAIVLV | 454 |
| STEAP1 | GVIAAIVQL | 788 | FVIAAIVCV | 455 |
| STEAP1 | GVIAAIVQL | 788 | FIIAAIVAV | 456 |
| STEAP1 | GVIAAIVQL | 788 | AVIAAIVGV | 457 |
| STEAP1 | KIAAIIASL | 789 | YIAAIIAEA | 458 |
| STEAP1 | KIAAIIASL | 789 | FVAAIIASL | 459 |
| STEAP1 | KIAAIIASL | 789 | FIAAIIAPI | 460 |
| STEAP1 | LIFKSILFL | 790 | GLFKSILFL | 461 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| STEAP1 | LLLGTIHAL | 791 | MLLGTIHGV | 462 |
| STEAP1 | LLSFFFAVL | 792 | LLSFFFAML | 463 |
| STEAP1 | LLSFFFAVL | 792 | LLSFFFAAL | 464 |
| STEAP1 | LLSFFFAVL | 792 | FLSFFFAAM | 465 |
| STEAP1 | MIAVFLPIV | 793 | FLAVFLPVL | 466 |
| STEAP1 | SLLLGTIHA | 794 | SLLLGTILV | 467 |
| STEAP1 | SLLLGTIHA | 794 | ILLLGTILL | 468 |
| TBL1Y | SLSLIVAVI | 795 | RLSLIVALV | 469 |
| TBL1Y | SLSLIVAVI | 795 | RLSLIVAFV | 470 |
| TDRD1 | IISPNLFYA | 796 | MISPNLFRV | 471 |
| TDRD1 | LLDHVLIEM | 797 | LLDHVLIAV | 472 |
| TDRD1 | VLIDEHLVL | 798 | RLIDEHLVV | 473 |
| TDRD1 | YSSEVLEYM | 799 | TLSEVLEYL | 474 |
| TOP2A | ILLRPDTYI | 800 | FLLRPDTFL | 475 |
| TOP2A | LMMTIINLA | 801 | LMMTIINQV | 476 |
| TOP2A | LMMTIINLA | 80 | LLMTIINQV | 477 |
| TOP2A | LMMTIINLA | 801 | FLMTIINQV | 478 |
| TOP2A | QLAGSVAEM | 802 | RLAGSVAGV | 479 |
| TOP2A | QLAGSVAEM | 802 | KLAGSVAGV | 480 |
| TOP2A | SLMMTIINL | 803 | LLMMTIITV | 481 |
| TOP2A | TMLSSLARL | 804 | AMLSSLAGV | 482 |
| TOP2A | YIFTMLSSL | 805 | YVFTMLSAV | 483 |
| TPTE | DLAGVIIEL | 806 | YLAGVIILI | 484 |
| TPTE | DLAGVIIEL | 806 | MLAGVIIYI | 485 |
| TPTE | DLAGVIIEL | 806 | MLAGVIIGI | 486 |
| TPTE | DLAGVIIEL | 806 | LLAGVIITI | 487 |
| TPTE | DLAGVIIEL | 806 | LLAGVIIGI | 488 |
| TPTE | DLAGVIIEL | 806 | GLAGVIITI | 489 |
| TPTE | DLAGVIIEL | 806 | GLAGVIIAV | 490 |
| TPTE | FGLFGVFLV | 807 | VMLFGVFMV | 491 |
| TPTE | FGLFGVFLV | 807 | VLLFGVFLV | 492 |
| TPTE | FGLFGVFLV | 807 | ILLFGVFMV | 493 |
| TPTE | FGLFGVFLV | 807 | FILFGVFML | 494 |
| TPTE | GLFGVFLVL | 808 | VLFGVFLGV | 495 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| TPTE | GLFGVFLVL | 808 | GMFGVFLTL | 496 |
| TPTE | GLFGVFLVL | 808 | FLFGVFLAM | 497 |
| TPTE | ILDTAIIVI | 809 | VLDTAHIYI | 498 |
| TPTE | ILDTAIIVI | 809 | KLDTAIIHV | 499 |
| TPTE | IVSSFAFGL | 810 | LISSFAFLV | 500 |
| TPTE | IVSSFAFGL | 810 | LISSFAFLL | 501 |
| TPTE | RLLRLIILL | 811 | FMLRLIINL | 502 |
| TPTE | SLAIALFFL | 812 | ALAIALFPV | 503 |
| TPTE | YFWLHTSFI | 813 | ALWLHTSFA | 504 |
| TRPM8 | AMFGYTVGT | 814 | TMFGYTVFL | 505 |
| TRPM8 | FIAGIVFRL | 815 | YLAGIVFTL | 506 |
| TRPM8 | FLLLFAYVL | 816 | LMLLFAYYL | 507 |
| TRPM8 | LLFAYVLLM | 817 | YLFAYVLIV | 508 |
| TRPM8 | LLFAYVLLM | 817 | TLFAYVLGL | 509 |
| TRPM8 | LLLFAYVLL | 818 | GLLFAYVEV | 510 |
| TRPM8 | LVLYSLVFV | 819 | KILYSLVEV | 511 |
| TRPM8 | NILLVNLLV | 820 | FLLLVNLLV | 512 |
| TRPM8 | QIADVIASL | 821 | VIADVIALL | 513 |
| TRPM8 | QIADVIASL | 821 | QIADVIAFL | 514 |
| TRPM8 | QIADVIASL | 821 | LVADVIASV | 515 |
| TRPM8 | QIADVIASL | 821 | LIADVIALL | 516 |
| TRPM8 | VLYSLVFVL | 822 | LLYSLVFFL | 517 |
| TRPM8 | YLVKINTKA | 823 | FLVKINTNI | 518 |
| TYMS | FLDSLGFST | 824 | KLDSLGFTL | 519 |
| TYMS | FLDSLGFST | 824 | KLDSLGFSL | 520 |
| TYMS | FLDSLGFST | 824 | FLDSLGFSL | 521 |
| TYMS | SLRDEFPLL | 825 | FMRDEFPDV | 522 |
| TYMS | SLRDEFPLL | 825 | FLRDEFPEA | 523 |
| TYMS | VLEELLWFI | 826 | SMEELLWFV | 524 |
| TYR | ALLAGLVSL | 827 | YLLAGLVLL | 525 |
| TYR | ALLAGLVSL | 827 | YLLAGLVLI | 526 |
| TYR | AMVGAVLTA | 828 | WLVGAVLTL | 527 |
| TYR | AMVGAVLTA | 828 | LLVGAVLTV | 528 |
| TYR | AMVGAVLTA | 828 | ALVGAVLTV | 529 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| TYR | AMVGAVLTA | 828 | ALVGAVLLV | 530 |
| TYR | ISSDYVIPI | 829 | CLSDYVIPV | 531 |
| TYR | LLAGLVSLL | 830 | KLAGLVSSV | 532 |
| TYR | LLSPASFFS | 831 | GMSPASFFA | 533 |
| TYR | MVGAVLTAL | 832 | ALGAVLTAV | 534 |
| TYR | VLTALLAGL | 833 | YLTALLAEM | 535 |
| TYR | VLTALLAGL | 833 | VLTALLAAV | 536 |
| TYR | VLTALLAGL | 833 | RLTALLAAV | 537 |
| TYR | VLTALLAGL | 833 | GLTALLAPV | 538 |
| TYR | VLTALLAGL | 833 | FLTALLATV | 539 |
| UPK2 | ALTESLLVA | 834 | TLTESLLYL | 540 |
| UPK2 | ALTESLLVA | 834 | KLTESLLTI | 541 |
| UPK2 | ALTESLLVA | 834 | ILTESLLFL | 542 |
| UPK2 | LLALLSPGA | 835 | RLALLSPYI | 543 |
| UPK2 | LVLGFIIAL | 836 | SILGFIIAA | 544 |
| UPK2 | LVLGFIIAL | 836 | LILGFIIAV | 545 |
| UPK2 | LVLGFIIAL | 836 | FVLGFIITI | 546 |
| UPK2 | LVLGFIIAL | 836 | FILGFIITI | 547 |
| UPK2 | SLSGLLSPA | 837 | SLSGLLSGV | 548 |
| UPK2 | SLSGLLSPA | 837 | FLSGLLSAL | 549 |
| UPK2 | TLPLILILL | 838 | ILPLILITV | 550 |
| UPK2 | VLGFIIALA | 839 | MLGFIIAFL | 551 |
| UPK2 | VLGFIIALA | 839 | LLGFIIAEV | 552 |
| UPK2 | VLGFIIALA | 839 | ILGFIIAAV | 553 |
| UPK2 | VLGFIIALA | 839 | FLGFIIADV | 554 |
| UPK2 | VVITVLLSV | 840 | MIITVLLLV | 555 |
| UPK2 | VVITVLLSV | 840 | FIITVLLGL | 556 |
| VCAM1 | AQIGDSVML | 841 | YQIGDSVLL | 557 |
| VCAM1 | FASSLIIPA | 842 | MLSSLIIPL | 558 |
| VCAM1 | KSIDGAYTI | 843 | ILIDGAYTV | 559 |
| VCAM1 | SILEEGSSV | 844 | YLLEEGSSV | 560 |
| WFDC2 | LLFGFTLVS | 845 | YMFGFTLTM | 561 |
| WFDC2 | LLFGFTLVS | 845 | YLFGFTLGM | 562 |
| WFDC2 | LLFGFTLVS | 845 | VLFGFTLSI | 563 |

TABLE 1A-continued

Antigenic peptides according to the invention

| Tumor antigen | Sequence human reference peptide | SEQ ID NO. human reference peptide | Sequence antigenic peptide | SEQ ID NO. antigenic peptide |
|---|---|---|---|---|
| WFDC2 | LLFGFTLVS | 845 | RMFGFTLML | 564 |
| WFDC2 | LLFGFTLVS | 845 | LMFGFTLRT | 565 |
| WFDC2 | LLLFGFTLV | 846 | YLLFGFTRV | 566 |
| WFDC2 | RLGPLAAAL | 847 | VLGPLAALV | 567 |
| WFDC2 | RLGPLAAAL | 847 | ILGPLAAWL | 568 |
| WT1 | DLNALLPAV | 848 | SLNALLPYV | 569 |
| ZEB1 | ILIPQVAYT | 849 | MMIPQVATL | 570 |
| ZEB1 | ILIPQVAYT | 849 | MMIPQVATI | 571 |
| ZEB1 | NLSDIQNVL | 850 | YLSDIQNAI | 572 |
| ZEB1 | NLSDIQNVL | 850 | VMSDIQNRV | 573 |
| ZEB1 | VQAVVLPTV | 851 | YQAVVLPGL | 574 |
| ZNF165 | LVLEQFLTI | 852 | LLLEQFLSV | 575 |
| ZNF165 | LVLEQFLTI | 852 | LLLEQFLAI | 576 |
| ZNF165 | LVLEQFLTI | 852 | ALLEQFLTA | 577 |
| ZNF165 | RISGYISEA | 853 | GVSGYISPV | 578 |
| ZNF280A | AMTDISSLA | 854 | KLTDISSLV | 579 |
| ZNF280A | VLLSNFYYG | 855 | YLLSNFYTV | 580 |

As can be retrieved from Table 1A, the antigenic peptides according to the present invention can be categorized according to the respective "human reference peptide" and according to the respective tumor antigen.

In one embodiment, the antigenic peptide according to the present invention is a microbiota sequence variant of a fragment of the tumor antigen ACPP (human reference peptide), such as "FLFLLFFWL" (SEQ ID NO: 581), "SLSLGFLFL" (SEQ ID NO: 582) or "LSLGFLFLL" (SEQ ID NO: 583). In a preferred embodiment, the antigenic peptide according to the present invention is a sequence variant of a fragment of the tumor antigen ACPP, such as antigenic peptides comprising or consisting of an amino acid sequence as set forth in any one of SEQ ID NOs 1-4. More preferably, the antigenic peptide according to the present invention is a sequence variant of the ACPP fragment (human reference peptide) "FLFLLFFWL" (SEQ ID NO: 581), such as an antigenic peptide comprising or consisting of an amino acid sequence as set forth in SEQ ID NO: 1. It is also more preferred that the antigenic peptide according to the present invention is a sequence variant of the ACPP fragment (human reference peptide) "SLSLGFLFL" (SEQ ID NO: 582), such as an antigenic peptide comprising or consisting of an amino acid sequence as set forth in SEQ ID NO: 2 or 3. It is also more preferred that the antigenic peptide according to the present invention is a sequence variant of the ACPP fragment (human reference peptide)

"LSLGFLFLL" (SEQ ID NO: 583), such as an antigenic peptide comprising or consisting of an amino acid sequence as set forth in SEQ ID NO: 4.

In another embodiment, the antigenic peptide according to the present invention is a microbiota sequence variant of a fragment of the tumor antigen ANKRD30A (human reference peptide), such as "YTSNDSYIV" (SEQ ID NO: 584), "ILIDSGADI" (SEQ ID NO: 585), "SLFESSAKI" (SEQ ID NO: 586) or "SLTPLLLSI" (SEQ ID NO: 587). In another preferred embodiment, the antigenic peptide according to the present invention is a sequence variant of a fragment of the tumor antigen ANKRD30A, such as antigenic peptides comprising or consisting of an amino acid sequence as set forth in any one of SEQ ID NOs 5-15. More preferably, the antigenic peptide according to the present invention is a sequence variant of the ANKRD30A fragment (human reference peptide) "YTSNDSYIV" (SEQ ID NO: 584), such as an antigenic peptide comprising or consisting of an amino acid sequence as set forth in SEQ ID NO: 5. It is also more preferred that the antigenic peptide according to the present invention is a sequence variant of the ANKRD30A fragment (human reference peptide) "ILIDSGADI" (SEQ ID NO: 585), such as an antigenic peptide comprising or consisting of an amino acid sequence as set forth in SEQ ID NO: 6, 7 or 8. It is also more preferred that the antigenic peptide according to the present invention is a sequence variant of the ANKRD30A fragment (human reference peptide) "SLFESSAKI" (SEQ ID NO: 586), such as an antigenic peptide comprising or consisting of an amino acid sequence as set forth in SEQ ID NO: 9 or 10. It is also more preferred that the antigenic peptide according to the present invention is a sequence variant of the ANKRD30A fragment (human reference peptide) "SLTPLLLSI" (SEQ ID NO: 587), such as an antigenic peptide comprising or consisting of an amino acid sequence as set forth in SEQ ID NO: 11, 12, 13, 14 or 15.

In another embodiment, the antigenic peptide according to the present invention is a microbiota sequence variant of a fragment of the tumor antigen AREG (human reference peptide), such as "MSAVILTAV" (SEQ ID NO: 588) or "ALAAIAAFM" (SEQ ID NO: 589). In another preferred embodiment, the antigenic peptide according to the present invention is a sequence variant of a fragment of the tumor antigen AREG, such as antigenic peptides comprising or consisting of an amino acid sequence as set forth in any one of SEQ ID NOs 16-24. More preferably, the antigenic peptide according to the present invention is a sequence variant of the AREG fragment (human reference peptide) "MSAVILTAV" (SEQ ID NO: 588), such as an antigenic peptide comprising or consisting of an amino acid sequence as set forth in SEQ ID NO: 16 or 17. It is also more preferred that the antigenic peptide according to the present invention is a sequence variant of the AREG fragment (human reference peptide) "ALAAIAAFM" (SEQ ID NO: 589), such as an antigenic peptide comprising or consisting of an amino acid sequence as set forth in SEQ ID NO: 18, 19, 20, 21, 22, 23 or 24.

In another embodiment, the antigenic peptide according to the present invention is a microbiota sequence variant of a fragment of the tumor antigen ASCL1 (human reference peptide), such as "VSAAFQAGV" (SEQ ID NO: 590). In another preferred embodiment, the antigenic peptide according to the present invention is a sequence variant of a fragment of the tumor antigen ASCL1, such as the antigenic peptide comprising or consisting of an amino acid sequence as set forth in SEQ ID NO: 25. Namely, the antigenic peptide according to the present invention, which comprises or consists of an amino acid sequence as set forth in SEQ ID NO: 25 is a sequence variant of the ASCL1 fragment (human reference peptide) "VSAAFQAGV" (SEQ ID NO: 590).

In another embodiment, the antigenic peptide according to the present invention is a microbiota sequence variant of a fragment of the tumor antigen ASCL2 (human reference peptide), such as "KLVNLGFQA" (SEQ ID NO: 591) or "ELLDFSSWL" (SEQ ID NO: 592). In another preferred embodiment, the antigenic peptide according to the present invention is a sequence variant of a fragment of the tumor antigen ASCL2, such as antigenic peptides comprising or consisting of an amino acid sequence as set forth in any one of SEQ ID NOs 26-29. More preferably, the antigenic peptide according to the present invention is a sequence variant of the ASCL2 fragment (human reference peptide) "KLVNLGFQA" (SEQ ID NO: 591), such as an antigenic peptide comprising or consisting of an amino acid sequence as set forth in SEQ ID NO: 26 or 27. It is also more preferred that the antigenic peptide according to the present invention is a sequence variant of the ASCL2 fragment (human reference peptide) "ELLDFSSWL" (SEQ ID NO: 592), such as an antigenic peptide comprising or consisting of an amino acid sequence as set forth in SEQ ID NO: 28 or 29.

In another embodiment, the antigenic peptide according to the present invention is a microbiota sequence variant of a fragment of the tumor antigen BIRC5 (human reference peptide), such as "LTLGEFLKL" (SEQ ID NO: 593). In another preferred embodiment, the antigenic peptide according to the present invention is a sequence variant of a fragment of the tumor antigen BIRC5, such as antigenic peptides comprising or consisting of an amino acid sequence as set forth in any one of SEQ ID NOs 30-32. More preferably, the antigenic peptide according to the present invention is a sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32. Even more preferably, the antigenic peptide comprises or consists of SEQ ID NO: 32.

In another embodiment, the antigenic peptide according to the present invention is a microbiota sequence variant of a fragment of the tumor antigen CA9 (human reference peptide), such as "AAGDILALV" (SEQ ID NO: 594), "ALVFGLLFA" (SEQ ID NO: 595), "FQYEGSLTT" (SEQ ID NO: 596), "HLSTAFARV" (SEQ ID NO: 597), "LSLLLLVPV" (SEQ ID NO: 598), "QLLLSLLLL" (SEQ ID NO: 599) or "VQLLLSLLL" (SEQ ID NO: 600). In another preferred embodiment, the antigenic peptide according to the present invention is a sequence variant of a fragment of the tumor antigen CA9, such as antigenic peptides comprising or consisting of an amino acid sequence as set forth in any one of SEQ ID NOs 33-50. More preferably, the antigenic peptide according to the present invention is a sequence variant of the CA9 fragment (human reference peptide) "AAGDILALV" (SEQ ID NO: 594), such as an antigenic peptide comprising or consisting of an amino acid sequence as set forth in SEQ ID NO: 33 or 34. It is also more preferred that the antigenic peptide according to the present invention is a sequence variant of the CA9 fragment (human reference peptide) "ALVFGLLFA" (SEQ ID NO: 595), such as an antigenic peptide comprising or consisting of an amino acid sequence as set forth in SEQ ID NO: 35, 36 or 37. It is also more preferred that the antigenic peptide according to the present invention is a sequence variant of the CA9 fragment (human reference peptide) "FQYEGSLTT" (SEQ ID NO: 596), such as an antigenic peptide comprising or consisting of an amino acid sequence as set forth in SEQ ID NO: 38. It is also more preferred that the antigenic peptide according to the present invention is a sequence variant of the CA9 fragment (human reference peptide) "HLSTAFARV" (SEQ ID NO: 597), such as an antigenic peptide comprising or consisting of an amino acid sequence as set forth in SEQ ID NO: 39, 40 or 41. It is also more preferred that the antigenic peptide according to the present invention is a sequence variant of the CA9 fragment (human reference peptide) "LSLLLLVPV" (SEQ ID NO: 598), such as an antigenic peptide comprising or consisting of an amino acid sequence as set forth in SEQ ID NO: 42, 43 or 44. It is also more preferred that the antigenic peptide according to the present invention is a sequence variant of the CA9 fragment (human reference peptide) "QLLLSLLLL" (SEQ ID NO: 599), such as an antigenic peptide comprising or consisting of an amino acid sequence as set forth in SEQ ID NO: 45, 46 or 47. It is also more preferred that the antigenic peptide according to the present invention is a sequence variant of the CA9 fragment (human reference peptide) "VQLLLSLLL" (SEQ ID NO: 600), such as an antigenic peptide comprising or consisting of an amino acid sequence as set forth in SEQ ID NO: 48, 49 or 50.

In another embodiment, the antigenic peptide according to the present invention is a microbiota sequence variant of a fragment of the tumor antigen CCNA1 (human reference peptide), such as "NLAKYVAEL" (SEQ ID NO: 601) or "LIAAAAFCL" (SEQ ID NO: 602). In another preferred embodiment, the antigenic peptide according to the present invention is a sequence variant of a fragment of the tumor antigen CCNA1, such as antigenic peptides comprising or consisting of an amino acid sequence as set forth in any one of SEQ ID NOs 51-55. More preferably, the antigenic peptide according to the present invention is a sequence variant of the CCNA1 fragment (human reference peptide) "NLAKYVAEL" (SEQ ID NO: 601), such as an antigenic peptide comprising or consisting of an amino acid sequence as set forth in SEQ ID NO: 51. It is also more preferred that the antigenic peptide according to the present invention is a sequence variant of the CCNA1 fragment (human reference peptide) "LIAAAAFCL" (SEQ ID NO: 602), such as an antigenic peptide comprising or consisting of an amino acid sequence as set forth in SEQ ID NO: 52, 53, 54 or 55.

In another embodiment, the antigenic peptide according to the present invention is a microbiota sequence variant of a fragment of the tumor antigen CCND1 (human reference peptide), such as "LLNDRVLRA" (SEQ ID NO: 603). In another preferred embodiment, the antigenic peptide according to the present invention is a sequence variant of a fragment of the tumor antigen CCND1, such as the antigenic peptide comprising or consisting of an amino acid sequence as set forth in SEQ ID NO: 56. Namely, the antigenic peptide according to the present invention, which comprises or consists of an amino acid sequence as set forth in SEQ ID NO: 56 is a sequence variant of the CCND1 fragment (human reference peptide) "LLNDRVLRA" (SEQ ID NO: 603).

In another embodiment, the antigenic peptide according to the present invention is a microbiota sequence variant of a fragment of the tumor antigen CDH17 (human reference peptide), such as "GILLTTLLV" (SEQ ID NO: 604), "ILAVVFIRI" (SEQ ID NO: 605), "ILLTTLLVI" (SEQ ID NO: 606) or "LVIGIILAV" (SEQ ID NO: 607). In another preferred embodiment, the antigenic peptide according to the present invention is a sequence variant of a fragment of the tumor antigen CDH17, such as antigenic peptides comprising or consisting of an amino acid sequence as set forth in any one of SEQ ID NOs 57-63. More preferably, the antigenic peptide according to the present invention is a sequence variant of the CDH17 fragment (human reference peptide) “GILLTTLLV” (SEQ ID NO: 604), such as an antigenic peptide comprising or consisting of an amino acid sequence as set forth in SEQ ID NO: 57. It is also more preferred that the antigenic peptide according to the present invention is a sequence variant of the CDH17 fragment (human reference peptide) “ILAVVFIRI” (SEQ ID NO: 605), such as an antigenic peptide comprising or consisting of an amino acid sequence as set forth in SEQ ID NO: 58 or 59. It is also more preferred that the antigenic peptide according to the present invention is a sequence variant of the CDH17 fragment (human reference peptide) “ILLTTLLVI” (SEQ ID NO: 606), such as an antigenic peptide comprising or consisting of an amino acid sequence as set forth in SEQ ID NO: 60, 61 or 62. It is also more preferred that the antigenic peptide according to the present invention is a sequence variant of the CDH17 fragment (human reference peptide) “LVIGIILAV” (SEQ ID NO: 607), such as an antigenic peptide comprising or consisting of an amino acid sequence as set forth in SEQ ID NO: 63.

In another embodiment, the antigenic peptide according to the present invention is a microbiota sequence variant of a fragment of the tumor antigen CDH6 (human reference peptide), such as “ALVAILLCI” (SEQ ID NO: 608), “EMSDVGTFV” (SEQ ID NO: 609), “EMSTYLLPV” (SEQ ID NO: 610), “FLLEEYTGS” (SEQ ID NO: 611), “ILLCIVILL” (SEQ ID NO: 612), or “LLVTVVLFA” (SEQ ID NO: 613). In another preferred embodiment, the antigenic peptide according to the present invention is a sequence variant of a fragment of the tumor antigen CDH6, such as antigenic peptides comprising or consisting of an amino acid sequence as set forth in any one of SEQ ID NOs 64-81. More preferably, the antigenic peptide according to the present invention is a sequence variant of the CDH6 fragment (human reference peptide) “ALVAILLCI” (SEQ ID NO: 608), such as an antigenic peptide comprising or consisting of an amino acid sequence as set forth in SEQ ID NO: 64, 65, 66, 67, 68, 69 or 70. It is also more preferred that the antigenic peptide according to the present invention is a sequence variant of the CDH6 fragment (human reference peptide) “EMSDVGTFV” (SEQ ID NO: 609), such as an antigenic peptide comprising or consisting of an amino acid sequence as set forth in SEQ ID NO: 71. It is also more preferred that the antigenic peptide according to the present invention is a sequence variant of the CDH6 fragment (human reference peptide) “EMSTYLLPV” (SEQ ID NO: 610), such as an antigenic peptide comprising or consisting of an amino acid sequence as set forth in SEQ ID NO: 72. It is also more preferred that the antigenic peptide according to the present invention is a sequence variant of the CDH6 fragment (human reference peptide) “FLLEEYTGS” (SEQ ID NO: 611), such as an antigenic peptide comprising or consisting of an amino acid sequence as set forth in SEQ ID NO: 73. It is also more preferred that the antigenic peptide according to the present invention is a sequence variant of the CDH6 fragment (human reference peptide) “ILLCIVILL” (SEQ ID NO: 612), such as an antigenic peptide comprising or consisting of an amino acid sequence as set forth in SEQ ID NO: 74 or 75. It is also more preferred that the antigenic peptide according to the present invention is a sequence variant of the CDH6 fragment (human reference peptide) “LLVTVVLFA” (SEQ ID NO: 613), such as an antigenic peptide comprising or consisting of an amino acid sequence as set forth in SEQ ID NO: 76, 77, 78, 79, 80 or 81.

In another embodiment, the antigenic peptide according to the present invention is a microbiota sequence variant of a fragment of the tumor antigen CDKN2A (human reference peptide), such as “AVALVLMLL” (SEQ ID NO: 614). In another preferred embodiment, the antigenic peptide according to the present invention is a sequence variant of a fragment of the tumor antigen CDKN2A, such as the antigenic peptide comprising or consisting of an amino acid sequence as set forth in SEQ ID NO: 82. Namely, the antigenic peptide according to the present invention, which comprises or consists of an amino acid sequence as set forth in SEQ ID NO: 82 is a sequence variant of the CDKN2A fragment (human reference peptide) “AVALVLMLL” (SEQ ID NO: 614).

In another embodiment, the antigenic peptide according to the present invention is a microbiota sequence variant of a fragment of the tumor antigen CEACAM5 (human reference peptide), such as “LLTFWNPPT” (SEQ ID NO: 615). In another preferred embodiment, the antigenic peptide according to the present invention is a sequence variant of a fragment of the tumor antigen CEACAM5, such as the antigenic peptide comprising or consisting of an amino acid sequence as set forth in SEQ ID NO: 83. Namely, the antigenic peptide according to the present invention, which comprises or consists of an amino acid sequence as set forth in SEQ ID NO: 83 is a sequence variant of the CEACAM5 fragment (human reference peptide) “LLTFWNPPT” (SEQ ID NO: 615).

In another embodiment, the antigenic peptide according to the present invention is a microbiota sequence variant of a fragment of the tumor antigen CHI3L (human reference peptide), such as “KQLLLSAAL” (SEQ ID NO: 616), “LLLSAALSA” (SEQ ID NO: 617), “QLAGAMVWA” (SEQ ID NO: 618), “SQTGFVVLV” (SEQ ID NO: 619) or “TLASSETGV” (SEQ ID NO: 620). In another preferred embodiment, the antigenic peptide according to the present invention is a sequence variant of a fragment of the tumor antigen CHI3L, such as antigenic peptides comprising or consisting of an amino acid sequence as set forth in any one of SEQ ID NOs 84-114. More preferably, the antigenic peptide according to the present invention is a sequence variant of the CHI3L1 fragment (human reference peptide) “KQLLLSAAL” (SEQ ID NO: 616), such as an antigenic peptide comprising or consisting of an amino acid sequence as set forth in SEQ ID NO: 84 or 85. It is also more preferred that the antigenic peptide according to the present invention is a sequence variant of the CHI3L1 fragment (human reference peptide) “LLLSAALSA” (SEQ ID NO: 617), such as an antigenic peptide comprising or consisting of an amino acid sequence as set forth in SEQ ID NO: 86, 87, 88, 89, 90, 91, 92, 93, 94, 95, 96, 97, 98, 99, 100, 101, 102, 103, 104, 105, 106, 107, 108, or 109. It is also more preferred that the antigenic peptide according to the present invention is a sequence variant of the CHI3L1 fragment (human reference peptide) “QLAGAMVWA” (SEQ ID NO: 618), such as an antigenic peptide comprising or consisting of an amino acid sequence as set forth in SEQ ID NO: 110, 111 or 112. It is also more preferred that the antigenic peptide according to the present invention is a sequence variant of the CHI3L1 fragment (human reference peptide) “SQTGFVVLV” (SEQ ID NO: 619), such as an antigenic peptide comprising or consisting of an amino acid sequence as set forth in SEQ ID NO: 113. It is also more preferred that the antigenic peptide according to the present invention is a sequence variant of the CHI3L1 fragment (human reference peptide) “TLAS- SETGV" (SEQ ID NO: 620), such as an antigenic peptide comprising or consisting of an amino acid sequence as set forth in SEQ ID NO: 114.

In another embodiment, the antigenic peptide according to the present invention is a microbiota sequence variant of a fragment of the tumor antigen CHI3L2 (human reference peptide), such as "ILLSIGGYL" (SEQ ID NO: 621), "HLIYSFASI" (SEQ ID NO: 622), "VLIHELAEA" (SEQ ID NO: 623), or "SLWAGVVVL" (SEQ ID NO: 624). In another preferred embodiment, the antigenic peptide according to the present invention is a sequence variant of a fragment of the tumor antigen CHI3L2, such as antigenic peptides comprising or consisting of an amino acid sequence as set forth in any one of SEQ ID NOs 115-119. More preferably, the antigenic peptide according to the present invention is a sequence variant of the CHI3L2 fragment (human reference peptide) "ILLSIGGYL" (SEQ ID NO: 621), such as an antigenic peptide comprising or consisting of an amino acid sequence as set forth in SEQ ID NO: 115. It is also more preferred that the antigenic peptide according to the present invention is a sequence variant of the CHI3L2 fragment (human reference peptide) "HLIYSFASI" (SEQ ID NO: 622), such as an antigenic peptide comprising or consisting of an amino acid sequence as set forth in SEQ ID NO: 116. It is also more preferred that the antigenic peptide according to the present invention is a sequence variant of the CHI3L2 fragment (human reference peptide) "VLIHELAEA" (SEQ ID NO: 623), such as an antigenic peptide comprising or consisting of an amino acid sequence as set forth in SEQ ID NO: 117 or 118. It is also more preferred that the antigenic peptide according to the present invention is a sequence variant of the CHI3L2 fragment (human reference peptide) "SLWAGVVVL" (SEQ ID NO: 624), such as an antigenic peptide comprising or consisting of an amino acid sequence as set forth in SEQ ID NO: 119.

In another embodiment, the antigenic peptide according to the present invention is a microbiota sequence variant of a fragment of the tumor antigen COL11A1 (human reference peptide), such as "WLWDFTVTT" (SEQ ID NO: 625). In another preferred embodiment, the antigenic peptide according to the present invention is a sequence variant of a fragment of the tumor antigen COL11A1, such as the antigenic peptide comprising or consisting of an amino acid sequence as set forth in SEQ ID NO: 120. Namely, the antigenic peptide according to the present invention, which comprises or consists of an amino acid sequence as set forth in SEQ ID NO: 120 is a sequence variant of the COL11A1 fragment (human reference peptide) "WLWDFTVTT" (SEQ ID NO: 625).

In another embodiment, the antigenic peptide according to the present invention is a microbiota sequence variant of a fragment of the tumor antigen CT83 (human reference peptide), such as "LLASSILCA" (SEQ ID NO: 626). In another preferred embodiment, the antigenic peptide according to the present invention is a sequence variant of a fragment of the tumor antigen CT83, such as antigenic peptides comprising or consisting of an amino acid sequence as set forth in any one of SEQ ID NOs 121-123. More preferably, the antigenic peptide according to the present invention is a sequence variant of the CT83 fragment (human reference peptide) "LLASSILCA" (SEQ ID NO: 626), such as an antigenic peptide comprising or consisting of an amino acid sequence as set forth in SEQ ID NO: 121, 122 or 123.

In another embodiment, the antigenic peptide according to the present invention is a microbiota sequence variant of a fragment of the tumor antigen CTCFL (human reference peptide), such as "KLAVSLAET" (SEQ ID NO: 627). In another preferred embodiment, the antigenic peptide according to the present invention is a sequence variant of a fragment of the tumor antigen CTCFL, such as the antigenic peptide comprising or consisting of an amino acid sequence as set forth in SEQ ID NO: 124. Namely, the antigenic peptide according to the present invention, which comprises or consists of an amino acid sequence as set forth in SEQ ID NO: 124 is a sequence variant of the CTCFL fragment (human reference peptide) "KLAVSLAET" (SEQ ID NO: 627).

In another embodiment, the antigenic peptide according to the present invention is a microbiota sequence variant of a fragment of the tumor antigen DCT (human reference peptide), such as "ALVGLFVLL" (SEQ ID NO: 628), "GLFVLLAFL" (SEQ ID NO: 629), "SVYDFFVWL" (SEQ ID NO: 630) or "VVMGTLVAL" (SEQ ID NO: 631). In another preferred embodiment, the antigenic peptide according to the present invention is a sequence variant of a fragment of the tumor antigen DCT, such as antigenic peptides comprising or consisting of an amino acid sequence as set forth in any one of SEQ ID NOs 125-132. More preferably, the antigenic peptide according to the present invention is a sequence variant of the DCT fragment (human reference peptide) "ALVGLFVLL" (SEQ ID NO: 628), such as an antigenic peptide comprising or consisting of an amino acid sequence as set forth in SEQ ID NO: 125 or 126. It is also more preferred that the antigenic peptide according to the present invention is a sequence variant of the DCT fragment (human reference peptide) "GLFVLLAFL" (SEQ ID NO: 629), such as an antigenic peptide comprising or consisting of an amino acid sequence as set forth in SEQ ID NO: 127, 128 or 129. It is also more preferred that the antigenic peptide according to the present invention is a sequence variant of the DCT fragment (human reference peptide) "SVYDFFVWL" (SEQ ID NO: 630), such as an antigenic peptide comprising or consisting of an amino acid sequence as set forth in SEQ ID NO: 130. It is also more preferred that the antigenic peptide according to the present invention is a sequence variant of the DCT fragment (human reference peptide) "VVMGTLVAL" (SEQ ID NO: 631), such as an antigenic peptide comprising or consisting of an amino acid sequence as set forth in SEQ ID NO: 131 or 132.

In another embodiment, the antigenic peptide according to the present invention is a microbiota sequence variant of a fragment of the tumor antigen DMRTA2 (human reference peptide), such as "GTAEGLALA" (SEQ ID NO: 632) or "GLAAGLGPA" (SEQ ID NO: 633). In another preferred embodiment, the antigenic peptide according to the present invention is a sequence variant of a fragment of the tumor antigen DMRTA2, such as antigenic peptides comprising or consisting of an amino acid sequence as set forth in any one of SEQ ID NOs 133-134. More preferably, the antigenic peptide according to the present invention is a sequence variant of the DMRTA2 fragment (human reference peptide) "GTAEGLALA" (SEQ ID NO: 632), such as an antigenic peptide comprising or consisting of an amino acid sequence as set forth in SEQ ID NO: 133. It is also more preferred that the antigenic peptide according to the present invention is a sequence variant of the DMRTA2 fragment (human reference peptide) "GLAAGLGPA" (SEQ ID NO: 633), such as an antigenic peptide comprising or consisting of an amino acid sequence as set forth in SEQ ID NO: 134.

In another embodiment, the antigenic peptide according to the present invention is a microbiota sequence variant of a fragment of the tumor antigen EGFR (human reference peptide), such as "ALESILHRI" (SEQ ID NO: 634), "ALLAALCPA" (SEQ ID NO: 635), "ALLALLAAL" (SEQ ID NO: 636), "ILDEAYVMA" (SEQ ID NO: 637), "LLLLLVVAL" (SEQ ID NO: 638), "MVGALLLLL" (SEQ ID NO: 639), "NLQEILHGA" (SEQ ID NO: 640) or "SLAVVSLNI" (SEQ ID NO: 641). In another preferred embodiment, the antigenic peptide according to the present invention is a sequence variant of a fragment of the tumor antigen EGFR, such as antigenic peptides comprising or consisting of an amino acid sequence as set forth in any one of SEQ ID NOs 135-150. More preferably, the antigenic peptide according to the present invention is a sequence variant of the EGFR fragment (human reference peptide) "ALESILHRI" (SEQ ID NO: 634), such as an antigenic peptide comprising or consisting of an amino acid sequence as set forth in SEQ ID NO: 135 or 136. It is also more preferred that the antigenic peptide according to the present invention is a sequence variant of the EGFR fragment (human reference peptide) "ALLAALCPA" (SEQ ID NO: 635), such as an antigenic peptide comprising or consisting of an amino acid sequence as set forth in SEQ ID NO: 137. It is also more preferred that the antigenic peptide according to the present invention is a sequence variant of the EGFR fragment (human reference peptide) "ALLALLAAL" (SEQ ID NO: 636), such as an antigenic peptide comprising or consisting of an amino acid sequence as set forth in SEQ ID NO: 138, 139, 140, 141, 142, 143 or 144. It is also more preferred that the antigenic peptide according to the present invention is a sequence variant of the EGFR fragment (human reference peptide) "ILDEAYVMA" (SEQ ID NO: 637), such as an antigenic peptide comprising or consisting of an amino acid sequence as set forth in SEQ ID NO: 145. It is also more preferred that the antigenic peptide according to the present invention is a sequence variant of the EGFR fragment (human reference peptide) "LLLLLVVAL" (SEQ ID NO: 638), such as an antigenic peptide comprising or consisting of an amino acid sequence as set forth in SEQ ID NO: 146. It is also more preferred that the antigenic peptide according to the present invention is a sequence variant of the EGFR fragment (human reference peptide) "MVGALLLLL" (SEQ ID NO: 639), such as an antigenic peptide comprising or consisting of an amino acid sequence as set forth in SEQ ID NO: 147. It is also more preferred that the antigenic peptide according to the present invention is a sequence variant of the EGFR fragment (human reference peptide) "NLQEILHGA" (SEQ ID NO: 640), such as an antigenic peptide comprising or consisting of an amino acid sequence as set forth in SEQ ID NO: 148. It is also more preferred that the antigenic peptide according to the present invention is a sequence variant of the EGFR fragment (human reference peptide) "SLAVVSLNI" (SEQ ID NO: 641), such as an antigenic peptide comprising or consisting of an amino acid sequence as set forth in SEQ ID NO: 149 or 150.

In another embodiment, the antigenic peptide according to the present invention is a microbiota sequence variant of a fragment of the tumor antigen ERBB2 (human reference peptide), such as "AVVGILLVV" (SEQ ID NO: 642), "ILDEAYVMA" (SEQ ID NO: 643), "LLALLPPGA" (SEQ ID NO: 644), "SIISAVVGI" (SEQ ID NO: 645) or "VVLGVVFGI" (SEQ ID NO: 646). In another preferred embodiment, the antigenic peptide according to the present invention is a sequence variant of a fragment of the tumor antigen ERBB2, such as antigenic peptides comprising or consisting of an amino acid sequence as set forth in any one of SEQ ID NOs 151-162. More preferably, the antigenic peptide according to the present invention is a sequence variant of the ERBB2 fragment (human reference peptide) "AVVGILLVV" (SEQ ID NO: 642), such as an antigenic peptide comprising or consisting of an amino acid sequence as set forth in SEQ ID NO: 151, 152, 153 or 154. It is also more preferred that the antigenic peptide according to the present invention is a sequence variant of the ERBB2 fragment (human reference peptide) "ILDEAYVMA" (SEQ ID NO: 643), such as an antigenic peptide comprising or consisting of an amino acid sequence as set forth in SEQ ID NO: 155. It is also more preferred that the antigenic peptide according to the present invention is a sequence variant of the ERBB2 fragment (human reference peptide) "LLALLPPGA" (SEQ ID NO: 644), such as an antigenic peptide comprising or consisting of an amino acid sequence as set forth in SEQ ID NO: 156, 157, 158 or 159. It is also more preferred that the antigenic peptide according to the present invention is a sequence variant of the ERBB2 fragment (human reference peptide) "SIISAVVGI" (SEQ ID NO: 645), such as an antigenic peptide comprising or consisting of an amino acid sequence as set forth in SEQ ID NO: 160. It is also more preferred that the antigenic peptide according to the present invention is a sequence variant of the ERBB2 fragment (human reference peptide) "VVLGVVFGI" (SEQ ID NO: 646), such as an antigenic peptide comprising or consisting of an amino acid sequence as set forth in SEQ ID NO: 161 or 162, in particular an antigenic peptide comprising or consisting of an amino acid sequence as set forth in SEQ ID NO: 162.

In another embodiment, the antigenic peptide according to the present invention is a microbiota sequence variant of a fragment of the tumor antigen ERG (human reference peptide), such as "FLLELLSDS" (SEQ ID NO: 647) or "QLWQFLLEL" (SEQ ID NO: 857). In another preferred embodiment, the antigenic peptide according to the present invention is a sequence variant of a fragment of the tumor antigen ERG, such as antigenic peptides comprising or consisting of an amino acid sequence as set forth in any one of SEQ ID NOs 163-164. More preferably, the antigenic peptide according to the present invention is a sequence variant of the ERG fragment (human reference peptide) "FLLELLSDS" (SEQ ID NO: 647), such as an antigenic peptide comprising or consisting of an amino acid sequence as set forth in SEQ ID NO: 163. It is also more preferred that the antigenic peptide according to the present invention is a sequence variant of the ERG fragment (human reference peptide) "QLWQFLLEL" (SEQ ID NO: 857), such as an antigenic peptide comprising or consisting of an amino acid sequence as set forth in SEQ ID NO: 164.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen ESR1, such as antigenic peptides comprising or consisting of an amino acid sequence as set forth in any one of SEQ ID NOs 165-192. More preferably, the antigenic peptide according to the present invention is a sequence variant of the ESR1 fragment (human reference peptide) "ALLDAEPPI" (SEQ ID NO: 648), such as an antigenic peptide comprising or consisting of an amino acid sequence as set forth in SEQ ID NO: 165. It is also more preferred that the antigenic peptide according to the present invention is a sequence variant of the ESR1 fragment (human reference peptide) "KITDT-LIHL" (SEQ ID NO: 649), such as an antigenic peptide comprising or consisting of an amino acid sequence as set forth in SEQ ID NO: 166 or 167. It is also more preferred that the antigenic peptide according to the present invention is a sequence variant of the ESR1 fragment (human reference peptide) "KLLFAPNLL" (SEQ ID NO: 650), such as an antigenic peptide comprising or consisting of an amino acid sequence as set forth in SEQ ID NO: 168 or 169. It is also more preferred that the antigenic peptide according to the present invention is a sequence variant of the ESR1 fragment (human reference peptide) "LLDAEPPIL" (SEQ ID NO: 651), such as an antigenic peptide comprising or consisting of an amino acid sequence as set forth in SEQ ID NO: 170. It is also more preferred that the antigenic peptide according to the present invention is a sequence variant of the ESR1 fragment (human reference peptide) "LLNSGVYTF" (SEQ ID NO: 652), such as an antigenic peptide comprising or consisting of an amino acid sequence as set forth in SEQ ID NO: 171 or 172. It is also more preferred that the antigenic peptide according to the present invention is a sequence variant of the ESR1 fragment (human reference peptide) "LMIGLVWRS" (SEQ ID NO: 653), such as an antigenic peptide comprising or consisting of an amino acid sequence as set forth in SEQ ID NO: 173. It is also more preferred that the antigenic peptide according to the present invention is a sequence variant of the ESR1 fragment (human reference peptide) "PLYDLLLEM" (SEQ ID NO: 654), such as an antigenic peptide comprising or consisting of an amino acid sequence as set forth in SEQ ID NO: 174, 175, 176, 177, 178, 179, 180 or 181. It is also more preferred that the antigenic peptide according to the present invention is a sequence variant of the ESR1 fragment (human reference peptide) "QLLLILSHI" (SEQ ID NO: 655), such as an antigenic peptide comprising or consisting of an amino acid sequence as set forth in SEQ ID NO: 182, 183, 184, 185, 186, 187 or 188. It is also more preferred that the antigenic peptide according to the present invention is a sequence variant of the ESR1 fragment (human reference peptide) "RLAQLLLIL" (SEQ ID NO: 656), such as an antigenic peptide comprising or consisting of an amino acid sequence as set forth in SEQ ID NO: 189 or 190. It is also more preferred that the antigenic peptide according to the present invention is a sequence variant of the ESR1 fragment (human reference peptide) "TLIHLMAKA" (SEQ ID NO: 657), such as an antigenic peptide comprising or consisting of an amino acid sequence as set forth in SEQ ID NO: 191. It is also more preferred that the antigenic peptide according to the present invention is a sequence variant of the ESR1 fragment (human reference peptide) "VLDKITDTL" (SEQ ID NO: 658), such as an antigenic peptide comprising or consisting of an amino acid sequence as set forth in SEQ ID NO: 192.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen EZH2, such as antigenic peptides comprising or consisting of an amino acid sequence as set forth in any one of SEQ ID NOs 193-194. More preferably, the antigenic peptide according to the present invention is a sequence variant of the EZH2 fragment (human reference peptide) "FMVEDETVL" (SEQ ID NO: 659), such as an antigenic peptide comprising or consisting of an amino acid sequence as set forth in SEQ ID NO: 193. It is also more preferred that the antigenic peptide according to the present invention is a sequence variant of the EZH2 fragment (human reference peptide) "SMFRVLIGT" (SEQ ID NO: 660), such as an antigenic peptide comprising or consisting of an amino acid sequence as set forth in SEQ ID NO: 194.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen FAP, such as antigenic peptides comprising or consisting of an amino acid sequence as set forth in any one of SEQ ID NOs 195-201. More preferably, the antigenic peptide according to the present invention is a sequence variant of the FAP fragment (human reference peptide) "ATSAVLALL" (SEQ ID NO: 661), such as an antigenic peptide comprising or consisting of an amino acid sequence as set forth in SEQ ID NO: 195, 196 or 197. It is also more preferred that the antigenic peptide according to the present invention is a sequence variant of the FAP fragment (human reference peptide) "TGWAGGFFV" (SEQ ID NO: 662), such as an antigenic peptide comprising or consisting of an amino acid sequence as set forth in SEQ ID NO: 198. It is also more preferred that the antigenic peptide according to the present invention is a sequence variant of the FAP fragment (human reference peptide) "VLALLVMCI" (SEQ ID NO: 663), such as an antigenic peptide comprising or consisting of an amino acid sequence as set forth in SEQ ID NO: 199, 200 or 201.

In another embodiment, the antigenic peptide according to the present invention is a microbiota sequence variant of a fragment of the tumor antigen CDH17 (human reference peptide), such as In another preferred embodiment the antigenic peptide according to the present invention is a sequence variant of a fragment of the tumor antigen FLT1, such as antigenic peptides comprising or consisting of an amino acid sequence as set forth in any one of SEQ ID NOs 202-216. More preferably, the antigenic peptide according to the present invention is a sequence variant of the FLT1 fragment (human reference peptide) "ALLSCLLLT" (SEQ ID NO: 664), such as an antigenic peptide comprising or consisting of an amino acid sequence as set forth in SEQ ID NO: 202, 203, 204, 205, 206, 207 or 208. It is also more preferred that the antigenic peptide according to the present invention is a sequence variant of the FLT1 fragment (human reference peptide) "CVAATLFWL" (SEQ ID NO: 665), such as an antigenic peptide comprising or consisting of an amino acid sequence as set forth in SEQ ID NO: 209. It is also more preferred that the antigenic peptide according to the present invention is a sequence variant of the FLT1 fragment (human reference peptide) "EMYSEIPEI" (SEQ ID NO: 666), such as an antigenic peptide comprising or consisting of an amino acid sequence as set forth in SEQ ID NO: 210. It is also more preferred that the antigenic peptide according to the present invention is a sequence variant of the FLT1 fragment (human reference peptide) "KMASTLVVA" (SEQ ID NO: 667), such as an antigenic peptide comprising or consisting of an amino acid sequence as set forth in SEQ ID NO: 211 or 212. It is also more preferred that the antigenic peptide according to the present invention is a sequence variant of the FLT1 fragment (human reference peptide) "SIFDKIYST" (SEQ ID NO: 668), such as an antigenic peptide comprising or consisting of an amino acid sequence as set forth in SEQ ID NO: 213. It is also more preferred that the antigenic peptide according to the present invention is a sequence variant of the FLT1 fragment (human reference peptide) "TLFWLLLTL" (SEQ ID NO: 669), such as an antigenic peptide comprising or consisting of an amino acid sequence as set forth in SEQ ID NO: 214. It is also more preferred that the antigenic peptide according to the present invention is a sequence variant of the FLT1 fragment (human reference peptide) "VLLWEIFSL" (SEQ ID NO: 670), such as an antigenic peptide comprising or consisting of an amino acid sequence as set forth in SEQ ID NO: 215. It is also more preferred that the antigenic peptide according to the present invention is a sequence variant of the FLT1 fragment (human reference peptide) "WLKDGLPAT" (SEQ ID NO: 671), such as an antigenic peptide comprising or consisting of an amino acid sequence as set forth in SEQ ID NO: 216.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen FOXM1, such as antigenic peptides comprising or consisting of an amino acid sequence as set forth in any one of SEQ ID NOs 217-227 and 861-877, for example as set forth in any one of SEQ ID NOs 217-227. More preferably, the antigenic peptide according to the present invention is a sequence variant of the FOXM1 fragment (human reference peptide) "ILLDISFPG" (SEQ ID NO: 672), such as an antigenic peptide comprising or consisting of an amino acid sequence as set forth in SEQ ID NO: 217 or 218. Further examples of antigenic peptides according to the present invention, which are sequence variants of the FOXM1 fragment (human reference peptide) "ILLDISFPG" (SEQ ID NO: 672), include antigenic peptides comprising or consisting of an amino acid sequence as set forth in SEQ ID NO: 861, 862, 863, 864, 865 or 866. It is also more preferred that the antigenic peptide according to the present invention is a sequence variant of the FOXM1 fragment (human reference peptide) "LLDISFPGL" (SEQ ID NO: 673), such as an antigenic peptide comprising or consisting of an amino acid sequence as set forth in SEQ ID NO: 219. Another example of an antigenic peptide according to the present invention, which is a sequence variant of the FOXM1 fragment (human reference peptide) "LLDISFPGL" (SEQ ID NO: 673), includes antigenic peptides comprising or consisting of an amino acid sequence as set forth in SEQ ID NO: 867. It is also more preferred that the antigenic peptide according to the present invention is a sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220. Another example of an antigenic peptide according to the present invention, which is a sequence variant of the FOXM1 fragment (human reference peptide) "LMDLSTTPL" (SEQ ID NO: 674), includes antigenic peptides comprising or consisting of an amino acid sequence as set forth in SEQ ID NO: 868. It is also more preferred that the antigenic peptide according to the present invention is a sequence variant of the FOXM1 fragment (human reference peptide) "RVSSYLVPI" (SEQ ID NO: 675), such as an antigenic peptide comprising or consisting of an amino acid sequence as set forth in SEQ ID NO: 221, 222 or 223. Further examples of antigenic peptides according to the present invention, which are sequence variants of the FOXM1 fragment (human reference peptide) "RVSSYLVPI" (SEQ ID NO: 675), include antigenic peptides comprising or consisting of an amino acid sequence as set forth in SEQ ID NO: 869, 870 or 871. It is also more preferred that the antigenic peptide according to the present invention is a sequence variant of the FOXM1 fragment (human reference peptide) "SLSKILLDI" (SEQ ID NO: 676), such as an antigenic peptide comprising or consisting of an amino acid sequence as set forth in SEQ ID NO: 224. It is also more preferred that the antigenic peptide according to the present invention is a sequence variant of the FOXM1 fragment (human reference peptide) "SQLSYSQEV" (SEQ ID NO: 677), such as an antigenic peptide comprising or consisting of an amino acid sequence as set forth in SEQ ID NO: 225 or 226. It is also more preferred that the antigenic peptide according to the present invention is a sequence variant of the FOXM1 fragment (human reference peptide) "WAAELPFPA" (SEQ ID NO: 678), such as an antigenic peptide comprising or consisting of an amino acid sequence as set forth in SEQ ID NO: 227. It is also more preferred that the antigenic peptide according to the present invention is a sequence variant of the FOXM1 fragment (human reference peptide) "NLSLHDMFV" (SEQ ID NO: 888), such as an antigenic peptide comprising or consisting of an amino acid sequence as set forth in SEQ ID NO: 872. It is also more preferred that the antigenic peptide according to the present invention is a sequence variant of the FOXM1 fragment (human reference peptide) "KMKPLLPRV" (SEQ ID NO: 889), such as an antigenic peptide comprising or consisting of an amino acid sequence as set forth in SEQ ID NO: 873 or 874. It is also more preferred that the antigenic peptide according to the present invention is a sequence variant of the FOXM1 fragment (human reference peptide) "YLVPIQFPV" (SEQ ID NO: 890), such as an antigenic peptide comprising or consisting of an amino acid sequence as set forth in SEQ ID NO: 875 or 876. It is also more preferred that the antigenic peptide according to the present invention is a sequence variant of the FOXM1 fragment (human reference peptide) "YMAMIQFAI" (SEQ ID NO: 891), such as an antigenic peptide comprising or consisting of an amino acid sequence as set forth in SEQ ID NO: 877. Even more preferably, the antigenic peptide comprises or consists of SEQ ID NO: 32.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen FSIP1, such as antigenic peptides comprising or consisting of an amino acid sequence as set forth in any one of SEQ ID NOs 228-231. More preferably, the antigenic peptide according to the present invention is a sequence variant of the FSIP1 fragment (human reference peptide) "LLNESETKV" (SEQ ID NO: 679), such as an antigenic peptide comprising or consisting of an amino acid sequence as set forth in SEQ ID NO: 228. It is also more preferred that the antigenic peptide according to the present invention is a sequence variant of the FSIP1 fragment (human reference peptide) "RLVELLKDL" (SEQ ID NO: 680), such as an antigenic peptide comprising or consisting of an amino acid sequence as set forth in SEQ ID NO: 229, 230 or 231.

In another embodiment, the antigenic peptide according to the present invention is a microbiota sequence variant of a fragment of the tumor antigen GAL3ST1 (human reference peptide), such as "GLASTTPEA" (SEQ ID NO: 681) or "RMAREVAAL" (SEQ ID NO: 682). In another preferred embodiment, the antigenic peptide according to the present invention is a sequence variant of a fragment of the tumor antigen GAL3ST1, such as antigenic peptides comprising or consisting of an amino acid sequence as set forth in any one of SEQ ID NOs 232-234. More preferably, the antigenic peptide according to the present invention is a sequence variant of the GAL3ST1 fragment (human reference peptide) "GLASTTPEA" (SEQ ID NO: 681), such as an antigenic peptide comprising or consisting of an amino acid sequence as set forth in SEQ ID NO: 232. It is also more preferred that the antigenic peptide according to the present invention is a sequence variant of the GAL3ST1 fragment (human reference peptide) "RMAREVAAL" (SEQ ID NO: 682), such as an antigenic peptide comprising or consisting of an amino acid sequence as set forth in SEQ ID NO: 233 or 234.

In another embodiment, the antigenic peptide according to the present invention is a microbiota sequence variant of a fragment of the tumor antigen GPR143 (human reference peptide), such as "FLLSLAFYG" (SEQ ID NO: 683), "ILNPAQGFL" (SEQ ID NO: 684), "MAWGLATLL" (SEQ ID NO: 685) or "RLALGLLQL" (SEQ ID NO: 686). In another preferred embodiment, the antigenic peptide according to the present invention is a sequence variant of a fragment of the tumor antigen GPR143, such as antigenic peptides comprising or consisting of an amino acid sequence as set forth in any one of SEQ ID NOs 235-247. More preferably, the antigenic peptide according to the present invention is a sequence variant of the GPR143 fragment (human reference peptide) "FLLSLAFYG" (SEQ ID NO: 683), such as an antigenic peptide comprising or consisting of an amino acid sequence as set forth in SEQ ID NO: 235, 236 or 237. It is also more preferred that the antigenic peptide according to the present invention is a sequence variant of the GPR143 fragment (human reference peptide) "ILNPAQGFL" (SEQ ID NO: 684), such as an antigenic peptide comprising or consisting of an amino acid sequence as set forth in SEQ ID NO: 238. It is also more preferred that the antigenic peptide according to the present invention is a sequence variant of the GPR143 fragment (human reference peptide) "MAWGLATLL" (SEQ ID NO: 685), such as an antigenic peptide comprising or consisting of an amino acid sequence as set forth in SEQ ID NO: 239. It is also more preferred that the antigenic peptide according to the present invention is a sequence variant of the GPR143 fragment (human reference peptide) "RLALGLLQL" (SEQ ID NO: 686), such as an antigenic peptide comprising or consisting of an amino acid sequence as set forth in SEQ ID NO: 240, 241, 242, 243, 245, 246 or 247.

In another embodiment, the antigenic peptide according to the present invention is a microbiota sequence variant of a fragment of the tumor antigen HES6 (human reference peptide), such as "RLLLAGAEV" (SEQ ID NO: 687). In another preferred embodiment, the antigenic peptide according to the present invention is a sequence variant of a fragment of the tumor antigen HES6, such as the antigenic peptide comprising or consisting of an amino acid sequence as set forth in SEQ ID NO: 248. Namely, the antigenic peptide according to the present invention, which comprises or consists of an amino acid sequence as set forth in SEQ ID NO: 248 is a sequence variant of the HES6 fragment (human reference peptide) "RLLLAGAEV" (SEQ ID NO: 687).

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen IL13RA2, such as antigenic peptides comprising or consisting of an amino acid sequence as set forth in any one of SEQ ID NOs 249-255. More preferably, the antigenic peptide according to the present invention is a sequence variant of the IL13RA2 fragment (human reference peptide) "CLYTFLIST" (SEQ ID NO: 688), such as an antigenic peptide comprising or consisting of an amino acid sequence as set forth in SEQ ID NO: 249, 250 or 251. It is also more preferred that the antigenic peptide according to the present invention is a sequence variant of the IL13RA2 fragment (human reference peptide) "FLISTTFGC" (SEQ ID NO: 689), such as an antigenic peptide comprising or consisting of an amino acid sequence as set forth in SEQ ID NO: 252. It is also more preferred that the antigenic peptide according to the present invention is a sequence variant of the IL13RA2 fragment (human reference peptide) "VLLDTNYNL" (SEQ ID NO: 690), such as an antigenic peptide comprising or consisting of an amino acid sequence as set forth in SEQ ID NO: 253. It is also more preferred that the antigenic peptide according to the present invention is a sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254 or 255, in particular an antigenic peptide comprising or consisting of an amino acid sequence as set forth in SEQ ID NO: 255. Further examples of antigenic peptides according to the present invention, which are sequence variants of the IL13RA2 fragment (human reference peptide) "WLPFGFILIL" (SEQ ID NO: 692), include antigenic peptides comprising or consisting of an amino acid sequence as set forth in SEQ ID NO: 878 or 879. It is also more preferred that the antigenic peptide according to the present invention is a sequence variant of the IL13RA2 fragment (human reference peptide) "FLISTTFGCT" (SEQ ID NO: 892), such as an antigenic peptide comprising or consisting of an amino acid sequence as set forth in SEQ ID NO: 880, 881 or 882. It is also more preferred that the antigenic peptide according to the present invention is a sequence variant of the IL13RA2 fragment (human reference peptide) "YLYLQWQPPL" (SEQ ID NO: 893), such as an antigenic peptide comprising or consisting of an amino acid sequence as set forth in SEQ ID NO: 883. It is also more preferred that the antigenic peptide according to the present invention is a sequence variant of the IL13RA2 fragment (human reference peptide) "GVLLDTNYNL" (SEQ ID NO: 894), such as an antigenic peptide comprising or consisting of an amino acid sequence as set forth in SEQ ID NO: 884 or 885. It is also more preferred that the antigenic peptide according to the present invention is a sequence variant of the IL13RA2 fragment (human reference peptide) "FQLQNIVKPL" (SEQ ID NO: 895), such as an antigenic peptide comprising or consisting of an amino acid sequence as set forth in SEQ ID NO: 886 or 887. Even more preferably, the antigenic peptide comprises or consists of SEQ ID NO: 255.

In another embodiment, the antigenic peptide according to the present invention is a microbiota sequence variant of a fragment of the tumor antigen KISS1R (human reference peptide), such as "ALYLLPLLA" (SEQ ID NO: 693), "FALYNLLAL" (SEQ ID NO: 694), "QLFLVLQAL" (SEQ ID NO: 695), "RLVAAVVLL" (SEQ ID NO: 696), "VLAERAGAV" (SEQ ID NO: 697), "WLVPLFFAA" (SEQ ID NO: 698) or "YLLPLLATC" (SEQ ID NO: 699). In another preferred embodiment, the antigenic peptide according to the present invention is a sequence variant of a fragment of the tumor antigen KISS1R, such as antigenic peptides comprising or consisting of an amino acid sequence as set forth in any one of SEQ ID NOs 256-287. More preferably, the antigenic peptide according to the present invention is a sequence variant of the KISS1R fragment (human reference peptide) "ALYLLPLLA" (SEQ ID NO: 693), such as an antigenic peptide comprising or consisting of an amino acid sequence as set forth in SEQ ID NO: 256, 257 or 258. It is also more preferred that the antigenic peptide according to the present invention is a sequence variant of the KISS1R fragment (human reference peptide) “FALYNLLAL” (SEQ ID NO: 694), such as an antigenic peptide comprising or consisting of an amino acid sequence as set forth in SEQ ID NO: 259, 260 or 261. It is also more preferred that the antigenic peptide according to the present invention is a sequence variant of the KISS1R fragment (human reference peptide) “QLFLVLQAL” (SEQ ID NO: 695), such as an antigenic peptide comprising or consisting of an amino acid sequence as set forth in SEQ ID NO: 262. It is also more preferred that the antigenic peptide according to the present invention is a sequence variant of the KISS1R fragment (human reference peptide) “RLVAAVVLL” (SEQ ID NO: 696), such as an antigenic peptide comprising or consisting of an amino acid sequence as set forth in SEQ ID NO: 263. It is also more preferred that the antigenic peptide according to the present invention is a sequence variant of the KISS1R fragment (human reference peptide) “VLAERAGAV” (SEQ ID NO: 697), such as an antigenic peptide comprising or consisting of an amino acid sequence as set forth in SEQ ID NO: 264. It is also more preferred that the antigenic peptide according to the present invention is a sequence variant of the KISS1R fragment (human reference peptide) “WLVPLFFAA” (SEQ ID NO: 698), such as an antigenic peptide comprising or consisting of an amino acid sequence as set forth in SEQ ID NO: 266, 267, 268 or 269. It is also more preferred that the antigenic peptide according to the present invention is a sequence variant of the KISS1R fragment (human reference peptide) “YLLPLLATC” (SEQ ID NO: 699), such as an antigenic peptide comprising or consisting of an amino acid sequence as set forth in SEQ ID NO: 270, 271, 272, 273, 274, 275, 276, 277, 278, 279, 280, 281, 282, 283, 284, 285, 286 or 287.

In another embodiment, the antigenic peptide according to the present invention is a microbiota sequence variant of a fragment of the tumor antigen KLHDC8A (human reference peptide), such as “GLSDAVEAL” (SEQ ID NO: 700) or “MLREAAMGI” (SEQ ID NO: 701). In another preferred embodiment, the antigenic peptide according to the present invention is a sequence variant of a fragment of the tumor antigen KLHDC8A, such as antigenic peptides comprising or consisting of an amino acid sequence as set forth in any one of SEQ ID NOs 288-289. More preferably, the antigenic peptide according to the present invention is a sequence variant of the KLHDC8A fragment (human reference peptide) “GLSDAVEAL” (SEQ ID NO: 700), such as an antigenic peptide comprising or consisting of an amino acid sequence as set forth in SEQ ID NO: 288. It is also more preferred that the antigenic peptide according to the present invention is a sequence variant of the KLHDC8A fragment (human reference peptide) “MLREAAMGI” (SEQ ID NO: 701), such as an antigenic peptide comprising or consisting of an amino acid sequence as set forth in SEQ ID NO: 289.

In another embodiment, the antigenic peptide according to the present invention is a microbiota sequence variant of a fragment of the tumor antigen KLHL14 (human reference peptide), such as “ALIPAPELV” (SEQ ID NO: 702), “NLLHGLNLL” (SEQ ID NO: 703) or “YVSSLPQPL” (SEQ ID NO: 704). In another preferred embodiment, the antigenic peptide according to the present invention is a sequence variant of a fragment of the tumor antigen KLHL14, such as antigenic peptides comprising or consisting of an amino acid sequence as set forth in any one of SEQ ID NOs 290-292. More preferably, the antigenic peptide according to the present invention is a sequence variant of the KLHL14 fragment (human reference peptide) “ALIPAPELV” (SEQ ID NO: 702), such as an antigenic peptide comprising or consisting of an amino acid sequence as set forth in SEQ ID NO: 290. It is also more preferred that the antigenic peptide according to the present invention is a sequence variant of the KLHL14 fragment (human reference peptide) “NLLHGLNLL” (SEQ ID NO: 703), such as an antigenic peptide comprising or consisting of an amino acid sequence as set forth in SEQ ID NO: 291. It is also more preferred that the antigenic peptide according to the present invention is a sequence variant of the KLHL14 fragment (human reference peptide) “YVSSLPQPL” (SEQ ID NO: 704), such as an antigenic peptide comprising or consisting of an amino acid sequence as set forth in SEQ ID NO: 292.

In another embodiment, the antigenic peptide according to the present invention is a microbiota sequence variant of a fragment of the tumor antigen KLK4 (human reference peptide), such as “YLILGVAGS” (SEQ ID NO: 705). In another preferred embodiment, the antigenic peptide according to the present invention is a sequence variant of a fragment of the tumor antigen KLK4, such as antigenic peptides comprising or consisting of an amino acid sequence as set forth in any one of SEQ ID NOs 293-296. More preferably, the antigenic peptide according to the present invention is a sequence variant of the KLK4 fragment (human reference peptide) “YLILGVAGS” (SEQ ID NO: 705), such as an antigenic peptide comprising or consisting of an amino acid sequence as set forth in SEQ ID NO: 293, 294, 295 or 296.

In another embodiment, the antigenic peptide according to the present invention is a microbiota sequence variant of a fragment of the tumor antigen KRT81 (human reference peptide), such as “NMDCIIAEI” (SEQ ID NO: 706). In another preferred embodiment, the antigenic peptide according to the present invention is a sequence variant of a fragment of the tumor antigen KRT81, such as the antigenic peptide comprising or consisting of an amino acid sequence as set forth in SEQ ID NO: 297. Namely, the antigenic peptide according to the present invention, which comprises or consists of an amino acid sequence as set forth in SEQ ID NO: 297 is a sequence variant of the KRT81 fragment (human reference peptide) “NMDCIIAEI” (SEQ ID NO: 706).

In another embodiment, the antigenic peptide according to the present invention is a microbiota sequence variant of a fragment of the tumor antigen LEMD1 (human reference peptide), such as “AVLGIFIIV” (SEQ ID NO: 707) or “KLAVLGIFI” (SEQ ID NO: 708). In another preferred embodiment, the antigenic peptide according to the present invention is a sequence variant of a fragment of the tumor antigen LEMD1, such as antigenic peptides comprising or consisting of an amino acid sequence as set forth in any one of SEQ ID NOs 298-299. More preferably, the antigenic peptide according to the present invention is a sequence variant of the LEMD1 fragment (human reference peptide) “AVLGIFIIV” (SEQ ID NO: 707), such as an antigenic peptide comprising or consisting of an amino acid sequence as set forth in SEQ ID NO: 298. It is also more preferred that the antigenic peptide according to the present invention is a sequence variant of the LEMD1 fragment (human reference peptide) “KLAVLGIFI” (SEQ ID NO: 708), such as an antigenic peptide comprising or consisting of an amino acid sequence as set forth in SEQ ID NO: 299.

In another embodiment, the antigenic peptide according to the present invention is a microbiota sequence variant of a fragment of the tumor antigen LRRC15 (human reference peptide), such as “AIAAIVIGI” (SEQ ID NO: 709), “ALACSLAAC” (SEQ ID NO: 710), “IVIGIVALA” (SEQ ID NO: 711), “RIVAVPTPL” (SEQ ID NO: 712) or “SLKELSPGI” (SEQ ID NO: 713). In another preferred embodiment, the antigenic peptide according to the present invention is a sequence variant of a fragment of the tumor antigen LRRC15, such as antigenic peptides comprising or consisting of an amino acid sequence as set forth in any one of SEQ ID NOs 300-307. More preferably, the antigenic peptide according to the present invention is a sequence variant of the LRRC15 fragment (human reference peptide) “AIAAIVIGI” (SEQ ID NO: 709), such as an antigenic peptide comprising or consisting of an amino acid sequence as set forth in SEQ ID NO: 300. It is also more preferred that the antigenic peptide according to the present invention is a sequence variant of the LRRC15 fragment (human reference peptide) “ALACSLAAC” (SEQ ID NO: 710), such as an antigenic peptide comprising or consisting of an amino acid sequence as set forth in SEQ ID NO: 301. It is also more preferred that the antigenic peptide according to the present invention is a sequence variant of the LRRC15 fragment (human reference peptide) “IVIGIVALA” (SEQ ID NO: 711), such as an antigenic peptide comprising or consisting of an amino acid sequence as set forth in SEQ ID NO: 302. It is also more preferred that the antigenic peptide according to the present invention is a sequence variant of the LRRC15 fragment (human reference peptide) “RIVAVPTPL” (SEQ ID NO: 712), such as an antigenic peptide comprising or consisting of an amino acid sequence as set forth in SEQ ID NO: 303, 304 or 305. It is also more preferred that the antigenic peptide according to the present invention is a sequence variant of the LRRC15 fragment (human reference peptide) “SLKELSPGI” (SEQ ID NO: 713), such as an antigenic peptide comprising or consisting of an amino acid sequence as set forth in SEQ ID NO: 306 or 307.

In another embodiment, the antigenic peptide according to the present invention is a microbiota sequence variant of a fragment of the tumor antigen MAGEA1 (human reference peptide), such as “KVADLVGFL” (SEQ ID NO: 714) or “LVLGTLEEV” (SEQ ID NO: 858). In another preferred embodiment, the antigenic peptide according to the present invention is a sequence variant of a fragment of the tumor antigen MAGEA1, such as antigenic peptides comprising or consisting of an amino acid sequence as set forth in any one of SEQ ID NOs 308-309. More preferably, the antigenic peptide according to the present invention is a sequence variant of the MAGEA1 fragment (human reference peptide) “KVADLVGFL” (SEQ ID NO: 714), such as an antigenic peptide comprising or consisting of an amino acid sequence as set forth in SEQ ID NO: 308. It is also more preferred that the antigenic peptide according to the present invention is a sequence variant of the MAGEA1 fragment (human reference peptide) “LVLGTLEEV” (SEQ ID NO: 858), such as an antigenic peptide comprising or consisting of an amino acid sequence as set forth in SEQ ID NO: 309.

In another embodiment, the antigenic peptide according to the present invention is a microbiota sequence variant of a fragment of the tumor antigen MAGEA4 (human reference peptide), such as “AVSSSSPLV” (SEQ ID NO: 722), “KVDELAHFL” (SEQ ID NO: 723) or “KVLEHVVRV” (SEQ ID NO: 724). In another preferred embodiment, the antigenic peptide according to the present invention is a sequence variant of a fragment of the tumor antigen MAGEA4, such as antigenic peptides comprising or consisting of an amino acid sequence as set forth in any one of SEQ ID NOs 320-322. More preferably, the antigenic peptide according to the present invention is a sequence variant of the MAGEA4 fragment (human reference peptide) “AVSSSSPLV” (SEQ ID NO: 722), such as an antigenic peptide comprising or consisting of an amino acid sequence as set forth in SEQ ID NO: 320. It is also more preferred that the antigenic peptide according to the present invention is a sequence variant of the MAGEA4 fragment (human reference peptide) “KVDELAHFL” (SEQ ID NO: 723), such as an antigenic peptide comprising or consisting of an amino acid sequence as set forth in SEQ ID NO: 321. It is also more preferred that the antigenic peptide according to the present invention is a sequence variant of the MAGEA4 fragment (human reference peptide) “KVLEHVVRV” (SEQ ID NO: 724), such as an antigenic peptide comprising or consisting of an amino acid sequence as set forth in SEQ ID NO: 322.

In another embodiment, the antigenic peptide according to the present invention is a microbiota sequence variant of a fragment of the tumor antigen MAGEA10 (human reference peptide), such as “GMLSDVQSM” (SEQ ID NO: 715) or “ILILILSIV” (SEQ ID NO: 716). In another preferred embodiment, the antigenic peptide according to the present invention is a sequence variant of a fragment of the tumor antigen MAGEA10, such as antigenic peptides comprising or consisting of an amino acid sequence as set forth in any one of SEQ ID NOs 310-313. More preferably, the antigenic peptide according to the present invention is a sequence variant of the MAGEA10 fragment (human reference peptide) “GMLSDVQSM” (SEQ ID NO: 715), such as an antigenic peptide comprising or consisting of an amino acid sequence as set forth in SEQ ID NO: 310 or 311. It is also more preferred that the antigenic peptide according to the present invention is a sequence variant of the MAGEA10 fragment (human reference peptide) “ILILILSIV” (SEQ ID NO: 716), such as an antigenic peptide comprising or consisting of an amino acid sequence as set forth in SEQ ID NO: 312 or 313.

In another embodiment, the antigenic peptide according to the present invention is a microbiota sequence variant of a fragment of the tumor antigen MAGEA11 (human reference peptide), such as “AMDAIFGSL” (SEQ ID NO: 717), “GLITKAEML” (SEQ ID NO: 718), “GTLEELPAA” (SEQ ID NO: 719) or “KVLEYIANA” (SEQ ID NO: 720). In another preferred embodiment, the antigenic peptide according to the present invention is a sequence variant of a fragment of the tumor antigen MAGEA11, such as antigenic peptides comprising or consisting of an amino acid sequence as set forth in any one of SEQ ID NOs 314-318. More preferably, the antigenic peptide according to the present invention is a sequence variant of the MAGEA11 fragment (human reference peptide) “AMDAIFGSL” (SEQ ID NO: 717), such as an antigenic peptide comprising or consisting of an amino acid sequence as set forth in SEQ ID NO: 314. It is also more preferred that the antigenic peptide according to the present invention is a sequence variant of the MAGEA11 fragment (human reference peptide) “GLITKAEML” (SEQ ID NO: 718), such as an antigenic peptide comprising or consisting of an amino acid sequence as set forth in SEQ ID NO: 315. It is also more preferred that the antigenic peptide according to the present invention is a sequence variant of the MAGEA11 fragment (human reference peptide) “GTLEELPAA” (SEQ ID NO: 719), such as an antigenic peptide comprising or consisting of an amino acid sequence as set forth in SEQ ID NO: 316 or 317. It is also more preferred that the antigenic peptide according to the present invention is a sequence variant of the MAGEA11 fragment (human reference peptide) “KVLEYIANA” (SEQ ID NO: 720), such as an antigenic peptide comprising or consisting of an amino acid sequence as set forth in SEQ ID NO: 318.

In another embodiment, the antigenic peptide according to the present invention is a microbiota sequence variant of a fragment of the tumor antigen MAGEA12 (human reference peptide), such as "QLVFGIEVV" (SEQ ID NO: 721). In another preferred embodiment, the antigenic peptide according to the present invention is a sequence variant of a fragment of the tumor antigen MAGEA12, such as the antigenic peptide comprising or consisting of an amino acid sequence as set forth in SEQ ID NO: 319. Namely, the antigenic peptide according to the present invention, which comprises or consists of an amino acid sequence as set forth in SEQ ID NO: 319 is a sequence variant of the MAGEA12 fragment (human reference peptide) "QLVFGIEVV" (SEQ ID NO: 721).

In another embodiment, the antigenic peptide according to the present invention is a microbiota sequence variant of a fragment of the tumor antigen MLANA (human reference peptide), such as "VILGVLLLI" (SEQ ID NO: 725). In another preferred embodiment, the antigenic peptide according to the present invention is a sequence variant of a fragment of the tumor antigen MLANA, such as antigenic peptides comprising or consisting of an amino acid sequence as set forth in any one of SEQ ID NOs 323-334. More preferably, the antigenic peptide according to the present invention is a sequence variant of the MLANA fragment (human reference peptide) "VILGVLLLI" (SEQ ID NO: 725), such as an antigenic peptide comprising or consisting of an amino acid sequence as set forth in SEQ ID NO: 323, 324, 325, 326, 327, 328, 329, 330, 331, 332, 333 or 334.

In another embodiment, the antigenic peptide according to the present invention is a microbiota sequence variant of a fragment of the tumor antigen NKX2-1 (human reference peptide), such as "MTAAGVPQL" (SEQ ID NO: 726) or "SVSDILSPL" (SEQ ID NO: 727). In another preferred embodiment, the antigenic peptide according to the present invention is a sequence variant of a fragment of the tumor antigen NKX2-1, such as antigenic peptides comprising or consisting of an amino acid sequence as set forth in any one of SEQ ID NOs 335-340. More preferably, the antigenic peptide according to the present invention is a sequence variant of the NKX2-1 fragment (human reference peptide) "MTAAGVPQL" (SEQ ID NO: 726), such as an antigenic peptide comprising or consisting of an amino acid sequence as set forth in SEQ ID NO: 335. It is also more preferred that the antigenic peptide according to the present invention is a sequence variant of the NKX2-1 fragment (human reference peptide) "SVSDILSPL" (SEQ ID NO: 727), such as an antigenic peptide comprising or consisting of an amino acid sequence as set forth in SEQ ID NO: 336, 337, 338, 339 or 340.

In another embodiment, the antigenic peptide according to the present invention is a microbiota sequence variant of a fragment of the tumor antigen NPTX2 (human reference peptide), such as "ALLAASVAL" (SEQ ID NO: 728), "LLAASVALA" (SEQ ID NO: 729), "QLLRKVAEL" (SEQ ID NO: 730), "TLPELYAFT" (SEQ ID NO: 731) or "YLYGKIKKT" (SEQ ID NO: 732). In another preferred embodiment, the antigenic peptide according to the present invention is a sequence variant of a fragment of the tumor antigen NPTX2, such as antigenic peptides comprising or consisting of an amino acid sequence as set forth in any one of SEQ ID NOs 341-351. More preferably, the antigenic peptide according to the present invention is a sequence variant of the NPTX2 fragment (human reference peptide) "ALLAASVAL" (SEQ ID NO: 728), such as an antigenic peptide comprising or consisting of an amino acid sequence as set forth in SEQ ID NO: 341, 342, 343 or 344. It is also more preferred that the antigenic peptide according to the present invention is a sequence variant of the NPTX2 fragment (human reference peptide) "LLAASVALA" (SEQ ID NO: 729), such as an antigenic peptide comprising or consisting of an amino acid sequence as set forth in SEQ ID NO: 345, 346, 347 or 348. It is also more preferred that the antigenic peptide according to the present invention is a sequence variant of the NPTX2 fragment (human reference peptide) "QLLRKVAEL" (SEQ ID NO: 730), such as an antigenic peptide comprising or consisting of an amino acid sequence as set forth in SEQ ID NO: 349. It is also more preferred that the antigenic peptide according to the present invention is a sequence variant of the NPTX2 fragment (human reference peptide) "TLPELYAFT" (SEQ ID NO: 731), such as an antigenic peptide comprising or consisting of an amino acid sequence as set forth in SEQ ID NO: 350. It is also more preferred that the antigenic peptide according to the present invention is a sequence variant of the NPTX2 fragment (human reference peptide) "YLYGKIKKT" (SEQ ID NO: 732), such as an antigenic peptide comprising or consisting of an amino acid sequence as set forth in SEQ ID NO: 351.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen PAGE3, such as antigenic peptides comprising or consisting of an amino acid sequence as set forth in any one of SEQ ID NOs 352-354. More preferably, the antigenic peptide according to the present invention is a sequence variant of the PAGE3 fragment (human reference peptide) "QVLGLAAYL" (SEQ ID NO: 733), such as an antigenic peptide comprising or consisting of an amino acid sequence as set forth in SEQ ID NO: 352, 353 or 354.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen PAX2, such as antigenic peptides comprising or consisting of an amino acid sequence as set forth in any one of SEQ ID NOs 355-358. More preferably, the antigenic peptide according to the present invention is a sequence variant of the PAX2 fragment (human reference peptide) "GLDEVKSSL" (SEQ ID NO: 734), such as an antigenic peptide comprising or consisting of an amino acid sequence as set forth in SEQ ID NO: 355, 356, 357 or 358.

In another embodiment, the antigenic peptide according to the present invention is a microbiota sequence variant of a fragment of the tumor antigen CDH17 (human reference peptide), such as In another preferred embodiment, the antigenic peptide according to the present invention is a sequence variant of a fragment of the tumor antigen PCDHB16, such as antigenic peptides comprising or consisting of an amino acid sequence as set forth in any one of SEQ ID NOs 359-365. More preferably, the antigenic peptide according to the present invention is a sequence variant of the PCDHB16 fragment (human reference peptide) "FVLLSLSGA" (SEQ ID NO: 735), such as an antigenic peptide comprising or consisting of an amino acid sequence as set forth in SEQ ID NO: 359. It is also more preferred that the antigenic peptide according to the present invention is a sequence variant of the PCDHB16 fragment (human reference peptide) "SLFLFSVLL" (SEQ ID NO: 736), such as an antigenic peptide comprising or consisting of an amino acid sequence as set forth in SEQ ID NO: 360. It is also more preferred that the antigenic peptide according to the present invention is a sequence variant of the PCDHB16 fragment (human reference peptide) "SLTVYLVVA" (SEQ ID NO: 737), such as an antigenic peptide comprising or consisting of an amino acid sequence as set forth in SEQ ID NO: 361. It is also more preferred that the antigenic peptide according to the present invention is a sequence variant of the PCDHB16 fragment (human reference peptide) "VLLFVA-VRL" (SEQ ID NO: 738), such as an antigenic peptide comprising or consisting of an amino acid sequence as set forth in SEQ ID NO: 362, 363 or 364. It is also more preferred that the antigenic peptide according to the present invention is a sequence variant of the PCDHB16 fragment (human reference peptide) "VSSLFLFSV" (SEQ ID NO: 739), such as an antigenic peptide comprising or consisting of an amino acid sequence as set forth in SEQ ID NO: 365.

In another embodiment, the antigenic peptide according to the present invention is a microbiota sequence variant of a fragment of the tumor antigen PIWIL1 (human reference peptide), such as "SIAGFVASI" (SEQ ID NO: 740). In another preferred embodiment, the antigenic peptide according to the present invention is a sequence variant of a fragment of the tumor antigen PIWIL1, such as the antigenic peptide comprising or consisting of an amino acid sequence as set forth in SEQ ID NO: 366. Namely, the antigenic peptide according to the present invention, which comprises or consists of an amino acid sequence as set forth in SEQ ID NO: 366 is a sequence variant of the PIWIL1 fragment (human reference peptide) "SIAGFVASI" (SEQ ID NO: 740).

In another embodiment, the antigenic peptide according to the present invention is a microbiota sequence variant of a fragment of the tumor antigen PMEL (human reference peptide), such as "ILLVLMAVV" (SEQ ID NO: 741), "LIVGILLVL" (SEQ ID NO: 742), "LMAVVLASL" (SEQ ID NO: 743), "PLLDGTATL" (SEQ ID NO: 744), "SLADTNSLA" (SEQ ID NO: 745) or "VLQAAIPLT" (SEQ ID NO: 746). In another preferred embodiment, the antigenic peptide according to the present invention is a sequence variant of a fragment of the tumor antigen PMEL, such as antigenic peptides comprising or consisting of an amino acid sequence as set forth in any one of SEQ ID NOs 367-379. More preferably, the antigenic peptide according to the present invention is a sequence variant of the PMEL fragment (human reference peptide) "ILLVLMAVV" (SEQ ID NO: 741), such as an antigenic peptide comprising or consisting of an amino acid sequence as set forth in SEQ ID NO: 367. It is also more preferred that the antigenic peptide according to the present invention is a sequence variant of the PMEL fragment (human reference peptide) "LIVGILLVL" (SEQ ID NO: 742), such as an antigenic peptide comprising or consisting of an amino acid sequence as set forth in SEQ ID NO: 368, 369, 370, 371, 372 or 373. It is also more preferred that the antigenic peptide according to the present invention is a sequence variant of the PMEL fragment (human reference peptide) "LMAVVLASL" (SEQ ID NO: 743), such as an antigenic peptide comprising or consisting of an amino acid sequence as set forth in SEQ ID NO: 374 or 375. It is also more preferred that the antigenic peptide according to the present invention is a sequence variant of the PMEL fragment (human reference peptide) "PLLDGTATL" (SEQ ID NO: 744), such as an antigenic peptide comprising or consisting of an amino acid sequence as set forth in SEQ ID NO: 376. It is also more preferred that the antigenic peptide according to the present invention is a sequence variant of the PMEL fragment (human reference peptide) "SLADTNSLA" (SEQ ID NO: 745), such as an antigenic peptide comprising or consisting of an amino acid sequence as set forth in SEQ ID NO: 377 or 378. It is also more preferred that the antigenic peptide according to the present invention is a sequence variant of the PMEL fragment (human reference peptide) "VLQAAIPLT" (SEQ ID NO: 746), such as an antigenic peptide comprising or consisting of an amino acid sequence as set forth in SEQ ID NO: 379.

In another embodiment, the antigenic peptide according to the present invention is a microbiota sequence variant of a fragment of the tumor antigen PRAME (human reference peptide), such as "AVLDGLDVL" (SEQ ID NO: 747), "QLLALLPSL" (SEQ ID NO: 748), "RLRELLCEL" (SEQ ID NO: 749) or "VLYPVPLES" (SEQ ID NO: 750). In another preferred embodiment, the antigenic peptide according to the present invention is a sequence variant of a fragment of the tumor antigen PRAME, such as antigenic peptides comprising or consisting of an amino acid sequence as set forth in any one of SEQ ID NOs 380-387. More preferably, the antigenic peptide according to the present invention is a sequence variant of the PRAME fragment (human reference peptide) "AVLDGLDVL" (SEQ ID NO: 747), such as an antigenic peptide comprising or consisting of an amino acid sequence as set forth in SEQ ID NO: 380 or 381. It is also more preferred that the antigenic peptide according to the present invention is a sequence variant of the PRAME fragment (human reference peptide) "QLLALLPSL" (SEQ ID NO: 748), such as an antigenic peptide comprising or consisting of an amino acid sequence as set forth in SEQ ID NO: 382, 383, 384 or 385. It is also more preferred that the antigenic peptide according to the present invention is a sequence variant of the PRAME fragment (human reference peptide) "RLRELLCEL" (SEQ ID NO: 749), such as an antigenic peptide comprising or consisting of an amino acid sequence as set forth in SEQ ID NO: 386. It is also more preferred that the antigenic peptide according to the present invention is a sequence variant of the PRAME fragment (human reference peptide) "VLYPVPLES" (SEQ ID NO: 750), such as an antigenic peptide comprising or consisting of an amino acid sequence as set forth in SEQ ID NO: 387.

In another embodiment, the antigenic peptide according to the present invention is a microbiota sequence variant of a fragment of the tumor antigen PTHLH (human reference peptide), such as "AVFLLSYAV" (SEQ ID NO: 751). In another preferred embodiment, the antigenic peptide according to the present invention is a sequence variant of a fragment of the tumor antigen PTHLH, such as the antigenic peptide comprising or consisting of an amino acid sequence as set forth in SEQ ID NO: 388. Namely, the antigenic peptide according to the present invention, which comprises or consists of an amino acid sequence as set forth in SEQ ID NO: 388 is a sequence variant of the PTHLH fragment (human reference peptide) "AVFLLSYAV" (SEQ ID NO: 751).

In another embodiment, the antigenic peptide according to the present invention is a microbiota sequence variant of a fragment of the tumor antigen SEMG1 (human reference peptide), such as "FVLSLLLIL" (SEQ ID NO: 752), "IIFVLSLLL" (SEQ ID NO: 753) or "LILEKQAAV" (SEQ ID NO: 754). In another preferred embodiment, the antigenic peptide according to the present invention is a sequence variant of a fragment of the tumor antigen SEMG1, such as antigenic peptides comprising or consisting of an amino acid sequence as set forth in any one of SEQ ID NOs 389-400. More preferably, the antigenic peptide according to the present invention is a sequence variant of the SEMG1 fragment (human reference peptide) "FVLSLL- LIL" (SEQ ID NO: 752), such as an antigenic peptide comprising or consisting of an amino acid sequence as set forth in SEQ ID NO: 389, 390, 391, 392, 393, 394, 395, 396 or 397. It is also more preferred that the antigenic peptide according to the present invention is a sequence variant of the SEMG1 fragment (human reference peptide) "IIFVLSLLL" (SEQ ID NO: 753), such as an antigenic peptide comprising or consisting of an amino acid sequence as set forth in SEQ ID NO: 398 or 399. It is also more preferred that the antigenic peptide according to the present invention is a sequence variant of the SEMG1 fragment (human reference peptide) "LILEKQAAV" (SEQ ID NO: 754), such as an antigenic peptide comprising or consisting of an amino acid sequence as set forth in SEQ ID NO: 400.

In another embodiment, the antigenic peptide according to the present invention is a microbiota sequence variant of a fragment of the tumor antigen SERHL2 (human reference peptide), such as "LISELKLAV" (SEQ ID NO: 755), "RAIEHVLQV" (SEQ ID NO: 756), "SSFDRLIPL" (SEQ ID NO: 757) or "TLKEQFQFV" (SEQ ID NO: 758). In another preferred embodiment, the antigenic peptide according to the present invention is a sequence variant of a fragment of the tumor antigen SERHL2, such as antigenic peptides comprising or consisting of an amino acid sequence as set forth in any one of SEQ ID NOs 401-405. More preferably, the antigenic peptide according to the present invention is a sequence variant of the SERHL2 fragment (human reference peptide) "LISELKLAV" (SEQ ID NO: 755), such as an antigenic peptide comprising or consisting of an amino acid sequence as set forth in SEQ ID NO: 401. It is also more preferred that the antigenic peptide according to the present invention is a sequence variant of the SERHL2 fragment (human reference peptide) "RAIEHVLQV" (SEQ ID NO: 756), such as an antigenic peptide comprising or consisting of an amino acid sequence as set forth in SEQ ID NO: 402. It is also more preferred that the antigenic peptide according to the present invention is a sequence variant of the SERHL2 fragment (human reference peptide) "SSFDRLIPL" (SEQ ID NO: 757), such as an antigenic peptide comprising or consisting of an amino acid sequence as set forth in SEQ ID NO: 403 or 404. It is also more preferred that the antigenic peptide according to the present invention is a sequence variant of the SERHL2 fragment (human reference peptide) "TLKEQFQFV" (SEQ ID NO: 758), such as an antigenic peptide comprising or consisting of an amino acid sequence as set forth in SEQ ID NO: 405.

In another embodiment, the antigenic peptide according to the present invention is a microbiota sequence variant of a fragment of the tumor antigen SLC45A3 (human reference peptide), such as "AILDSAFLL" (SEQ ID NO: 759), "AISLVFSLV" (SEQ ID NO: 760), "ALQILPYTL" (SEQ ID NO: 761), "ALTGFTFSA" (SEQ ID NO: 762), "AQLLLVNLL" (SEQ ID NO: 763), "CLFGLLTLI" (SEQ ID NO: 764), "GILLSLFLI" (SEQ ID NO: 765), "GLLPPPPAL" (SEQ ID NO: 766), "GLLTLIFLT" (SEQ ID NO: 767), "GLVAIYFAT" (SEQ ID NO: 768), "NLGALLPRL" (SEQ ID NO: 769) or "SVAAFPVAA" (SEQ ID NO: 770). In another preferred embodiment, the antigenic peptide according to the present invention is a sequence variant of a fragment of the tumor antigen SLC45A3, such as antigenic peptides comprising or consisting of an amino acid sequence as set forth in any one of SEQ ID NOs 406-427. More preferably, the antigenic peptide according to the present invention is a sequence variant of the SLC45A3 fragment (human reference peptide) "AILDSAFLL" (SEQ ID NO: 759), such as an antigenic peptide comprising or consisting of an amino acid sequence as set forth in SEQ ID NO: 406. It is also more preferred that the antigenic peptide according to the present invention is a sequence variant of the SLC45A3 fragment (human reference peptide) "AISLVFSLV" (SEQ ID NO: 760), such as an antigenic peptide comprising or consisting of an amino acid sequence as set forth in SEQ ID NO: 407 or 408. It is also more preferred that the antigenic peptide according to the present invention is a sequence variant of the SLC45A3 fragment (human reference peptide) "ALQILPYTL" (SEQ ID NO: 761), such as an antigenic peptide comprising or consisting of an amino acid sequence as set forth in SEQ ID NO: 409. It is also more preferred that the antigenic peptide according to the present invention is a sequence variant of the SLC45A3 fragment (human reference peptide) "ALTGFTFSA" (SEQ ID NO: 762), such as an antigenic peptide comprising or consisting of an amino acid sequence as set forth in SEQ ID NO: 410. It is also more preferred that the antigenic peptide according to the present invention is a sequence variant of the SLC45A3 fragment (human reference peptide) "AQLLLVNLL" (SEQ ID NO: 763), such as an antigenic peptide comprising or consisting of an amino acid sequence as set forth in SEQ ID NO: 411. It is also more preferred that the antigenic peptide according to the present invention is a sequence variant of the SLC45A3 fragment (human reference peptide) "CLFGLLTLI" (SEQ ID NO: 764), such as an antigenic peptide comprising or consisting of an amino acid sequence as set forth in SEQ ID NO: 412, 413, 414 or 415. It is also more preferred that the antigenic peptide according to the present invention is a sequence variant of the SLC45A3 fragment (human reference peptide) "GILLSLFLI" (SEQ ID NO: 765), such as an antigenic peptide comprising or consisting of an amino acid sequence as set forth in SEQ ID NO: 416 or 417. It is also more preferred that the antigenic peptide according to the present invention is a sequence variant of the SLC45A3 fragment (human reference peptide) "GLLPPPPAL" (SEQ ID NO: 766), such as an antigenic peptide comprising or consisting of an amino acid sequence as set forth in SEQ ID NO: 418. It is also more preferred that the antigenic peptide according to the present invention is a sequence variant of the SLC45A3 fragment (human reference peptide) "GLLTLIFLT" (SEQ ID NO: 767), such as an antigenic peptide comprising or consisting of an amino acid sequence as set forth in SEQ ID NO: 419, 420, 421, 422 or 423. It is also more preferred that the antigenic peptide according to the present invention is a sequence variant of the SLC45A3 fragment (human reference peptide) "GLVAIYFAT" (SEQ ID NO: 768), such as an antigenic peptide comprising or consisting of an amino acid sequence as set forth in SEQ ID NO: 424. It is also more preferred that the antigenic peptide according to the present invention is a sequence variant of the SLC45A3 fragment (human reference peptide) "NLGALLPRL" (SEQ ID NO: 769), such as an antigenic peptide comprising or consisting of an amino acid sequence as set forth in SEQ ID NO: 425 or 426. It is also more preferred that the antigenic peptide according to the present invention is a sequence variant of the SLC45A3 fragment (human reference peptide) "SVAAFPVAA" (SEQ ID NO: 770), such as an antigenic peptide comprising or consisting of an amino acid sequence as set forth in SEQ ID NO: 427.

In another embodiment, the antigenic peptide according to the present invention is a microbiota sequence variant of a fragment of the tumor antigen SLC6A3 (human reference peptide), such as "FLLSLFCVT" (SEQ ID NO: 771), "FSLGVGFGV" (SEQ ID NO: 772), "GLIDEFQLL" (SEQ ID NO: 773), "GMESVITGL" (SEQ ID NO: 774),) "ILFGVLIEA" (SEQ ID NO: 775), "KIDFLLSVI" (SEQ ID NO: 776), "LLFMVIAGM" (SEQ ID NO: 777), "LVPYLLFMV" (SEQ ID NO: 778) or "QLTACLVLV" (SEQ ID NO: 779). In another preferred embodiment, the antigenic peptide according to the present invention is a sequence variant of a fragment of the tumor antigen SLC6A3, such as antigenic peptides comprising or consisting of an amino acid sequence as set forth in any one of SEQ ID NOs 428-441. More preferably, the antigenic peptide according to the present invention is a sequence variant of the SLC6A3 fragment (human reference peptide) "FLLSLFCVT" (SEQ ID NO: 771), such as an antigenic peptide comprising or consisting of an amino acid sequence as set forth in SEQ ID NO: 428, 429 or 430. It is also more preferred that the antigenic peptide according to the present invention is a sequence variant of the SLC6A3 fragment (human reference peptide) "FSLGVGFGV" (SEQ ID NO: 772), such as an antigenic peptide comprising or consisting of an amino acid sequence as set forth in SEQ ID NO: 431 or 432. It is also more preferred that the antigenic peptide according to the present invention is a sequence variant of the SLC6A3 fragment (human reference peptide) "GLIDEFQLL" (SEQ ID NO: 773), such as an antigenic peptide comprising or consisting of an amino acid sequence as set forth in SEQ ID NO: 433. It is also more preferred that the antigenic peptide according to the present invention is a sequence variant of the SLC6A3 fragment (human reference peptide) "GMESVITGL" (SEQ ID NO: 774), such as an antigenic peptide comprising or consisting of an amino acid sequence as set forth in SEQ ID NO: 434. It is also more preferred that the antigenic peptide according to the present invention is a sequence variant of the SLC6A3 fragment (human reference peptide) "ILFGVLIEA" (SEQ ID NO: 775), such as an antigenic peptide comprising or consisting of an amino acid sequence as set forth in SEQ ID NO: 435 or 436. It is also more preferred that the antigenic peptide according to the present invention is a sequence variant of the SLC6A3 fragment (human reference peptide) "KIDFLLSVI" (SEQ ID NO: 776), such as an antigenic peptide comprising or consisting of an amino acid sequence as set forth in SEQ ID NO: 437. It is also more preferred that the antigenic peptide according to the present invention is a sequence variant of the SLC6A3 fragment (human reference peptide) "LLFMVIAGM" (SEQ ID NO: 777), such as an antigenic peptide comprising or consisting of an amino acid sequence as set forth in SEQ ID NO: 438 or 439. It is also more preferred that the antigenic peptide according to the present invention is a sequence variant of the SLC6A3 fragment (human reference peptide) "LVPYLLFMV" (SEQ ID NO: 778), such as an antigenic peptide comprising or consisting of an amino acid sequence as set forth in SEQ ID NO: 440. It is also more preferred that the antigenic peptide according to the present invention is a sequence variant of the SLC6A3 fragment (human reference peptide) "QLTACLVLV" (SEQ ID NO: 779), such as an antigenic peptide comprising or consisting of an amino acid sequence as set forth in SEQ ID NO: 441.

In another embodiment, the antigenic peptide according to the present invention is a microbiota sequence variant of a fragment of the tumor antigen SNX31 (human reference peptide), such as "MISEKMVKL" (SEQ ID NO: 780). In another preferred embodiment, the antigenic peptide according to the present invention is a sequence variant of a fragment of the tumor antigen SNX31, such as the antigenic peptide comprising or consisting of an amino acid sequence as set forth in SEQ ID NO: 442. Namely, the antigenic peptide according to the present invention, which comprises or consists of an amino acid sequence as set forth in SEQ ID NO: 442 is a sequence variant of the SNX31 fragment (human reference peptide) "MISEKMVKL" (SEQ ID NO: 780).

In another embodiment, the antigenic peptide according to the present invention is a microbiota sequence variant of a fragment of the tumor antigen SOX11 (human reference peptide), such as "LMFDLSLNF" (SEQ ID NO: 781). In another preferred embodiment, the antigenic peptide according to the present invention is a sequence variant of a fragment of the tumor antigen SOX11, such as antigenic peptides comprising or consisting of an amino acid sequence as set forth in any one of SEQ ID NOs 443-445. More preferably, the antigenic peptide according to the present invention is a sequence variant of the SOX11 fragment (human reference peptide) "LMFDLSLNF" (SEQ ID NO: 781), such as an antigenic peptide comprising or consisting of an amino acid sequence as set forth in SEQ ID NO: 443, 444 or 445.

In another embodiment, the antigenic peptide according to the present invention is a microbiota sequence variant of a fragment of the tumor antigen SOX17 (human reference peptide), such as "ALPAVMAGL" (SEQ ID NO: 782) or "GLAEPQAAA" (SEQ ID NO: 783). In another preferred embodiment, the antigenic peptide according to the present invention is a sequence variant of a fragment of the tumor antigen SOX17, such as antigenic peptides comprising or consisting of an amino acid sequence as set forth in any one of SEQ ID NOs 446-449. More preferably, the antigenic peptide according to the present invention is a sequence variant of the SOX17 fragment (human reference peptide) "ALPAVMAGL" (SEQ ID NO: 782), such as an antigenic peptide comprising or consisting of an amino acid sequence as set forth in SEQ ID NO: 446. It is also more preferred that the antigenic peptide according to the present invention is a sequence variant of the SOX17 fragment (human reference peptide) "GLAEPQAAA" (SEQ ID NO: 783), such as an antigenic peptide comprising or consisting of an amino acid sequence as set forth in SEQ ID NO: 447, 448 or 449.

In another embodiment, the antigenic peptide according to the present invention is a microbiota sequence variant of a fragment of the tumor antigen SPINK1 (human reference peptide), such as "GIFLLSALA" (SEQ ID NO: 784). In another preferred embodiment the antigenic peptide according to the present invention is a sequence variant of a fragment of the tumor antigen SPINK1, such as the antigenic peptide comprising or consisting of an amino acid sequence as set forth in SEQ ID NO: 450. Namely, the antigenic peptide according to the present invention, which comprises or consists of an amino acid sequence as set forth in SEQ ID NO: 450 is a sequence variant of the SPINK1 fragment (human reference peptide) "GIFLLSALA" (SEQ ID NO: 784).

In another embodiment, the antigenic peptide according to the present invention is a microbiota sequence variant of a fragment of the tumor antigen STEAP1 (human reference peptide), such as "ASLTFLYTL" (SEQ ID NO: 785), "AVLHAIYSL" (SEQ ID NO: 786), "FFFAVLHAI" (SEQ ID NO: 787), "GVIAAIVQL" (SEQ ID NO: 788), "KIAAIIASL" (SEQ ID NO: 789), "LIFKSILFL" (SEQ ID NO: 790), "LLLGTIHAL" (SEQ ID NO: 791), "LLSFFFAVL" (SEQ ID NO: 792), "MIAVFLPIV" (SEQ ID NO: 793) or "SLLLGTIHA" (SEQ ID NO: 794). In another preferred embodiment, the antigenic peptide according to the present invention is a sequence variant of a fragment of the tumor antigen STEAP1, such as antigenic peptides comprising or consisting of an amino acid sequence as set forth in any one of SEQ ID NOs 451-468. More preferably, the antigenic peptide according to the present invention is a sequence variant of the STEAP1 fragment (human reference peptide) “ASLTFLYTL” (SEQ ID NO: 785), such as an antigenic peptide comprising or consisting of an amino acid sequence as set forth in SEQ ID NO: 451. It is also more preferred that the antigenic peptide according to the present invention is a sequence variant of the STEAP1 fragment (human reference peptide) “AVLHAIYSL” (SEQ ID NO: 786), such as an antigenic peptide comprising or consisting of an amino acid sequence as set forth in SEQ ID NO: 452. It is also more preferred that the antigenic peptide according to the present invention is a sequence variant of the STEAP1 fragment (human reference peptide) “FFFAVLHAI” (SEQ ID NO: 787), such as an antigenic peptide comprising or consisting of an amino acid sequence as set forth in SEQ ID NO: 453. It is also more preferred that the antigenic peptide according to the present invention is a sequence variant of the STEAP1 fragment (human reference peptide) “GVIAAIVQL” (SEQ ID NO: 788), such as an antigenic peptide comprising or consisting of an amino acid sequence as set forth in SEQ ID NO: 454, 455, 456 or 457. It is also more preferred that the antigenic peptide according to the present invention is a sequence variant of the STEAP1 fragment (human reference peptide) “KIAAIIASL” (SEQ ID NO: 789), such as an antigenic peptide comprising or consisting of an amino acid sequence as set forth in SEQ ID NO: 458, 459 or 460. It is also more preferred that the antigenic peptide according to the present invention is a sequence variant of the STEAP1 fragment (human reference peptide) “LIFKSILFL” (SEQ ID NO: 790), such as an antigenic peptide comprising or consisting of an amino acid sequence as set forth in SEQ ID NO: 461. It is also more preferred that the antigenic peptide according to the present invention is a sequence variant of the STEAP1 fragment (human reference peptide) “LLLGTIHAL” (SEQ ID NO: 791), such as an antigenic peptide comprising or consisting of an amino acid sequence as set forth in SEQ ID NO: 462. It is also more preferred that the antigenic peptide according to the present invention is a sequence variant of the STEAP1 fragment (human reference peptide) “LLSFFFAVL” (SEQ ID NO: 792), such as an antigenic peptide comprising or consisting of an amino acid sequence as set forth in SEQ ID NO: 463, 464 or 465. It is also more preferred that the antigenic peptide according to the present invention is a sequence variant of the STEAP1 fragment (human reference peptide) “MIAVFLPIV” (SEQ ID NO: 793), such as an antigenic peptide comprising or consisting of an amino acid sequence as set forth in SEQ ID NO: 466. It is also more preferred that the antigenic peptide according to the present invention is a sequence variant of the STEAP1 fragment (human reference peptide) “SLLLGTIHA” (SEQ ID NO: 794), such as an antigenic peptide comprising or consisting of an amino acid sequence as set forth in SEQ ID NO: 467 or 468.

In another embodiment, the antigenic peptide according to the present invention is a microbiota sequence variant of a fragment of the tumor antigen TBL1Y (human reference peptide), such as “SLSLIVAVI” (SEQ ID NO: 795). In another preferred embodiment, the antigenic peptide according to the present invention is a sequence variant of a fragment of the tumor antigen TBL1Y, such as antigenic peptides comprising or consisting of an amino acid sequence as set forth in any one of SEQ ID NOs 469-470. More preferably, the antigenic peptide according to the present invention is a sequence variant of the TBL1Y fragment (human reference peptide) “SLSLIVAVI” (SEQ ID NO: 795), such as an antigenic peptide comprising or consisting of an amino acid sequence as set forth in SEQ ID NO: 469 or 470.

In another embodiment, the antigenic peptide according to the present invention is a microbiota sequence variant of a fragment of the tumor antigen TDRD1 (human reference peptide), such as “IISPNLFYA” (SEQ ID NO: 796), “LLDHVLIEM” (SEQ ID NO: 797), “VLIDEHLVL” (SEQ ID NO: 798), “YSSEVLEYM” (SEQ ID NO: 799). In another preferred embodiment, the antigenic peptide according to the present invention is a sequence variant of a fragment of the tumor antigen TDRD1, such as antigenic peptides comprising or consisting of an amino acid sequence as set forth in any one of SEQ ID NOs 471-474. More preferably, the antigenic peptide according to the present invention is a sequence variant of the TDRD1 fragment (human reference peptide) “IISPNLFYA” (SEQ ID NO: 796), such as an antigenic peptide comprising or consisting of an amino acid sequence as set forth in SEQ ID NO: 471. It is also more preferred that the antigenic peptide according to the present invention is a sequence variant of the TDRD1 fragment (human reference peptide) “LLDHVLIEM” (SEQ ID NO: 797), such as an antigenic peptide comprising or consisting of an amino acid sequence as set forth in SEQ ID NO: 472. It is also more preferred that the antigenic peptide according to the present invention is a sequence variant of the TDRD1 fragment (human reference peptide) “VLIDEHLVL” (SEQ ID NO: 798), such as an antigenic peptide comprising or consisting of an amino acid sequence as set forth in SEQ ID NO: 473. It is also more preferred that the antigenic peptide according to the present invention is a sequence variant of the TDRD1 fragment (human reference peptide) “YSSEVLEYM” (SEQ ID NO: 799), such as an antigenic peptide comprising or consisting of an amino acid sequence as set forth in SEQ ID NO: 474.

In another embodiment, the antigenic peptide according to the present invention is a microbiota sequence variant of a fragment of the tumor antigen TOP2A (human reference peptide), such as “ILLRPDTYI” (SEQ ID NO: 800), “LMMTIINLA” (SEQ ID NO: 801), “QLAGSVAEM” (SEQ ID NO: 802), “SLMMTIINL” (SEQ ID NO: 803), “TMLSSLARL” (SEQ ID NO: 804) or “YIFTMLSSL” (SEQ ID NO: 805). In another preferred embodiment, the antigenic peptide according to the present invention is a sequence variant of a fragment of the tumor antigen TOP2A, such as antigenic peptides comprising or consisting of an amino acid sequence as set forth in any one of SEQ ID NOs 475-483. More preferably, the antigenic peptide according to the present invention is a sequence variant of the TOP2A fragment (human reference peptide) “ILLRPDTYI” (SEQ ID NO: 800), such as an antigenic peptide comprising or consisting of an amino acid sequence as set forth in SEQ ID NO: 475. It is also more preferred that the antigenic peptide according to the present invention is a sequence variant of the TOP2A fragment (human reference peptide) “LMMTIINLA” (SEQ ID NO: 801), such as an antigenic peptide comprising or consisting of an amino acid sequence as set forth in SEQ ID NO: 476, 477 or 478. It is also more preferred that the antigenic peptide according to the present invention is a sequence variant of the TOP2A fragment (human reference peptide) “QLAGSVAEM” (SEQ ID NO: 802), such as an antigenic peptide comprising or consisting of an amino acid sequence as set forth in SEQ ID NO: 479 or 480. It is also more preferred that the antigenic peptide according to the present invention is a sequence variant of the TOP2A fragment (human reference peptide) “SLMMTIINL” (SEQ ID NO: 803), such as an antigenic peptide comprising or consisting of an amino acid sequence as set forth in SEQ ID NO: 481. It is also more preferred that the antigenic peptide according to the present invention is a sequence variant of the TOP2A fragment (human reference peptide) "TMLSSLARL" (SEQ ID NO: 804), such as an antigenic peptide comprising or consisting of an amino acid sequence as set forth in SEQ ID NO: 482. It is also more preferred that the antigenic peptide according to the present invention is a sequence variant of the TOP2A fragment (human reference peptide) "YIFTMLSSL" (SEQ ID NO: 805), such as an antigenic peptide comprising or consisting of an amino acid sequence as set forth in SEQ ID NO: 483.

In another embodiment, the antigenic peptide according to the present invention is a microbiota sequence variant of a fragment of the tumor antigen TPTE (human reference peptide), such as "DLAGVIIEL" (SEQ ID NO: 806), "FGLFGVFLV" (SEQ ID NO: 807), "GLFGVFLVL" (SEQ ID NO: 808), "ILDTAIIVI" (SEQ ID NO: 809), "IVSSFAFGL" (SEQ ID NO: 810), "RLLRLIILL" (SEQ ID NO: 811), "SLAIALFFL" (SEQ ID NO: 812) or "YFWLHTSFI" (SEQ ID NO: 813). In another preferred embodiment, the antigenic peptide according to the present invention is a sequence variant of a fragment of the tumor antigen TPTE, such as antigenic peptides comprising or consisting of an amino acid sequence as set forth in any one of SEQ ID NOs 484-504. More preferably, the antigenic peptide according to the present invention is a sequence variant of the TPTE fragment (human reference peptide) "DLAGVIIEL" (SEQ ID NO: 806), such as an antigenic peptide comprising or consisting of an amino acid sequence as set forth in SEQ ID NO: 484, 485, 486, 487, 488, 489 or 490. It is also more preferred that the antigenic peptide according to the present invention is a sequence variant of the TPTE fragment (human reference peptide) "FGLFGVFLV" (SEQ ID NO: 807), such as an antigenic peptide comprising or consisting of an amino acid sequence as set forth in SEQ ID NO: 491, 492, 493 or 494. It is also more preferred that the antigenic peptide according to the present invention is a sequence variant of the TPTE fragment (human reference peptide) "GLFGVFLVL" (SEQ ID NO: 808), such as an antigenic peptide comprising or consisting of an amino acid sequence as set forth in SEQ ID NO: 495, 496 or 497. It is also more preferred that the antigenic peptide according to the present invention is a sequence variant of the TPTE fragment (human reference peptide) "ILDTAIIVI" (SEQ ID NO: 809), such as an antigenic peptide comprising or consisting of an amino acid sequence as set forth in SEQ ID NO: 498 or 499. It is also more preferred that the antigenic peptide according to the present invention is a sequence variant of the TPTE fragment (human reference peptide) "IVSSFAFGL" (SEQ ID NO: 810), such as an antigenic peptide comprising or consisting of an amino acid sequence as set forth in SEQ ID NO: 500 or 501. It is also more preferred that the antigenic peptide according to the present invention is a sequence variant of the TPTE fragment (human reference peptide) "RLLRLIILL" (SEQ ID NO: 811), such as an antigenic peptide comprising or consisting of an amino acid sequence as set forth in SEQ ID NO: 502. It is also more preferred that the antigenic peptide according to the present invention is a sequence variant of the TPTE fragment (human reference peptide) "SLAIALFFL" (SEQ ID NO: 812), such as an antigenic peptide comprising or consisting of an amino acid sequence as set forth in SEQ ID NO: 503. It is also more preferred that the antigenic peptide according to the present invention is a sequence variant of the TPTE fragment (human reference peptide) "YFWLHTSFI" (SEQ ID NO: 813), such as an antigenic peptide comprising or consisting of an amino acid sequence as set forth in SEQ ID NO: 504.

In another embodiment, the antigenic peptide according to the present invention is a microbiota sequence variant of a fragment of the tumor antigen TRPM8 (human reference peptide), such as "AMFGYTVGT" (SEQ ID NO: 814), "FIAGIVFRL" (SEQ ID NO: 815), "FLLLFAYVL" (SEQ ID NO: 816), "LLFAYVLLM" (SEQ ID NO: 817), "LLLFAYVLL" (SEQ ID NO: 818), "LVLYSLVFV" (SEQ ID NO: 819), "NILLVNLLV" (SEQ ID NO: 820), "QIADVIASL" (SEQ ID NO: 821), "VLYSLVFVL" (SEQ ID NO: 822) or "YLVKINTKA" (SEQ ID NO: 823). In another preferred embodiment, the antigenic peptide according to the present invention is a sequence variant of a fragment of the tumor antigen TRPM8, such as antigenic peptides comprising or consisting of an amino acid sequence as set forth in any one of SEQ ID NOs 505-518. More preferably, the antigenic peptide according to the present invention is a sequence variant of the TRPM8 fragment (human reference peptide) "AMFGYTVGT" (SEQ ID NO: 814), such as an antigenic peptide comprising or consisting of an amino acid sequence as set forth in SEQ ID NO: 505. It is also more preferred that the antigenic peptide according to the present invention is a sequence variant of the TRPM8 fragment (human reference peptide) "FIAGIVFRL" (SEQ ID NO: 815), such as an antigenic peptide comprising or consisting of an amino acid sequence as set forth in SEQ ID NO: 506. It is also more preferred that the antigenic peptide according to the present invention is a sequence variant of the TRPM8 fragment (human reference peptide) "FLLLFAYVL" (SEQ ID NO: 816), such as an antigenic peptide comprising or consisting of an amino acid sequence as set forth in SEQ ID NO: 507. It is also more preferred that the antigenic peptide according to the present invention is a sequence variant of the TRPM8 fragment (human reference peptide) "LLFAYVLLM" (SEQ ID NO: 817), such as an antigenic peptide comprising or consisting of an amino acid sequence as set forth in SEQ ID NO: 508 or 509. It is also more preferred that the antigenic peptide according to the present invention is a sequence variant of the TRPM8 fragment (human reference peptide) "LLLFAYVLL" (SEQ ID NO: 818), such as an antigenic peptide comprising or consisting of an amino acid sequence as set forth in SEQ ID NO: 510. It is also more preferred that the antigenic peptide according to the present invention is a sequence variant of the TRPM8 fragment (human reference peptide) "LVLYSLVFV" (SEQ ID NO: 819), such as an antigenic peptide comprising or consisting of an amino acid sequence as set forth in SEQ ID NO: 511. It is also more preferred that the antigenic peptide according to the present invention is a sequence variant of the TRPM8 fragment (human reference peptide) "NILLVNLLV" (SEQ ID NO: 820), such as an antigenic peptide comprising or consisting of an amino acid sequence as set forth in SEQ ID NO: 512. It is also more preferred that the antigenic peptide according to the present invention is a sequence variant of the TRPM8 fragment (human reference peptide) "QIADVIASL" (SEQ ID NO: 821), such as an antigenic peptide comprising or consisting of an amino acid sequence as set forth in SEQ ID NO: 513, 514, 515 or 516. It is also more preferred that the antigenic peptide according to the present invention is a sequence variant of the TRPM8 fragment (human reference peptide) "VLYSLVFVL" (SEQ ID NO: 822), such as an antigenic peptide comprising or consisting of an amino acid sequence as set forth in SEQ ID NO: 517. It is also more preferred that the antigenic peptide according to the present invention is a sequence variant of the TRPM8 fragment (human reference peptide) "YLVKINTKA" (SEQ ID NO: 823), such as an antigenic peptide comprising or consisting of an amino acid sequence as set forth in SEQ ID NO: 518.

In another embodiment, the antigenic peptide according to the present invention is a microbiota sequence variant of a fragment of the tumor antigen TYMS (human reference peptide), such as "FLDSLGFST" (SEQ ID NO: 824), "SLRDEFPLL" (SEQ ID NO: 825) or "VLEELLWFI" (SEQ ID NO: 826). In another preferred embodiment, the antigenic peptide according to the present invention is a sequence variant of a fragment of the tumor antigen TYMS, such as antigenic peptides comprising or consisting of an amino acid sequence as set forth in any one of SEQ ID NOs 519-524. More preferably, the antigenic peptide according to the present invention is a sequence variant of the TYMS fragment (human reference peptide) "FLDSLGFST" (SEQ ID NO: 824), such as an antigenic peptide comprising or consisting of an amino acid sequence as set forth in SEQ ID NO: 519, 520 or 521. It is also more preferred that the antigenic peptide according to the present invention is a sequence variant of the TYMS fragment (human reference peptide) "SLRDEFPLL" (SEQ ID NO: 825), such as an antigenic peptide comprising or consisting of an amino acid sequence as set forth in SEQ ID NO: 522 or 523. It is also more preferred that the antigenic peptide according to the present invention is a sequence variant of the TYMS fragment (human reference peptide) "VLEELLWFI" (SEQ ID NO: 826), such as an antigenic peptide comprising or consisting of an amino acid sequence as set forth in SEQ ID NO: 524.

In another embodiment, the antigenic peptide according to the present invention is a microbiota sequence variant of a fragment of the tumor antigen TYR (human reference peptide), such as "ALLAGLVSL" (SEQ ID NO: 827), "AMVGAVLTA" (SEQ ID NO: 828), "ISSDYVIPI" (SEQ ID NO: 829), "LLAGLVSLL" (SEQ ID NO: 830), "LLSPASFFS" (SEQ ID NO: 831), "MVGAVLTAL" (SEQ ID NO: 832) or "VLTALLAGL" (SEQ ID NO: 833). In another preferred embodiment, the antigenic peptide according to the present invention is a sequence variant of a fragment of the tumor antigen TYR, such as antigenic peptides comprising or consisting of an amino acid sequence as set forth in any one of SEQ ID NOs 525-539. More preferably, the antigenic peptide according to the present invention is a sequence variant of the TYR fragment (human reference peptide) "ALLAGLVSL" (SEQ ID NO: 827), such as an antigenic peptide comprising or consisting of an amino acid sequence as set forth in SEQ ID NO: 525 or 526. It is also more preferred that the antigenic peptide according to the present invention is a sequence variant of the TYR fragment (human reference peptide) "AMVGAVLTA" (SEQ ID NO: 828), such as an antigenic peptide comprising or consisting of an amino acid sequence as set forth in SEQ ID NO: 527, 528, 529 or 530. It is also more preferred that the antigenic peptide according to the present invention is a sequence variant of the TYR fragment (human reference peptide) "ISSDYVIPI" (SEQ ID NO: 829), such as an antigenic peptide comprising or consisting of an amino acid sequence as set forth in SEQ ID NO: 531. It is also more preferred that the antigenic peptide according to the present invention is a sequence variant of the TYR fragment (human reference peptide) "LLAGLVSLL" (SEQ ID NO: 830), such as an antigenic peptide comprising or consisting of an amino acid sequence as set forth in SEQ ID NO: 532. It is also more preferred that the antigenic peptide according to the present invention is a sequence variant of the TYR fragment (human reference peptide) "LLSPASFFS" (SEQ ID NO: 831), such as an antigenic peptide comprising or consisting of an amino acid sequence as set forth in SEQ ID NO: 533. It is also more preferred that the antigenic peptide according to the present invention is a sequence variant of the TYR fragment (human reference peptide) "MVGAVLTAL" (SEQ ID NO: 832), such as an antigenic peptide comprising or consisting of an amino acid sequence as set forth in SEQ ID NO: 534. It is also more preferred that the antigenic peptide according to the present invention is a sequence variant of the TYR fragment (human reference peptide) "VLTALLAGL" (SEQ ID NO: 833), such as an antigenic peptide comprising or consisting of an amino acid sequence as set forth in SEQ ID NO: 535, 536, 537, 538 or 539.

In another embodiment, the antigenic peptide according to the present invention is a microbiota sequence variant of a fragment of the tumor antigen UPK2 (human reference peptide), such as "ALTESLLVA" (SEQ ID NO: 834), "LLALLSPGA" (SEQ ID NO: 835), "LVLGFIIAL" (SEQ ID NO: 836), "SLSGLLSPA" (SEQ ID NO: 837), "TLPLILILL" (SEQ ID NO: 838), "VLGFIIALA" (SEQ ID NO: 839) or "VVITVLLSV" (SEQ ID NO: 840). In another preferred embodiment, the antigenic peptide according to the present invention is a sequence variant of a fragment of the tumor antigen UPK2, such as antigenic peptides comprising or consisting of an amino acid sequence as set forth in any one of SEQ ID NOs 540-556. More preferably, the antigenic peptide according to the present invention is a sequence variant of the UPK2 fragment (human reference peptide) "ALTESLLVA" (SEQ ID NO: 834), such as an antigenic peptide comprising or consisting of an amino acid sequence as set forth in SEQ ID NO: 540, 541 or 542. It is also more preferred that the antigenic peptide according to the present invention is a sequence variant of the UPK2 fragment (human reference peptide) "LLALLSPGA" (SEQ ID NO: 835), such as an antigenic peptide comprising or consisting of an amino acid sequence as set forth in SEQ ID NO: 543. It is also more preferred that the antigenic peptide according to the present invention is a sequence variant of the UPK2 fragment (human reference peptide) "LVLGFIIAL" (SEQ ID NO: 836), such as an antigenic peptide comprising or consisting of an amino acid sequence as set forth in SEQ ID NO: 544, 545, 546 or 547. It is also more preferred that the antigenic peptide according to the present invention is a sequence variant of the UPK2 fragment (human reference peptide) "SLSGLLSPA" (SEQ ID NO: 837), such as an antigenic peptide comprising or consisting of an amino acid sequence as set forth in SEQ ID NO: 548 or 549. It is also more preferred that the antigenic peptide according to the present invention is a sequence variant of the UPK2 fragment (human reference peptide) "TLPLILILL" (SEQ ID NO: 838), such as an antigenic peptide comprising or consisting of an amino acid sequence as set forth in SEQ ID NO: 550. It is also more preferred that the antigenic peptide according to the present invention is a sequence variant of the UPK2 fragment (human reference peptide) "VLGFIIALA" (SEQ ID NO: 839), such as an antigenic peptide comprising or consisting of an amino acid sequence as set forth in SEQ ID NO: 551, 552, 553 or 554. It is also more preferred that the antigenic peptide according to the present invention is a sequence variant of the UPK2 fragment (human reference peptide) "VVITVLLSV" (SEQ ID NO: 840), such as an antigenic peptide comprising or consisting of an amino acid sequence as set forth in SEQ ID NO: 555 or 556.

In another embodiment, the antigenic peptide according to the present invention is a microbiota sequence variant of a fragment of the tumor antigen VCAM1 (human reference peptide), such as "AQIGDSVML" (SEQ ID NO: 841), "FASSLIIPA" (SEQ ID NO: 842), "KSIDGAYTI" (SEQ ID NO: 843) or "SILEEGSSV" (SEQ ID NO: 844). In another preferred embodiment, the antigenic peptide according to the present invention is a sequence variant of a fragment of the tumor antigen VCAM1, such as antigenic peptides comprising or consisting of an amino acid sequence as set forth in any one of SEQ ID NOs 557-560. More preferably, the antigenic peptide according to the present invention is a sequence variant of the VCAM1 fragment (human reference peptide) "AQIGDSVML" (SEQ ID NO: 841), such as an antigenic peptide comprising or consisting of an amino acid sequence as set forth in SEQ ID NO: 557. It is also more preferred that the antigenic peptide according to the present invention is a sequence variant of the VCAM1 fragment (human reference peptide) "FASSLIIPA" (SEQ ID NO: 842), such as an antigenic peptide comprising or consisting of an amino acid sequence as set forth in SEQ ID NO: 558. It is also more preferred that the antigenic peptide according to the present invention is a sequence variant of the VCAM1 fragment (human reference peptide) "KSIDGAYTI" (SEQ ID NO: 843), such as an antigenic peptide comprising or consisting of an amino acid sequence as set forth in SEQ ID NO: 559. It is also more preferred that the antigenic peptide according to the present invention is a sequence variant of the VCAM1 fragment (human reference peptide) "SILEEGSSV" (SEQ ID NO: 844), such as an antigenic peptide comprising or consisting of an amino acid sequence as set forth in SEQ ID NO: 560.

In another embodiment, the antigenic peptide according to the present invention is a microbiota sequence variant of a fragment of the tumor antigen WFDC2 (human reference peptide), such as "LLFGFTLVS" (SEQ ID NO: 845), "LLLFGFTLV" (SEQ ID NO: 846) or "RLGPLAAAL" (SEQ ID NO: 847). In another preferred embodiment, the antigenic peptide according to the present invention is a sequence variant of a fragment of the tumor antigen WFDC2, such as antigenic peptides comprising or consisting of an amino acid sequence as set forth in any one of SEQ ID NOs 561-568. More preferably, the antigenic peptide according to the present invention is a sequence variant of the WFDC2 fragment (human reference peptide) "LLFGFTLVS" (SEQ ID NO: 845), such as an antigenic peptide comprising or consisting of an amino acid sequence as set forth in SEQ ID NO: 561, 562, 563, 564 or 565. It is also more preferred that the antigenic peptide according to the present invention is a sequence variant of the WFDC2 fragment (human reference peptide) "LLLFGFTLV" (SEQ ID NO: 846), such as an antigenic peptide comprising or consisting of an amino acid sequence as set forth in SEQ ID NO: 566. It is also more preferred that the antigenic peptide according to the present invention is a sequence variant of the WFDC2 fragment (human reference peptide) "RLGPLAAAL" (SEQ ID NO: 847), such as an antigenic peptide comprising or consisting of an amino acid sequence as set forth in SEQ ID NO: 567 or 568.

In another embodiment, the antigenic peptide according to the present invention is a microbiota sequence variant of a fragment of the tumor antigen WT1 (human reference peptide), such as "DLNALLPAV" (SEQ ID NO: 848). In another preferred embodiment, the antigenic peptide according to the present invention is a sequence variant of a fragment of the tumor antigen WT1, such as the antigenic peptide comprising or consisting of an amino acid sequence as set forth in SEQ ID NO: 569. Namely, the antigenic peptide according to the present invention, which comprises or consists of an amino acid sequence as set forth in SEQ ID NO: 569 is a sequence variant of the WT1 fragment (human reference peptide) "DLNALLPAV" (SEQ ID NO: 848).

In another embodiment, the antigenic peptide according to the present invention is a microbiota sequence variant of a fragment of the tumor antigen ZEB1 (human reference peptide), such as "ILIPQVAYT" (SEQ ID NO: 849), "NLSDIQNVL" (SEQ ID NO: 850) or "VQAVVLPTV" (SEQ ID NO: 851). In another preferred embodiment, the antigenic peptide according to the present invention is a sequence variant of a fragment of the tumor antigen ZEB1, such as antigenic peptides comprising or consisting of an amino acid sequence as set forth in any one of SEQ ID NOs 570-574. More preferably, the antigenic peptide according to the present invention is a sequence variant of the ZEB1 fragment (human reference peptide) "ILIPQVAYT" (SEQ ID NO: 849), such as an antigenic peptide comprising or consisting of an amino acid sequence as set forth in SEQ ID NO: 570 or 571. It is also more preferred that the antigenic peptide according to the present invention is a sequence variant of the ZEB1 fragment (human reference peptide) "NLSDIQNVL" (SEQ ID NO: 850), such as an antigenic peptide comprising or consisting of an amino acid sequence as set forth in SEQ ID NO: 572 or 573. It is also more preferred that the antigenic peptide according to the present invention is a sequence variant of the ZEB1 fragment (human reference peptide) "VQAVVLPTV" (SEQ ID NO: 851), such as an antigenic peptide comprising or consisting of an amino acid sequence as set forth in SEQ ID NO: 574.

In another embodiment, the antigenic peptide according to the present invention is a microbiota sequence variant of a fragment of the tumor antigen ZNF165 (human reference peptide), such as "LVLEQFLTI" (SEQ ID NO: 852) or "RISGYISEA" (SEQ ID NO: 853). In another preferred embodiment, the antigenic peptide according to the present invention is a sequence variant of a fragment of the tumor antigen ZNF165, such as antigenic peptides comprising or consisting of an amino acid sequence as set forth in any one of SEQ ID NOs 575-578. More preferably, the antigenic peptide according to the present invention is a sequence variant of the ZNF165 fragment (human reference peptide) "LVLEQFLTI" (SEQ ID NO: 852), such as an antigenic peptide comprising or consisting of an amino acid sequence as set forth in SEQ ID NO: 575, 576 or 577. It is also more preferred that the antigenic peptide according to the present invention is a sequence variant of the ZNF165 fragment (human reference peptide) "RISGYISEA" (SEQ ID NO: 853), such as an antigenic peptide comprising or consisting of an amino acid sequence as set forth in SEQ ID NO: 578.

In another embodiment, the antigenic peptide according to the present invention is a microbiota sequence variant of a fragment of the tumor antigen ZNF280A (human reference peptide), such as "AMTDISSLA" (SEQ ID NO: 854) or "VLLSNFYYG" (SEQ ID NO: 855). In another preferred embodiment, the antigenic peptide according to the present invention is a sequence variant of a fragment of the tumor antigen ZNF280A, such as antigenic peptides comprising or consisting of an amino acid sequence as set forth in any one of SEQ ID NOs 579-580. More preferably, the antigenic peptide according to the present invention is a sequence variant of the ZNF280A fragment (human reference peptide) "AMTDISSLA" (SEQ ID NO: 854), such as an antigenic peptide comprising or consisting of an amino acid sequence as set forth in SEQ ID NO: 579. It is also more preferred that the antigenic peptide according to the present invention is a sequence variant of the ZNF280A fragment (human reference peptide) "VLLSNFYYG" (SEQ ID NO: 855), such as an antigenic peptide comprising or consisting of an amino acid sequence as set forth in SEQ ID NO: 580.

Preferably, the antigenic peptide according to the present invention comprises or consists of an amino acid sequence as set forth in any one of SEQ ID NOs 1-160, 162-253 and 255-580. More preferably, the antigenic peptide according to the present invention comprises or consists of an amino acid sequence as set forth in any one of SEQ ID NOs 30, 31, 32, 87, 97, 145, 193, 194, 220, 221, 255, 521 and 524. Even more preferably, the antigenic peptide according to the present invention comprises or consists of an amino acid sequence as set forth in any one of SEQ ID NOs 30, 31, 32, 87, 97, 193, 194, 220, 255, 521 and 524. Still more preferably, the antigenic peptide according to the present invention comprises or consists of an amino acid sequence as set forth in any one of SEQ ID NOs 30, 31, 32, 87, 97, 194, 220, 255, 521 and 524. Most preferably, the antigenic peptide according to the present invention comprises or consists of an amino acid sequence as set forth in any one of SEQ ID NOs 30, 32, 87, 97, and 194.

Moreover, the antigenic peptide according to the present invention comprises or consists of an amino acid sequence as set forth in any one of SEQ ID NOs 30, 32, 194, 220, 254 or 255 is particularly preferred. Most preferably, the antigenic peptide according to the present invention comprises or consists of an amino acid sequence as set forth in SEQ ID NO: 30 or 32. Most preferably, the antigenic peptide according to the present invention comprises or consists of an amino acid sequence as set forth in SEQ ID NO: 194 or 220. Most preferably, the antigenic peptide according to the present invention comprises or consists of an amino acid sequence as set forth in SEQ ID NO: 254 or 255.

As shown in the examples herein, the specific antigenic peptides according to the present invention allow the raise of a strong immune response against themselves, and most importantly, allow the raise of a strong immune response against peptides having amino acid similarity therewith which are comprised in the tumor antigen, even if the human reference peptides comprised in the tumor antigen may be tolerogenic.

Advantageously, the antigenic peptides according to the present invention may be in the form of immunogenic compounds, in particular for use in the prevention or in the treatment of a cancer.

Immunogenic Compounds Comprising the Antigenic Peptide According to the Invention In a further aspect, the present invention also provides an immunogenic compound comprising an antigenic peptide according to the present invention as described above. In particular, preferred embodiments of the antigenic peptide as described above also apply for the immunogenic compound according to the present invention. For example, the antigenic peptide comprised in the immunogenic compound preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, immunogenic compound comprising distinct antigenic peptides according to the present invention.

As used herein, the term "immunogenic compound" refers to a compound that is able to induce, increase, prolong or maintain an immune response, in particular which induces, increases, prolongs or maintains an immune response, when it is administered to a mammal, and especially when it is administered to a human individual.

In general, the term "immunogenic compound" includes all kinds of compounds comprising the antigenic peptide according to the present invention. For example, the antigenic peptide according to the present invention may be linked to a carrier molecule or the antigenic peptide according to the present invention may be comprised in a polypeptide or protein (which polypeptide or protein may occur "separately", i.e. not linked to any other compound, or the polypeptide or protein comprising the antigenic peptide may be linked to a carrier molecule).

Preferably, the immunogenic compound according to present invention comprises the antigenic peptide and a carrier molecule, in particular wherein the antigenic peptide (or a polypeptide or protein comprising the antigenic peptide) is linked to a carrier molecule. A preferred carrier molecule is a carrier protein or a carrier peptide. According to a preferred embodiment, the antigenic peptide as above defined, or a polypeptide/protein comprising said antigenic peptide, is linked to a carrier protein or a carrier peptide, for example by a covalent or non-covalent bond. Alternatively, such a carrier protein or carrier peptide as described herein) may be (separately) co-administered in the form of immune adjuvant (i.e., not as an "immunogenic compound", but as co-administration/combination therapy as described herein below).

The carrier molecule may also be a lipid or a lipid-like moiety. In this case, the immunogenic compound may be a lipopeptide. As used herein, the term "lipopeptide" refers to a molecule that comprises a lipid or a lipid-like moiety covalently linked to a peptide moiety. In general, a "lipid" is soluble in nonpolar solvents, but usually a "lipid" does not (or does not easily) dissolve in water. Examples of a lipid or a lipid-like moiety include, but are not limited to, fatty acids, waxes, sterols, monoglycerides, diglycerides, triglycerides and phospolipids. The lipid may be a fatty acid, a glycerolipid, a gylcerophospholipid, a sphingolipid, a sterol lipid, a prenol lipid, a saccharolipid, or a polyketide. Preferably, the lipid is a fatty acid or a derivative thereof (including monoglycerides, diglycerides, triglycerides and phospolipids). Fatty acids typically contain a hydrocarbon chain that terminates with a carboxylic group. Fatty acids may be saturated or unsaturated. Fatty acids may be attached to functional groups, e.g., containing oxygens, halogens, nitrogen or sulfur. Preferred fatty acids are saturated or unsaturated long-chain fatty acids, such as myristic acid with 14 carbon atoms ($CH_3(CH_2)_{12}COOH$) or palmitic acid with 16 carbon atoms ($CH_3(CH_2)_{14}COOH$), as well as phospholipids, such as phosphatidylglycerol (PG).

Preferably, the antigenic peptide as described herein, or a polypeptide/protein comprising the antigenic peptide, may be co-administrated or linked, for example by covalent or non-covalent bond, to a protein/peptide having immuno-adjuvant properties, such as providing stimulation of CD4+ Th1 cells. While the antigenic peptide as described herein preferably binds to MHC class I, CD4+ helper epitopes may be additionally used to provide an efficient immune response. Th1 helper cells are able to sustain efficient dendritic cell (DC) activation and specific CTL activation by secreting interferon-gamma (IFN-γ), tumor necrosis factor-alpha (TNF-α) and interleukin-2 (IL-2) and enhancing expression of costimulatory signal on DCs and T cells (Galaine et al., Interest of Tumor-Specific CD4 T Helper 1 Cells for Therapeutic Anticancer Vaccine. Vaccines (Basel). 2015 Jun. 30; 3(3):490-502).

For example, the adjuvant peptide/protein may preferably be a non-tumor antigen that recalls immune memory or provides a non-specific help or could be a specific tumor-derived helper peptide. Several helper peptides have been described in the literature for providing a nonspecific T cell help, such as tetanus helper peptide, keyhole limpet hemocyanin peptide or PADRE peptide (Adotévi et al., Targeting antitumor CD4 helper T cells with universal tumor-reactive helper peptides derived from telomerase for cancer vaccine. Hum Vaccin Immunother. 2013 May; 9(5):1073-7, Slingluff C L, The present and future of peptide vaccines for cancer: single or multiple, long or short, alone or in combination? Cancer J. 2011 September-October; 17(5):343-50). Accordingly, tetanus helper peptide, keyhole limpet hemocyanin peptide and PADRE peptide are preferred examples of such adjuvant peptide/proteins. Moreover, specific tumor derived helper peptides are preferred. Specific tumor derived helper peptides are typically presented by MHC class II, in particular by HLA-DR, HLA-DP or HLA-DQ. Specific tumor derived helper peptides may be fragments of sequences of shared overexpressed tumor antigens, such as HER2, NY-ESO-1, hTERT or IL13RA2. Such fragments have preferably a length of at least 10 amino acids, more preferably of at least 11 amino acids, even more preferably of at least 12 amino acids and most preferably of at least 13 amino acids. In particular, fragments of shared overexpressed tumor antigens, such as HER2, NY-ESO-1, hTERT or IL13RA2, having a length of 13 to 24 amino acids are preferred. Preferred fragments bind to MHC class II and may, thus, be identified using, for example, the MHC class II binding prediction tools of IEDB (Immune epitope database and analysis resource; Supported by a contract from the National Institute of Allergy and Infectious Diseases, a component of the National Institutes of Health in the Department of Health and Human Services; URL: http://www.iedb.org/; http://tools.iedb.org/mhcii/). Preferably, the adjuvant peptide/protein may be the HHD-DR3 peptide of sequence MAKTIAYDEEARRGLERGLN (SEQ ID NO: 856). Another preferred example is h-pAg T13L (sequence: TPPAYRPPNAPIL; SEQ ID NO: 860; Bhasin M, Singh H, Raghava G P (2003) MHCBN: a comprehensive database of MHC binding and non-binding peptides. Bioinformatics 19: 665-666). Further examples of preferred adjuvant peptides/proteins, in particular of helper peptides, include the UCP2 peptide (for example as described in WO 2013/135553 A1 or in Dosset et al. Clin Cancer Res. 2012 Nov. 15; 18(22): 6284-95) and the BIRC5 peptide (for example as described in EP2119726 A1 or in Widenmeyer et al. Int J Cancer. 2012 Jul. 1; 131(1):140-9). The most preferred helper peptide is the UCP2 peptide (amino acid sequence: KSVWSKLQSIGIRQH; SEQ ID NO: 859, for example as described in WO 2013/135553 A1 or in Dosset et al., Clin Cancer Res. 2012 Nov. 15; 18(22):6284-95).

It is also preferred that the immunogenic compound according to the present invention is a polypeptide or a protein comprising the antigenic peptide according to the present invention. Preferably, such a protein or polypeptide is a recombinant protein or polypeptide, for example a fusion protein. The term "recombinant" means that it does not occur in nature.

In a preferred embodiment, the immunogenic compound according to the present invention comprises or consists of a polypeptide of formula (I)

PepNt-CORE-PepCt (I)

wherein:

"PepNt" consists of a polypeptide having a length varying from 0 to 500 amino acid residues and is located at the N-terminal end of the polypeptide of formula (I);

"CORE" consists of an antigenic peptide according to the present invention as defined above; and "PepCt" consists of a polypeptide having a length varying from 0 to 500 amino acid residues and is located at the C-terminal end of the polypeptide of formula (I).

For example, the immunogenic compound may comprise or consist of a polypeptide of formula (La) or (Ib):

PepNt-CORE (Ia); or

CORE-PepCt (Ib)

wherein "PepNt" and "PepCt" and "CORE" are as defined above.

Preferably, the polypeptide of formula (I), (Ia) or (Ib) is a fusion peptide or fusion protein, in particular a recombinant fusion peptide or protein.

It is also preferred that the polypeptide or the immunogenic compound as defined above, comprises from 9 to 1000 amino acids; which includes 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67? 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, 500, 600, 700, 800, 900 and 1000 amino acids. Accordingly, the length of "PepNt" and "PepCt", if applicable, may be defined accordingly.

Thus, "PepNt" and "PepCt", as defined above, may comprise from 0 to 500 amino acid residues; which includes 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 250, 300, 350, 400, 450, and 500 amino acid residues.

The types of carrier molecules used for generating an immunogenic compound of the invention, such as an immunogenic compound comprising or consisting of a polypeptide of formula (I) linked to a carrier molecule, are well in the general knowledge of the one skilled in the art. In particular, the function of the carrier molecule is to provide cytokine help (or T-cell help) in order to enhance the immune response against tumor antigen.

Preferably, the antigenic peptide is linked to a carrier molecule, in particular to a carrier protein, preferably by covalent or non-covalent bond. The carrier molecule to which the peptide is optionally bound can be selected from a wide variety of known carriers. Examples of carrier molecules for vaccine purposes encompass proteins such as human or bovine serum albumin and keyhole limpet haemocyanin (KLH) and fatty acids. Other embodiments of carrier molecules to which an antigenic peptide of formula (I) may be covalently linked include bacterial toxins or toxoids, such as diphtheria, cholera, *E. coli* heat labile or tetanus toxoids, the *N. meningitidis* outer membrane protein (European patent application n° EP0372501), synthetic peptides (European patent applications n° EP0378881 and n° EP0427347), heat shock proteins (PCT application n° WO93/17712), *Pertussis* proteins (PCT application n° WO98/58668), protein D from *H. influenzae* (PCT application n° WO00/56360.) and toxin A or B from *C. difficile* (International patent application WO00/61761).

More preferably, the carrier protein or carrier peptide is a protein/peptide having immuno-adjuvant properties, such as providing stimulation of CD4+Th1 cells as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above. In a preferred embodiment, the carrier protein or carrier peptide is a protein/peptide having immuno-adjuvant properties may be a HHD-DR3 carrier peptide MAKTIAYDEEARRGLERGLN (SEQ ID NO: 856). In particular, "PepNt" and/or "PepCt" may correspond to a carrier protein or carrier peptide, such as the HHD-DR3 carrier peptide MAKTIAYDEEARRGLERGLN (SEQ ID NO: 856). Another preferred example is h-pAg T13L (sequence: TPPAYRPPNAPIL; SEQ ID NO: 860; Bhasin M, Singh H, Raghava G P (2003) MHCBN: a comprehensive database of MHC binding and non-binding peptides. Bioinformatics 19: 665-666). Further examples of preferred carrier proteins/peptides, in particular of helper peptides, include the UCP2 peptide (for example as described in WO 2013/135553 A1 or in Dosset et al., Clin Cancer Res. 2012 Nov. 15; 18(22): 6284-95) and the BIRC5 peptide (for example as described in EP2119726 A1 or in Widenmeyer et al., Int J Cancer. 2012 Jul. 1; 131(1):140-9). The most preferred helper peptide is the UCP2 peptide (amino acid sequence: KSVWSKLQSIGIRQH; SEQ ID NO: 859).

Moreover, in the polypeptide according to formula (I), (Ia) or (Ib), "PepNt" and/or "PepCt" may preferably correspond to such a protein/peptide having immuno-adjuvant properties, such as providing stimulation of CD4+Th1 cells as described herein.

Moreover, the immunogenic compound may comprise or consist of such a protein/peptide having immuno-adjuvant properties, such as providing stimulation of CD4+Th1 cells as described herein, linked covalently to the N-terminus of the antigenic peptide according to the present invention or to the N-Terminus of a polypeptide/protein comprising said antigenic peptide.

Preferably, the antigenic peptide according to the present invention (or the polypeptide/protein comprising said antigenic peptide) is covalently bound to the carrier molecule through a linker moiety.

Preferred linker agents encompass the linker agents named GMBS, sulfo-GMBS, SMPB and sulfo-SMPB.

In some embodiments of an immunogenic compound as defined above, the linker agent is selected from the group consisting of GMBS (N-[γ-maleimidobutyryl-oxy]succinimide ester), Sulfo-GMBS (N-[γ-maleimidobutyryl-oxy]sulfosuccinimide ester), SMPB (succinimidyl 4-[p-maleimidophenyl]butyrate) and Sulfo-SMPB (sulfosuccinimidyl 4-[p-maleimidophenyl]butyrate).

Methods for conjugating two proteins with a linker agent in general, and more particularly with a linker agent selected from the group consisting of GMBS, Sulfo-GMBS, SMPB and Sulfo-SMPB, are well known by the one skilled in the art. Illustratively, such protocols are disclosed in the leaflets that are made publicly available by the Pierce Company (Illinois, USA).GMBS, Sulfo-GMBS, SMPB and Sulfo-SMPB consist of heterobifunctional linker agents that contain both a N-hydroxysuccinimide (NHS) ester group and a maleimide group. Conjugation using GMBS, Sulfo-GMBS, SMPB or Sulfo-SMPB is usually performed by a two-step procedure. In a first step, the amine-containing protein is reacted with a several-fold molar excess of the linker agent at pH 7-9 to form amide bonds, followed by removal of excess non-reacted linker agent, usually by desalting or dialysis. In a second step, the sulfhydryl-containing molecule (e.g. peptide of formula (I)) is added to react with the maleimide groups already attached to the first protein at pH 6.5-7.5 to form stable thioether bonds.

Using SMPB or Sulfo-SMPB as linker agents for covalently linking the antigenic peptide according to the present invention (or the polypeptide/protein comprising said antigenic peptide, such as the polypeptide of formula (I)) to the amine-containing carrier protein, leads to a conjugate of formula (II) below:

(II)

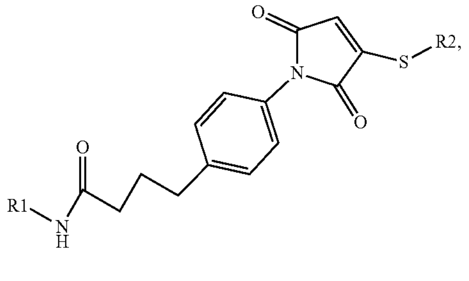

wherein:

R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Using GMBS or Sulfo-GMBS as linker agents for covalently linking the antigenic peptide according to the present invention (or the polypeptide/protein comprising said antigenic peptide, such as a polypeptide of formula (I)) to the amine-containing carrier protein, in particular the CRM197 carrier, protein leads to a conjugate of formula (III) below:

(III)

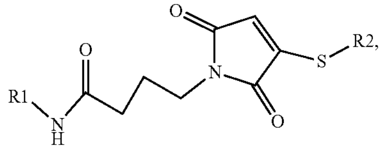

wherein:

R1 consists of one reactive group of the amine-containing carrier protein, and wherein the NH group attached thereto derives from (i) the alpha amino group located at the N-terminal end of the amine-containing carrier protein or (ii) a lateral chain amino group from a Lysine (K) amino acid residue of the amine-containing carrier protein; and R2 consists of the antigenic peptide according to the present invention (or the polypeptide/protein comprising said antigenic peptide, such as a polypeptide of formula (I)), and wherein the sulphur (S) atom attached thereto derives from a sulfhydryl (SH) group of a cysteine residue located at the N-terminal end or at the C-terminal end of a peptide of formula (I). In some embodiments, the sulfhydryl moiety could be part of an unnatural amino acid, or any other molecule present at the end of the peptide of formula (I).

Peptide-MHC (pMHC) Multimers Comprising the Antigenic Peptide

In a further aspect, the present invention also provides a Peptide-MHC (pMHC) multimer comprising an antigenic peptide according to the present invention.

As used herein, the term "peptide-MHC multimer" (pMHC) refers to a stable multimeric complex composed of major histocompatibility complex (MHC) protein subunits loaded with an antigenic peptide of the invention. In general, "MHC multimers" are oligomeric forms of MHC molecules. The main function of an MHC molecule is to bind to an antigen. According to the invention, said antigen is the antigenic peptide according to the invention. Accordingly, a complex of MHC proteins "loaded" with the antigenic peptide of the invention typically means that the antigenic peptide of the invention is bound to one or more of the MHC proteins. The "peptide-MHC multimers" (pMHC) of the invention include, but are not limited to, a peptide-MHC dimer, trimer, tetramer, pentamer, hexamer, heptamer or octamer. MHC tetramers and pentamers are preferred. The term "Major Histocompatibility Complex" (MHC) is a generic designation meant to encompass the histo-compatibility antigen systems described in different species including the human leucocyte antigens (HLA). In humans there are three major different genetic loci that encode MHC class I molecules: HLA-A, HLA-B, and HLA-C. HLA-A*01, HLA-A*02, and HLA-A*11 are examples of different MHC class I alleles that can be expressed from these loci.

In one embodiment of the invention, the pMHC multimer is a peptide/MHC class I multimer. In another particular embodiment, the pMHC multimer is a HLA corresponding to MHC class I/peptide multimer. Accordingly, the pMHC multimer may be a HLA-peptide multimer selected from the group consisting of HLA-A-peptide multimer, HLA-B-peptide multimer, HLA-C-peptide multimer, HLA-E-peptide multimer, MICA-peptide multimer and MICB-peptide multimer.

Methods for obtaining pHMC multimers are known in the art and described, for example, in WO96/26962 and WO01/18053, which are incorporated herein by reference.

In addition to the MHC molecule and the antigenic peptide of the invention, the pMHC may contain further components, such as a multimerization agent and/or a label (e.g., for visualization). Examples of labels include, but are not limited to, fluorescent labels, e.g. fluorescently labelled proteins, such as streptavidin. Fluorescent labels include allophycocyanin (APC), phycoerythrin (PE), R-phycoerythrin (R-PE) and fluorescein isothiocyanate (FITC). A preferred label is biotin.

In one embodiment of the invention, said pMHC multimer can be used to visualize T cell populations that are specific for the MHC class I peptide complex or a HLAs corresponding to MHC class I/peptide complex as described here above. For example, the pMHC multimer may be a multimer where the heavy chain of the MHC is biotinylated, which allows combination as a tetramer with streptavidine. Such pMHC tetramer has an increased avidity for the appropriate TCR-carrier T lymphocytes and can therefore be used to visualize reactive populations by immunofluorescence. In another embodiment of the invention, said pMHC multimer can be used for the detection and/or isolation by screening (in flow cytometry or by immunomagnetic screening) of T cell populations that are specific for a pMHC complex as described here above.

Cells Loaded with the Antigenic Peptide or the Immunogenic Compound

In a further aspect, the present invention also provides a cell loaded with an antigenic peptide according to the present invention or with the immunogenic compound comprising an antigenic peptide according to the present invention as described above. In particular, preferred embodiments of the antigenic peptide as described above also apply for such a cell according to the present invention. For example, the antigenic peptide loaded to the cell or comprised in the immunogenic compound loaded to the cell preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred.

For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, cells loaded with distinct antigenic peptides according to the present invention (or with the respective immunogenic compound(s)).

A preferred cell loaded with the antigenic peptide according to the present invention or with the immunogenic compound according to the present invention is an antigen presenting cell (APC), more preferably a dendritic cell (DC).

APCs are of particular interest, as their main function is to process antigens and present it on the cell surface to the T cells of the immune system, so as to initiate and modulate T-cell responses in vivo. In the context of the present invention, it is preferred that the APCs are loaded with the antigenic peptide(s) and/or immunogenic compound(s) according to the invention. This may be done by exposing APCs in vitro with said antigenic peptide(s) and/or immunogenic compound(s) (as described in Rizzo M M, Alaniz L, Mazzolini G. Ex vivo loading of autologous dendritic cells with tumor antigens. Methods Mol Biol. 2014; 1139:41-4; Rolinski J, Hus I. Breaking immunotolerance of tumors: a new perspective for dendritic cell therapy. J Immunotoxicol. 2014 October; 11(4):311-8).

Preferred APCs according to the invention are dendritic cells (DCs). It can indeed be advantageous to combine at least one antigenic peptide or immunogenic compound according to the invention with DCs, as those are the most potent APCs and have been reported to be frequently functionally defective in cancer patients. DCs can be easily obtained by the skilled person in the art from either healthy compatible donors (i.e. the DCs are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Figdor C G, de Vries I J, Lesterhuis W J, Melief C J. Dendritic cell immunotherapy: mapping the way. Nat Med. 2004 May; 10(5):475-80). DCs can indeed be distinguished from other cells of peripheral blood by their surface markers, such as S100, p55, CD83, and/or OX62, and may thus be isolated and purified based on said markers using cell cultures techniques well-known in the art.

Nucleic Acids Encoding the Antigenic Peptides and Host Cells Comprising Nucleic Acids In a further aspect, the present invention also provides nucleic acid encoding the antigenic peptide according to the present invention, the polypeptide of formula (I) as defined above, or the immunogenic compound according to the present invention, wherein the immunogenic compound is a peptide or a protein. In particular, preferred embodiments of the antigenic peptide as described above also apply for such a nucleic acid according to the present invention. For example, the antigenic peptide encoded by the nucleic acid preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, nucleic acids encoding distinct antigenic peptides according to the present invention.

Nucleic acids preferably comprise single stranded, double stranded or partially double stranded nucleic acids, preferably selected from gDNA, cDNA, RNA, antisense DNA, antisense RNA, complementary RNA/DNA sequences with or without expression elements, a mini-gene, gene fragments, regulatory elements, promoters, and combinations thereof. Further preferred examples of nucleic acid (molecules) and/or polynucleotides include, e.g., a recombinant polynucleotide, a vector, an oligonucleotide, an RNA molecule such as an rRNA, an mRNA, or a tRNA, or a DNA molecule as described above. It is thus preferred that the nucleic acid (molecule) is a DNA molecule or an RNA molecule; preferably selected from gDNA; cDNA; rRNA; mRNA; antisense DNA; antisense RNA; complementary RNA and/or DNA sequences; RNA and/or DNA sequences with or without expression elements, regulatory elements, and/or promoters; a vector; and combinations thereof.

It is of great interest in the fields of therapeutics, diagnostics, reagents and for biological assays to be able to deliver a nucleic acid, e.g., a ribonucleic acid (RNA) inside a cell, whether in vitro, in vivo, in situ or ex vivo, such as to cause intracellular translation of the nucleic acid and production of an encoded peptide of interest. Of particular importance is the delivery and function of a non-integrative polynucleotide. Accordingly, nucleic acids, which do not integrate into the chromosomes of the host, are preferred, such as mRNA. In general, nucleic acids, such as mRNA, may be optimized for expression of the antigenic peptide of the invention, e.g. by methods known in the art, such as codon optimization. In addition, the nucleic acid may be modified, for example, in order to enhance its stability, prolong its lifetime and/or to increase the expression of the antigenic peptide of the invention. Accordingly, optimized or modified mRNA (mmRNA), which encodes an antigenic peptide according to the present invention, is preferred. The mmRNA are distinguished from wild type mRNA in their functional and/or structural design features for optimal delivery of the mRNA and/or for optimal expression of the antigenic peptide of the invention (for example as described in WO 2013/151672 A2, WO 2013/101690 A1, WO2013/052523 A, which are incorporated herein by reference). In general, nucleic acids may be delivered "naked" or associated with a carrier, e.g., a cationic carrier. Cationic carriers (positively charged) typically associate easily with nucleic acids, which are negatively charged. The carrier may be any of any kind including, for example, polymers, proteins, lipids and nanoparticles. Cationic lipids and nanoparticles (in particular lipid nanoparticles, LNPs) are preferred for nucleic acid delivery. Accordingly, the present invention also provides a nucleic acid as described herein associated with a carrier (e.g., a lipid, in particular a cationic lipid or an LNP).

In some embodiments, the nucleic acid molecule may be a vector. The term "vector", as used in the context of the present invention, refers to a nucleic acid molecule, preferably to an artificial nucleic acid molecule, i.e. a nucleic acid molecule which does not occur in nature. A vector in the context of the present invention is suitable for incorporating or harboring a desired nucleic acid sequence. Such vectors may be storage vectors, expression vectors, cloning vectors, transfer vectors etc. A storage vector is a vector which allows the convenient storage of a nucleic acid molecule. Thus, the vector may comprise a sequence corresponding, e.g., to a desired antigenic peptide according to the present invention. An expression vector may be used for production of expression products such as RNA, e.g. mRNA, or peptides, polypeptides or proteins. For example, an expression vector may comprise sequences needed for transcription of a sequence stretch of the vector, such as a promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector which is suitable for transferring nucleic acid molecules into cells or organisms, for example, viral vectors. A vector in the context of the present invention may be, e.g., an RNA vector or a DNA vector. Preferably, a vector is a DNA molecule. For example, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector. Preferably, a vector in the context of the present application is an expression vector. A preferred vector is a vector for expression in bacterial cells. More preferably, the vector is useful for expression in so-called "live bacterial vaccine vectors", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview; Braz J Microbiol. 2015 Mar. 4; 45(4):1117-29.

Nucleic acids encoding antigenic peptides according to the invention may be in the form of naked nucleic acids, or nucleic acids cloned into plasmids or viral vectors (Tregoning and Kinnear, Using Plasmids as DNA Vaccines for Infectious Diseases. Microbiol Spectr. 2014 December; 2(6). doi: 10.1128/microbiolspec.PLAS-0028-2014), the latter being particularly preferred. Examples of suitable viral vectors according to the invention include, without limitation, retrovirus, adenovirus, adeno-associated virus (AAV), herpes virus and poxvirus vectors. It is within the skill of the person in the art to clone a nucleic acid into a plasmid or viral vector, using standard recombinant techniques in the art.

In a further aspect, the present invention also provides a host cell comprising the nucleic acid according to the present invention. Also combinations thereof are preferred, namely, host cells comprising distinct nucleic acids according to the present invention, for example encoding distinct antigenic peptides according to the present invention.

Preferably, the nucleic acid comprised in the host cell is preferably a vector. Preferably, the host cell is a bacterial cell. Such a host cell may be preferably used for production of the antigenic peptide according to the present invention or the immunogenic compound according to the present invention. Moreover, such a host cell may also be an active component in a vaccine.

Preferably, the host cell is a bacterial cell, more preferably a gut bacterial cell. The term "gut bacterial cell" refers to bacteria residing in the (human) gut.

Such a bacterial host cell may serve as "live bacterial vaccine vector", wherein live bacterial cells (such as bacteria or bacterial spores, e.g., endospores, exospores or microbial cysts) can serve as vaccines. Preferred examples thereof are described in da Silva et al., Live bacterial vaccine vectors: an overview-; Braz J Microbiol. 2015 Mar. 4; 45(4):1117-29.

Bacterial cells (such as bacteria or bacterial spores, e.g., endospores, exospores or microbial cysts), in particular (entire) gut bacterial species, can be advantageous, as they have the potential to trigger a greater immune response than the (poly)peptides or nucleic acids they contain.

Alternatively, bacterial cells, in particular gut bacteria, according to the invention may be in the form of probiotics, i.e. of live gut bacterium, which can thus be used as food additive due to the health benefits it can provide. Those can be for example lyophilized in granules, pills or capsules, or directly mixed with dairy products for consumption.

Nanoparticles Comprising the Antigenic Peptide or the Immunogenic Compound

In a further aspect, the present invention also provides a nanoparticle comprising, in particular a nanoparticle loaded with,

- at least one of the antigenic peptides according to the present invention, or
- at least one of the immunogenic compounds according to the present invention;
- and, optionally, with an adjuvant.

In particular, preferred embodiments of the antigenic peptide as described above also apply for such a nanoparticle according to the present invention. For example, the antigenic peptide loaded to the nanoparticle or comprised in the immunogenic compound loaded to the nanoparticle preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred. Also combinations thereof are preferred, namely, nanoparticles loaded with distinct antigenic peptides according to the present invention (or with the respective immunogenic compound (s)).

Nanoparticles, in particular for use as vaccines, are known in the art and described, for example, in Shao et al., Nanoparticle-based immunotherapy for cancer, ACS Nano 2015, 9(1):16-30; Zhao et al., Nanoparticle vaccines, Vaccine 2014, 32(3):327-37; and Gregory et al., Vaccine delivery using nanoparticles, Front Cell Infect Microbiol. 2013, 3:13, doi: 10.3389/fcimb.2013.00013. eCollection 2013, Review. In particular, the nanoparticle is used for delivery of the antigenic peptide (or the immunogenic compound/polypeptide/protein/nucleic acid comprising the antigenic peptide) and may optionally also act as an adjuvant. The antigenic peptide (the immunogenic compound/polypeptide/protein/nucleic acid comprising the antigenic peptide) is typically either encapsulated within the nanoparticle or linked/bound to (decorated onto) the surface of the nanoparticle ("coating"). Compared to conventional approaches, nanoparticles can protect the payload (antigen/adjuvant) from the surrounding biological milieu, increase the half-life, minimize the systemic toxicity, promote the delivery to APCs, or even directly trigger the activation of TAA-specific T-cells. Preferably, the nanoparticle has a size (diameter) of no more than 300 nm, more preferably of no more than 200 nm and most preferably of no more than 100 nm. Such nanoparticles are adequately sheltered from phagocyte uptake, with high structural integrity in the circulation and long circulation times, capable of accumulating at sites of tumor growth, and able to penetrate deep into the tumor mass.

Examples of nanoparticles include polymeric nanoparticles such as poly(ethylene glycol) (PEG) and poly (D,L-lactic-coglycolic acid) (PLGA); inorganic nanoparticles such as gold nanoparticles, iron oxide beads, iron-oxide zinc-oxide nanoparticles, carbon nanotubes and mesoporous silica nanoparticles; liposomes, such as cationic liposomes; immunostimulating complexes (ISCOM); virus-like particles (VLP); and self-assembled proteins.

Polymeric nanoparticles are nanoparticles based on/comprising polymers, such as poly(D,L-lactide-co-glycolide) (PLG), poly(D,L-lactic-coglycolic acid)(PLGA), poly(γ-glutamic acid) (γ-PGA), poly(ethylene glycol) (PEG), and polystyrene. Polymeric nanoparticles may entrap an antigen (e.g., the antigenic peptide or a (poly)peptide comprising the same) or bind to/conjugate to an antigen (e.g., the antigenic peptide or a (poly)peptide comprising the same). Polymeric nanoparticles may be used for delivery, e.g. to certain cells, or sustain antigen release by virtue of their slow biodegradation rate. For example, g-PGA nanoparticles may be used to encapsulate hydrophobic antigens. Polystyrene nanoparticles can conjugate to a variety of antigens as they can be surface-modified with various functional groups. Polymers, such as Poly(L-lactic acid) (PLA), PLGA, PEG, and natural polymers such as polysaccharides may also be used to synthesize hydrogel nanoparticles, which are a type of nano-sized hydrophilic three-dimensional polymer network. Nanogels have favorable properties including flexible mesh size, large surface area for multivalent conjugation, high water content, and high loading capacity for antigens. Accordingly, a preferred nanoparticle is a nanogel, such as a chitosan nanogel. Preferred polymeric nanoparticles are nanoparticles based on/comprising PEG and PLGA.

Inorganic nanoparticles are nanoparticles based on/comprising inorganic substances, and examples of such nanoparticles include gold nanoparticles, iron oxide beads, iron-oxide zinc-oxide nanoparticles, carbon nanoparticles (e.g., carbon nanotubes) and mesoporous silica nanoparticles. Inorganic nanoparticles provide a rigid structure and controllable synthesis. For example, gold nanoparticles can be easily produced in different shapes, such as spheres, rods, cubes. Inorganic nanoparticles may be surface-modified, e.g. with carbohydrates. Carbon nanoparticles provide good biocompatibility and may be produced, for example, as nanotubes or (mesoporous) spheres. For example, multiple copies of the antigenic peptide according to the present invention (or a (poly)peptide comprising the same) may be conjugated onto carbon nanoparticles, e.g. carbon nanotubes. Mesoporous carbon nanoparticles are preferred for oral administration. Silica-based nanoparticles (SiNPs) are also preferred. SiNPs are biocompatible and show excellent properties in selective tumor targeting and vaccine delivery. The abundant silanol groups on the surface of SiNPs may be used for further modification to introduce additional functionality, such as cell recognition, absorption of specific biomolecules, improvement of interaction with cells, and enhancement of cellular uptake. Mesoporous silica nanoparticles are particularly preferred.

Liposomes are typically formed by phospholipids, such as 1,2-dioleoyl-3-trimethylammonium propane (DOTAP). In general, cationic liposomes are preferred. Liposomes are self-assembling with a phospholipid bilayer shell and an aqueous core. Liposomes can be generated as unilameller vesicles (having a single phospholipid bilayer) or as multilameller vesicles (having several concentric phospholipid shells separated by layers of water). Accordingly, antigens can be encapsulated in the core or between different layers/shells. Preferred liposome systems are those approved for human use, such as Inflexal® V and Epaxal®.

Immunostimulating complexes (ISCOM) are cage like particles of about 40 nm (diameter), which are colloidal saponin containing micelles, for example made of the saponin adjuvant Quil-A, cholesterol, phospholipids, and the (poly)peptide antigen (such as the antigenic peptide or a polypeptide comprising the same). These spherical particles can trap the antigen by apolar interactions. Two types of ISCOMs have been described, both of which consist of cholesterol, phospholipid (typically either phosphatidylethanolamine or phosphatidylcholine) and saponin (such as Quil-A).

Virus-like particles (VLP) are self-assembling nanoparticles formed by self-assembly of biocompatible capsid proteins. Due to the naturally-optimized nanoparticle size and repetitive structural order VLPs can induce potent immune responses. VLPs can be derived from a variety of viruses with sizes ranging from 20 nm to 800 nm, typically in the range of 20-150 nm. VLPs can be engineered to express additional peptides or proteins either by fusing these peptides/proteins to the particle or by expressing multiple antigens. Moreover, antigens can be chemically coupled onto the viral surface to produce bioconjugate VLPs.

Examples of self-assembled proteins include ferritin and major vault protein (MVP). Ferritin is a protein that can self-assemble into nearly-spherical 10 nm structure. Ninety-six units of MVP can self-assemble into a barrel-shaped vault nanoparticle, with a size of approximately 40 nm wide and 70 nm long. Antigens that are genetically fused with a minimal interaction domain can be packaged inside vault nanoparticles by self-assembling process when mixed with MVPs. Accordingly, the antigen (such as the antigenic peptide according to the present invention of a polypeptide comprising the same) may be fused to a self-assembling protein or to a fragment/domain thereof, such as the minimal interaction domain of MVP. Accordingly, the present invention also provides a fusion protein comprising a self-assembling protein (or a fragment/domain thereof) and the antigenic peptide according to the present invention.

In general, preferred examples of nanoparticles (NPs) include iron oxide beads, polystyrene microspheres, poly(γ-glutamic acid) (7-PGA) NPs, iron oxide-zinc oxide NPs, cationized gelatin NPs, pluronic-stabilized poly(propylene sulfide) (PPS) NPs, PLGA NPs, (cationic) liposomes, (pH-responsive) polymeric micelles, PLGA, cancer cell membrane coated PLGA, lipid-calcium-phosphate (LCP) NPs, liposome-protamine-hyaluronic acid (LPH) NPs, polystyrene latex beads, magnetic beads, iron-dextran particles and quantum dot nanocrystals.

Preferably, the nanoparticle further comprises an adjuvant, for example a toll-like receptor (TLR) agonist. Thereby, the antigenic peptide (the immunogenic compound/polypeptide/protein/nucleic acid comprising the antigenic peptide) can be delivered together with an adjuvant, for example to antigen-presenting cells (APCs), such as dendritic cells (DCs). The adjuvant may be encapsulated by the nanoparticle or bound to/conjugated to the surface of the nanoparticle, preferably similarly to the antigenic peptide.

Particularly preferred adjuvants are polyinosinic: polycytidylic acid (also referred to as "poly L:C") and/or its derivative poly-ICLC. Poly I:C is a mismatched double-stranded RNA with one strand being a polymer of inosinic acid, the other a polymer of cytidylic acid. Poly L:C is an immunostimulant known to interact with toll-like receptor 3 (TLR3). Poly I: C is structurally similar to double-stranded RNA, which is the "natural" stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly 1:C and poly-ICLC typically stimulate the release of cytotoxic cytokines. A preferred example of poly-ICLC is Hiltonol®.

Pharmaceutical Compositions

In a further aspect, the present invention also provides a pharmaceutical composition comprising at least one of the following:

- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein, and/or
- the host cell according to the present invention as described herein, and, optionally, one or more pharmaceutically acceptable excipients or carriers.

In particular, preferred embodiments of the antigenic peptide as described above also apply for such a pharmaceutical composition according to the present invention. For example, the antigenic peptide comprised in the pharmaceutical composition or the antigenic peptide comprised in any of the immunogenic compound, the nanoparticle, the cell, the nucleic acid or the host cell comprised by the pharmaceutical composition preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred.

Also combinations thereof are preferred, namely, pharmaceutical compositions comprising distinct antigenic peptides according to the present invention. For example, the pharmaceutical composition may comprise (i) at least two distinct antigenic peptides according to the present invention;
(ii) at least two distinct immunogenic compounds according to the present invention;
(iii) at least two distinct nanoparticles according to the present invention; and/or
(iv) at least two distinct nucleic acids according to the present invention.

Accordingly, the present invention provides a pharmaceutical composition comprising (at least) one antigenic peptide according to the present invention as described herein. Moreover, the present invention also provides a pharmaceutical composition comprising (at least) one immunogenic compound according to the present invention as described herein. Moreover, the present invention also provides a pharmaceutical composition comprising (at least) one nanoparticle according to the present invention as described herein. Moreover, the present invention also provides a pharmaceutical composition comprising (at least) one cell according to the present invention as described herein. Moreover, the present invention also provides a pharmaceutical composition comprising (at least) one nucleic acid according to the present invention as described herein. Moreover, the present invention also provides a pharmaceutical composition comprising (at least) one host cell according to the present invention as described herein.

Preferably, the pharmaceutical composition comprises at least two distinct antigenic peptides according to the present invention.

In particular, the present invention provides a pharmaceutical composition comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the human tumor antigen FOXM1. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868. Even more preferably, the pharmaceutical composition comprises an antigenic peptide comprising or consisting of SEQ ID NO: 32 and an antigenic peptide comprising or consisting of SEQ ID NO: 220.

In particular, the present invention also provides a pharmaceutical composition comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the pharmaceutical composition comprises an antigenic peptide comprising or consisting of SEQ ID NO: 32 and an antigenic peptide comprising or consisting of SEQ ID NO: 255.

In particular, the present invention also provides a pharmaceutical composition comprising a first antigenic peptide according to the present invention, which comprises or consists of a microbiota sequence variant of a fragment of the human tumor antigen FOXM1, and a second antigenic peptide according to the present invention, which comprises or consists of a microbiota sequence variant of a fragment of the human tumor antigen IL13RA2. Preferably, the first antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the pharmaceutical composition comprises an antigenic peptide comprising or consisting of SEQ ID NO: 220 and an antigenic peptide comprising or consisting of SEQ ID NO: 255.

More preferably, the pharmaceutical composition comprises at least three distinct antigenic peptides according to the present invention.

In particular, the present invention also provides a pharmaceutical composition comprising a first antigenic peptide according to the present invention, which comprises or consists of a microbiota sequence variant of a fragment of the human tumor antigen BIRC5, a second antigenic peptide according to the present invention, which comprises or consists of a microbiota sequence variant of a fragment of the human tumor antigen FOXM1, and a third antigenic peptide according to the present invention, which comprises or consists of a microbiota sequence variant of a fragment of the human tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; the second antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868; and the third antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the pharmaceutical composition comprises an antigenic peptide comprising or consisting of an amino acid sequence as set forth in SEQ ID NO: 30, an antigenic peptide comprising or consisting of an amino acid sequence as set forth in SEQ ID NO: 220, and an antigenic peptide comprising or consisting of an amino acid sequence as set forth in SEQ ID NO: 255.

It is understood that the pharmaceutical composition may also contain—instead of the above-described preferred combinations of antigenic peptides—a respective combination of immunogenic compounds of the invention, a respective combination of nanoparticles of the invention or a respective combination of nucleic acids of the invention.

Preferably, the pharmaceutical composition further comprises one or more pharmaceutically acceptable excipients or carriers.

The pharmaceutical composition of the invention may be in any form suitable for the purposes of the invention. For example, said composition may be in a form suitable for parenteral, enteral or topical administration, such as a liquid suspension, a solid dosage form (granules, pills, capsules or tablets), or a paste or gel. It is within the skill of the person in the art to select the appropriate form of the composition for the intended purpose.

The composition according to the invention can further comprise other active agents, for example such, which can enhance the effects of the antigenic peptide or immunogenic compound. Alternatively, the composition may not comprise any other active agents (i.e., other than the antigenic peptide according to the present invention, the immunogenic compound according to the present invention, the nanoparticle according to the present invention, the cell according to the present invention, the nucleic acid according to the present invention, and/or the host cell according to the present invention).

The pharmaceutical composition as defined herein is preferably an immunogenic composition, i.e. a composition that is able to induce, increase, prolong or maintain an immune response. This may be achieved by an antigenic peptide according to the present invention or by an immunogenic compound according to the present invention comprised in said composition. Preferably, the pharmaceutical composition further comprises one or more immuno-adjuvant substances. A pharmaceutical composition, in particular an immunogenic composition, may also be termed "vaccine composition" in the present specification.

Preferably, the pharmaceutical composition further comprises at least one immunostimulatory agent, in particular so as to increase, potentiate, prolong or maintain the immune response mediated by the antigenic peptide. Preferred immunostimulatory agents according to the invention include, without limitation, immune adjuvants, antigen-presenting cells, and combinations thereof. Preferably, the immunostimulatory agent is an immune adjuvant or an antigen-presenting cell (APC).

Preferably, the immunostimulatory agent is an immune adjuvant. Some immune adjuvants are capable of favoring and prolonging the duration of interaction between an antigen and the immune system, while others are capable of recruiting and activating cells of the natural immunity so as to induce an adaptive response. The adjuvants belonging to the former category include, without limitation, mineral compounds such as alum, aluminum hydroxide, aluminum phosphate, calcium phosphate hydroxide; and oil-based emulsions such as paraffin oil, starch oil, Freund's complete/incomplete adjuvant (FCA/FIA), saponins (e.g. from the plants Quillaja, Soybean, Polygala senega). The adjuvants of belonging to the latter category include, without limitation, immunostimulatory complexes (ISCOMs) such as cytokines (e.g. GM-CSF; Interleukins such as IL-1, IL-2, IL6, IL8, or IL12; Tumor necrosis factors (TNFs) such as TNFα or TNFβ; Interferons IFNδ such as IFNα, IFNβ, IFNγ or IFNβ, etc); ligands of toll-like receptors (TLRs) such as imiquimod, resiquimod or MPL; exosomes such as exosomes derived from dendritic cells (DCs) or from tumor cells; bacterial products such as heat-shock proteins (HSPs such as gp96, hsp90, hsp70, calreticulin, hsp110, hsp170), pathogen-associated molecular patterns (PAMPs), trehalose dimicolate (TDM), mummyldipeptide (MDP), polysaccharide (PLS) such as polysaccharide-K.

More preferably, the immune adjuvant is a protein/peptide having immuno-adjuvant properties, such as providing stimulation of CD4+ Th1 cells, as described herein. A preferred example thereof is a non-tumor antigen that recalls immune memory or provides a non-specific help or could be a specific tumor-derived helper peptide, such as tetanus helper peptide, keyhole limpet hemocyanin peptide or PADRE peptide, as described herein. Another preferred example is a specific tumor derived helper peptide, which may be presented by MHC II, in particular by HLA-DR, HLA-DP or HLA-DQ, such as fragments of shared overexpressed tumor antigens, e.g. HER2, NY-ESO-1, hTERT or IL13RA2, as described above. In particular, the immune adjuvant may be the HHD-DR3 peptide of sequence MAKTIAYDEEARRGLERGLN (SEQ ID NO: 856). This peptide represents another example of a helper peptide (having immuno-adjuvant properties), which is preferred in the context of the present invention. Another preferred example is h-pAg T13L (sequence: TPPAYRPPNAPIL; SEQ ID NO: 860; Bhasin M, Singh H, Raghava G P (2003) MHCBN: a comprehensive database of MHC binding and non-binding peptides. Bioinformatics 19: 665-666). Further examples of preferred immune adjuvants, in particular of helper peptides, include the UCP2 peptide (for example as described in WO 2013/135553 A1 or in Dosset et al., Clin Cancer Res. 2012 Nov. 15; 18(22):6284-95) and the BIRC5 peptide (for example as described in EP2119726 A1 or in Widenmeyer et al., Int J Cancer. 2012 Jul. 1; 131(1):140-9). The most preferred helper peptide is the UCP2 peptide (amino acid sequence: KSVWSKLQSIGIRQH; SEQ ID NO: 859).

Preferably, the pharmaceutical composition comprises at least two distinct antigenic peptides according to the present invention and a helper peptide, preferably the UCP2 peptide (SEQ ID NO: 859).

Preferably, the pharmaceutical composition comprises a first antigenic peptide according to the present invention comprising or consisting of a microbiota sequence variant of a fragment of the human tumor antigen BIRC5, a second antigenic peptide according to the present invention comprising or consisting of a microbiota sequence variant of a fragment of the human tumor antigen FOXM1 and a helper peptide, preferably the UCP2 peptide (SEQ ID NO: 859). More preferably, the pharmaceutical composition comprises a first antigenic peptide according to the present invention comprising or consisting of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; a second antigenic peptide according to the present invention comprising or consisting of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868; and a helper peptide, preferably the UCP2 peptide (SEQ ID NO: 859). Even more preferably, the pharmaceutical composition comprises an antigenic peptide comprising or consisting of SEQ ID NO: 32; an antigenic peptide comprising or consisting of SEQ ID NO: 220; and the UCP2 helper peptide (SEQ ID NO: 859).

It is also preferred, that the pharmaceutical composition comprises a first antigenic peptide according to the present invention comprising or consisting of a microbiota sequence variant of a fragment of the human tumor antigen BIRC5, a second antigenic peptide according to the present invention comprising or consisting of a microbiota sequence variant of a fragment of the human tumor antigen IL13RA2, and a helper peptide, preferably the UCP2 peptide (SEQ ID NO: 859). More preferably, the pharmaceutical composition comprises a first antigenic peptide according to the present invention comprising or consisting of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; a second antigenic peptide according to the present invention comprising or consisting of a microbiota sequence variant of a fragment of the tumor antigen IL13RA2 (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879; and a helper peptide, preferably the UCP2 peptide (SEQ ID NO: 859). Even more preferably, the pharmaceutical composition comprises an antigenic peptide comprising or consisting of SEQ ID NO: 32; an antigenic peptide comprising or consisting of SEQ ID NO: 255; and the UCP2 helper peptide (SEQ ID NO: 859).

It is also preferred, that the pharmaceutical composition comprises a first antigenic peptide according to the present invention comprising or consisting of a microbiota sequence variant of a fragment of the human tumor antigen FOXM1; a second antigenic peptide according to the present invention comprising or consisting of a microbiota sequence variant of a fragment of the tumor antigen IL13RA2; and a helper peptide, preferably the UCP2 peptide (SEQ ID NO: 859). More preferably, the pharmaceutical composition comprises a first antigenic peptide according to the present invention comprising or consisting of a microbiota sequence variant of the FOXM1 fragment (human reference peptide) “LMDLSTTPL” (SEQ ID NO: 674), such as an antigenic peptide comprising or consisting of an amino acid sequence as set forth in SEQ ID NO: 220 or 868; a second antigenic peptide according to the present invention comprising or consisting of a microbiota sequence variant of the IL13RA2 fragment (human reference peptide) “WLPFGFILI” (SEQ ID NO: 691) or “WLPFGFILIL” (SEQ ID NO: 692), such as an antigenic peptide comprising or consisting of an amino acid sequence as set forth in SEQ ID NO: 254, 255, 878 or 879; and a helper peptide, preferably the UCP2 peptide (SEQ ID NO: 859). Even more preferably, the pharmaceutical composition comprises an antigenic peptide comprising or consisting of SEQ ID NO: 220; an antigenic peptide comprising or consisting of SEQ ID NO: 255; and the UCP2 helper peptide (SEQ ID NO: 859).

More preferably, the pharmaceutical composition comprises at least three distinct antigenic peptides according to the present invention and a helper peptide, preferably the UCP2 peptide (SEQ ID NO: 859).

In particular, the pharmaceutical composition may comprise a first antigenic peptide according to the present invention comprising or consisting of a microbiota sequence variant of a fragment of the human tumor antigen BIRC5, a second antigenic peptide according to the present invention comprising or consisting of a microbiota sequence variant of a fragment of the human tumor antigen FOXM1, a third antigenic peptide according to the present invention comprising or consisting of a microbiota sequence variant of a fragment of the human tumor antigen IL13RA2 and a helper peptide, preferably the UCP2 peptide (SEQ ID NO: 859). Even more preferably, the pharmaceutical composition comprises a first antigenic peptide according to the present invention comprising or consisting of a microbiota sequence variant of the BIRC5 fragment (human reference peptide) “LTLGEFLKL” (SEQ ID NO: 593), such as an antigenic peptide comprising or consisting of an amino acid sequence as set forth in SEQ ID NO: 30, 31 or 32; a second antigenic peptide according to the present invention comprising or consisting of a microbiota sequence variant of the FOXM1 fragment (human reference peptide) “LMDLSTTPL” (SEQ ID NO: 674), such as an antigenic peptide comprising or consisting of an amino acid sequence as set forth in SEQ ID NO: 220 or 868; a third antigenic peptide according to the present invention comprising or consisting of a microbiota sequence variant of the IL13RA2 fragment (human reference peptide) “WLPFGFILI” (SEQ ID NO: 691) or “WLPFGFILIL” (SEQ ID NO: 692), such as an antigenic peptide comprising or consisting of an amino acid sequence as set forth in SEQ ID NO: 254, 255, 878 or 879; and a helper peptide, preferably the UCP2 peptide (SEQ ID NO: 859). Still more preferably, the pharmaceutical composition comprises the antigenic peptide comprising or consisting of an amino acid sequence as set forth in SEQ ID NO: 30, the antigenic peptide comprising or consisting of an amino acid sequence as set forth in SEQ ID NO: 220, the antigenic peptide comprising or consisting of an amino acid sequence as set forth in SEQ ID NO: 255, and a helper peptide, preferably the UCP2 peptide (SEQ ID NO: 859).

Particularly preferred immune adjuvants are polyinosinic: polycytidylic acid (also referred to as “poly I:C”) and/or its derivative poly-ICLC. Poly L:C is a mismatched double-stranded RNA with one strand being a polymer of inosinic acid, the other a polymer of cytidylic acid. Poly I:C is an immunostimulant known to interact with toll-like receptor 3 (TLR3). Poly I: C is structurally similar to double-stranded RNA, which is the “natural” stimulant of TLR3. Accordingly, poly I:C may be considered a synthetic analog of double-stranded RNA. Poly-ICLC is a synthetic complex of carboxymethylcellulose, polyinosinic-polycytidylic acid, and poly-L-lysine double-stranded RNA. Similar to poly I:C, also poly-ICLC is a ligand for TLR3. Poly I:C and poly-ICLC typically stimulate the release of cytotoxic cytokines. A preferred example of poly-ICLC is Hiltonol®.

Most preferably, the adjuvant is Montanide, such as Montanide ISA 51 VG and/or Montanide ISA 720 VG. Those adjuvants are rendering stable water-in-oil emulsions when mixed with water based antigenic media. Montanide ISA 51 VG is based on a blend of mannide monooleate surfactant and mineral oil, whereas Montanide ISA 720 VG uses a non-mineral oil (Aucouturier J, Dupuis L, Deville S, Ascarateil S, Ganne V. Montanide ISA 720 and 51: a new generation of water in oil emulsions as adjuvants for human vaccines. Expert Rev Vaccines. 2002 June, 1(1):111-8; Ascarateil S, Puget A, Koziol M-E. Safety data of Montanide ISA 51 VG and Montanide ISA 720 VG, two adjuvants dedicated to human therapeutic vaccines. Journal for Immunotherapy of Cancer. 2015; 3(Suppl 2):P428. doi:10.1186/2051-1426-3-S2-P428).

It is also preferred that the immunostimulatory agent is an antigen-presenting cell (APC). APCs are also of particular interest, as their main function is to process antigens and present it on the cell surface to the T cells of the immune system, so as to initiate and modulate T-cell responses in vivo.

In the present composition, it is preferred that the APCs are loaded with the antigenic peptide(s) and/or immunogenic compound(s) according to the invention, which can be done by exposing APCs in vitro with said antigenic peptide(s) and/or immunogenic compound(s) (Rizzo et al., Methods Mol Biol. 2014; 1139:41-4; Rolinski and Hus, J Immunotoxicol. 2014 October; 11(4):311-8).

Preferably, the APC is a dendritic cell (DC). DCs are the most potent APCs and have been reported to be frequently functionally defective in cancer patients. DCs can be easily obtained by the skilled person in the art from either healthy compatible donors (i.e. the dendritic cells are HLA-related) or from the patient himself provided that they are functional (i.e. the DCs are autologous), for example by direct isolation from the peripheral blood, or by derivation from peripheral blood cells such as CD14+ monocytes or CD34+ hematopoietic precursors (Emens et al., 2008). DCs can indeed be distinguished from other cells of peripheral blood by their surface markers, such as S100, p55, CD83, and/or OX62, and may thus be isolated and purified based on said markers using cell cultures techniques well-known in the art.

According to a preferred embodiment, the pharmaceutical composition may further comprise at least one anti-cancer therapeutic agent. Said therapeutic agent is thus preferably capable of preventing and/or treating the same type of cancer than the one for which the antigenic peptide according to the invention is used. Preferably, the anti-cancer therapeutic agent is selected from antibodies, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumor antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(15):5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March, 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA-4, B7H3, B7H4, PVR, TIGIT, GAL9, LAG-3, GITR, CD137, TIM3, VISTA, VISTA-R (Pico de Coaña et al., Checkpoint blockade for cancer therapy: revitalizing a suppressed immune system. Trends Mol Med. 2015 August; 21(8):482-91; Pardoll D M. The blockade of immune checkpoints in cancer immunotherapy. Nat Rev Cancer. 2012 Mar. 22; 112(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-oeasophageal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-oeasophageal cancers); while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MEDI4736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al., Trial Watch: Immunomodulatory monoclonal antibodies for oncological indications. Oncoimmunology. 2015 Mar. 2; 4(4):e1008814. eCollection 2015 April; Redman et al., Mechanisms of action of therapeutic antibodies for cancer. Mol Immunol. 2015 October; 67(2 Pt A): 28-45; Simpson and Caballero, Monoclonal antibodies for the therapy of cancer MC Proc. 2014; 8(Suppl 4): 06 as well as on the antibody society website (list of therapeutic monoclonal antibodies approved or in review in the European Union or United States available on the weblink http://www.antibodysociety.org/news/approved_mabs.php).

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al., (Paci et al., Review of therapeutic drug monitoring of anticancer drugs part 1—cytotoxics. Eur J Cancer. 2014 August; 50(12):2010-9) and Widmer et al. (Widmer et al., Review of therapeutic drug monitoring of anticancer drugs part two-targeted therapies. Eur J Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1, PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy© (Ipilimumab; Bristol Myers Squibb) and Tremelimumab (Pfizer/MedImmune) as well as Opdivo© (Nivolumab; Bristol Myers Squibb), Keytruda® (Pembrolizumab, also known as Lambrolizumab or MK-3475; Merck), Imfinzi© (Durvalumab, also known as MED14736; Medimmune/AstraZeneca), Tecentriq© (Atezolizumab, also known as MPDL3280A; Roche/Genentech), Pidilizumab (CT-011; CureTech), MEDI0680 (AMP-514; AstraZeneca), Bavencio® (Avelumab; Merck KGaA/Pfizer, also known as MSB-0010718C), MIH1 (Affymetrix), LY3300054 (Eli Lilly) and Spartalizumab (also known as PDR001; Novartis). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZencca), AMP-224 (a PD-L2 Fc fusion protein: MedImmune).

It is also preferred that the immune checkpoint modulator for combination with the antigenic peptide as defined herein is selected from the group consisting of Pembrolizumab, Ipilimumab, Nivolumab, Atezolizumab. Durvalumab, Tremelimumab, Avelumab, Spartalizumab, LAG525 (an anti-LAG-3 monoclonal antibody), Epacadostat (also known as INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention. For example, should one wish to prevent or treat melanoma, a lysate from melanoma cells and/or the antibody Ipilimumab can preferably be used, along with an appropriate antigenic peptide. Appropriate antigenic peptides may be selected by (i) selecting an appropriate tumor antigen for a certain type of cancer as known in the art and/or as described herein in Table 1B and (ii) selecting an appropriate antigenic peptide according to the invention for the selected tumor antigen, as described above, e.g. in Table 1A.

The anti-cancer therapeutic agent can also be administered in combination with the composition of the invention, either simultaneously, separately, or sequentially. Should the composition and the therapeutic agent be administered in a separate or sequential manner, those may be administered in distinct pharmaceutical forms.

Thus, in another aspect, the invention relates to a composition of the invention and at least one anti-cancer therapeutic agent as described above, as a combined preparation for a simultaneous, separate, or sequential administration. In other terms, the invention proposes a combined use of the composition the invention and least one anti-cancer therapeutic agent as described above, for a simultaneous, separate, or sequential administration.

Kits-of-Parts

In a further aspect, the present invention also provides a kit-of-parts (also referred to herein as "kit") comprising at least one of the following:

- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein,
- the host cell according to the present invention as described herein, and/or
- the pharmaceutical composition according to the present invention as described herein.

In particular, preferred embodiments of the antigenic peptide as described above also apply for such a kit according to the present invention. For example, the antigenic peptide comprised in the kit or the antigenic peptide comprised in any of the immunogenic compound, the nanoparticle, the cell, the nucleic acid, the host cell or the pharmaceutical composition comprised in the kit preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred.

Also combinations thereof are preferred, namely, kits comprising distinct antigenic peptides according to the present invention. In particular, the kit-of-parts of the invention may comprise more than one of the above described components, e.g. 2, 3, 4, 5, 6, 7, 8, 9, or 10 distinct components. For example, the kit-of-parts according to the present invention may comprise at least two (e.g. 2, 3, 4, 5, 6, 7, 8, 9, or 10) different immunogenic compounds, at least two (e.g. 2, 3, 4, 5, 6, 7, 8, 9, or 10) different antigenic peptides, at least two (e.g. 2, 3, 4, 5, 6, 7, 8, 9, or 10) different nanoparticles, at least two (e.g. 2, 3, 4, 5, 6, 7, 8, 9, or 10) different cells, at least two (e.g. 2, 3, 4, 5, 6, 7, 8, 9, or 10) different nucleic acids, at least two (e.g. 2, 3, 4, 5, 6, 7, 8, 9, or 10) different host cells, and/or at least two (e.g. 2, 3, 4, 5, 6, 7, 8, 9, or 10) different pharmaceutical compositions. Preferably, such different components comprised by the kit-of-parts as described above differ in the antigenic peptides according to the present invention, for example one component relating to a first antigenic peptide, and one component relating to a second antigenic peptide (distinct from the first antigenic peptide). For example, the kit may comprise at least two distinct immunogenic compounds according to the present invention. For example, the kit may comprise at least two distinct antigenic peptides according to the present invention. For example, the kit may comprise at least two distinct nanoparticles according to the present invention. For example, the kit may comprise at least two distinct nucleic acids according to the present invention.

Preferred combinations of antigenic peptides according to the present invention included in the kit correspond to the preferred combinations of antigenic peptides according to the present invention included in the pharmaceutical composition as described above.

Accordingly, the present invention provides a kit comprising (at least one) antigenic peptide according to the present invention as described herein. Moreover, the present invention also provides a kit comprising (at least one) immunogenic compound according to the present invention as described herein. Moreover, the present invention also provides a kit comprising (at least one) nanoparticle according to the present invention as described herein. Moreover, the present invention also provides a kit comprising (at least one) cell according to the present invention as described herein. Moreover, the present invention also provides a kit comprising (at least one) nucleic acid according to the present invention as described herein. Moreover, the present invention also provides a kit comprising (at least one) host cell according to the present invention as described herein.

The various components of the kit-of-parts may be packaged in one or more containers. The above components may be provided in a lyophilized or dry form or dissolved in a suitable buffer. The kit may also comprise additional reagents including, for instance, preservatives, growth media, and/or buffers for storage and/or reconstitution of the above-referenced components, washing solutions, and the like.

Accordingly, the present invention provides a kit comprising at least two, preferably three distinct antigenic peptides according to the present invention as described herein (or immunogenic compounds, nanoparticles, nucleic acids, cells, etc. as described above, which differ regarding the antigenic peptide), and, optionally, a helper peptide, such as the UCP2 peptide, and/or an adjuvant, such as MONTANIDE ISA 51. Distinct antigenic peptides (or immunogenic compounds, nanoparticles, nucleic acids, cells, etc. as described above, which differ regarding the antigenic peptide) may be contained in the same or in distinct containers. For example, the kit may comprise a (single) container containing a first antigenic peptide as described herein and a second antigenic peptide as described herein. Said (single) container may additionally also comprise a helper peptide, such as UCP2. Optionally, the first and second antigenic peptide (and optionally the helper peptide) contained in the (single) container may be formulated together, e.g. in water for injection and/or Dimethyl sulfoxide (DMSO). Additionally, the kit may comprise a further container (distinct from the container containing the antigenic peptides), which contains the adjuvant, e.g. MONTANIDE ISA 51.

It is thus preferred that the kit comprises (i) a first vial comprising one or more antigenic peptides of the invention (e.g., at least 200 or 300 μg of each antigenic peptide), and, optionally, a helper peptide, such as UCP2 (e.g., at least 200 or 300 μg of the helper peptide), optionally formulated in water for injection and dimethyl sulfoxide (DMSO); and (ii) a second vial comprising MONTANIDE ISA 51 (e.g., at least 0.4 or 0.5 ml).

In addition, the kit may comprise one or more (e.g., 2 or 3) syringes, for example silicon- and rubber-free syringes. The kit may also comprise a connector, such as an I-connector.

Non-limiting examples of such connectors are:

the I-connector developed by Green Peptide (Japan), the connector of reference DIDRACDLLFT from Didanorm (France), the I-connector (ref: ODG0015ST) from Promepla (Monaco), and the I-connector (ref: MX494) from Smiths medical (US).

The syringes are preferably suitable for MONTANIDE, i.e., silicon-free and rubber free (i.e., without any rubber tip free on the plunger), and preferably also latex-free. Non-limiting examples of such syringes are:

2 ml INKJET (Ref: 4606701V from B-Braun, Germany), 5 ml INKJET (Ref: 4606710V from B-Braun, Germany), 2 ml Norm-Ject (Ref: 4020.000V0 from Henke Sass Wolf GMBH, Germany), and 5 ml Norm-Ject (Ref: 4050.000V0 from Henke Sass Wolf GMBH, Germany).

For example, the kit may comprise (i) a first vial comprising at least 300 μg of an antigenic peptide of the invention (or two or three antigenic peptides, at least 300 μg of each), and optionally at least 300 μg of UCP2, formulated in water for Injection and Dimethyl sulfoxide (DMSO), (ii) a second vial comprising at least 0.5 ml of MONTANIDE ISA 51, (iii) two silicon- and rubber-free syringes, and (iv) an I-connector.

Optionally, the kit can also comprise a vial of water for injection and/or a vial adapter. A sterile needle can also be comprised, e.g. for vaccinating the patient after obtaining the emulsion. The syringes in the kit can be, for example, 2 ml syringes.

In one particular embodiment, the kit comprises three distinct antigenic peptides according to the present invention, the UCP2 peptide, and MONTANIDE ISA 51, wherein said kit comprises (i) a first vial comprising at least 300 μg of each of the three antigenic peptides of the invention, at least 300 μg of UCP2 (SEQ ID NO: 859), formulated in water for injection and DMSO, (ii) a second vial comprising at least 0.5 ml of MONTANIDE ISA 51, (iii) two silicon- and rubber-free syringes, and (iv) an I-connector. The three antigenic peptides of the invention included in the kit are preferably an antigenic peptide comprising or consisting of an amino acid sequence as set forth in SEQ ID NO: 32, an antigenic peptide comprising or consisting of an amino acid sequence as set forth in SEQ ID NO: 220 and an antigenic peptide comprising or consisting of an amino acid sequence as set forth in SEQ ID NO: 255.

In addition, the kit-of-parts according to the present invention may optionally contain instructions of use. Accordingly, it is preferred that the kit comprises a package insert or instruction leaflet with directions to prevent or to treat a cancer by using the immunogenic compound according to the present invention, the antigenic peptide according to the present invention, the nanoparticle according to the present invention, the cell according to the present invention, the nucleic acid according to the present invention, the host cell according to the present invention, or the pharmaceutical composition according to the present invention.

It is also preferred that, in addition to any of components as described above, the kit comprises an anti-cancer therapeutic agent as described herein.

Moreover, the present invention also provides a vaccination kit for treating, preventing and/or stabilizing a cancer, comprising the pharmaceutical composition as described herein or a vaccine as described herein and instructions for use of said pharmaceutical composition or of said vaccine in the prevention and/or treatment of a cancer.

Medical Treatment and Uses

As stated above, the composition of the invention can be particularly useful for therapeutic purposes, notably for triggering a specific immune response towards a particular tumor antigen/protein, for example to prevent or treat cancer in a patient in need thereof.

In view thereof, the present invention provides

- the antigenic peptide according to the present invention as described herein,
- the immunogenic compound according to the present invention as described herein,
- the nanoparticle according to the present invention as described herein,
- the cell according to the present invention as described herein,
- the nucleic acid according to the present invention as described herein,
- the host cell according to the present invention as described herein,
- the pharmaceutical composition according to the present invention as described herein, or
- the kit according to the present invention as described herein for use in the prevention and/or in the treatment of a cancer.

In particular, preferred embodiments of the antigenic peptide as described above also apply for the use according to the present invention in the prevention and/or in the treatment of a cancer. For example, the antigenic peptide used in the prevention and/or in the treatment of a cancer or the antigenic peptide comprised in any of the immunogenic compound, the nanoparticle, the cell, the nucleic acid, the host cell or the pharmaceutical composition used in the prevention and/or in the treatment of a cancer preferably comprises or consists of an amino acid sequence as set forth in any one of SEQ ID NOs 1 to 580 and 861 to 887, such as an antigenic peptide comprising or consisting of an amino acid sequence as set forth in any one of SEQ ID NOs 1 to 580. For example, antigenic peptides according to the present invention comprising or consisting of an amino acid sequence as set forth in any one of SEQ ID NOs 1-160, 162-253 and 255-580 are more preferred. For example, antigenic peptides according to the present invention comprising or consisting of an amino acid sequence as set forth in any one of SEQ ID NOs 30, 31, 32, 87, 97, 145, 193, 194, 220, 221, 255, 521 and 524 are even more preferred. For example, antigenic peptides according to the present invention comprising or consisting of an amino acid sequence as set forth in any one of SEQ ID NOs 30, 31, 32, 87, 97, 193, 194, 220, 255, 521 and 524 are still more preferred. For example, antigenic peptides according to the present invention comprising or consisting of an amino acid sequence as set forth in any one of SEQ ID NOs 30, 31, 32, 87, 97, 194, 220, 255, 521 and 524 are still more preferred. For example, antigenic peptides according to the present invention comprising or consisting of an amino acid sequence as set forth in any one of SEQ ID NOs 30, 32, 87, 97, and 194 are most preferred. For example, antigenic peptides according to the present invention comprising or consisting of an amino acid sequence as set forth in any one of SEQ ID NOs 30, 32, 194, 220, 254 or 255 are particularly preferred.

Also combinations thereof are preferred, namely, distinct antigenic peptides according to the present invention for use in the prevention and/or in the treatment of a cancer. In particular, more than one of the above described components may be used in the prevention and/or in the treatment of a cancer. For example, at least two different antigenic peptides, at least two different immunogenic compounds, at least two different nanoparticles, at least two different cells, at least two different nucleic acids, at least two different host cells, and/or at least two different pharmaceutical compositions may be used in the prevention and/or in the treatment of a cancer. Preferably, such different components used in the prevention and/or in the treatment of a cancer as described above differ in the antigenic peptides according to the present invention, for example one component relating to a first antigenic peptide, and one component relating to a second antigenic peptide (distinct from the first antigenic peptide). For example, at least two distinct immunogenic compounds according to the present invention may be used in the prevention and/or in the treatment of a cancer. For example, at least two distinct antigenic peptides according to the present invention may be used in the prevention and/or in the treatment of a cancer. For example, at least two distinct nanoparticles according to the present invention may be used in the prevention and/or in the treatment of a cancer. For example, at least two distinct nucleic acids according to the present invention may be used in the prevention and/or in the treatment of a cancer.

Accordingly, the present invention provides (at least one) antigenic peptide according to the present invention as described herein for use in the prevention and/or in the treatment of a cancer. Moreover, the present invention also provides (at least one) immunogenic compound according to the present invention as described herein for use in the prevention and/or in the treatment of a cancer. Moreover, the present invention also provides (at least one) nanoparticle according to the present invention as described herein for use in the prevention and/or in the treatment of a cancer. Moreover, the present invention also provides (at least one) cell according to the present invention as described herein for use in the prevention and/or in the treatment of a cancer. Moreover, the present invention also provides (at least one) nucleic acid according to the present invention as described herein for use in the prevention and/or in the treatment of a cancer. Moreover, the present invention also provides (at least one) host cell according to the present invention as described herein for use in the prevention and/or in the treatment of a cancer. Moreover, the present invention also provides (at least one) pharmaceutical composition according to the present invention as described herein for use in the prevention and/or in the treatment of a cancer. Moreover, the present invention also provides a kit according to the present invention as described herein for use in the prevention and/or in the treatment of a cancer.

Accordingly, the present invention also provides a method for preventing and/or treating a cancer or initiating, enhancing or prolonging an anti-tumor-response in a subject in need thereof comprising administering to the subject

- the antigenic peptide according to the present invention,
- the immunogenic compound according to the present invention,
- the nanoparticle according to the present invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein.

Preferably, the cancer to be prevented and/or treated is selected from glioma, kidney cancer, skin cancer, in particular melanoma, lung cancer, ovarian cancer, breast cancer, colorectal cancer, liver cancer, pancreatic cancer, head and neck cancer, urothelial cancer and prostate cancer.

Moreover, the present invention provides a method for eliciting or improving, in a subject, an immune response against one or multiple epitopes that is dependent on CD8+ cytotoxic T cells, wherein said method comprises administering to said subject any one of:

- the antigenic peptide according to the present invention,
- the immunogenic compound according to the present invention,
- the nanoparticle according to the present invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein.

An immune response that is dependent on $CD8^+$ response can be determined by evaluating an inflammatory response, a pro-inflammatory cytokine response, including an increase in the expression of one or more of IFN-γ, TNF-α and IL-2 mRNA or protein relative to the level before administration of the compounds of the invention. It can also be measured by an increase in the frequency or absolute number of antigen-specific T cells after administration of the compounds of the invention, measured by HLA-peptide multimer staining, ELISPOT assays, and delayed type hypersensitivity tests. It can also be indirectly measured by an increase in antigen-specific serum antibodies that are dependent on antigen-specific T helper cells.

The present invention also provides a method for eliciting or improving, in a subject, an immune response against one or multiple antigens or antigenic epitopes that is restricted by multiple MHC class I molecules, wherein said method comprises administering to said subject any one of:

- the antigenic peptide according to the present invention,
- the immunogenic compound according to the present invention,
- the nanoparticle according to the present invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein.

A method for eliciting or improving, in a subject, an immune response against multiple epitopes as described herein, that is restricted by multiple MHC class I molecules can be determined by evaluating a cytokine response, including an increase in the expression of one or more of IFN-γ, TNF-α and IL-2 mRNA or protein relative to the level before administration of the compounds of the invention, after in vitro stimulation of T cells with individual peptides binding to discrete MHC class I molecules on antigen presenting cells. Restriction to MHC class I molecules can also be validated by using antigen presenting cells expressing MHC class I molecules, or by using MHC class I blocking antibodies. It can also be measured by an increase in the frequency or absolute number of antigen-specific T cells after administration of the compounds of the invention, measured by HLA-peptide multimer staining, using multimers assembled with MHC class I molecules.

Thus, in another aspect, the present invention also provides

- the antigenic peptide according to the present invention,
- the immunogenic compound according to the present invention,
- the nanoparticle according to the present invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein.

for use as a medicament.

The invention relates more particularly to a composition as defined above, for use as a vaccine for immunotherapy. Moreover,

- the antigenic peptide according to the present invention,
- the immunogenic compound according to the present invention,
- the nanoparticle according to the present invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein
- may be used as vaccine, in particular for (cancer) immunotherapy.

As used in the context of the present invention, the term "vaccine" refers to a (biological) preparation that provides innate and/or adaptive immunity, typically to a particular disease, preferably cancer. Thus, a vaccine supports in particular an innate and/or an adaptive immune response of the immune system of a subject to be treated. For example, the antigenic peptide according to the present invention typically leads to or supports an adaptive immune response in the patient to be treated.

In the context of the present invention, the vaccine (composition) can induce a specific immune response against a tumor antigen, and is thus preferably used to prevent or treat cancer. A vaccine for preventing or treating cancer may also be referred to as "cancer vaccine".

Accordingly, in a preferred embodiment, the invention relates to a composition as defined above, for use in the prevention and/or treatment of cancer in a subject in need thereof. More preferably, the invention relates to the use of the composition of the invention for manufacturing a medicament to prevent or treat cancer in a subject in need thereof. In other words, the invention relates to a method for preventing or treating cancer in a subject in need thereof, comprising administering an effective amount of the composition of the invention, to said subject.

Preferably the cancer to be prevented and/or treated by
- the antigenic peptide according to the present invention,
- the immunogenic compound according to the present invention,
- the nanoparticle according to the present invention,
- the cell according to the present invention,
- the nucleic acid according to the present invention,
- the host cell according to the present invention,
- the pharmaceutical composition according to the present invention,
- the kit according to the present invention, or
- the combination according to the present invention as described herein relates to the (reference) tumor antigen of the antigenic peptide as described herein. Namely, appropriate antigenic peptides may be selected by (i) selecting an appropriate tumor antigen for a certain type of cancer as known in the art and/or as described herein in Table 1B (below) and (ii) selecting an appropriate antigenic peptide according to the invention for the selected tumor antigen, as described above, e.g. in Table 1A. One skilled in the art will readily understand that an antigenic peptide of the invention can be selected based upon the nature of the cancer to be prevented or treated, and/or on the human gene/human tumor antigen involved in said cancer.

Accordingly, preferred examples of cancer are shown in Table 1B below. In particular, the antigenic peptides according to the present invention are sequence variants of fragments of the tumor antigens shown in Table 1B and may be used in particular in the disease outlined for the respective tumor antigen in Table 1B.

TABLE 1B list of tumor antigens and associated therapeutic indications

| Tumor antigen | Full name tumor antigen | Cancers associated with tumor antigen |
|---|---|---|
| ACPP | acid phosphatase, prostate | Diseases associated with ACPP include prostate cancer, ovarian cancer and prostatic adenoma |
| ANKRD30A | ankyrin repeat domain 30A | Diseases associated with ANKRD30A include breast cancer |
| AREG | amphiregulin | Diseases associated with AREG include colorectal cancer |
| ASCL1 | achaete-scute family bHLH transcription factor 1 | Diseases associated with ASCL1 include glioma and lung cancer |
| ASCL2 | achaete-scute family bHLH transcription factor 2 | Diseases associated with ASCL2 include colorectal cancer and stomach cancer |
| BIRC5 | baculoviral IAP repeat containing 5 | Diseases associated with BIRC5 include glioma, kidney cancer, lung cancer, ovarian cancer, breast cancer, colorectal cancer and head and neck cancer |
| CA9 | carbonic anhydrase 9 | Diseases associated with CA9 include kidney cancer |
| CCNA1 | cyclin A1 | Diseases associated with CCNA1 include ovarian cancer and head and neck cancer |
| CCND1 | cyclin D1 | Diseases associated with CCND1 include kidney cancer, skin cancer and breast cancer |
| CDH17 | cadherin 17 | Diseases associated with CDH17 include colorectal cancer, pancreatic cancer and stomach cancer |
| CDH6 | cadherin 6 | Diseases associated with CDH6 include kidney cancer and ovarian cancer |
| CDKN2A | cyclin dependent kinase inhibitor 2A | Diseases associated with CDKN2A include glioma, skin cancer, lung cancer, ovarian cancer, breast cancer, head and neck cancer and stomach cancer |
| CEACAM5 | carcinoembryonic antigen related cell adhesion molecule 5 | Diseases associated with CEACAM5 include gut carcinoma, colorectal cancer, urachal cancer, gastrointestinal cancer and pancreatic cancer |
| CHI3L1 | chitinase 3 like 1 | Diseases associated with CHI3L1 include glioma and kidney cancer |
| CHI3L2 | chitinase 3 like 2 | Diseases associated with CHI3L2 include glioma |
| COL11A1 | collagen type XI alpha 1 chain | Diseases associated with COL11A1 include breast cancer and pancreatic cancer |
| CT83 | cancer/testis antigen 83 | Diseases associated with CT83 include lung cancer and stomach cancer |
| CTCFL | CCCTC-binding factor like | Diseases associated with CTCFL include skin cancer and ovarian cancer |
| DCT | dopachrome tautomerase | Diseases associated with DCT include skin cancer |
| DMRTA2 | DMRT like family A2 | Diseases associated with DMRTA2 include glioma |
| EGFR | epidermal growth factor receptor | Diseases associated with EGFR include numerous cancers, including glioma, kidney cancer, lung cancer, head and neck cancer and urothelial cancer |
| ERBB2 | erb-b2 receptor tyrosine kinase 2 | Diseases associated with ERBB2 include numerous cancers, including breast cancer, glioma, urothelial cancer and ovarian cancer |

TABLE 1B-continued list of tumor antigens and associated therapeutic indications

| Tumor antigen | Full name tumor antigen | Cancers associated with tumor antigen |
|---|---|---|
| ERG | ERG, ETS transcription factor | Diseases associated with ERG include prostate cancer |
| ESR1 | estrogen receptor 1 | Diseases associated with ESR1 include breast cancer |
| EZH2 | enhancer of zeste 2 polycomb repressive complex 2 subunit | Diseases associated with EZH2 include many forms of cancers, including lung cancer, lymphoblastoma, glioma, kidney cancer, skin cancer, ovarian cancer, breast cancer, colorectal cancer, head and neck cancer, stomach cancer, urothelial cancer and prostate cancer |
| FAP | fibroblast activation protein alpha | Diseases associated with FAP include lung cancer, colorectal cancer, pancreatic cancer and head and neck cancer |
| FLT1 | fms related tyrosine kinase 1 | Diseases associated with FLT1 include kidney cancer |
| FOXM1 | forkhead box M1 | Diseases associated with FOXM1 include numerous types of cancer including glioma, kidney cancer, skin cancer, lung cancer, ovarian cancer, breast cancer, colorectal cancer and head and neck cancer |
| FSIP1 | fibrous sheath interacting protein 1 | Diseases associated with FSIP1 include breast cancer |
| GAL3ST1 | galactose-3-O-sulfotransferase 1 | Diseases associated with GAL3ST1 include kidney cancer |
| GPR143 | G protein-coupled receptor 143 | Diseases associated with GPR143 include skin cancer |
| HES6 | hes family bHLH transcription factor 6 | Diseases associated with HES6 include various cancers including glioma, kidney cancer, skin cancer, lung cancer, breast cancer, colorectal cancer and pancreatic cancer |
| IL13RA2 | interleukin 13 receptor subunit alpha 2 | Diseases associated with IL13RA2 include colorectal cancer, ovarian cancer, testis cancer, renal cell carcinoma, prostate cancer, glioma, skin cancer, head and neck cancer, astrocytoma, melanoma, pancreatic cancer and breast cancer metastasis |
| KISS1R | KISS1 receptor | Diseases associated with KISS1R include kidney cancer |
| KLHDC8A | kelch domain containing 8A | Diseases associated with KLHDC8A include glioma |
| KLHL14 | kelch like family member 14 | Diseases associated with KLHL14 include ovarian cancer |
| KLK4 | kallikrein related peptidase 4 | Diseases associated with KLK4 include prostate cancer |
| KRT81 | keratin 81 | Diseases associated with KRT81 include breast cancer |
| LEMD1 | LEM domain containing 1 | Diseases associated with LEMD1 include lung cancer, ovarian cancer, colorectal cancer and pancreatic cancer |
| LRRC15 | leucine rich repeat containing 15 | Diseases associated with LRRC15 include breast cancer |
| MAGEA1 | MAGE family member A1 | Diseases associated with MAGEA1 include melanoma and hemangioma of liver, non-small cell lung cancer, gastric cancer, head and neck cancer and melanoma |
| MAGEA4 | MAGE family member A4 | Diseases associated with MAGEA4 include melanoma and testicular leukemia, thyroid cancer, breast cancer including estrogen receptor negative breast cancer and non-small cell lung cancer |
| MAGEA10 | MAGE family member A10 | Diseases associated with MAGEA10 include glioma and lung cancer |
| MAGEA11 | MAGE family member A11 | Diseases associated with MAGEA11 include skin cancer, lung cancer and colorectal cancer |
| MAGEA12 | MAGE family member A12 | Diseases associated with MAGEA12 include skin cancer |
| MLANA | melan-A | Diseases associated with MLANA include melanoma |
| NKX2-1 | NK2 homeobox 1 | Diseases associated with NKX2-1 include lung cancer |
| NPTX2 | neuronal pentraxin 2 | Diseases associated with NPTX2 include kidney cancer |
| PAGE3 | PAGE family member 3 | Diseases associated with PAGE3 include numerous types of cancer including glioma, kidney cancer, skin cancer, lung cancer, ovarian cancer, breast cancer, colorectal cancer, liver cancer, pancreatic cancer, stomach cancer, urothelial cancer, prostate cancer and head and neck cancer |
| PAX2 | paired box 2 | Diseases associated with PAX2 include kidney cancer |
| PCDHB16 | protocadherin beta 16 | Diseases associated with PCDHB16 include glioma, kidney cancer and breast cancer |

TABLE 1B-continued list of tumor antigens and associated therapeutic indications

| Tumor antigen | Full name tumor antigen | Cancers associated with tumor antigen |
|---|---|---|
| PIWIL1 | piwi like RNA-mediated gene silencing 1 | Diseases associated with PIWIL1 include colorectal cancer and stomach cancer |
| PMEL | premelanosome protein | Diseases associated with PMEL include melanoma |
| PRAME | preferentially expressed antigen in melanoma | Diseases associated with PRAME include skin cancer |
| PTHLH | parathyroid hormone like hormone | Diseases associated with PTHLH include breast cancer |
| SEMG1 | semenogelin 1 | Diseases associated with SEMG1 include prostate cancer |
| SERHL2 | serine hydrolase like 2 | Diseases associated with SERHL2 include breast cancer |
| SLC45A3 | solute carrier family 45 member 3 | Diseases associated with SLC45A3 include prostate cancer |
| SLC6A3 | solute carrier family 6 member 3 | Diseases associated with SLC6A3 include kidney cancer |
| SNX31 | sorting nexin 31 | Diseases associated with SNX31 include urothelial cancer |
| SOX11 | SRY-box 11 | Diseases associated with SOX11 include glioma |
| SOX17 | SRY-box 17 | Diseases associated with SOX17 include ovarian cancer |
| SPINK1 | serine peptidase inhibitor, Kazal type 1 | Diseases associated with SPINK1 include pancreatic cancer |
| STEAP1 | STEAP family member 1 | Diseases associated with STEAP1 include prostate cancer |
| TBL1Y | transducin beta like 1 Y-linked | Diseases associated with TBL1Y include prostate cancer |
| TDRD1 | tudor domain containing 1 | Diseases associated with TDRD1 include prostate cancer |
| TOP2A | DNA topoisomerase II alpha | Diseases associated with TOP2A include lung cancer and breast cancer |
| TPTE | transmembrane phosphatase with tensin homology | Diseases associated with TPTE include skin cancer, lung cancer and breast cancer |
| TRPM8 | transient receptor potential cation channel subfamily M member 8 | Diseases associated with TRPM8 include prostate cancer |
| TYMS | thymidylate synthetase | Diseases associated with TYMS include glioma, kidney cancer and skin cancer |
| TYR | tyrosinase | Diseases associated with TYR include skin cancer and melanoma |
| UPK2 | uroplakin 2 | Diseases associated with UPK2 include kidney cancer |
| VCAM1 | vascular cell adhesion molecule 1 | Diseases associated with VCAM1 include kidney cancer |
| WFDC2 | WAP four-disulfide core domain 2 | Diseases associated with WFDC2 include ovarian cancer |
| WT1 | Wilms tumor 1 | Diseases associated with WT1 include glioma, kidney cancer and ovarian cancer |
| ZEB1 | zinc finger E-box binding homeobox 1 | Diseases associated with ZEB1 include glioma |
| ZNF165 | zinc finger protein 165 | Diseases associated with ZNF165 include pancreatic cancer |
| ZNF280A | zinc finger protein 280A | Diseases associated with ZNF280A include include glioma, skin cancer, lung cancer and ovarian cancer |

In general, antigenic peptides of the invention may be administered "naked" or in the form of immunogenic compounds according to the present invention, cells loaded therewith according to the present invention, nanoparticles according to the present invention, nucleic acids according to the present invention, host cells according to the present invention and/or pharmaceutical compositions according to the present invention.

In a preferred embodiment, they may be administered in the form of a micro-organism such as a gut bacterial species. Entire gut bacterial species can also be advantageous as they have the potential to trigger a greater immune response than the (poly)peptides or nucleic acids they contain. Alternatively, gut bacteria according to the invention may be in the form of probiotics, i.e. of live gut bacterium, which can thus be used as food additive thanks to the health benefits it can provide. Those can be for example lyophilized in granules, pills or capsules, or directly mixed with dairy products for consumption.

Methods of administration are well-known to the skilled person in the art. With regard to the composition of the invention, it can be directly administered into the subject, into the affected organ (i.e. local administration) or systemically (i.e. enteral or parenteral administration), or even applied ex vivo to cells derived from the subject or a human cell line which are subsequently administered to the subject, or even used in vitro to select a subpopulation of immune cells derived from the subject, which are then re-administered to the said subject. Enteral administrations include oral and rectal administrations, as well as administrations via gastric feeding tubes, duodenal feeding tubes or gastrostomy, while parenteral administrations includes, among others, subcutaneous, intravenous, intramuscular, intra-arterial, intradermal, intraosseous, intracerebral, and intrathecal injections. The administration method will often depend upon the antigenic peptide(s) and/or immunogenic compound(s) present in the composition, and the type of cancer to be treated and other active agents that may be contained in said composition. For example, the administration is preferably an intramuscular or an intradermal injection if the immunogenic compound is a nucleic acid as defined above, the oral/nasal administration being particularly preferred if said nucleic acid is cloned into a viral vector. Alternatively, the administration is preferably an intramuscular, an intradermal or an oral administration if the antigenic peptide and/or immunogenic compound is a (poly)peptide as defined above or if it is loaded in/on a nanoparticle as described herein. Yet, still alternatively, the administration is preferably an oral administration if the antigenic peptide and/or immunogenic compound is delivered in the form of a gut bacterium as defined above, notably if the gut bacterium is in the form of probiotics.

The antigenic peptides, the immunogenic compounds and the nucleic acids according to the invention can further be encapsulated so as to facilitate their administration to the subject in need thereof. For example, those may be encapsulated into peptide nanocarriers (preferable if the immunogenic compound is a nucleic acid or a (poly)peptide), into virosomes (preferable if the immunogenic compound is a nucleic acid or a (poly)peptide), or into lipid-based carrier systems such as liposome-polycation-DNA complex (preferable if the immunogen is a nucleic acid or a (poly)peptide) (Trovato M, De Berardinis P. Novel antigen delivery systems. World J Virol. 2015 Aug. 12; 4(3):156-68; Saade F, Petrovsky N. Technologies for enhanced efficacy of DNA vaccines. Expert Rev Vaccines. 2012 February; 11(2):189-209; Li et al., Peptide Vaccine: Progress and Challenges. Vaccines (Basel). 2014 Jul. 2; 2(3):515-36).

The composition may also be administered more than once so as to achieve the desired effect. In a preferred embodiment, said composition is administered repeatedly, at least twice, and preferably more than twice. This can be done over an extended period of time, such as weekly, every other week, monthly, yearly, or even several years after the first administration to ensure that the subject is properly immunized.

Combination Therapy

The administration of the antigenic peptide according to the present invention, the immunogenic compound according to the present invention, the nanoparticle according to the present invention, the cell according to the present invention, the nucleic acid according to the present invention, the host cell according to the present invention, and the pharmaceutical composition according to the present invention, in particular in the methods and uses according to the invention, can be carried out alone or in combination with a co-agent useful for treating and/or preventing cancer, such as an anti-cancer therapeutic agent.

Said therapeutic agent is thus preferably capable of preventing and/or treating the same type of cancer as the one for which the antigenic peptide according to the invention is used. Particularly preferred anti-cancer therapeutic agents according to the invention include, without limitation, antibodies, tumor cell lysates, chemotherapeutic agents, radiotherapeutic agents, immune checkpoint modulators and combinations thereof.

Antibodies are particularly advantageous in cancer therapy as they can either bind to specific antigens on cancer cell surfaces, thereby directing the therapy to the tumor (i.e. these are referred as tumor-targeting antibodies), or block immune checkpoints that are dysregulated in cancer (i.e. these are referred herein as immunomodulatory antibodies). The purpose of the later type of antibodies is to inhibit cancer immune resistance, which can notably be observed against T cells that are specific for tumour antigens. Indeed, as well-known in the art, under normal physiological conditions, immune checkpoints are crucial for the maintenance of self-tolerance (i.e. prevention of autoimmunity) and protect tissues from damage when the immune system is responding to pathogenic infection. However, in cancer, immune-checkpoints expression can be dysregulated as an important mechanism of immune resistance. Said resistance has notably been observed in melanoma, ovarian, lung, glioblastoma, breast, and pancreatic cancers with regard to the PD-L1 checkpoint (Konishi et al., B7-H1 expression on non-small cell lung cancer cells and its relationship with tumor-infiltrating lymphocytes and their PD-1 expression. Clin Cancer Res. 2004 Aug. 1; 10(15):5094-100; Ghebeh et al., The B7-H1 (PD-L1) T lymphocyte-inhibitory molecule is expressed in breast cancer patients with infiltrating ductal carcinoma: correlation with important high-risk prognostic factors. Neoplasia. 2006 March; 8(3):190-8; Hino et al., Tumor cell expression of programmed cell death-1 ligand 1 is a prognostic factor for malignant melanoma. Cancer. 2010 Apr. 1; 116(7):1757-66). Other examples of immune checkpoints include, without limitation, PD-L2, PD-1, CD80, CD86, CTLA4, B7H3, B7H4, PVR, TIGIT, GAL9, LAG-3, GITR, CD137, TIM3, VISTA, VISTA-R (Pico de Coaña et al., Checkpoint blockade for cancer therapy: revitalizing a suppressed immune system. Trends Mol Med. 2015 August; 21(8):482-91; Pardoll D M1. The blockade of immune checkpoints in cancer immunotherapy. Nat Rev Cancer. 2012 Mar. 22; 12(4):252-64).

Antibodies are usually employed for the above purposes either in the form of naked monoclonal antibodies (i.e. non-conjugated), or conjugated to another molecule which can be toxic to cells or radioactive.

Examples of well-known monoclonal tumor-targeting antibodies used in cancer immunotherapy include, without limitation, alemtuzumab (chronic lymphocytic leukemia), bevacizumab (colorectal cancer, glioblastoma multiforme, cervical cancer, lung cancer, renal cancer), brentuximab/vedotin (lymphomas), blinatumumab (acute lymphoblastic leukemia), catumaxomab (malignant ascites in EPCAM+ cancers), cetuximab (head and neck cancer, colorectal cancer), denosumab (breast, prostate and bone cancers), Gemtuzumab/ozogamicin (acute myeloid keulemia), ibritumomab/tiuxetan (non-Hodgkin lymphoma), panitumumab (colorectal cancer), pertuzumab (breast cancer), obinutuzumab (chronic lymphocytic leukemia), ofatumumab (chronic lymphocytic leukemia), opilimumab (melanoma), ramucirumab (gastric and gastro-ocasophagcal cancers), rituximab (chronic lymphocytic leukemia and non-Hodgkin lymphoma), siltuximab (multicentric's Catsleman's disease), tositumomab (non-Hodgkin lymphoma), and trastuzumab (breast, gastric and gastro-ocasophageal cancers): while examples of immunomodulatory antibodies include, without limitation, ipilimumab (melanoma) which blocks the CTLA4-dependent immune checkpoint, nivolumab (melanoma, lung cancer) and prembrolizubmab (melanoma) which both block the PDCD1-dependent immune checkpoint, as well as MPDL3280A, MED14736, MEDI0680, and MSB0010718C which all block the PD-L1-dependent immune checkpoint (Sharma and Allison, The future of immune checkpoint therapy. Science. 2015 Apr. 3; 348(6230):56-61).

Other antibodies for cancer immunotherapy have been described in Buqué et al. (Buqué et al., Trial Watch: Immunomodulatory monoclonal antibodies for oncological indications. Oncoimmunology. 2015 Mar. 2; 4(4):e1008814. eCollection 2015 April), Redman et al. (Redman et al., Mechanisms of action of therapeutic antibodies for cancer. Mol Immunol. 2015 October; 67(2 Pt A): 28-45), and in Simpson and Caballero, Monoclonal antibodies for the therapy of cancer MC Proc. 2014; 8(Suppl 4): 06 as well as on the antibody society website (list of therapeutic monoclonal antibodies approved or in review in the European Union or United States available on the weblink http://www.antibodysociety.org/news/approved_mabs.php).

Tumor cell lysates may also be combined with the antigenic peptide(s) according to the invention. Tumor cells are indeed capable of priming the immune response, by presenting endogenous peptides-MHC complexes, as well as via dendritic cells (DCs) of the host which can process and present the antigen delivered by said lysates. The range of antigens against which an immune response can be induced is thereby increased. Tumor cell lysates can be easily obtained by treating tumor cells with a heat shock and/or a chemical treatment, and can be autologous (i.e. isolated from the patient), or allogeneic (i.e. isolated from another subject).

Standard chemotherapeutic drugs and radiotherapeutic agents need not be further described herein as they have been extensively described in the literature, notably by Baskar et al. (Baskar et al., Cancer and radiation therapy: current advances and future directions. Int J Med Sci. 2012; 9(3):193-9), Paci et al. (Paci et al., Review of therapeutic drug monitoring of anticancer drugs part 1—cytotoxics. Eur J Cancer. 2014 August; 50(12):2010-9) and Widmer et al. (Widmer et al., Review of therapeutic drug monitoring of anticancer drugs part two-targeted therapies. Eur J Cancer. 2014 August; 50(12):2020-36). A list of such drugs and agents is also available on the cancer.gov website (http://www.cancer.gov/about-cancer/treatment/drugs).

Preferably, the immune checkpoint modulator for combination with the antigenic peptide as defined herein is an activator or an inhibitor of one or more immune checkpoint point molecule(s) selected from CD27, CD28, CD40, CD122, CD137, OX40, GITR, ICOS, A2AR, B7-H3, B7-H4, BTLA, CD40, CTLA-4, IDO, KIR, LAG3, PD-1, TIM-3, VISTA, CEACAM1, GARP, PS, CSF1R, CD94/NKG2A, TDO, GITR, TNFR and/or FasR/DcR3; or an activator or an inhibitor of one or more ligands thereof.

More preferably, the immune checkpoint modulator is an activator of a (co-)stimulatory checkpoint molecule or an inhibitor of an inhibitory checkpoint molecule or a combination thereof. Accordingly, the immune checkpoint modulator is more preferably (i) an activator of CD27, CD28, CD40, CD122, CD137, OX40, GITR and/or ICOS or (ii) an inhibitor of A2AR, B7-H3, B7-H4, BTLA, CD40, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or FasR/DcR3.

Even more preferably, the immune checkpoint modulator is an inhibitor of an inhibitory checkpoint molecule (but preferably no inhibitor of a stimulatory checkpoint molecule). Accordingly, the immune checkpoint modulator is even more preferably an inhibitor of A2AR, B7-H3, B7-H4, BTLA, CTLA-4, IDO, KIR, LAG3, PD-1, PDL-1, PD-L2, TIM-3, VISTA, CEACAM1, GARP, PS, CSF1R, CD94/NKG2A, TDO, TNFR and/or DcR3 or of a ligand thereof.

It is also preferred that the immune checkpoint modulator is an activator of a stimulatory or costimulatory checkpoint molecule (but preferably no activator of an inhibitory checkpoint molecule). Accordingly, the immune checkpoint modulator is more preferably an activator of CD27, CD28, CD40, CD122, CD137, OX40, GITR and/or ICOS or of a ligand thereof.

It is even more preferred that the immune checkpoint modulator is a modulator of the CD40 pathway, of the IDO pathway, of the LAG3 pathway, of the CTLA-4 pathway and/or of the PD-1 pathway. In particular, the immune checkpoint modulator is preferably a modulator of CD40, LAG3, CTLA-4, PD-L1, PD-L2, PD-1 and/or IDO, more preferably the immune checkpoint modulator is an inhibitor of CTLA-4, PD-L1, PD-L2, PD-1, LAG3, and/or IDO or an activator of CD40, even more preferably the immune checkpoint modulator is an inhibitor of CTLA-4, PD-L1. PD-1, LAG3 and/or IDO, even more preferably the immune checkpoint modulator is an inhibitor of LAG3, CTLA-4 and/or PD-1, and most preferably the immune checkpoint modulator is an inhibitor of CTLA-4 and/or PD-1.

Accordingly, the checkpoint modulator for combination with the antigenic peptide may be selected from known modulators of the CTLA-4 pathway or the PD-1 pathway. Preferably, the checkpoint modulator for combination with the antigenic peptide as defined herein may be selected from known modulators of the CTLA-4 pathway or the PD-1 pathway. Particularly preferably, the immune checkpoint modulator is a PD-1 inhibitor. Preferred inhibitors of the CTLA-4 pathway and of the PD-1 pathway include the monoclonal antibodies Yervoy® (Ipilimumab; Bristol Myers Squibb) and Tremelimumab (Pfizer/MedImmune) as well as Opdivo® (Nivolumab; Bristol Myers Squibb), Keytruda® (Pembrolizumab; also known as Lambrolizumab or MK-3475; Merck), Imfinzi® (Durvalumab also known as MEDI4736; MedImmune/AstraZeneca), Tecentriq® (Atezolizumab also known as MPDL3280A; Roche/Genentech), Pidilizumab (CT-011; CureTech), MEDI0680 (AMP-514; AstraZeneca), Bavencio® (Avelumab; Merck KGaA/Pfizer also known as MSB-0010718C), MIH1 (Affymetrix), LY3300054 (Eli Lilly) and and Spartalizumab (also known as PDR001; Novartis). More preferred checkpoint inhibitors include the CTLA-4 inhibitors Yervoy® (Ipilimumab; Bristol Myers Squibb) and Tremelimumab (Pfizer/MedImmune) as well as the PD-1 inhibitors Opdivo® (Nivolumab; Bristol Myers Squibb), Keytruda® (Pembrolizumab; Merck), Pidilizumab (CT-011; CureTech), MEDI0680 (AMP-514; AstraZeneca), AMP-224 (a PD-L2 Fc fusion protein; MedImmune).

It is also preferred that the immune checkpoint modulator for combination with the antigenic peptide as defined herein is selected from the group consisting of Pembrolizumab, Ipilimumab, Nivolumab, Atezolizumab. MED14736. Tremelimumab, Avelumab, Spartalizumab, LAG525 (an anti-LAG3 monoclonal antibody), Epacadostat (formerly INCB24360; an IDO inhibitor), Varlilumab (an anti-CD27 monoclonal antibody), Urelumab (an anti-CD137 monoclonal antibody), AMP-224 and CM-24 (an anti-CEACAM1 monoclonal antibody).

It is within the skill of ordinary person in the art to select the appropriate immune anti-cancer therapeutic agent for the purposes of the invention. For example, should one wish to prevent or treat melanoma, a lysate from melanoma cells and/or the antibody Ipilimumab can preferably be used, along with the corresponding antigenic peptide according to the present invention as described herein.

The anti-cancer therapeutic agent can also be administered in association with the antigenic peptide according to the present invention, the immunogenic compound according to the present invention, the nanoparticle according to the present invention, the cell according to the present invention, the nucleic acid according to the present invention, the host cell according to the present invention, or the pharmaceutical composition according to the present invention, either at about the same time or consecutively as described herein and in the same or distinct pharmaceutical forms. Thus, the invention proposes a combined use of the composition the invention and least one anti-cancer therapeutic agent as described above, for a simultaneous, separate, or sequential administration as described herein.

Furthermore, the present invention also relates to a combination of at least two distinct antigenic peptides according to the present invention, e.g. for use in the prevention and/or treatment of a cancer. Furthermore, the present invention also relates to a combination of at least two distinct immunogenic compounds according to the present invention, e.g. for use in the prevention and/or treatment of a cancer. Furthermore, the present invention also relates to a combination of at least two distinct nanoparticles according to the present invention, e.g. for use in the prevention and/or treatment of a cancer. Furthermore, the present invention also relates to a combination of at least two distinct nucleic acids according to the present invention, e.g. for use in the prevention and/or treatment of a cancer.

Thus, according to a preferred embodiment, at least two antigenic peptides according to the present invention may be administered in combination, for example in the same pharmaceutical composition. For example, at least 3 antigenic peptides, at least 4 antigenic peptides, at least 5 antigenic peptides, at least 6 antigenic peptides, at least 7 antigenic peptides, at least 8 antigenic peptides, at least 9 antigenic peptides, at least 10 antigenic peptides, at least 11 antigenic peptides, at least 12 antigenic peptides, at least 13 antigenic peptides, at least 14 antigenic peptides, at least 15 antigenic peptides, at least 20 antigenic peptides, at least 25 antigenic peptides, at least 50 antigenic peptides, at least 100 antigenic peptides, at least 500 antigenic peptides, at least 1000 antigenic peptides, or at least 1500 antigenic peptides are administered in combination, for example in the same pharmaceutical composition. It is within the skill of the person in the art to select the combination of antigenic peptides and/or immunogenic compounds that is suitable for the intended purpose. For example, should one wish to prevent or treat melanoma which involves a tumor antigen encoded by a gene according to Table 1B, one can select any combination of the corresponding antigenic peptides as described in Table 1A.

In a particularly preferred embodiment two distinct antigenic peptides according to the present invention (e.g., relating to the same type of cancer and/or to the same reference antigen) are combined. For example, (i) at least two distinct immunogenic compounds according to the present invention;

(ii) at least two distinct antigenic peptides according to the present invention;

(iii) at least two distinct nanoparticles according to the present invention; or (iv) at least two distinct nucleic acids according to the present invention may be combined.

For example, the present invention provides a combination of (i) a first antigenic peptide according to the present invention, and (ii) a second antigenic peptide according to the present invention (distinct from the first) preferably for use in the prevention and/or treatment of a cancer.

For example, the present invention provides a combination of (i) an immunogenic compound according to the present invention comprising a first antigenic peptide according to the present invention, and (ii) an immunogenic compound according to the present invention comprising a second antigenic peptide according to the present invention (distinct from the first) preferably for use in the prevention and/or treatment of a cancer.

For example, the present invention provides a combination of (i) a nanoparticle according to the present invention comprising a first antigenic peptide according to the present invention, and (ii) a nanoparticle according to the present invention comprising a second antigenic peptide according to the present invention (distinct from the first) preferably for use in the prevention and/or treatment of a cancer.

For example, the present invention provides a combination of (i) a nucleic acid according to the present invention comprising a polynucleotide encoding a first antigenic peptide according to the present invention and (ii) a nucleic acid according to the present invention comprising a polynucleotide encoding a second antigenic peptide according to the present invention (distinct from the first) preferably for use in the prevention and/or treatment of a cancer.

Moreover, the antigenic peptide according to the present invention may also be combined with the corresponding (human) tumor antigen epitope (as described above regarding the peptide "families"). Thereby, selection of T-cell clones, which are very efficient against the tumor, is obtained/supported. In particular, the antigenic peptide according to the present invention and the corresponding (human) tumor antigen epitope may be co-administered. Such co-administration may be at about the same time (simultaneously) or consecutively, whereby in consecutive administration it is preferred that the antigenic peptide according to the present invention is administered first and the corresponding (human) tumor antigen epitope is administered thereafter. In particular, the antigenic peptide according to the present invention may be administered first, and the corresponding (human) tumor antigen epitope may be used as (re)boost. For example, the antigenic peptide according to SEQ ID NO: 30, 31 or 32 may be combined with the reference peptide according to SEQ ID NO: 593. In another example, the antigenic peptide according to SEQ ID NO: 87 or 97 may be combined with the reference peptide according to SEQ ID NO: 617. In another example, the antigenic peptide according to SEQ ID NO: 145 may be combined with the reference peptide according to SEQ ID NO: 637. In another example, the antigenic peptide according to SEQ ID NO: 193 may be combined with the reference peptide according to SEQ ID NO: 659. In another example, the antigenic peptide according to SEQ ID NO: 194 may be combined with the reference peptide according to SEQ ID NO: 660. In another example, the antigenic peptide according to SEQ ID NO: 221 may be combined with the reference peptide according to SEQ ID NO: 675. In another example, the antigenic peptide according to SEQ ID NO: 220 may be combined with the reference peptide according to SEQ ID NO: 674. In another example, the antigenic peptide according to SEQ ID NO: 255 may be combined with the reference peptide according to SEQ ID NO: 691. In another example, the antigenic peptide according to SEQ ID NO: 524 may be combined with the reference peptide according to SEQ ID NO: 826. In another example, the antigenic peptide according to SEQ ID NO: 521 may be combined with the reference peptide according to SEQ ID NO: 824.

The peptides, which are to be combined, such as (a) the antigenic peptide according to the present invention and the corresponding (human) tumor antigen epitope or (b) two distinct antigenic peptides according to the present invention, may be administered

- in the same immunogenic compound according to the present invention or in distinct immunogenic compounds according to the present invention,
- (loaded) in the same nanoparticle according to the present invention or in distinct nanoparticles according to the present invention,
- (loaded) in the same cell according to the present invention or in distinct cells according to the present invention,
- (encoded by) the same nucleic acid according to the present invention or by distinct nucleic acids according to the present invention,
- (expressed by) the same host cell according to the present invention or by distinct host cells according to the present invention, or
- (comprised) in the same pharmaceutical composition according to the present invention or in distinct pharmaceutical composition according to the present invention.

In the following it may be referred to "two distinct components" (of a combination for use according to the present invention). In general, the expression "two distinct components" in the context of a combination, e.g. for use according to the present invention (a combination therapy), refers to

- (1) a first component, such as the antigenic peptide according to the present invention as described herein, the immunogenic compound according to the present invention as described herein, the nanoparticle according to the present invention as described herein, the cell according to the present invention as described herein, the nucleic acid according to the present invention as described herein, the host cell according to the present invention as described herein, or the pharmaceutical composition according to the present invention as described herein; and
- (2) a second component (which is distinct from the first component), such as the anti-cancer therapeutic agent as described above, a distinct antigenic peptide according to the present invention as described herein, a distinct immunogenic compound according to the present invention as described herein, a distinct nanoparticle according to the present invention as described herein, a distinct cell according to the present invention as described herein, a distinct nucleic acid according to the present invention as described herein, a distinct host cell according to the present invention as described herein, a distinct pharmaceutical composition according to the present invention as described herein, or one or more (fragments of) human tumor antigens in any form ("naked", as immunogenic compound as described herein, as nanoparticle as described herein, as (host) cell as described herein, as nucleic acid as described herein or as pharmaceutical composition as described herein).

Accordingly, the "two distinct components", as referred to herein in the context of a combination for use according to the present invention (a combination therapy), are preferably active components in the context of the disease (cancer) to be prevented and/or treated. In other words, each of the at least two distinct components may also be useful for preventing and/or treating said cancer, if administered separately (not in combination as described herein)—although the combination (i.e. combined administration) typically potentiates their preventive and/or therapeutic effect (such as the immune response), in particular in a synergistic manner.

Accordingly, the present invention also provides the combination of (at least) two distinct antigenic peptides according to the present invention as described herein. In this context, the (at least) two distinct antigenic peptides may be in any form, e.g., "naked", comprised in immunogenic compounds, nanoparticles, (pharmaceutical) compositions or cells loaded therewith, or encoded by nucleic acids (e.g., vectors). Accordingly, the (at least) two distinct antigenic peptides may be comprised in (at least) two distinct components (to be combined). In a preferred embodiment, the at least two distinct components of the combination according to the present invention are at least distinct antigenic peptides according to the present invention (in any form, e.g. comprised in immunogenic compounds, nanoparticles, cells, pharmaceutical compositions, encoded by the nucleic acids, etc.).

Preferably, the at least two distinct components of the combination for use according to the present invention relate to the same type of cancer, for example to the same or distinct antigens associated with this cancer and/or to the same or distinct (reference) epitopes within an antigen associated with this cancer. More preferably, the at least two distinct components relate to the same tumor antigen.

In certain embodiments, the at least two distinct components of the combination for use according to the present invention are comprised in the same or distinct compositions. In certain embodiments, the at least two distinct components of the combination for use according to the present invention are administered via the same or distinct routes of administration. In certain embodiments, the at least two distinct components of the combination for use according to the present invention are administered at about the same time (simultaneously) or consecutively.

Preferably, the at least two distinct components of the combination for use according to the present invention are administered at about the same time. In more general, it is preferred that the first component is administered at about the same time as the second component, wherein the at least two distinct components of the combination for use according to the present invention are preferably administered in the same form (i.e., in the same type of formulation, e.g., as nanoparticles, as pharmaceutical compositions, etc.).

"At about the same time", as used herein, means in particular simultaneous administration or that directly after administration of the first component, the second component is administered or directly after administration of the second component, the first component is administered. The skilled person understands that "directly after" includes the time necessary to prepare the second administration—in particular the time necessary for exposing and disinfecting the location for the second administration as well as appropriate preparation of the "administration device" (e.g., syringe, pump, etc.). Simultaneous administration also includes if the periods of administration of the first component and of the second component overlap or if, for example, one component is administered over a longer period of time, such as 30 min, 1 h, 2 h or even more, e.g. by infusion, and the other component is administered at some time during such a long period. Administration of the first component and of the second component at about the same time is in particular preferred if different routes of administration and/or different administration sites are used.

It is also preferred that the at least two distinct components of the combination for use according to the present invention are administered consecutively. In more general, it is preferred that the first component and the second component are administered consecutively, wherein the at least two distinct components of the combination for use according to the present invention are preferably administered in the same form (i.e., in the same type of formulation, e.g., as nanoparticles, as pharmaceutical compositions, etc.).

This means that the first component is administered before or after the second component. In consecutive administration, the time between administration of the first component and administration of the second component is preferably no more than one week, more preferably no more than 3 days, even more preferably no more than 2 days and most preferably no more than 24 h. It is particularly preferred that the first component and the second component are administered at the same day with the time between administration of the first component and administration of the second component being preferably no more than 6 hours, more preferably no more than 3 hours, even more preferably no more than 2 hours and most preferably no more than 1 h.

Preferably, the first component and the second component are administered via the same route of administration. In more general, it is preferred that the first component and the second component are administered via the same route of administration, wherein the at least two distinct components of the combination for use according to the present invention are preferably administered in the same form (i.e., in the same type of formulation, e.g., as nanoparticles, as pharmaceutical compositions, etc.).

It is also preferred that the at least two distinct components of the combination for use according to the present invention are administered via distinct routes of administration. In more general, it is preferred that the first component and the second component are administered via distinct routes of administration, wherein the at least two distinct components of the combination for use according to the present invention are preferably administered in the same form (i.e., in the same type of formulation, e.g., as nanoparticles, as pharmaceutical compositions, etc.).

Preferably, the at least two distinct components of the combination for use according to the present invention are comprised in the same composition. In more general, it is preferred that the first component and the second component are comprised in the same composition, wherein the at least two distinct components of the combination for use according to the present invention are preferably administered in the same form (i.e., in the same type of formulation, e.g., as nanoparticles, etc.).

It is also preferred that the at least two distinct components of the combination for use according to the present invention are comprised in distinct compositions. In more general, it is preferred that the first component and the second component are comprised in distinct compositions, wherein the at least two distinct components of the combination for use according to the present invention are preferably administered in the same form (i.e., in the same type of formulation, e.g., as nanoparticles, etc.).

In particular, the present invention provides a combination, e.g. for use in the prevention and/or treatment of a cancer, comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the human tumor antigen FOXM1. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868. Even more preferably, the combination, e.g. for use in the prevention and/or treatment of a cancer, comprises an antigenic peptide comprising or consisting of SEQ ID NO: 32 and an antigenic peptide comprising or consisting of SEQ ID NO: 220.

In particular, the present invention also provides a combination, e.g. for use in the prevention and/or treatment of a cancer, comprising a first antigenic peptide according to the present invention, which comprises or consists of a microbiota sequence variant of a fragment of the human tumor antigen BIRC5, and a second antigenic peptide according to the present invention, which comprises or consists of a microbiota sequence variant of a fragment of the tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the combination, e.g. for use in the prevention and/or treatment of a cancer, comprises an antigenic peptide comprising or consisting of SEQ ID NO: 32 and an antigenic peptide comprising or consisting of SEQ ID NO: 255.

In particular, the present invention also provides a combination, e.g. for use in the prevention and/or treatment of a cancer, comprising a first antigenic peptide according to the present invention, which comprises or consists of a microbiota sequence variant of a fragment of the human tumor antigen FOXM1, and a second antigenic peptide according to the present invention, which comprises or consists of a microbiota sequence variant of a fragment of the human tumor antigen IL13RA2. Preferably, the first antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868, and the second antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the combination, e.g. for use in the prevention and/or treatment of a cancer, comprises an antigenic peptide comprising or consisting of SEQ ID NO: 220 and an antigenic peptide comprising or consisting of SEQ ID NO: 255.

More preferably, the combination according to the present invention (e.g. for use in the prevention and/or treatment of a cancer) comprises at least three distinct components as described above, in particular at least three distinct antigenic peptides according to the present invention. The above description regarding the combination of two distinct components applies accordingly for three distinct components.

Accordingly, the present invention also provides a combination, e.g. for use in the prevention and/or treatment of a cancer, comprising a first antigenic peptide according to the present invention, which comprises or consists of a microbiota sequence variant of a fragment of the human tumor antigen BIRC5, a second antigenic peptide according to the present invention, which comprises or consists of a microbiota sequence variant of a fragment of the human tumor antigen FOXM1, and a third antigenic peptide according to the present invention, which comprises or consists of a microbiota sequence variant of a fragment of the human tumor antigen IL13RA2. Preferably, the first antigenic peptide comprises or consists of a microbiota sequence variant of the BIRC5 fragment (human reference peptide) "LTLGEFLKL" (SEQ ID NO: 593), such as an antigenic peptide comprising or consisting of an amino acid sequence as set forth in SEQ ID NO: 30, 31 or 32; the second antigenic peptide comprises or consists of a microbiota sequence variant of the FOXM1 fragment (human reference peptide) "LMDLSTTPL" (SEQ ID NO: 674), such as an antigenic peptide comprising or consisting of an amino acid sequence as set forth in SEQ ID NO: 220 or 868; and the third antigenic peptide comprises or consists of a microbiota sequence variant of the IL13RA2 fragment (human reference peptide) "WLPFGFILI" (SEQ ID NO: 691) or "WLPFGFILIL" (SEQ ID NO: 692), such as an antigenic peptide comprising or consisting of an amino acid sequence as set forth in SEQ ID NO: 254, 255, 878 or 879. Even more preferably, the combination, e.g. for use in the prevention and/or treatment of a cancer, comprises an antigenic peptide comprising or consisting of an amino acid sequence as set forth in SEQ ID NO: 30, an antigenic peptide comprising or consisting of an amino acid sequence as set forth in SEQ ID NO: 220, and an antigenic peptide comprising or consisting of an amino acid sequence as set forth in SEQ ID NO: 255.

It is understood that the combination, e.g. for use in the prevention and/or treatment of a cancer, may also contain—instead of the above-described preferred combinations of antigenic peptides—a respective combination of immunogenic compounds of the invention, a respective combination of nanoparticles of the invention or a respective combination of nucleic acids of the invention.

EXAMPLES

In the following, particular examples illustrating various embodiments and aspects of the invention are presented. However, the present invention shall not to be limited in scope by the specific embodiments described herein. The following preparations and examples are given to enable those skilled in the art to more clearly understand and to practice the present invention. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become readily apparent to those skilled in the art from the foregoing description, accompanying figures and the examples below. All such modifications fall within the scope of the appended claims.

Example 1: Antigenic Peptides have Superior Binding Affinity Compared to Human Peptides Binding affinity of the exemplified antigenic peptides of the present invention and of the corresponding fragments of human tumor antigens (human reference peptides) to MHC class I was predicted in silico.

Such prediction has been obtained by using NetMHC 4.0 Server (www.cbs.dtu.dk/services/NetMHC/) and as described in Andreatta M, Nielsen M Gapped sequence alignment using artificial neural networks: application to the MHC class I system. Bioinformatics (2016) February 15; 32(4):511-7. This method generates high-accuracy predictions of major histocompatibility complex (MHC): peptide binding, in particular for peptides having a length of 8-11 amino acids.

Table 2 below shows the results, i.e. information about prediction of peptide-MHC class I binding.

TABLE 2

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| ACPP | 581 | 7.84 | 1 | 6.81 |
| ACPP | 582 | 70.75 | 2 | 19.02 |
| ACPP | 582 | 70.75 | 3 | 8.76 |
| ACPP | 583 | 186.03 | 4 | 5.16 |
| ANKRD30A | 584 | 94.32 | 5 | 6.03 |
| ANKRD30A | 585 | 210.49 | 6 | 17.64 |
| ANKRD30A | 585 | 210.49 | 7 | 11.20 |
| ANKRD30A | 585 | 210.49 | 8 | 22.76 |
| ANKRD30A | 586 | 19.65 | 9 | 7.27 |
| ANKRD30A | 586 | 19.65 | 10 | 12.28 |
| ANKRD30A | 587 | 27.61 | 11 | 13.89 |
| ANKRD30A | 587 | 27.61 | 12 | 17.81 |
| ANKRD30A | 587 | 27.61 | 13 | 4.93 |
| ANKRD30A | 587 | 27.61 | 14 | 7.60 |
| ANKRD30A | 587 | 27.61 | 15 | 6.72 |
| AREG | 588 | 638.46 | 16 | 34.31 |
| AREG | 588 | 638.46 | 17 | 19.29 |
| AREG | 589 | 55.99 | 18 | 12.69 |
| AREG | 589 | 55.99 | 19 | 16.12 |
| AREG | 589 | 55.99 | 20 | 8.29 |
| AREG | 589 | 55.99 | 21 | 11.08 |
| AREG | 589 | 55.99 | 22 | 15.31 |
| AREG | 589 | 55.99 | 23 | 12.64 |
| AREG | 589 | 55.99 | 24 | 12.77 |
| ASCL1 | 590 | 1467.39 | 25 | 18.36 |
| ASCL2 | 591 | 102.76 | 26 | 29.90 |
| ASCL2 | 591 | 102.76 | 27 | 51.07 |
| ASCL2 | 592 | 80.88 | 28 | 11.95 |
| ASCL2 | 592 | 80.88 | 29 | 5.31 |
| BIRC5 | 593 | 1413.34 | 30 | 17.18 |
| BIRC5 | 593 | 1413.34 | 31 | 48.50 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| BIRC5 | 593 | 1413.34 | 32 | 5.40 |
| CA9 | 594 | 261.09 | 33 | 17.82 |
| CA9 | 594 | 261.09 | 34 | 28.33 |
| CA9 | 595 | 105.51 | 35 | 22.38 |
| CA9 | 595 | 105.51 | 36 | 9.88 |
| CA9 | 595 | 105.51 | 37 | 40.34 |
| CA9 | 596 | 44.01 | 38 | 21.18 |
| CA9 | 597 | 83.40 | 39 | 20.04 |
| CA9 | 597 | 83.40 | 40 | 22.39 |
| CA9 | 597 | 83.40 | 41 | 37.70 |
| CA9 | 598 | 639.25 | 42 | 6.03 |
| CA9 | 598 | 639.25 | 43 | 11.77 |
| CA9 | 598 | 639.25 | 44 | 44.14 |
| CA9 | 599 | 250.07 | 45 | 17.99 |
| CA9 | 599 | 250.07 | 46 | 13.94 |
| CA9 | 599 | 250.07 | 47 | 28.39 |
| CA9 | 600 | 926.80 | 48 | 38.72 |
| CA9 | 600 | 926.80 | 49 | 50.95 |
| CA9 | 600 | 926.80 | 50 | 19.91 |
| CCNA1 | 601 | 23.44 | 51 | 7.14 |
| CCNA1 | 602 | 125.47 | 52 | 19.85 |
| CCNA1 | 602 | 125.47 | 53 | 19.59 |
| CCNA1 | 602 | 125.47 | 54 | 29.54 |
| CCNA1 | 602 | 125.47 | 55 | 4.69 |
| CCND1 | 603 | 146.91 | 56 | 39.32 |
| CDH17 | 604 | 256.56 | 57 | 19.45 |
| CDH17 | 605 | 176.80 | 58 | 25.52 |
| CDH17 | 605 | 176.80 | 59 | 13.81 |
| CDH17 | 606 | 55.58 | 60 | 8.96 |
| CDH17 | 606 | 55.58 | 61 | 10.34 |
| CDH17 | 606 | 55.58 | 62 | 18.19 |
| CDH17 | 607 | 31.40 | 63 | 10.43 |
| CDH6 | 608 | 70.52 | 64 | 5.24 |
| CDH6 | 608 | 70.52 | 65 | 18.50 |
| CDH6 | 608 | 70.52 | 66 | 7.58 |
| CDH6 | 608 | 70.52 | 67 | 10.94 |
| CDH6 | 608 | 70.52 | 68 | 8.93 |
| CDH6 | 608 | 70.52 | 69 | 27.51 |
| CDH6 | 608 | 70.52 | 70 | 45.84 |
| CDH6 | 609 | 149.17 | 71 | 31.98 |
| CDH6 | 610 | 20.01 | 72 | 4.27 |
| CDH6 | 611 | 106.71 | 73 | 16.73 |
| CDH6 | 612 | 19.90 | 74 | 11.85 |
| CDH6 | 612 | 19.90 | 75 | 12.92 |
| CDH6 | 613 | 85.54 | 76 | 12.49 |
| CDH6 | 613 | 85.54 | 77 | 14.18 |
| CDH6 | 613 | 85.54 | 78 | 11.69 |
| CDH6 | 613 | 85.54 | 79 | 26.76 |
| CDH6 | 613 | 85.54 | 80 | 13.91 |
| CDH6 | 613 | 85.54 | 81 | 64.63 |
| CDKN2A | 614 | 609.17 | 82 | 13.54 |
| CEACAM5 | 615 | 126.68 | 83 | 17.05 |
| CHI3L1 | 616 | 374.26 | 84 | 14.77 |
| CHI3L1 | 616 | 374.26 | 85 | 13.27 |
| CHI3L1 | 617 | 49.46 | 86 | 6.69 |
| CHI3L1 | 617 | 49.46 | 87 | 7.55 |
| CHI3L1 | 617 | 49.46 | 88 | 43.85 |
| CHI3L1 | 617 | 49.46 | 89 | 20.12 |
| CHI3L1 | 617 | 49.46 | 90 | 11.41 |
| CHI3L1 | 617 | 49.46 | 91 | 38.08 |
| CHI3L1 | 617 | 49.46 | 92 | 21.15 |
| CHI3L1 | 617 | 49.46 | 93 | 12.59 |
| CHI3L1 | 617 | 49.46 | 94 | 8.44 |
| CHI3L1 | 617 | 49.46 | 95 | 10.00 |
| CHI3L1 | 617 | 49.46 | 96 | 11.72 |
| CHI3L1 | 617 | 49.46 | 97 | 8.56 |
| CHI3L1 | 617 | 49.46 | 98 | 53.90 |
| CHI3L1 | 617 | 49.46 | 99 | 33.87 |
| CHI3L1 | 617 | 49.46 | 100 | 17.70 |
| CHI3L1 | 617 | 49.46 | 101 | 29.51 |
| CHI3L1 | 617 | 49.46 | 102 | 6.12 |
| CHI3L1 | 617 | 49.46 | 103 | 31.73 |
| CHI3L1 | 617 | 49.46 | 104 | 27.90 |
| CHI3L1 | 617 | 49.46 | 105 | 6.00 |
| CHI3L1 | 617 | 49.46 | 106 | 15.57 |
| CHI3L1 | 617 | 49.46 | 107 | 47.62 |
| CHI3L1 | 617 | 49.46 | 108 | 13.60 |
| CHI3L1 | 617 | 49.46 | 109 | 35.37 |
| CHI3L1 | 618 | 184.90 | 110 | 5.98 |
| CHI3L1 | 618 | 184.90 | 111 | 5.46 |
| CHI3L1 | 618 | 184.90 | 112 | 46.78 |
| CHI3L1 | 619 | 89.58 | 113 | 30.62 |
| CHI3L1 | 620 | 116.85 | 114 | 11.40 |
| CHI3L2 | 621 | 71.53 | 115 | 18.40 |
| CHI3L2 | 622 | 62.20 | 116 | 16.60 |
| CHI3L2 | 623 | 33.99 | 117 | 5.25 |
| CHI3L2 | 623 | 33.99 | 118 | 24.67 |
| CHI3L2 | 624 | 14.03 | 119 | 7.34 |
| COL11A1 | 625 | 8.14 | 120 | 2.73 |
| CT83 | 626 | 39.72 | 121 | 6.47 |
| CT83 | 626 | 39.72 | 122 | 18.16 |
| CT83 | 626 | 39.72 | 123 | 19.51 |
| CTCFL | 627 | 202.12 | 124 | 5.50 |
| DCT | 628 | 67.88 | 125 | 9.23 |
| DCT | 628 | 67.88 | 126 | 19.60 |
| DCT | 629 | 33.01 | 127 | 8.70 |
| DCT | 629 | 33.01 | 128 | 14.83 |
| DCT | 629 | 33.01 | 129 | 11.42 |
| DCT | 630 | 24.75 | 130 | 10.84 |
| DCT | 631 | 53.11 | 131 | 10.04 |
| DCT | 631 | 53.11 | 132 | 75.39 |
| DMRTA2 | 632 | 560.82 | 133 | 15.32 |
| DMRTA2 | 633 | 121.55 | 134 | 6.77 |
| EGFR | 634 | 262.29 | 135 | 12.94 |
| EGFR | 634 | 262.29 | 136 | 18.28 |
| EGFR | 635 | 13.68 | 137 | 4.03 |
| EGFR | 636 | 12.26 | 138 | 3.81 |
| EGFR | 636 | 12.26 | 139 | 4.70 |
| EGFR | 636 | 12.26 | 140 | 4.18 |
| EGFR | 636 | 12.26 | 141 | 5.65 |
| EGFR | 636 | 12.26 | 142 | 6.77 |
| EGFR | 636 | 12.26 | 143 | 3.75 |
| EGFR | 636 | 12.26 | 144 | 4.99 |
| EGFR | 637 | 61.00 | 145 | 11.98 |
| EGFR | 638 | 93.43 | 146 | 23.35 |
| EGFR | 639 | 226.82 | 147 | 25.04 |
| EGFR | 640 | 78.07 | 148 | 4.72 |
| EGFR | 641 | 116.72 | 149 | 45.62 |
| EGFR | 641 | 116.72 | 150 | 20.54 |
| ERBB2 | 642 | 271.92 | 151 | 17.06 |
| ERBB2 | 642 | 271.92 | 152 | 73.58 |
| ERBB2 | 642 | 271.92 | 153 | 31.31 |
| ERBB2 | 642 | 271.92 | 154 | 23.78 |
| ERBB2 | 643 | 61.00 | 155 | 11.98 |
| ERBB2 | 644 | 78.48 | 156 | 7.26 |
| ERBB2 | 644 | 78.48 | 157 | 17.51 |
| ERBB2 | 644 | 78.48 | 158 | 8.66 |
| ERBB2 | 644 | 78.48 | 159 | 5.60 |
| ERBB2 | 645 | 112.27 | 160 | 14.20 |
| ERBB2 | 646 | 43.79 | 161 | 10.47 |
| ERBB2 | 646 | 43.79 | 162 | 17.29 |
| ERG | 647 | 131.75 | 163 | 3.21 |
| ERG | 857 | 19.28 | 164 | 6.61 |
| ESR1 | 648 | 8.71 | 165 | 5.96 |
| ESR1 | 649 | 74.42 | 166 | 4.99 |
| ESR1 | 649 | 74.42 | 167 | 7.11 |
| ESR1 | 650 | 44.48 | 168 | 5.98 |
| ESR1 | 650 | 44.48 | 169 | 17.96 |
| ESR1 | 651 | 87.59 | 170 | 5.52 |
| ESR1 | 652 | 1197.89 | 171 | 15.76 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| ESR1 | 652 | 1197.89 | 172 | 16.48 |
| ESR1 | 653 | 150.15 | 173 | 4.45 |
| ESR1 | 654 | 353.62 | 174 | 2.20 |
| ESR1 | 654 | 353.62 | 175 | 2.89 |
| ESR1 | 654 | 353.62 | 176 | 5.67 |
| ESR1 | 654 | 353.62 | 177 | 31.36 |
| ESR1 | 654 | 353.62 | 178 | 8.16 |
| ESR1 | 654 | 353.62 | 179 | 8.17 |
| ESR1 | 654 | 353.62 | 180 | 7.28 |
| ESR1 | 654 | 353.62 | 181 | 2.81 |
| ESR1 | 655 | 255.96 | 182 | 23.09 |
| ESR1 | 655 | 255.96 | 183 | 15.10 |
| ESR1 | 655 | 255.96 | 184 | 13.13 |
| ESR1 | 655 | 255.96 | 185 | 11.02 |
| ESR1 | 655 | 255.96 | 186 | 59.71 |
| ESR1 | 655 | 255.96 | 187 | 17.37 |
| ESR1 | 655 | 255.96 | 188 | 9.52 |
| ESR1 | 656 | 131.20 | 189 | 32.95 |
| ESR1 | 656 | 131.20 | 190 | 6.68 |
| ESR1 | 657 | 126.34 | 191 | 5.67 |
| ESR1 | 658 | 159.50 | 192 | 5.57 |
| EZH2 | 659 | 20.00 | 193 | 25.28 |
| EZH2 | 660 | 63.82 | 194 | 22.39 |
| FAP | 661 | 512.58 | 195 | 10.02 |
| FAP | 661 | 512.58 | 196 | 42.73 |
| FAP | 661 | 512.58 | 197 | 47.13 |
| FAP | 662 | 1616.20 | 198 | 7.97 |
| FAP | 663 | 106.57 | 199 | 11.88 |
| FAP | 663 | 106.57 | 200 | 17.55 |
| FAP | 663 | 106.57 | 201 | 17.08 |
| FLT1 | 664 | 63.37 | 202 | 10.87 |
| FLT1 | 664 | 63.37 | 203 | 9.10 |
| FLT1 | 664 | 63.37 | 204 | 5.89 |
| FLT1 | 664 | 63.37 | 205 | 12.69 |
| FLT1 | 664 | 63.37 | 206 | 12.60 |
| FLT1 | 664 | 63.37 | 207 | 5.18 |
| FLT1 | 664 | 63.37 | 208 | 15.58 |
| FLT1 | 665 | 227.40 | 209 | 7.81 |
| FLT1 | 666 | 112.02 | 210 | 6.16 |
| FLT1 | 667 | 42.43 | 211 | 4.48 |
| FLT1 | 667 | 42.43 | 212 | 13.08 |
| FLT1 | 668 | 44.22 | 213 | 3.66 |
| FLT1 | 669 | 24.87 | 214 | 5.44 |
| FLT1 | 670 | 5.89 | 215 | 3.18 |
| FLT1 | 671 | 558.96 | 216 | 20.59 |
| FOXM1 | 672 | 36.15 | 217 | 5.22 |
| FOXM1 | 672 | 36.15 | 218 | 2.79 |
| FOXM1 | 672 | 36.15 | 861 | 2.42 |
| FOXM1 | 672 | 36.15 | 862 | 4.16 |
| FOXM1 | 672 | 36.15 | 863 | 15.79 |
| FOXM1 | 672 | 36.15 | 864 | 2.99 |
| FOXM1 | 672 | 36.15 | 865 | 2.98 |
| FOXM1 | 672 | 36.15 | 866 | 2.92 |
| FOXM1 | 673 | 46.25 | 219 | 13.40 |
| FOXM1 | 673 | 46.25 | 867 | 34.24 |
| FOXM1 | 674 | 26.60 | 220 | 15.68 |
| FOXM1 | 674 | 26.60 | 868 | 29.42 |
| FOXM1 | 675 | 53.72 | 221 | 7.72 |
| FOXM1 | 675 | 53.72 | 222 | 7.03 |
| FOXM1 | 675 | 53.72 | 223 | 11.75 |
| FOXM1 | 675 | 53.72 | 869 | 3.16 |
| FOXM1 | 675 | 53.72 | 870 | 4.76 |
| FOXM1 | 675 | 53.72 | 871 | 34.60 |
| FOXM1 | 676 | 203.88 | 224 | 43.00 |
| FOXM1 | 677 | 31.23 | 225 | 7.56 |
| FOXM1 | 677 | 31.23 | 226 | 6.92 |
| FOXM1 | 678 | 144.91 | 227 | 5.90 |
| FOXM1 | 888 | 48.87 | 872 | 48.49 |
| FOXM1 | 889 | 35.91 | 873 | 64.21 |
| FOXM1 | 889 | 35.91 | 874 | 25.70 |
| FOXM1 | 890 | 2.22 | 875 | 9.69 |
| FOXM1 | 890 | 2.22 | 876 | 15.82 |
| FOXM1 | 891 | 3.73 | 877 | 17.91 |
| FSIP1 | 679 | 70.88 | 228 | 21.67 |
| FSIP1 | 680 | 602.51 | 229 | 19.24 |
| FSIP1 | 680 | 602.51 | 230 | 51.70 |
| FSIP1 | 680 | 602.51 | 231 | 36.16 |
| GAL3ST1 | 681 | 71.36 | 232 | 8.07 |
| GAL3ST1 | 682 | 133.28 | 233 | 25.02 |
| GAL3ST1 | 682 | 133.28 | 234 | 35.65 |
| GPR143 | 683 | 27.67 | 235 | 8.90 |
| GPR143 | 683 | 27.67 | 236 | 9.55 |
| GPR143 | 683 | 27.67 | 237 | 21.93 |
| GPR143 | 684 | 345.70 | 238 | 74.50 |
| GPR143 | 685 | 274.36 | 239 | 12.76 |
| GPR143 | 686 | 108.41 | 240 | 21.48 |
| GPR143 | 686 | 108.41 | 241 | 26.02 |
| GPR143 | 686 | 108.41 | 242 | 20.01 |
| GPR143 | 686 | 108.41 | 243 | 5.57 |
| GPR143 | 686 | 108.41 | 244 | 15.06 |
| GPR143 | 686 | 108.41 | 245 | 24.30 |
| GPR143 | 686 | 108.41 | 246 | 6.35 |
| GPR143 | 686 | 108.41 | 247 | 30.08 |
| HES6 | 687 | 66.43 | 248 | 39.04 |
| IL13RA2 | 688 | 132.87 | 249 | 5.99 |
| IL13RA2 | 688 | 132.87 | 250 | 10.47 |
| IL13RA2 | 688 | 132.87 | 251 | 15.64 |
| IL13RA2 | 689 | 45.46 | 252 | 3.78 |
| IL13RA2 | 690 | 7.76 | 253 | 5.35 |
| IL13RA2 | 691 | 171.06 | 254 | 8.49 |
| IL13RA2 | 692 | 78.00 | 255 | 3.77 |
| IL13RA2 | 692 | 78.00 | 878 | 4.82 |
| IL13RA2 | 692 | 78.00 | 879 | 3.97 |
| IL13RA2 | 892 | 44.03 | 880 | 28.67 |
| IL13RA2 | 892 | 44.03 | 881 | 10.01 |
| IL13RA2 | 892 | 44.03 | 882 | 31.65 |
| IL13RA2 | 893 | 8.37 | 883 | 17.68 |
| IL13RA2 | 894 | 117.95 | 884 | 13.66 |
| IL13RA2 | 894 | 117.95 | 885 | 13.66 |
| IL13RA2 | 895 | 137.80 | 886 | 23.34 |
| IL13RA2 | 895 | 137.80 | 887 | 31.28 |
| KISS1R | 693 | 143.54 | 256 | 20.53 |
| KISS1R | 693 | 143.54 | 257 | 28.11 |
| KISS1R | 693 | 143.54 | 258 | 44.06 |
| KISS1R | 694 | 141.98 | 259 | 12.78 |
| KISS1R | 694 | 141.98 | 260 | 14.02 |
| KISS1R | 694 | 141.98 | 261 | 21.16 |
| KISS1R | 695 | 237.51 | 262 | 41.96 |
| KISS1R | 696 | 80.71 | 263 | 12.37 |
| KISS1R | 697 | 148.34 | 264 | 20.84 |
| KISS1R | 698 | 23.99 | 265 | 14.74 |
| KISS1R | 698 | 23.99 | 266 | 16.42 |
| KISS1R | 698 | 23.99 | 267 | 4.30 |
| KISS1R | 698 | 23.99 | 268 | 5.23 |
| KISS1R | 698 | 23.99 | 269 | 14.10 |
| KISS1R | 699 | 76.87 | 270 | 4.08 |
| KISS1R | 699 | 76.87 | 271 | 4.99 |
| KISS1R | 699 | 76.87 | 272 | 8.08 |
| KISS1R | 699 | 76.87 | 273 | 13.54 |
| KISS1R | 699 | 76.87 | 274 | 9.53 |
| KISS1R | 699 | 76.87 | 275 | 5.96 |
| KISS1R | 699 | 76.87 | 276 | 23.28 |
| KISS1R | 699 | 76.87 | 277 | 4.61 |
| KISS1R | 699 | 76.87 | 278 | 25.31 |
| KISS1R | 699 | 76.87 | 279 | 13.98 |
| KISS1R | 699 | 76.87 | 280 | 4.72 |
| KISS1R | 699 | 76.87 | 281 | 9.40 |
| KISS1R | 699 | 76.87 | 282 | 32.74 |
| KISS1R | 699 | 76.87 | 283 | 16.73 |
| KISS1R | 699 | 76.87 | 284 | 72.01 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| KISS1R | 699 | 76.87 | 285 | 6.18 |
| KISS1R | 699 | 76.87 | 286 | 20.88 |
| KISS1R | 699 | 76.87 | 287 | 18.73 |
| KLHDC8A | 700 | 35.26 | 288 | 3.46 |
| KLHDC8A | 701 | 172.00 | 289 | 35.47 |
| KLHL14 | 702 | 17.84 | 290 | 7.70 |
| KLHL14 | 703 | 34.68 | 291 | 8.63 |
| KLHL14 | 704 | 77.24 | 292 | 16.82 |
| KLK4 | 705 | 270.66 | 293 | 10.04 |
| KLK4 | 705 | 270.66 | 294 | 19.56 |
| KLK4 | 705 | 270.66 | 295 | 15.44 |
| KLK4 | 705 | 270.66 | 296 | 38.82 |
| KRT81 | 706 | 21.85 | 297 | 10.20 |
| LEMD1 | 707 | 136.71 | 298 | 15.87 |
| LEMD1 | 708 | 88.07 | 299 | 25.93 |
| LRRC15 | 709 | 82.50 | 300 | 6.46 |
| LRRC15 | 710 | 1001.18 | 301 | 21.72 |
| LRRC15 | 711 | 259.30 | 302 | 9.78 |
| LRRC15 | 712 | 258.37 | 303 | 11.59 |
| LRRC15 | 712 | 258.37 | 304 | 7.37 |
| LRRC15 | 712 | 258.37 | 305 | 18.92 |
| LRRC15 | 713 | 145.27 | 306 | 22.64 |
| LRRC15 | 713 | 145.27 | 307 | 13.47 |
| MAGEA1 | 714 | 165.35 | 308 | 20.56 |
| MAGEA1 | 858 | 59.75 | 309 | 17.40 |
| MAGEA10 | 715 | 94.39 | 310 | 7.76 |
| MAGEA10 | 715 | 94.39 | 311 | 32.14 |
| MAGEA10 | 716 | 98.71 | 312 | 17.05 |
| MAGEA10 | 716 | 98.71 | 313 | 15.58 |
| MAGEA11 | 717 | 102.07 | 314 | 43.72 |
| MAGEA11 | 718 | 455.06 | 315 | 13.01 |
| MAGEA11 | 719 | 324.53 | 316 | 4.07 |
| MAGEA11 | 719 | 324.53 | 317 | 7.58 |
| MAGEA11 | 720 | 27.38 | 318 | 9.42 |
| MAGEA12 | 721 | 243.84 | 319 | 9.58 |
| MAGEA4 | 722 | 257.20 | 320 | 12.43 |
| MAGEA4 | 723 | 60.75 | 321 | 5.71 |
| MAGEA4 | 724 | 16.67 | 322 | 4.57 |
| MLANA | 725 | 114.10 | 323 | 5.47 |
| MLANA | 725 | 114.10 | 324 | 20.46 |
| MLANA | 725 | 114.10 | 325 | 9.29 |
| MLANA | 725 | 114.10 | 326 | 15.44 |
| MLANA | 725 | 114.10 | 327 | 20.04 |
| MLANA | 725 | 114.10 | 328 | 19.83 |
| MLANA | 725 | 114.10 | 329 | 5.48 |
| MLANA | 725 | 114.10 | 330 | 21.30 |
| MLANA | 725 | 114.10 | 331 | 9.05 |
| MLANA | 725 | 114.10 | 332 | 19.05 |
| MLANA | 725 | 114.10 | 333 | 32.71 |
| MLANA | 725 | 114.10 | 334 | 26.26 |
| NKX2-1 | 726 | 138.71 | 335 | 5.30 |
| NKX2-1 | 727 | 54.26 | 336 | 3.57 |
| NKX2-1 | 727 | 54.26 | 337 | 2.92 |
| NKX2-1 | 727 | 54.26 | 338 | 31.31 |
| NKX2-1 | 727 | 54.26 | 339 | 16.53 |
| NKX2-1 | 727 | 54.26 | 340 | 32.65 |
| NPTX2 | 728 | 23.10 | 341 | 9.27 |
| NPTX2 | 728 | 23.10 | 342 | 10.16 |
| NPTX2 | 728 | 23.10 | 343 | 17.81 |
| NPTX2 | 728 | 23.10 | 344 | 11.59 |
| NPTX2 | 729 | 39.51 | 345 | 18.64 |
| NPTX2 | 729 | 39.51 | 346 | 8.01 |
| NPTX2 | 729 | 39.51 | 347 | 7.87 |
| NPTX2 | 729 | 39.51 | 348 | 5.76 |
| NPTX2 | 730 | 106.32 | 349 | 12.85 |
| NPTX2 | 731 | 268.65 | 350 | 34.09 |
| NPTX2 | 732 | 408.67 | 351 | 25.81 |
| PAGE3 | 733 | 379.62 | 352 | 8.32 |
| PAGE3 | 733 | 379.62 | 353 | 19.22 |
| PAGE3 | 733 | 379.62 | 354 | 16.27 |
| PAX2 | 734 | 99.81 | 355 | 5.65 |
| PAX2 | 734 | 99.81 | 356 | 11.74 |
| PAX2 | 734 | 99.81 | 357 | 26.27 |
| PAX2 | 734 | 99.81 | 358 | 19.79 |
| PCDHB16 | 735 | 205.70 | 359 | 7.64 |
| PCDHB16 | 736 | 53.23 | 360 | 23.60 |
| PCDHB16 | 737 | 413.71 | 361 | 25.77 |
| PCDHB16 | 738 | 234.89 | 362 | 50.41 |
| PCDHB16 | 738 | 234.89 | 363 | 97.85 |
| PCDHB16 | 738 | 234.89 | 364 | 6.18 |
| PCDHB16 | 739 | 452.03 | 365 | 5.49 |
| PIWIL1 | 740 | 51.24 | 366 | 16.50 |
| PMEL | 741 | 40.34 | 367 | 9.19 |
| PMEL | 742 | 483.91 | 368 | 17.06 |
| PMEL | 742 | 483.91 | 369 | 101.71 |
| PMEL | 742 | 483.91 | 370 | 29.33 |
| PMEL | 742 | 483.91 | 371 | 31.31 |
| PMEL | 742 | 483.91 | 372 | 79.31 |
| PMEL | 742 | 483.91 | 373 | 73.91 |
| PMEL | 743 | 27.82 | 374 | 13.22 |
| PMEL | 743 | 27.82 | 375 | 20.06 |
| PMEL | 744 | 322.67 | 376 | 35.49 |
| PMEL | 745 | 146.77 | 377 | 10.60 |
| PMEL | 745 | 146.77 | 378 | 17.17 |
| PMEL | 746 | 226.06 | 379 | 21.42 |
| PRAME | 747 | 282.46 | 380 | 14.96 |
| PRAME | 747 | 282.46 | 381 | 11.11 |
| PRAME | 748 | 8.33 | 382 | 2.65 |
| PRAME | 748 | 8.33 | 383 | 3.77 |
| PRAME | 748 | 8.33 | 384 | 4.71 |
| PRAME | 748 | 8.33 | 385 | 3.34 |
| PRAME | 749 | 175.38 | 386 | 46.71 |
| PRAME | 750 | 626.66 | 387 | 7.06 |
| PTHLH | 751 | 47.35 | 388 | 9.23 |
| SEMG1 | 752 | 43.54 | 389 | 15.12 |
| SEMG1 | 752 | 43.54 | 390 | 15.08 |
| SEMG1 | 752 | 43.54 | 391 | 30.58 |
| SEMG1 | 752 | 43.54 | 392 | 28.77 |
| SEMG1 | 752 | 43.54 | 393 | 29.87 |
| SEMG1 | 752 | 43.54 | 394 | 13.74 |
| SEMG1 | 752 | 43.54 | 395 | 24.69 |
| SEMG1 | 752 | 43.54 | 396 | 23.53 |
| SEMG1 | 752 | 43.54 | 397 | 34.57 |
| SEMG1 | 753 | 306.98 | 398 | 44.52 |
| SEMG1 | 753 | 306.98 | 399 | 83.94 |
| SEMG1 | 754 | 58.73 | 400 | 9.85 |
| SERHL2 | 755 | 125.11 | 401 | 21.05 |
| SERHL2 | 756 | 238.87 | 402 | 3.98 |
| SERHL2 | 757 | 133.08 | 403 | 20.14 |
| SERHL2 | 757 | 133.08 | 404 | 17.25 |
| SERHL2 | 758 | 125.30 | 405 | 69.45 |
| SLC45A3 | 759 | 13.80 | 406 | 4.22 |
| SLC45A3 | 760 | 528.37 | 407 | 111.79 |
| SLC45A3 | 760 | 528.37 | 408 | 51.45 |
| SLC45A3 | 761 | 119.20 | 409 | 38.29 |
| SLC45A3 | 762 | 11.94 | 410 | 2.83 |
| SLC45A3 | 763 | 963.46 | 411 | 17.62 |
| SLC45A3 | 764 | 37.99 | 412 | 7.52 |
| SLC45A3 | 764 | 37.99 | 413 | 26.14 |
| SLC45A3 | 764 | 37.99 | 414 | 4.86 |
| SLC45A3 | 764 | 37.99 | 415 | 10.47 |
| SLC45A3 | 765 | 147.42 | 416 | 29.12 |
| SLC45A3 | 765 | 147.42 | 417 | 21.68 |
| SLC45A3 | 766 | 53.08 | 418 | 20.75 |
| SLC45A3 | 767 | 29.75 | 419 | 7.15 |
| SLC45A3 | 767 | 29.75 | 420 | 7.33 |
| SLC45A3 | 767 | 29.75 | 421 | 5.53 |
| SLC45A3 | 767 | 29.75 | 422 | 3.97 |
| SLC45A3 | 767 | 29.75 | 423 | 2.84 |
| SLC45A3 | 768 | 166.51 | 424 | 14.86 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| SLC45A3 | 769 | 127.11 | 425 | 7.72 |
| SLC45A3 | 769 | 127.11 | 426 | 15.75 |
| SLC45A3 | 770 | 655.74 | 427 | 46.76 |
| SLC6A3 | 771 | 38.06 | 428 | 22.35 |
| SLC6A3 | 771 | 38.06 | 429 | 11.72 |
| SLC6A3 | 771 | 38.06 | 430 | 17.36 |
| SLC6A3 | 772 | 54.47 | 431 | 15.80 |
| SLC6A3 | 772 | 54.47 | 432 | 16.20 |
| SLC6A3 | 773 | 13.67 | 433 | 6.53 |
| SLC6A3 | 774 | 197.36 | 434 | 8.04 |
| SLC6A3 | 775 | 10.25 | 435 | 5.46 |
| SLC6A3 | 775 | 10.25 | 436 | 3.85 |
| SLC6A3 | 776 | 674.92 | 437 | 7.48 |
| SLC6A3 | 777 | 77.72 | 438 | 11.66 |
| SLC6A3 | 777 | 77.72 | 439 | 9.25 |
| SLC6A3 | 778 | 64.33 | 440 | 39.26 |
| SLC6A3 | 779 | 39.85 | 441 | 15.82 |
| SNX31 | 780 | 107.98 | 442 | 11.01 |
| SOX11 | 781 | 250.95 | 443 | 34.11 |
| SOX11 | 781 | 250.95 | 444 | 4.54 |
| SOX11 | 781 | 250.95 | 445 | 3.62 |
| SOX17 | 782 | 45.00 | 446 | 13.91 |
| SOX17 | 783 | 628.41 | 447 | 64.48 |
| SOX17 | 783 | 628.41 | 448 | 20.94 |
| SOX17 | 783 | 628.41 | 449 | 80.99 |
| SPINK1 | 784 | 683.89 | 450 | 62.86 |
| STEAP1 | 785 | 294.89 | 451 | 4.18 |
| STEAP1 | 786 | 46.06 | 452 | 15.04 |
| STEAP1 | 787 | 220.39 | 453 | 7.44 |
| STEAP1 | 788 | 549.08 | 454 | 49.18 |
| STEAP1 | 788 | 549.08 | 455 | 11.72 |
| STEAP1 | 788 | 549.08 | 456 | 5.65 |
| STEAP1 | 788 | 549.08 | 457 | 43.68 |
| STEAP1 | 789 | 27.88 | 458 | 10.31 |
| STEAP1 | 789 | 27.88 | 459 | 13.27 |
| STEAP1 | 789 | 27.88 | 460 | 5.52 |
| STEAP1 | 790 | 43.73 | 461 | 12.06 |
| STEAP1 | 791 | 11.48 | 462 | 3.54 |
| STEAP1 | 792 | 114.85 | 463 | 71.35 |
| STEAP1 | 792 | 114.85 | 464 | 45.04 |
| STEAP1 | 792 | 114.85 | 465 | 24.30 |
| STEAP1 | 793 | 17.41 | 466 | 5.58 |
| STEAP1 | 794 | 108.68 | 467 | 14.56 |
| STEAP1 | 794 | 108.68 | 468 | 38.72 |
| TBL1Y | 795 | 266.17 | 469 | 47.46 |
| TBL1Y | 795 | 266.17 | 470 | 24.18 |
| TDRD1 | 796 | 25.66 | 471 | 9.56 |
| TDRD1 | 797 | 39.35 | 472 | 8.52 |
| TDRD1 | 798 | 49.63 | 473 | 23.68 |
| TDRD1 | 799 | 518.24 | 474 | 9.97 |
| TOP2A | 800 | 111.32 | 475 | 14.85 |
| TOP2A | 801 | 8.69 | 476 | 3.98 |
| TOP2A | 801 | 8.69 | 477 | 4.60 |
| TOP2A | 801 | 8.69 | 478 | 2.56 |
| TOP2A | 802 | 209.11 | 479 | 16.24 |
| TOP2A | 802 | 209.11 | 480 | 8.73 |
| TOP2A | 803 | 13.42 | 481 | 7.20 |
| TOP2A | 804 | 22.95 | 482 | 4.92 |
| TOP2A | 805 | 9.84 | 483 | 7.56 |
| TPTE | 806 | 463.88 | 484 | 4.68 |
| TPTE | 806 | 463.88 | 485 | 3.96 |
| TPTE | 806 | 463.88 | 486 | 6.26 |
| TPTE | 806 | 463.88 | 487 | 13.78 |
| TPTE | 806 | 463.88 | 488 | 11.78 |
| TPTE | 806 | 463.88 | 489 | 15.72 |
| TPTE | 806 | 463.88 | 490 | 6.82 |
| TPTE | 807 | 288.31 | 491 | 4.57 |
| TPTE | 807 | 288.31 | 492 | 5.24 |
| TPTE | 807 | 288.31 | 493 | 5.23 |
| TPTE | 807 | 288.31 | 494 | 8.96 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| TPTE | 808 | 48.59 | 495 | 8.16 |
| TPTE | 808 | 48.59 | 496 | 14.63 |
| TPTE | 808 | 48.59 | 497 | 12.62 |
| TPTE | 809 | 51.09 | 498 | 10.30 |
| TPTE | 809 | 51.09 | 499 | 7.49 |
| TPTE | 810 | 98.14 | 500 | 13.70 |
| TPTE | 810 | 98.14 | 501 | 44.96 |
| TPTE | 811 | 26.77 | 502 | 5.21 |
| TPTE | 812 | 14.61 | 503 | 5.25 |
| TPTE | 813 | 655.75 | 504 | 29.36 |
| TRPM8 | 814 | 22.11 | 505 | 3.85 |
| TRPM8 | 815 | 6.88 | 506 | 2.87 |
| TRPM8 | 816 | 17.00 | 507 | 8.54 |
| TRPM8 | 817 | 20.72 | 508 | 3.08 |
| TRPM8 | 817 | 20.72 | 509 | 6.82 |
| TRPM8 | 818 | 97.59 | 510 | 16.59 |
| TRPM8 | 819 | 27.88 | 511 | 9.89 |
| TRPM8 | 820 | 396.02 | 512 | 8.37 |
| TRPM8 | 821 | 64.07 | 513 | 24.24 |
| TRPM8 | 821 | 64.07 | 514 | 27.93 |
| TRPM8 | 821 | 64.07 | 515 | 11.79 |
| TRPM8 | 821 | 64.07 | 516 | 18.44 |
| TRPM8 | 822 | 13.38 | 517 | 4.54 |
| TRPM8 | 823 | 80.70 | 518 | 19.78 |
| TYMS | 824 | 17.03 | 519 | 14.15 |
| TYMS | 824 | 17.03 | 520 | 11.59 |
| TYMS | 824 | 17.03 | 521 | 4.57 |
| TYMS | 825 | 104.14 | 522 | 21.32 |
| TYMS | 825 | 104.14 | 523 | 25.31 |
| TYMS | 826 | 10.01 | 524 | 3.45 |
| TYR | 827 | 7.58 | 525 | 3.75 |
| TYR | 827 | 7.58 | 526 | 3.96 |
| TYR | 828 | 89.30 | 527 | 57.36 |
| TYR | 828 | 89.30 | 528 | 20.14 |
| TYR | 828 | 89.30 | 529 | 19.81 |
| TYR | 828 | 89.30 | 530 | 23.50 |
| TYR | 829 | 172.53 | 531 | 3.17 |
| TYR | 830 | 22.89 | 532 | 6.48 |
| TYR | 831 | 454.20 | 533 | 20.88 |
| TYR | 832 | 239.36 | 534 | 18.48 |
| TYR | 833 | 42.36 | 535 | 11.41 |
| TYR | 833 | 42.36 | 536 | 14.65 |
| TYR | 833 | 42.36 | 537 | 16.03 |
| TYR | 833 | 42.36 | 538 | 7.40 |
| TYR | 833 | 42.36 | 539 | 4.75 |
| UPK2 | 834 | 107.50 | 540 | 9.06 |
| UPK2 | 834 | 107.50 | 541 | 12.77 |
| UPK2 | 834 | 107.50 | 542 | 9.19 |
| UPK2 | 835 | 62.49 | 543 | 12.45 |
| UPK2 | 836 | 46.89 | 544 | 42.83 |
| UPK2 | 836 | 46.89 | 545 | 10.01 |
| UPK2 | 836 | 46.89 | 546 | 10.53 |
| UPK2 | 836 | 46.89 | 547 | 7.26 |
| UPK2 | 837 | 27.00 | 548 | 12.89 |
| UPK2 | 837 | 27.00 | 549 | 6.74 |
| UPK2 | 838 | 366.36 | 550 | 54.32 |
| UPK2 | 839 | 210.79 | 551 | 22.97 |
| UPK2 | 839 | 210.79 | 552 | 16.83 |
| UPK2 | 839 | 210.79 | 553 | 26.98 |
| UPK2 | 839 | 210.79 | 554 | 17.24 |
| UPK2 | 840 | 50.83 | 555 | 16.79 |
| UPK2 | 840 | 50.83 | 556 | 14.52 |
| VCAM1 | 841 | 612.18 | 557 | 32.28 |
| VCAM1 | 842 | 97.02 | 558 | 4.32 |
| VCAM1 | 843 | 593.47 | 559 | 3.12 |
| VCAM1 | 844 | 207.18 | 560 | 5.51 |
| WFDC2 | 845 | 397.49 | 561 | 4.56 |
| WFDC2 | 845 | 397.49 | 562 | 5.04 |
| WFDC2 | 845 | 397.49 | 563 | 7.54 |
| WFDC2 | 845 | 397.49 | 564 | 8.54 |

TABLE 2-continued

In silico prediction of peptide-MHC class I binding.

| Tumor antigen | SEQ ID NO. human reference peptide | Binding affinity prediction human reference peptide (nM) | SEQ ID NO. antigenic peptide | Binding affinity prediction antigenic peptide (nM) |
|---|---|---|---|---|
| WFDC2 | 845 | 397.49 | 565 | 39.96 |
| WFDC2 | 846 | 10.86 | 566 | 4.19 |
| WFDC2 | 847 | 265.28 | 567 | 50.35 |
| WFDC2 | 847 | 265.28 | 568 | 114.90 |
| WT1 | 848 | 450.86 | 569 | 3.26 |
| ZEB1 | 849 | 44.34 | 570 | 9.16 |
| ZEB1 | 849 | 44.34 | 571 | 10.63 |
| ZEB1 | 850 | 246.22 | 572 | 7.49 |
| ZEB1 | 850 | 246.22 | 573 | 30.71 |
| ZEB1 | 851 | 58.11 | 574 | 20.17 |
| ZNF165 | 852 | 107.27 | 575 | 4.35 |
| ZNF165 | 852 | 107.27 | 576 | 11.00 |
| ZNF165 | 852 | 107.27 | 577 | 18.48 |
| ZNF165 | 853 | 375.88 | 578 | 29.16 |
| ZNF280A | 854 | 88.70 | 579 | 7.54 |
| ZNF280A | 855 | 340.56 | 580 | 2.32 |

A comparison between the binding affinity predicted for each antigenic peptide according to the invention and for the human reference peptide reveals a superior binding affinity of the antigenic peptide according to the present invention.

Example 2: Antigenic Peptides have Superior Affinity to the HLA-A*0201 Allele Next, binding affinity of various selected antigenic peptides and of the corresponding fragments of human tumor antigens (human reference peptides) to the HLA-A*0201 allele was confirmed in vitro. Namely, the antigenic peptides of sequence SEQ ID NO: 32 (<<FMLGEFLKL>> also referred herein as BIRC5-B31); SEQ ID NO: 30 (<<YTLGEFLYI>> also referred herein as BIRC5-1B2); and SEQ ID NO: 31 (<<GLLGEFLQI> also referred herein as BLRC5-B33) were compared to the corresponding reference human peptides derived from BIRC5 (<<LTLGEFLKL>> SEQ ID NO: 593, also referred herein as BIRC5-H). Moreover, antigenic peptides of sequence SEQ ID NO: 97 (<<LLLSAALSV>> also referred herein as CHI3L1B); and SEQ ID NO: 87 (<<YLLSAALTI>> also referred herein as CHI3L1B3) were compared to the corresponding reference human peptide derived from CHI3L1 (<<LLLSAALSA>>, SEQ ID NO: 617, also referred herein as CHI3L1H). Moreover, the antigenic peptide of sequence SEQ ID NO: 145 (<<ILDEAYVRV>> also referred herein as EGFR-B) was compared to the corresponding reference human peptide derived from EGFR (<<ILDEAYVMA>>, SEQ ID NO: 637, also referred herein as EGFR-H). Moreover, the antigenic peptides of sequence SEQ ID NO: 193 (<<FLVEDETVI>> also referred herein as EZH2-B) and sequence SEQ ID NO: 194 (<<AVFRVLIPV>> also referred herein as EZH2-B2) were compared to the corresponding reference human peptides derived from EZH2 (<<FMVEDETVL>>, SEQ ID NO: 659, also referred herein as EZH2-H and <<SMFRVLIGT>>, SEQ ID NO: 660, also referred herein as EZH2-H2, respectively). Moreover, the antigenic peptides of sequence SEQ ID NO: 221 (<<RLSSYLVEI>> also referred herein as FOXM1-B) and sequence SEQ ID NO: 220 (<<LMDLSTTEV>> also referred herein as FOXM1-B2) were compared to the corresponding reference human peptides derived from FOXM1 (<<RVSSYLVPI>>, SEQ ID NO: 675, also referred herein as FOXM1-H and <<LMDLSTTPL>>, SEQ ID NO: 674, also referred herein as FOXM1-H2, respectively). Moreover, the antigenic peptides of sequence SEQ ID NO: 254 (<<FLPFGFILV>> also referred herein as IL13RA2-B) and sequence SEQ ID NO: 255 (<<FLPFGFILPV>> also referred herein as IL13RA2-L) were compared to the corresponding reference human peptide derived from IL13RA2 (<<WLPFGFILI>>, SEQ ID NO: 691, also referred herein as IL13RA2-H). Moreover, the antigenic peptides of sequence SEQ ID NO: 524 (<<SMEELLWFV>> also referred herein as TYMS-B) and sequence SEQ ID NO: 521 (<<FLDSLGFSL>> also referred herein as TYMS-B2) were compared to the corresponding reference human peptides derived from TYMS (<<VLEELLWFL>>, SEQ ID NO: 826, also referred herein as TYMS-H, and <<FLDSLGFST>>, SEQ ID NO: 824, also referred herein as TYMS-H2, respectively).

A. Materials and Methods

A1. Measuring the Affinity of the Peptide to T2 Cell Line.

The experimental protocol is similar to the one that was validated for peptides presented by the HLA-A*0201 (Tourdot et al., A general strategy to enhance immunogenicity of low-affinity HLA-A2.1-associated peptides: implication in the identification of cryptic tumor epitopes. Eur J Immunol. 2000 Dee; 30(12):3411-21). Affinity measurement of the peptides is achieved with the human tumoral cell T2 which expresses the HLA-A*0201 molecule, but which is TAP1/2 negative and incapable of presenting endogenous peptides.

T2 cells ($2 \cdot 10^5$ cells per well) are incubated with decreasing concentrations of peptides from 100 μM to 1.5625 μM in a AIMV medium supplemented with 100 ng/l of human β2m at 37° C. for 16 hours. Cells are then washed two times and marked with the anti-HLA-A2 antibody coupled to PE (clone BB7.2, BD Pharmagen).

The analysis is achieved by FACS (Guava Easy Cyte).

For each peptide concentration, the geometric mean of the labelling associated with the peptide of interest is subtracted from background noise and reported as a percentage of the geometric mean of the HLA-A*0202 labelling obtained for the reference peptide HIV pol 589-597 at a concentration of 100 μM. The relative affinity is then determined as follows:

relative affinity=concentration of each peptide inducing 20% of expression of HLA-A*0201/concentration of the reference peptide inducing 20% of expression of HLA-A*0201.

A2. Solubilisation of Peptides

Each peptide is solubilized by taking into account the amino acid composition. For peptides which do not include any Cystein, Methionin, or Tryptophane, the addition of DMSO is possible to up to 10% of the total volume. Other peptides are resuspended in water or PBS pH7.4.

B. Results

The mean relative fluorescence intensity values (data are normalized to the mean fluorescence of HIV peptide, i.e. a value of 100 is equal to the best binding observed with HIV peptide) of T2 cells obtained for the various concentrations of each peptide are shown in Table 3 below:

TABLE 3

| Peptide | | Peptide concentration (µM) | | | | | |
|---|---|---|---|---|---|---|---|
| Name | SEQ ID NO. | 100 | 50 | 25 | 6.25 | 3.125 | 1.5625 |
| BIRC5-H | 593 | 35.6 | 18.9 | 9.8 | 10.8 | 1.4 | 1.7 |
| BIRC5-B1 | 32 | 117.0 | 77.1 | 61.7 | 36.1 | 22.3 | 1.9 |
| BIRC5-B2 | 30 | 58.0 | 54.4 | 29.6 | 9.0 | 6.6 | nd |
| BIRC5-B3 | 31 | 35.0 | 29.8 | 20.9 | nd | 8.9 | 9.4 |
| CHI3L1 H | 617 | 11.2 | 14.5 | 4.9 | 4.4 | 1.0 | −1.9 |
| CHI3L1 B | 97 | 58.9 | 85.0 | 45.3 | 44.0 | 23.9 | 13.5 |
| CHI3L1 B3 | 87 | 76.9 | 108.0 | 36.7 | 30.2 | 14.3 | 2.5 |
| EGFR-H | 637 | 87.4 | 107.4 | 91.5 | 33.7 | 28.6 | 12.0 |
| EGFR-B | 145 | 70.3 | 66.7 | 53.2 | 29.2 | 22.7 | 12.7 |
| EZH2-H | 659 | 95.4 | 66.0 | 40.7 | 10.6 | 0.7 | 0.0 |
| EZH2-B | 193 | 94.9 | 82.6 | 53.9 | 28.9 | 14.4 | 5.5 |
| EZH2-H2 | 660 | 78.2 | nd | 13.3 | 0.0 | 0.0 | 0.0 |
| EZH2-B2 | 194 | 112.4 | nd | 74.8 | 0.5 | 0.0 | 0.0 |
| FOXM1-H | 675 | 83.8 | 30.7 | 10.5 | 0.0 | 0.0 | 0.0 |
| FOXM1-B | 221 | 47.5 | 21.3 | 7.6 | 0.0 | 0.0 | 0.0 |
| FOXM1-H2 | 674 | 77.6 | 62.5 | 65.4 | 19.7 | 0.9 | 5.3 |
| FOXM1-B2 | 220 | 105.0 | 91.5 | 98.2 | 33.5 | 12.7 | 7.2 |
| IL13RA2-H | 691 | 26.5 | 14.2 | 11.2 | 9.6 | 3.7 | 3.0 |
| IL13RA2-B | 254 | 128.4 | 112.7 | 86.5 | 40.8 | 15.7 | 14.8 |
| IL13RA2-L | 255 | 107.7 | 85.5 | 77.3 | 30.4 | 19.8 | 13.3 |
| TYMS H | 826 | 50.2 | 40.4 | 38.1 | 26.6 | 15.3 | 8.6 |
| TYMS B | 524 | 80.9 | 65.7 | 49.3 | 36.0 | 30.4 | 15.9 |
| TYMS H2 | 824 | 50.6 | 37.2 | 32.5 | 6.1 | 4.5 | 1.6 |
| TYMS B2 | 521 | 71.3 | 62.0 | 61.1 | 27.5 | 21.5 | 10.7 |

Table 4 below summarizes for each tested peptide the concentration required to induce 20% of HLA-A2 expression and the in vitro binding affinity.

TABLE 4

| Peptide | SEQ ID NO | Concentration of peptide that induces 20% of HLA-A2 expression (µM) | In vitro binding affinity |
|---|---|---|---|
| BIRC5-H | 593 | 53.0 | 16.1 |
| BIRC5-B1 | 32 | 2.7 | 0.8 |
| BIRC5-B2 | 30 | 14.7 | 4.5 |
| BIRC5-B3 | 31 | 22.9 | 7.0 |
| CHI3L1 H | 617 | ND | ND |
| CHI3L1 B | 97 | 3.6 | 0.9 |
| CHI3L1 B3 | 87 | 8.6 | 2.2 |
| EGFR-H | 637 | 2.8 | 0.2 |
| EGFR-B | 145 | 3.1 | 0.2 |
| EZH2-H | 659 | 13.3 | 1.1 |
| EZH2-B | 193 | 8.8 | 0.7 |
| EZH2-H2 | 660 | 39.2 | 7.8 |
| EZH2-B2 | 194 | 8.3 | 1.7 |
| FOXM1-H | 675 | 37.6 | 3.7 |
| FOXM1-B | 221 | 46.7 | 4.6 |
| FOXM1-H2 | 674 | 12.6 | 2.5 |
| FOXM1-B2 | 220 | 6.7 | 1.3 |
| IL13RA2-H | 691 | ND | ND |
| IL13RA2-B | 254 | 2.9 | 0.3 |
| IL13RA2-L | 255 | 3.2 | 0.3 |
| TYMS H | 826 | 4.1 | 0.3 |
| TYMS B | 524 | 1.1 | 0.1 |
| TYMS H2 | 824 | 9.5 | 0.8 |
| TYMS B2 | 521 | 2.7 | 0.2 |

ND—not determined

Figure 6:
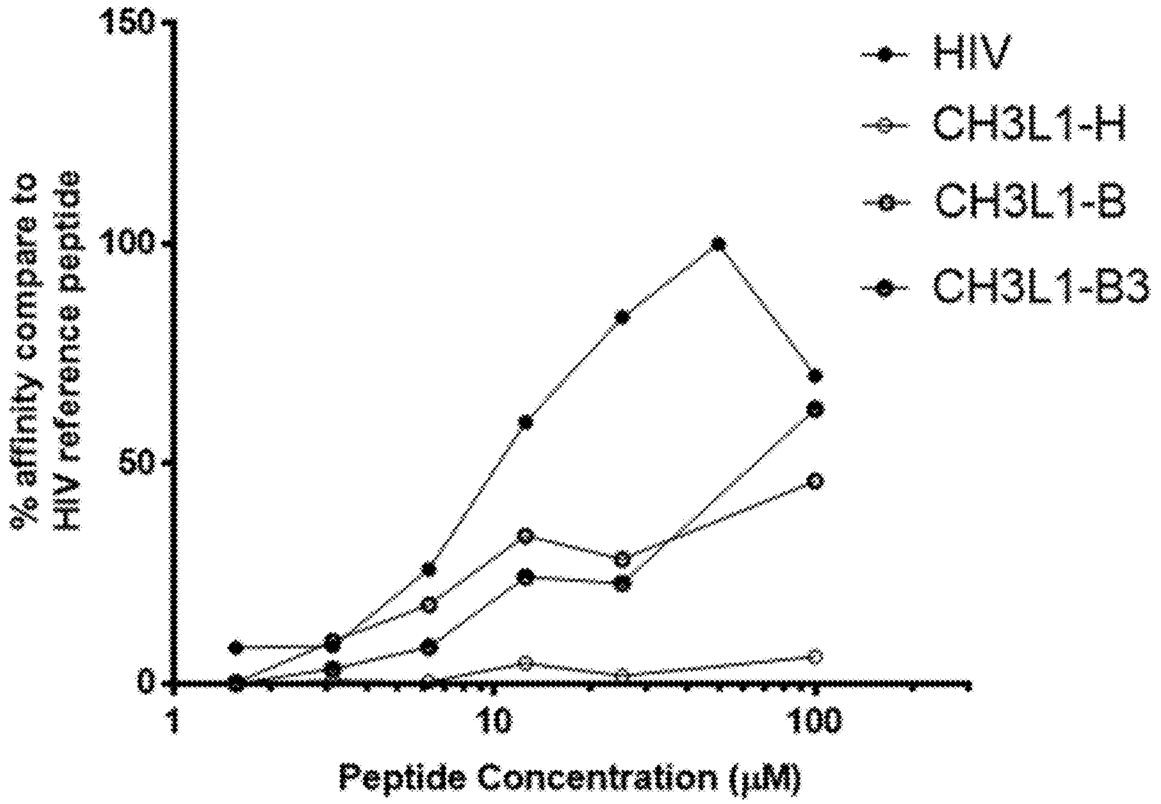
FIG. 6: shows for Example 2 in vitro affinity for antigenic peptides CHI3L1-B and CHI3L1-B3 in comparison to the corresponding human CHI3L1 epitope CHI3L1-H.

In addition, FIGS. 1-6 illustrate the results for selected examples, namely for antigenic peptides IL13RA2-B and IL13RA2-L in comparison to the corresponding human IL13RA2 fragment IL13RA2-H (FIG. 1), for antigenic peptides BIRC5-B1, BIRC5-B2 and BIRC5-B3 in comparison to the corresponding human BIRC5 fragment BIRC5-H (FIG. 2), for antigenic peptide EZH2-B in comparison to the corresponding human EZH2 fragment EZH2-H (FIG. 3A) and antigenic peptide EZH2-B2 in comparison to the corresponding human EZH2 fragment EZH2-H2 (FIG. 3B), for antigenic peptide TYMS-B in comparison to the corresponding human TYMS fragment TYMS-H (FIG. 4A) and antigenic peptide TYMS-B2 in comparison to the corresponding human TYMS fragment TYMS-H2 (FIG. 4B), for antigenic peptide FOXM1-B in comparison to the corresponding human FOXM1 fragment FOXM1-H (FIG. 5A) and antigenic peptide FOXM1-B2 in comparison to the corresponding human FOXM1 fragment FOXM1-H2 (FIG. 5B), and for antigenic peptides CHI3L1-B and CHI3L1-B3 in comparison to the corresponding human CHI3L1 fragment CHI3L1-H (FIG. 6).

In summary, the results show that the antigenic peptides according to the present invention show at least similar binding affinity to HLA-A*0201 as the corresponding human tumor antigen fragments. In most cases, the binding affinity observed for the antigenic peptides according to the present invention was stronger than that of the corresponding human epitopes. Without being bound to any theory it is assumed that such a strong binding affinity of the antigenic peptides according to the present invention reflects their ability to raise an immune response (i.e., their immunogenicity).

Example 3: Vaccination of Mice with Antigenic Peptides According to the Present Invention Induces Improved T Cell Responses in ELISPOT-IFNγ Assay

A. Materials and Methods

A.1 Mouse Model

Figure 7:
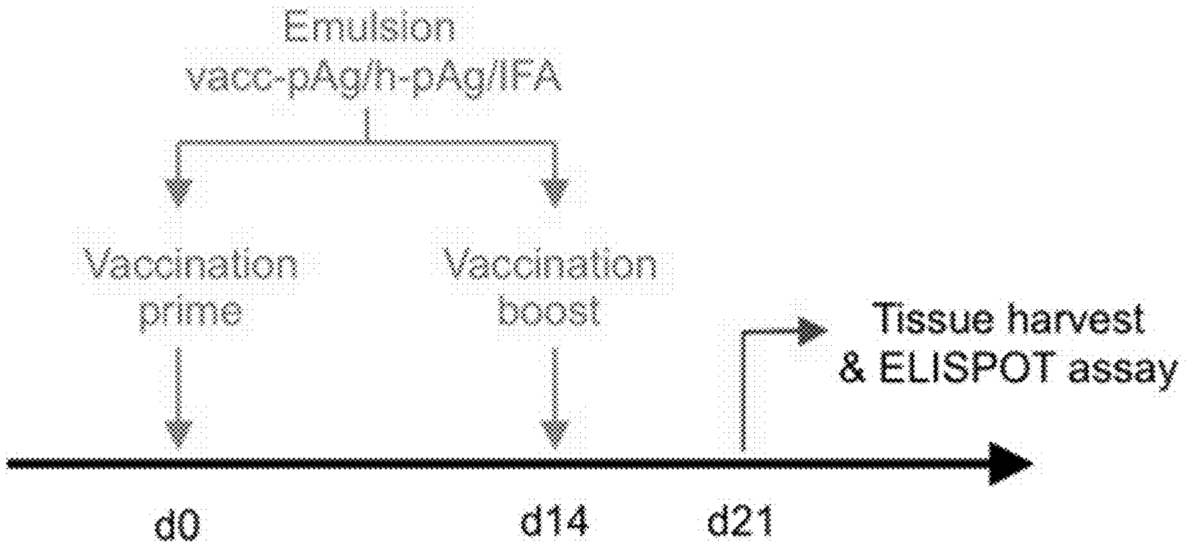
FIG. 7: shows for Example 3 a schematic view of the immunization scheme. d: day.

The immunization scheme is shown in FIG. 7. Briefly, HLA-A2 humanized mice (HLA-A2 (CB6F1-Tg(HLA-A*0201/H2-$K^b$)A*0201) were assigned randomly (based on mouse sex and age) to experimental groups, wherein each group was immunized with a specific vaccination peptide (vacc-pAg) combined to a common helper peptide (h-pAg T13L; sequence: TPPAYRPPNAPIL; SEQ ID NO: 860; Bhasin M, Singh H, Raghava G P (2003) MHCBN: a comprehensive database of MHC binding and non-binding peptides. Bioinformatics 19: 665-666) (as outlined in Table 5 below). The vacc-pAg were compared in couples (group 1 vs. group 2, group 1 vs. group 3: group 1 vs. group 4; group 5 vs. group 6; group 7 vs. group 8; group 9 vs. group 10). Thereby, both native and optimized versions of a single peptide were compared in each wave.

TABLE 5

Experimental group composition. h-pAg: 'helper' peptide; vacc-pAg: vaccination peptide. The number of boost injections is indicated into brackets.

| Group | Peptide (vacc-pAg) | Helper (h-Ag) | Prime | Boost | Animal Number |
|---|---|---|---|---|---|
| 1 | BIRC5-H (100 µg) | T13L (150 µg) | + | +(1X) | 5 |
| 2 | BIRC5-B1 (100 µg) | T13L (150 µg) | + | +(1X) | 5 |
| 3 | BIRC5-B2 (100 µg) | T13L (150 µg) | + | +(1X) | 5 |
| 4 | BIRC5-B3 (100 µg) | T13L (150 µg) | + | +(1X) | 5 |
| 5 | FOXM1-H2 (100 µg) | T13L (150 µg) | + | +(1X) | 5 |
| 6 | FOXMI-B2 (100 µg) | T13L (150 µg) | + | +(1X) | 5 |

TABLE 5-continued

Experimental group composition. h-pAg: 'helper' peptide; vacc-pAg: vaccination peptide. The number of boost injections is indicated into brackets.

| Group | Peptide (vacc-pAg) | Helper (h-Ag) | Prime | Boost | Animal Number |
|---|---|---|---|---|---|
| 7 | EZH2-H2 (100 µg) | T13L (150 µg) | + | +(1X) | 5 |
| 8 | EZH2-B2 (100 µg) | T13L (150 µg) | + | +(1X) | 5 |
| 9 | IL13RA2-H (100 µg) | T13L (150 µg) | + | +(1X) | 5 |
| 10 | IL 13RA2-B (100 µg) | T13L (150 µg) | + | +(1X) | 5 |

The peptides were provided as follows:

vacc-pAg: BIRC5-H, BIRC5-B1, BIRC5-B2, BIRC5-B3, FOXM1-H2, FOXM1-B2, EZH2-H2, EZH2-B2, IL13RA2-H and IL13RA2-B; all produced and provided at a 4 mg/ml (4 mM) concentration;

h-pAg: T13L; Eurogentec batch 1713334 re-suspended in pure distilled water at a 10 mg/mL concentration.

The animals were immunized on day 0 (d0) with a prime injection, and on d14 with a boost injection. Each mouse was injected s.c. at tail base with 100 µL of an oil-based emulsion that contained:

100 µg of vacc-pAg (25 µL of 4 mg/mL stock per mouse);

150 µg of h-pAg (15 µL of 10 mg/mL stock per mouse);

10 µL of PBS to reach a total volume of 50 µL (per mouse);

Incomplete Freund's Adjuvant (IFA) added at 1:1 (v:v) ratio (50 µL per mouse).

A separate emulsion was prepared for each vacc-pAg, as follows: IFA reagent was added to the vacc-pAg/h-pAg/PBS mixture in a 15 mL tube and mixed on vortex for repeated cycles of 1 min until forming a thick emulsion.

A.2 Analysis

Seven days after the boost injection (i.e. on d21), the animals were euthanized and the spleen was harvested. Splenocytes were prepared by mechanical disruption of the organ followed by 70 µm-filtering and Ficoll density gradient purification.

The splenocytes were immediately used in an ELISPOT-IFNγ assay (Table 6). Experimental conditions were repeated in triplicates, using $2*10^5$ total splenocytes per well, and were cultured in presence of vacc-pAg (10 µM), Ionomycin (0.1 µM) plus PMA (1 µM) or medium-only to assess for their capacity to secrete IFNγ. The commercial ELISPOT-IFNγ kit (Diaclone Kit Mujrine IFNγ ELISpot) was used following the manufacturer's instructions, and the assay was performed after about 19 h of incubation.

TABLE 6

Setup of the ELISPOT-IFNγ assay.

| Group | Stimulus | Wells | Animal | Total |
|---|---|---|---|---|
| 1 | BIRC5-H (10 µM) | 3 | 5 | 15 |
| | Ionomycin (0.1 µM) PMA 1 µM) | 3 | 5 | 15 |
| | Medium | 3 | 5 | 15 |
| 2 | BIRC5-B1 (10 µM) | 3 | 5 | 15 |
| | Ionomycin (0.1 µM) PMA 1 µM) | 3 | 5 | 15 |
| | Medium | 3 | 5 | 15 |
| 3 | BIRC5-B2 (10 µM) | 3 | 5 | 15 |
| | Ionomycin (0.1 µM) PMA 1 µM) | 3 | 5 | 15 |
| | Medium | 3 | 5 | 15 |

TABLE 6-continued

Setup of the ELISPOT-IFNγ assay.

| Group | Stimulus | Wells | Animal | Total |
|---|---|---|---|---|
| 4 | BIRC5-B3 (10 µM) | 3 | 5 | 15 |
| | Ionomycin (0.1 µM) PMA 1 µM) | 3 | 5 | 15 |
| | Medium | 3 | 5 | 15 |
| 5 | FOXM1-H2 (10 µM) | 3 | 5 | 15 |
| | Ionomycin (0.1 µM) PMA 1 µM) | 3 | 5 | 15 |
| | Medium | 3 | 5 | 15 |
| 6 | FOXM1-B2 (10 µM) | 3 | 5 | 15 |
| | Ionomycin (0.1 µM) PMA 1 µM) | 3 | 5 | 15 |
| | Medium | 3 | 5 | 15 |
| 7 | EZH2-H2 (10 µM) | 3 | 5 | 15 |
| | Ionomycin (0.1 µM) PMA 1 µM) | 3 | 5 | 15 |
| | Medium | 3 | 5 | 15 |
| 8 | EZH2-B2 (10 µM) | 3 | 5 | 15 |
| | Ionomycin (0.1 µM) PMA 1 µM) | 3 | 5 | 15 |
| | Medium | 3 | 5 | 15 |
| 9 | IL13RA2-H (10 µM) | 3 | 5 | 15 |
| | Ionomycin (0.1 µM) PMA 1 µM) | 3 | 5 | 15 |
| | Medium | 3 | 5 | 15 |
| 10 | IL13RA2-B (10 µM) | 3 | 5 | 15 |
| | Ionomycin (0.1 µM) PMA 1 µM) | 3 | 5 | 15 |
| | Medium | 3 | 5 | 15 |

Spots were counted on a CTL ELISpot reader. Data plotting and statistical analysis were performed with the Prism-5 software (GraphPad Software Inc.).

B. Results

A total of 50 HLA-A2 (CB6F1-Tg(HLA-A*0201/H2-$K^b$) A*0201) mice were used for these experiment. All mice were aged of 6 to 9 weeks at the experiment starting date. Both males and females were used in the study. Animals have been housed in groups of 5 per cage at maximum. At time of sacrifice, the spleen T cell population was analysed by flow cytometry, showing that the large majority belonged to the CD4+ T cell subset.

After plating and incubation with the appropriate stimuli, the IFNγ-producing cells were revealed and counted. The data were then normalized as a number of specific spots (the average counts obtained in the 'medium only' condition being subtracted) per $50*10^3$ total T cells.

Figure 8:
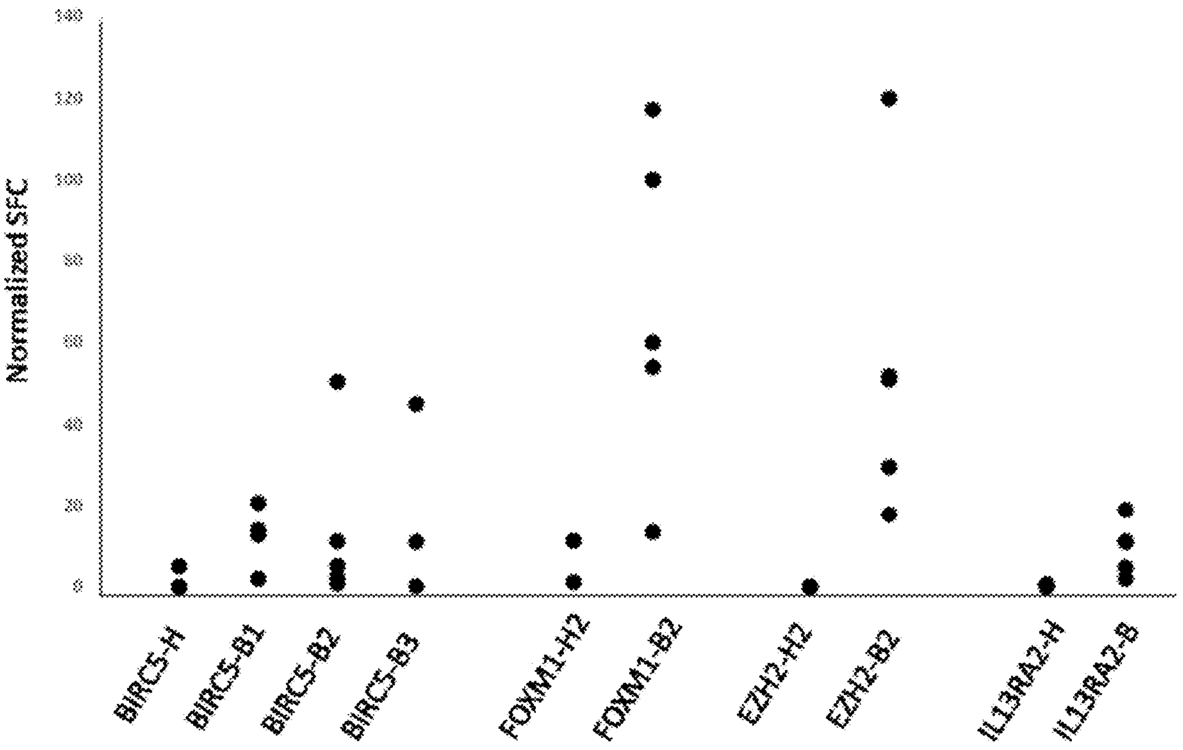
FIG. 8: shows for Example 3 ELISPOT results for mice vaccinated with the antigenic peptides as indicated in the figure (BIRC5-H, BIRC5-B1, BIRC5-B2, BIRC5-B3, FOXM1-H2, FOXM1-B2, EZH2-H2, EZH2-B2, IL13RA2-H, IL13RA2-B. For each group the normalized number of spot-forming cells (SFC) is shown. Each dot represents the average value for one individual/mouse.

The individual average values (obtained from the triplicates) were next used to plot the group average values. As the functional capacity of T cells might vary from individual to individual, the data were also expressed as the percentage of the ionomycin plus PMA response per individual (see FIG. 8).

Overall, vaccination with the antigenic peptides according to the present invention (BIRC5-B1, BIRC5-132, BIRC5-B3, FOXM1-B2, EZH2-B2 and IL13RA2-B) induced improved T cell responses in the ELISPOT-IFNγ assay, as compared to the respective human reference epitopes (BIRC5-H, FOXM1-H2, EZH2-H2 and IL13RA2-H).

Example 4: Immunogenicity of IL13R2A-L in HLA-A2 Transgenic Mice and Cross-Reactivity with the Corresponding Human Peptide

A. Materials and Methods

The antigenic peptide of the present invention 1L13RA2-L (SEQ ID NO: 255) and the corresponding human reference peptide IL13RA2-H (SEQ ID NO: 691) were tested in distinct groups of male and female HHD DR3 mice expressing human HLA-A2 and HLA-DR3 MHC and lacking the murine H-2 class I and class 11 MHCs. Groups of 5 mice (male and female) were subcutaneously injected on days 0 and 14 with 100 μg of IL13RA2-L (SEQ ID NO: 255) or IL13RA2-H (SEQ ID NO: 691), 150 μg of helper peptide (DR3) and IFA. On day 21, the mice were euthanized and splenocytes were prepared and stimulated in vitro with IL13RA2-L or the human corresponding peptide IL13RA2-H to assess their capacity to secrete IFN-γ as assessed by ELISpot. Concanavalin A (ConA) was used as a positive control.

B. Results

Figure 9:
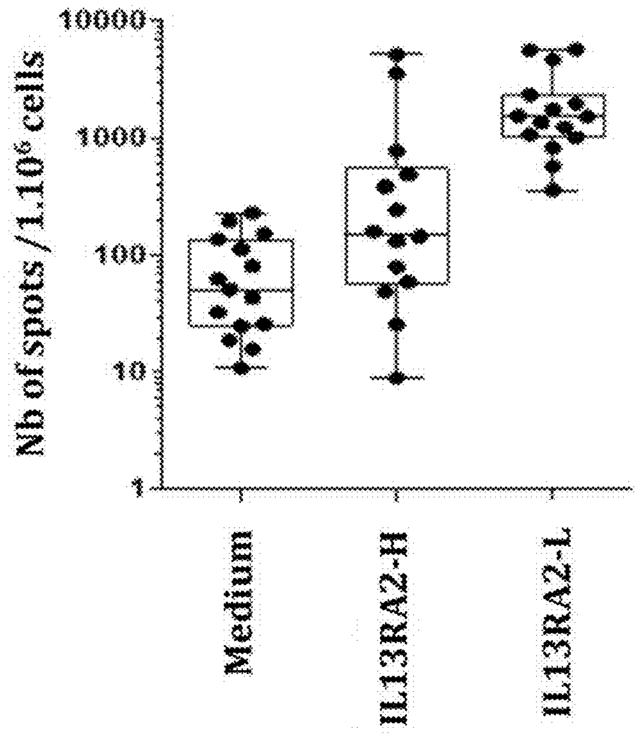
FIG. 9: shows for Example 4 ELISPOT results for HLA-A2 transgenic mice vaccinated with the antigenic peptide IL13R2A-L as indicated in the figure and cross-reactivity with the human corresponding peptide IL13RA2-H. For each group the normalized number of spot-forming cells (SFC) is shown.

The number of spot forming cells (SFC) (normalized to the number of CD8 cells) are depicted in FIG. 9. Results are shown for mice immunized with IL13RA2-L. The results show that immunisation of mice with IL13RA2-L allows to induce T-cells that are able to react strongly after challenge with either IL13RA2-L or the human corresponding peptide. Thus, IL13RA2-L is strongly immunogenic and is able to drive an effective immune response against the corresponding human peptide. As expected, the immunisation of mice with the human corresponding peptide IL13RA2-H does not induce an immune response after challenge with either IL13RA2-L or the human corresponding peptide IL13RA2-H (data not shown).

These results were confirmed in HHD DR1 mice expressing human HLA-A2 and HLA-DR1 MHC and lacking the murine H-2 class I and class II MHCs (groups of 5 mice).

Example 5: Immunogenicity of BIRC5-B1 in HLA-A2 Transgenic Mice and Cross-Reactivity with the Corresponding Human Peptide A. Materials and Methods The antigenic peptide of the invention BIRC5-B1 (SEQ ID NO: 32) and the corresponding human peptide BIRC5-H (SEQ ID NO: 593) were tested in distinct groups of male and female HHD DR3 mice expressing human HLA-A2 and HLA-DR3 MHC and lacking the murine H-2 class I and class II MHCs. Groups of 5 mice (male and female) were subcutaneously injected on days 0 and 14 with 100 μg of BIRC5-B1 or BIRC5-H, 150 μg of helper peptide (DR3) and IFA. On day 21, the mice were euthanized and splenocytes were prepared and stimulated in vitro with BIRC5-B1 or the human peptide BIRC5-H to assess their capacity to secrete IFN-γ as assessed by ELISpot. ConA was used as a positive control.

B. Results

Figure 10:
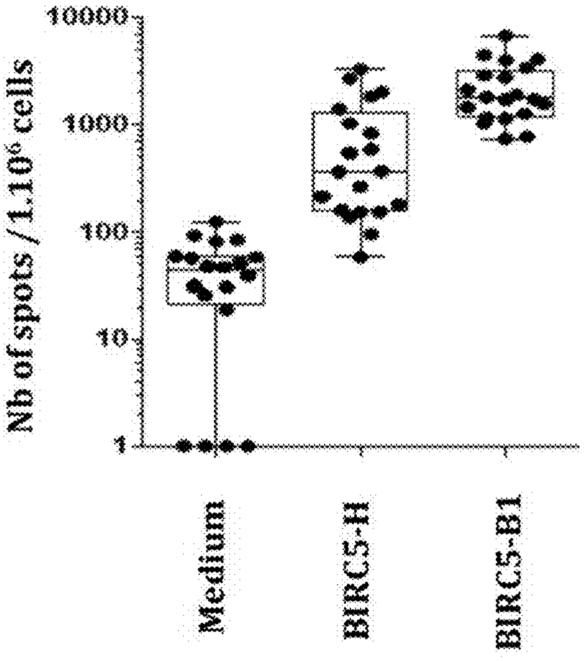
FIG. 10: shows for Example 5 ELISPOT results for HLA-A2 transgenic mice vaccinated with the antigenic peptide BIRC5-B1 as indicated in the figure and cross-reactivity with the human corresponding peptide BIRC5-H. For each group the normalized number of spot-forming cells (SFC) is shown.

The number of SFC (normalized to the number of CD8 cells) are depicted in FIG. 10. Results are shown for mice immunized with BIRC5-B1. The results show that immunisation of mice with BIRC5-B1 allows to induce T-cells that are able to react strongly after challenge with either BIRC5-B1 or the human corresponding peptide BIRC5-H. Thus, BIRC5-B1 is strongly immunogenic and is able to drive an effective immune response against human corresponding peptide. Immunisation of mice with the human corresponding peptide BIRC5-H does not induce any immune response against BIRC5-B1 or the human corresponding peptide (data not shown).

These results were confirmed in HHD DR1 mice expressing human HLA-A2 and HLA-DR1 MHC and lacking the murine H-2 class I and class II MHCs (groups of 5 mice).

Example 6: Immunogenicity of FOXM1-B2 in HLA-A2 Transgenic Mice and Cross-Reactivity with the Corresponding Human Peptide A. Materials and Methods The antigenic peptide of the invention FOXM1-B2 (SEQ ID NO: 220) and the corresponding human peptide FOXM1-H2 (SEQ ID NO: 674) were tested in distinct groups of male and female HHD DR3 mice expressing human HLA-A2 and HLA-DR3 MHC and lacking the murine H-2 class I and class II MHCs. Groups of 5 mice (male and female) were subcutaneously injected on days 0 and 14 with 100 μg of FOXM1-B2 or FOXM1-H2, 150 μg of helper peptide (DR3) and IFA. On day 21, the mice were euthanized and splenocytes were prepared and stimulated in vitro with FOXM1-B2 or the human corresponding peptide FOXM1-H2 to assess their capacity to secrete IFN-γ as assessed by ELISpot. ConA was used as a positive control.

B. Results

Figure 11:
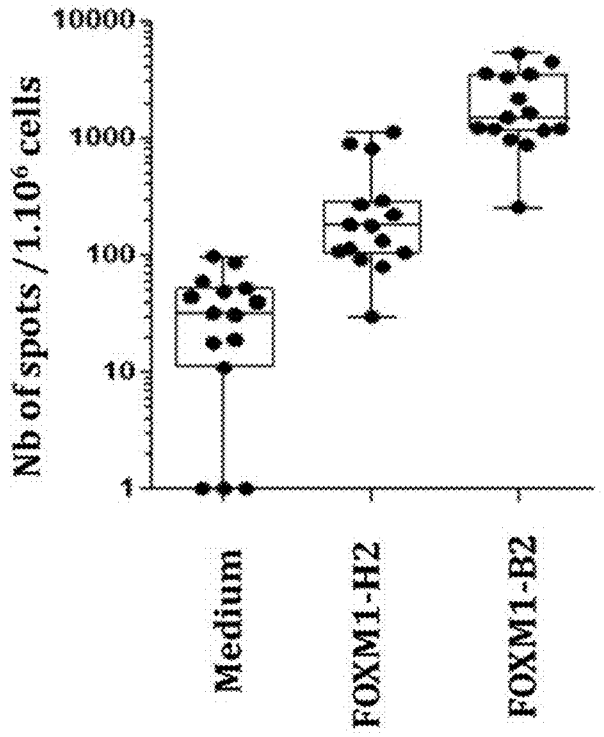
FIG. 11: shows for Example 6 ELISPOT results for HLA-A2 transgenic mice vaccinated with the antigenic peptide FOXM1-B2 as indicated in the figure and cross-reactivity with the human corresponding peptide FOXM1-H2. For each group the normalized number of spot-forming cells (SFC) is shown.

The number of SFC (normalized to the number of CD8 cells) are depicted in FIG. 11. Results are shown for mice immunized with FOXM1-B2. The results show that immunisation of mice with FOXM1-B2 allows to induce T-cells that are able to react strongly after challenge with either FOXM1-B2 or human corresponding peptide. Thus, FOXM1-B2 is strongly immunogenic and is able to drive an effective immune response against human corresponding peptide FOXM1-H2. Immunisation of mice with the human corresponding peptide FOXM1-H2 does not induce immune response against FOXM1-B2 or the human corresponding peptide (data not shown).

These results were confirmed in H4HD DR1 mice expressing human HLA-A2 and HLA-DR1 MHC and lacking the murine H-2 class I and class II MHCs (groups of 5 mice).

Altogether, these immunogenicity studies described in Examples 4 to 6 performed in HHD DR3 and HHD DR1 mice showed that the three antigenic peptides of the invention, IL13RA2-L, BIRC5-B1 and FOXM1-B2, induced strong immune responses. Cross-reactivity of the T cells generated against IL13RA2-L, BIRC5-B1 and FOXM1-B2 for the corresponding human peptides was shown in HHD DR3 and HHD DR1 mice.

Accordingly, those results provide experimental evidence that antigen-based immunotherapy is able to improve T cell response in vivo and that the antigenic peptides according to the present invention are particularly efficient for that purpose.

Example 7: IL13RA2-B has Superior Affinity to the HLA-A*0201 Allele

This Example provides evidence that the antigenic peptide of the invention as set forth in SEQ ID NO: 254 (FLPFGFILV, also referred to herein as IL13RA2-B) has higher affinity to the HLA-A*0201 allele than other sequence variants of the corresponding reference human peptide derived from IL13RA2 (IL13RA2-H, WLPFGFILI, SEQ ID NO: 691). In this experiment, the antigenic peptide of sequence SEQ ID NO: 254 (IL13RA2-B) was compared to the comparative peptide “1A9V” (SEQ ID NO: 896), as described by Eguchi Junichi et al., 2006, Identification of interleukin-13 receptor alpha 2 peptide analogues capable of inducing improved antiglioma CTL responses. Cancer Research 66(11): 5883-5891, in which the tryptophan at position 1 of SEQ ID NO: 691 was substituted by alanine (1A) and the isoleucine at position 9 of SEQ ID NO: 691 was substituted by valine (9V);

peptide "119A" (SEQ ID NO: 897), wherein the tryptophan at position 1 of SEQ ID NO: 691 was substituted by isoleucine (II) and the isoleucine at position 9 of SEQ ID NO: 691 was substituted by alanine (9A); and peptide "1F9M" (SEQ ID NO: 898), wherein the tryptophan at position 1 of SEQ ID NO: 691 was substituted by phenylalanine (1F) and the isoleucine at position 9 of SEQ ID NO: 691 was substituted by methionine (9M).

A. Materials and Methods

The experimental protocol, materials and methods correspond to those outlined in Example 2, with the only difference that the above mentioned (poly)peptides were used.

B. Results

The following in vitro binding affinities were obtained:

TABLE 7

| Peptide | In vitro binding affinity |
|---|---|
| IL13RA2-B (SEQ ID NO: 254) | 0.49 |
| 1A9V (SEQ ID NO: 896) | 3.06 |
| 1I9A (SEQ ID NO: 897) | 2.22 |
| 1F9M (SEQ ID NO: 898) | 2.62 |

Accordingly, the antigenic peptide according to the present invention (IL13RA2-B; SEQ ID NO: 254) showed considerably higher binding affinity to HLA-A*0201 than all other peptides tested, whereas the peptide "1A9V", as described by Eguchi Junichi et al., 2006, Identification of interleukin-13 receptor alpha 2 peptide analogues capable of inducing improved antiglioma CTL responses. Cancer Research 66(11): 5883-5891, showed the lowest affinity of the peptides tested.

Example 8: IL13RA2-L has Superior Affinity to the HLA-A*0201 Allele

This Example provides evidence that the antigenic peptide of the invention as set forth in SEQ ID NO: 255 (also referred to herein as IL13RA2-L) has a similarly high affinity to the HLA-A*0201 allele as the antigenic peptide of the invention as set forth in SEQ ID NO: 254 (FLPFGFILV, also referred to herein as IL13RA2-B)—and a higher affinity than the corresponding reference human peptide derived from IL13RA2 (IL13RA2-H, WLPFGFILI, SEQ ID NO: 691) and other sequence variants thereof. In this experiment, the antigenic peptide of sequence SEQ ID NO: 255 (IL13RA2-L) was compared to the comparative peptide "1A9V" (SEQ ID NO: 896), as described by Eguchi Junichi et al., 2006, Identification of interleukin-13 receptor alpha 2 peptide analogues capable of inducing improved antiglioma CTL responses. Cancer Research 66(11): 5883-5891, in which the tryptophan at position 1 of SEQ ID NO: 691 was substituted by alanine (1A) and the isoleucine at position 9 of SEQ ID NO: 691 was substituted by valine (9V);

the antigenic peptide of the invention as set forth in SEQ ID NO: 254 (IL13RA2-B);

the corresponding reference human peptide IL13RA2-H (SEQ ID NO: 691); and a positive control (HIV).

A. Materials and Methods

The experimental protocol, materials and methods correspond to those outlined in Example 2, with the only difference that the above mentioned (poly)peptides were used.

B. Results

The following in vitro binding affinities were obtained:

TABLE 8

| Peptide | SEQ ID NO | Concentration of peptide that induces 20% of HLA-A2 expression (μM) | In vitro binding affinity |
|---|---|---|---|
| IL13RA2-H | 691 | ND | ND |
| IL13RA2-B | 254 | 2.9 | 0.3 |
| IL13RA2-L | 255 | 3.2 | 0.3 |
| 1A9V | 896 | 36.5 | 3.6 |

Figure 12:
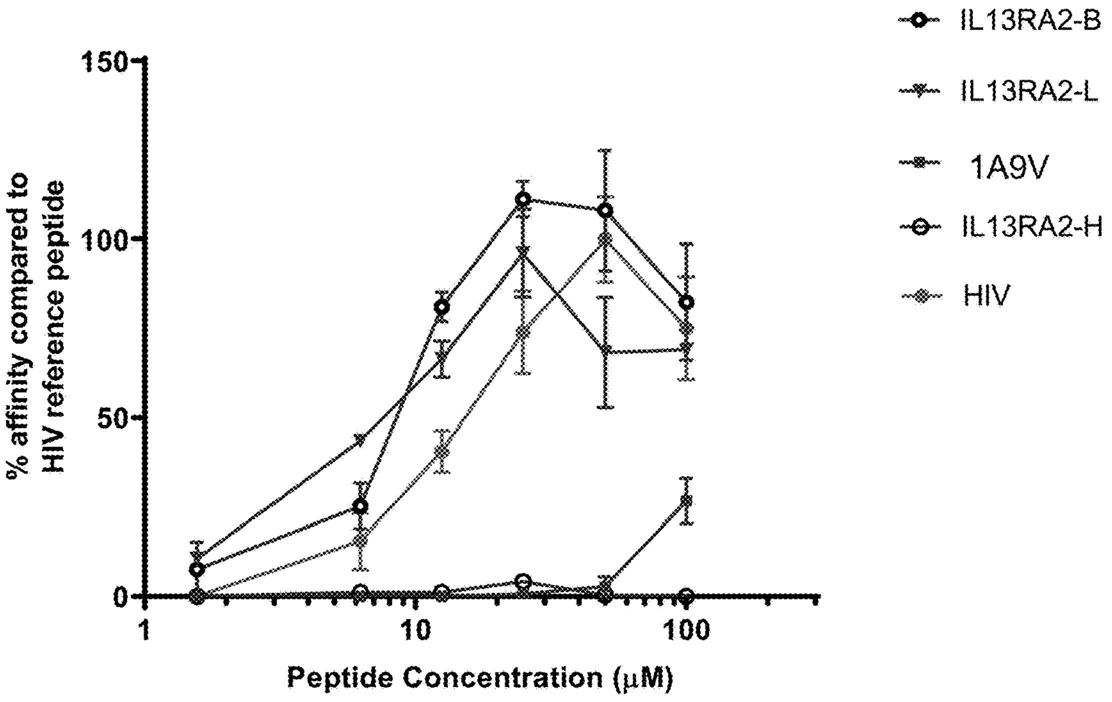
FIG. 12: shows for Example 8 in vitro affinity for antigenic peptides IL13RA2-B and IL13RA2-L in comparison to the corresponding human IL13RA2 epitope IL13RA2-H, to the comparative peptide 1A9V and to the positive control HIV.

Accordingly, the antigenic peptides according to the present invention (IL13RA2-B; SEQ ID NO: 254 and IL13RA2-L; SEQ ID NO: 255) showed considerably higher binding affinity to HLA-A*0201 than the corresponding human epitope (IL13RA2-H) and the comparative peptide "1A9V", as described by Eguchi Junichi et al., 2006, Identification of interleukin-13 receptor alpha 2 peptide analogues capable of inducing improved antiglioma CTL responses. Cancer Research 66(11): 5883-5891. In particular, the antigenic peptide IL13RA2-L (SEQ ID NO: 255) shows a strong binding affinity to HLA-A*0201, namely, 69% of maximum HIV pol 589-597 binding activity at 100 PM; 96% at 25 μM and 43% at 6.25 μM. Results are also shown in FIG. 12.

Example 9: BIRC5-B1 has Superior Affinity to the HLA-A*0201 Allele

This Example provides evidence that the antigenic peptide of the invention as set forth in SEQ ID NO: 32 (also referred to herein as BIRC5-B1) has a higher affinity than the corresponding reference human peptide derived from BIRC5 (BIRC5-H, SEQ ID NO: 593) and a comparative sequence variant thereof ("2M"; SEQ ID NO: 899). In this experiment, the antigenic peptide of sequence SEQ ID NO: 32 (BIRC5-B1) was compared to the peptide "2M" (LMLGEFLKL; SEQ ID NO: 899), in which the threonine at position 2 of SEQ ID NO: 593 was substituted by methionine (2M);

the corresponding reference human peptide BIRC5-H (SEQ ID NO: 593); and a positive control (HIV).

A. Materials and Methods

The experimental protocol, materials and methods correspond to those outlined in Example 2, with the only difference that the above mentioned (poly)peptides were used.

B. Results

The following in vitro binding affinities were obtained:

TABLE 9

| Peptide | SEQ ID NO | Concentration of peptide that induces 20% of HLA-A2 expression (μM) | In vitro binding affinity |
|---|---|---|---|
| BIRC5-H | 593 | 95.9 | 112.82 |
| BIRC5-B1 | 32 | 1.24 | 1.46 |
| 2M | 899 | 2.87 | 3.38 |
| HIV | | 0.85 | 1.00 |

TABLE 10

| Peptide | | Peptide concentration (μM) | | | |
|---|---|---|---|---|---|
| Name | SEQ ID NO. | 100 | 10 | 1 | 0.1 |
| HIV | | 100 | 84.725 | 22.14 | 2.405 |
| BIRC5-H | 593 | 20.545 | 3.515 | 0 | 0 |
| BIRC5-B | 32 | 101.845 | 65.06 | 17.42 | 1.07 |
| 2M | 899 | 75.22 | 48.465 | 8.37 | 0.76 |

Figure 13:
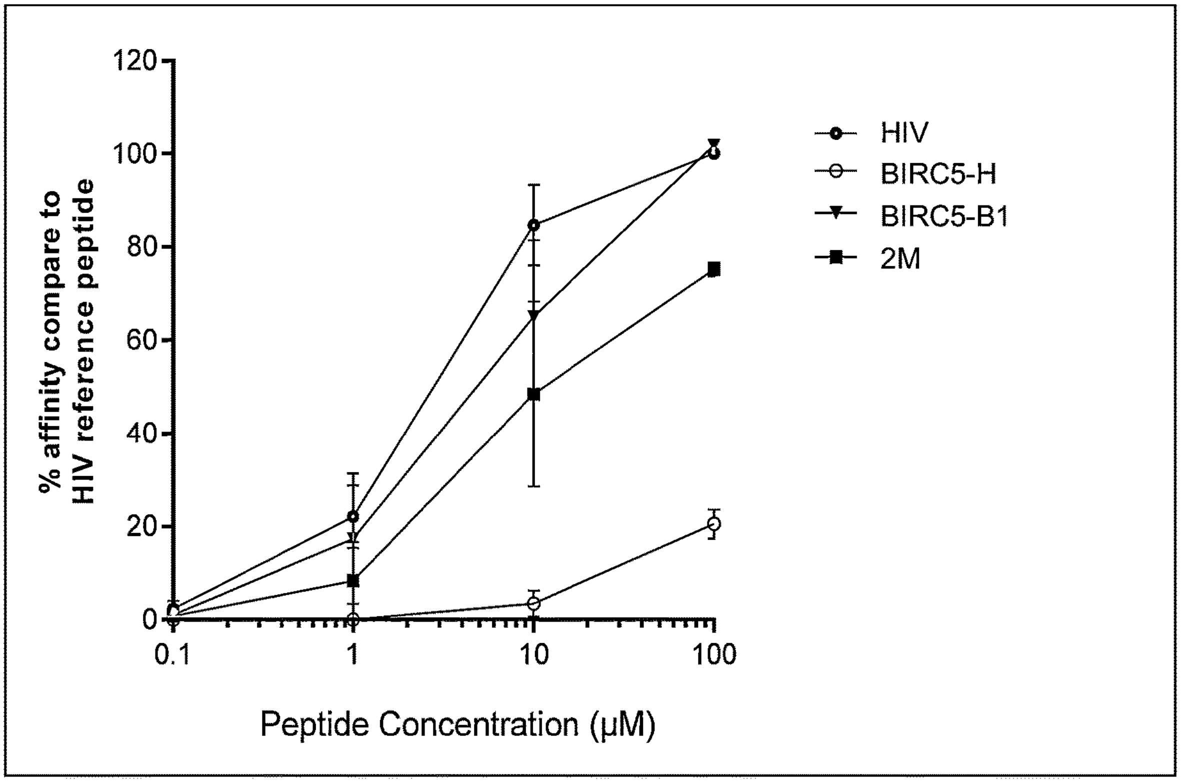
FIG. 13: shows for Example 9 in vitro affinity for the antigenic peptides BIRC5-B1 in comparison to the corresponding human BIRC5 epitope BIRC5-H, to the comparative peptide 2M and to the positive control HIV.

In summary, the antigenic peptide according to the present invention (BIRC5-B1; SEQ ID NO: 32) showed considerably higher in vitro binding affinity to HLA-A*0201 than the corresponding human epitope (BIRC5-H) and the comparative peptide “2M”. Results are also shown in FIG. 13.

SEQUENCE LISTING

```
Sequence total quantity: 899
SEQ ID NO: 1           moltype = AA  length = 9
FEATURE                Location/Qualifiers
REGION                 1..9
                       note = peptide
source                 1..9
                       mol_type = protein
                       organism = synthetic construct
SEQUENCE: 1
VLFLLFFPV                                                         9

SEQ ID NO: 2           moltype = AA  length = 9
FEATURE                Location/Qualifiers
REGION                 1..9
                       note = peptide
source                 1..9
                       mol_type = protein
                       organism = synthetic construct
SEQUENCE: 2
SMSLGFLSV                                                         9

SEQ ID NO: 3           moltype = AA  length = 9
FEATURE                Location/Qualifiers
REGION                 1..9
                       note = peptide
source                 1..9
                       mol_type = protein
                       organism = synthetic construct
SEQUENCE: 3
FLSLGFLAV                                                         9

SEQ ID NO: 4           moltype = AA  length = 9
FEATURE                Location/Qualifiers
REGION                 1..9
                       note = peptide
source                 1..9
                       mol_type = protein
                       organism = synthetic construct
SEQUENCE: 4
LLLGFLFLI                                                         9

SEQ ID NO: 5           moltype = AA  length = 9
FEATURE                Location/Qualifiers
REGION                 1..9
                       note = peptide
source                 1..9
                       mol_type = protein
                       organism = synthetic construct
SEQUENCE: 5
YLSNDSYRV                                                         9

SEQ ID NO: 6           moltype = AA  length = 9
FEATURE                Location/Qualifiers
REGION                 1..9
                       note = peptide
source                 1..9
                       mol_type = protein
                       organism = synthetic construct
SEQUENCE: 6
```

```
GLIDSGAFL                                                               9

SEQ ID NO: 7            moltype = AA  length = 9
FEATURE                 Location/Qualifiers
REGION                  1..9
                        note = peptide
source                  1..9
                        mol_type = protein
                        organism = synthetic construct
SEQUENCE: 7
LLIDSGALV                                                               9

SEQ ID NO: 8            moltype = AA  length = 9
FEATURE                 Location/Qualifiers
REGION                  1..9
                        note = peptide
source                  1..9
                        mol_type = protein
                        organism = synthetic construct
SEQUENCE: 8
RLIDSGATV                                                               9

SEQ ID NO: 9            moltype = AA  length = 9
FEATURE                 Location/Qualifiers
REGION                  1..9
                        note = peptide
source                  1..9
                        mol_type = protein
                        organism = synthetic construct
SEQUENCE: 9
KLFESSAAL                                                               9

SEQ ID NO: 10           moltype = AA  length = 9
FEATURE                 Location/Qualifiers
REGION                  1..9
                        note = peptide
source                  1..9
                        mol_type = protein
                        organism = synthetic construct
SEQUENCE: 10
TLFESSAFA                                                               9

SEQ ID NO: 11           moltype = AA  length = 9
FEATURE                 Location/Qualifiers
REGION                  1..9
                        note = peptide
source                  1..9
                        mol_type = protein
                        organism = synthetic construct
SEQUENCE: 11
MLTPLLLGL                                                               9

SEQ ID NO: 12           moltype = AA  length = 9
FEATURE                 Location/Qualifiers
REGION                  1..9
                        note = peptide
source                  1..9
                        mol_type = protein
                        organism = synthetic construct
SEQUENCE: 12
YLTPLLLIL                                                               9

SEQ ID NO: 13           moltype = AA  length = 9
FEATURE                 Location/Qualifiers
REGION                  1..9
                        note = peptide
source                  1..9
                        mol_type = protein
                        organism = synthetic construct
SEQUENCE: 13
IMTPLLLPV                                                               9

SEQ ID NO: 14           moltype = AA  length = 9
FEATURE                 Location/Qualifiers
REGION                  1..9
                        note = peptide
source                  1..9
                        mol_type = protein
                        organism = synthetic construct
```

```
SEQUENCE: 14
FMTPLLLCL                                                          9

SEQ ID NO: 15           moltype = AA  length = 9
FEATURE                 Location/Qualifiers
REGION                  1..9
                        note = peptide
source                  1..9
                        mol_type = protein
                        organism = synthetic construct
SEQUENCE: 15
FLTPLLLWL                                                          9

SEQ ID NO: 16           moltype = AA  length = 9
FEATURE                 Location/Qualifiers
REGION                  1..9
                        note = peptide
source                  1..9
                        mol_type = protein
                        organism = synthetic construct
SEQUENCE: 16
WMAVILTAL                                                          9

SEQ ID NO: 17           moltype = AA  length = 9
FEATURE                 Location/Qualifiers
REGION                  1..9
                        note = peptide
source                  1..9
                        mol_type = protein
                        organism = synthetic construct
SEQUENCE: 17
VLAVILTAV                                                          9

SEQ ID NO: 18           moltype = AA  length = 9
FEATURE                 Location/Qualifiers
REGION                  1..9
                        note = peptide
source                  1..9
                        mol_type = protein
                        organism = synthetic construct
SEQUENCE: 18
VLAAIAAGV                                                          9

SEQ ID NO: 19           moltype = AA  length = 9
FEATURE                 Location/Qualifiers
REGION                  1..9
                        note = peptide
source                  1..9
                        mol_type = protein
                        organism = synthetic construct
SEQUENCE: 19
LLAAIAAFL                                                          9

SEQ ID NO: 20           moltype = AA  length = 9
FEATURE                 Location/Qualifiers
REGION                  1..9
                        note = peptide
source                  1..9
                        mol_type = protein
                        organism = synthetic construct
SEQUENCE: 20
KLAAIAAAV                                                          9

SEQ ID NO: 21           moltype = AA  length = 9
FEATURE                 Location/Qualifiers
REGION                  1..9
                        note = peptide
source                  1..9
                        mol_type = protein
                        organism = synthetic construct
SEQUENCE: 21
ILAAIAAAV                                                          9

SEQ ID NO: 22           moltype = AA  length = 9
FEATURE                 Location/Qualifiers
REGION                  1..9
                        note = peptide
source                  1..9
                        mol_type = protein
```

```
                        organism = synthetic construct
SEQUENCE: 22
GMAAIAAFL                                                                9

SEQ ID NO: 23           moltype = AA  length = 9
FEATURE                 Location/Qualifiers
REGION                  1..9
                        note = peptide
source                  1..9
                        mol_type = protein
                        organism = synthetic construct
SEQUENCE: 23
FLAAIAAVL                                                                9

SEQ ID NO: 24           moltype = AA  length = 9
FEATURE                 Location/Qualifiers
REGION                  1..9
                        note = peptide
source                  1..9
                        mol_type = protein
                        organism = synthetic construct
SEQUENCE: 24
ALAAIAALV                                                                9

SEQ ID NO: 25           moltype = AA  length = 9
FEATURE                 Location/Qualifiers
REGION                  1..9
                        note = peptide
source                  1..9
                        mol_type = protein
                        organism = synthetic construct
SEQUENCE: 25
ALAAFQAGL                                                                9

SEQ ID NO: 26           moltype = AA  length = 9
FEATURE                 Location/Qualifiers
REGION                  1..9
                        note = peptide
source                  1..9
                        mol_type = protein
                        organism = synthetic construct
SEQUENCE: 26
SLVNLGFSL                                                                9

SEQ ID NO: 27           moltype = AA  length = 9
FEATURE                 Location/Qualifiers
REGION                  1..9
                        note = peptide
source                  1..9
                        mol_type = protein
                        organism = synthetic construct
SEQUENCE: 27
GLVNLGFAL                                                                9

SEQ ID NO: 28           moltype = AA  length = 9
FEATURE                 Location/Qualifiers
REGION                  1..9
                        note = peptide
source                  1..9
                        mol_type = protein
                        organism = synthetic construct
SEQUENCE: 28
QLLDFSSSL                                                                9

SEQ ID NO: 29           moltype = AA  length = 9
FEATURE                 Location/Qualifiers
REGION                  1..9
                        note = peptide
source                  1..9
                        mol_type = protein
                        organism = synthetic construct
SEQUENCE: 29
ILLDFSSVV                                                                9

SEQ ID NO: 30           moltype = AA  length = 9
FEATURE                 Location/Qualifiers
REGION                  1..9
                        note = peptide
source                  1..9
```

```
                        mol_type = protein
                        organism = synthetic construct
SEQUENCE: 30
YTLGEFLYI                                                                9

SEQ ID NO: 31           moltype = AA  length = 9
FEATURE                 Location/Qualifiers
REGION                  1..9
                        note = peptide
source                  1..9
                        mol_type = protein
                        organism = synthetic construct
SEQUENCE: 31
GLLGEFLQI                                                                9

SEQ ID NO: 32           moltype = AA  length = 9
FEATURE                 Location/Qualifiers
REGION                  1..9
                        note = peptide
source                  1..9
                        mol_type = protein
                        organism = synthetic construct
SEQUENCE: 32
FMLGEFLKL                                                                9

SEQ ID NO: 33           moltype = AA  length = 9
FEATURE                 Location/Qualifiers
REGION                  1..9
                        note = peptide
source                  1..9
                        mol_type = protein
                        organism = synthetic construct
SEQUENCE: 33
VLGDILALL                                                                9

SEQ ID NO: 34           moltype = AA  length = 9
FEATURE                 Location/Qualifiers
REGION                  1..9
                        note = peptide
source                  1..9
                        mol_type = protein
                        organism = synthetic construct
SEQUENCE: 34
KVGDILALV                                                                9

SEQ ID NO: 35           moltype = AA  length = 9
FEATURE                 Location/Qualifiers
REGION                  1..9
                        note = peptide
source                  1..9
                        mol_type = protein
                        organism = synthetic construct
SEQUENCE: 35
NLVFGLLPV                                                                9

SEQ ID NO: 36           moltype = AA  length = 9
FEATURE                 Location/Qualifiers
REGION                  1..9
                        note = peptide
source                  1..9
                        mol_type = protein
                        organism = synthetic construct
SEQUENCE: 36
FLVFGLLGL                                                                9

SEQ ID NO: 37           moltype = AA  length = 9
FEATURE                 Location/Qualifiers
REGION                  1..9
                        note = peptide
source                  1..9
                        mol_type = protein
                        organism = synthetic construct
SEQUENCE: 37
ALVFGLLRV                                                                9

SEQ ID NO: 38           moltype = AA  length = 9
FEATURE                 Location/Qualifiers
REGION                  1..9
                        note = peptide
```

```
source                  1..9
                        mol_type = protein
                        organism = synthetic construct
SEQUENCE: 38
GVYEGSLTV                                                                 9

SEQ ID NO: 39           moltype = AA  length = 9
FEATURE                 Location/Qualifiers
REGION                  1..9
                        note = peptide
source                  1..9
                        mol_type = protein
                        organism = synthetic construct
SEQUENCE: 39
VLSTAFALV                                                                 9

SEQ ID NO: 40           moltype = AA  length = 9
FEATURE                 Location/Qualifiers
REGION                  1..9
                        note = peptide
source                  1..9
                        mol_type = protein
                        organism = synthetic construct
SEQUENCE: 40
GLSTAFAAV                                                                 9

SEQ ID NO: 41           moltype = AA  length = 9
FEATURE                 Location/Qualifiers
REGION                  1..9
                        note = peptide
source                  1..9
                        mol_type = protein
                        organism = synthetic construct
SEQUENCE: 41
ALSTAFAVV                                                                 9

SEQ ID NO: 42           moltype = AA  length = 9
FEATURE                 Location/Qualifiers
REGION                  1..9
                        note = peptide
source                  1..9
                        mol_type = protein
                        organism = synthetic construct
SEQUENCE: 42
MLLLLLVPV                                                                 9

SEQ ID NO: 43           moltype = AA  length = 9
FEATURE                 Location/Qualifiers
REGION                  1..9
                        note = peptide
source                  1..9
                        mol_type = protein
                        organism = synthetic construct
SEQUENCE: 43
LLLLLLVPV                                                                 9

SEQ ID NO: 44           moltype = AA  length = 9
FEATURE                 Location/Qualifiers
REGION                  1..9
                        note = peptide
source                  1..9
                        mol_type = protein
                        organism = synthetic construct
SEQUENCE: 44
AILLLLVPV                                                                 9

SEQ ID NO: 45           moltype = AA  length = 9
FEATURE                 Location/Qualifiers
REGION                  1..9
                        note = peptide
source                  1..9
                        mol_type = protein
                        organism = synthetic construct
SEQUENCE: 45
YLLLSLLRL                                                                 9

SEQ ID NO: 46           moltype = AA  length = 9
FEATURE                 Location/Qualifiers
REGION                  1..9
```

```
                     note = peptide
source               1..9
                     mol_type = protein
                     organism = synthetic construct
SEQUENCE: 46
FLLLSLLTL                                                    9

SEQ ID NO: 47        moltype = AA  length = 9
FEATURE              Location/Qualifiers
REGION               1..9
                     note = peptide
source               1..9
                     mol_type = protein
                     organism = synthetic construct
SEQUENCE: 47
ALLLSLLPL                                                    9

SEQ ID NO: 48        moltype = AA  length = 9
FEATURE              Location/Qualifiers
REGION               1..9
                     note = peptide
source               1..9
                     mol_type = protein
                     organism = synthetic construct
SEQUENCE: 48
RLLLLSLLV                                                    9

SEQ ID NO: 49        moltype = AA  length = 9
FEATURE              Location/Qualifiers
REGION               1..9
                     note = peptide
source               1..9
                     mol_type = protein
                     organism = synthetic construct
SEQUENCE: 49
KLLLLSLLL                                                    9

SEQ ID NO: 50        moltype = AA  length = 9
FEATURE              Location/Qualifiers
REGION               1..9
                     note = peptide
source               1..9
                     mol_type = protein
                     organism = synthetic construct
SEQUENCE: 50
FLLLLSLLI                                                    9

SEQ ID NO: 51        moltype = AA  length = 9
FEATURE              Location/Qualifiers
REGION               1..9
                     note = peptide
source               1..9
                     mol_type = protein
                     organism = synthetic construct
SEQUENCE: 51
RLAKYVALV                                                    9

SEQ ID NO: 52        moltype = AA  length = 9
FEATURE              Location/Qualifiers
REGION               1..9
                     note = peptide
source               1..9
                     mol_type = protein
                     organism = synthetic construct
SEQUENCE: 52
LIAAAAFTV                                                    9

SEQ ID NO: 53        moltype = AA  length = 9
FEATURE              Location/Qualifiers
REGION               1..9
                     note = peptide
source               1..9
                     mol_type = protein
                     organism = synthetic construct
SEQUENCE: 53
GMAAAAFCL                                                    9

SEQ ID NO: 54        moltype = AA  length = 9
FEATURE              Location/Qualifiers
```

```
REGION                 1..9
                       note = peptide
source                 1..9
                       mol_type = protein
                       organism = synthetic construct
SEQUENCE: 54
GLAAAAFCI                                                    9

SEQ ID NO: 55          moltype = AA  length = 9
FEATURE                Location/Qualifiers
REGION                 1..9
                       note = peptide
source                 1..9
                       mol_type = protein
                       organism = synthetic construct
SEQUENCE: 55
FLAAAAFCL                                                    9

SEQ ID NO: 56          moltype = AA  length = 9
FEATURE                Location/Qualifiers
REGION                 1..9
                       note = peptide
source                 1..9
                       mol_type = protein
                       organism = synthetic construct
SEQUENCE: 56
WLNDRVLQL                                                    9

SEQ ID NO: 57          moltype = AA  length = 9
FEATURE                Location/Qualifiers
REGION                 1..9
                       note = peptide
source                 1..9
                       mol_type = protein
                       organism = synthetic construct
SEQUENCE: 57
KLLLTTLLV                                                    9

SEQ ID NO: 58          moltype = AA  length = 9
FEATURE                Location/Qualifiers
REGION                 1..9
                       note = peptide
source                 1..9
                       mol_type = protein
                       organism = synthetic construct
SEQUENCE: 58
GMAVVFINV                                                    9

SEQ ID NO: 59          moltype = AA  length = 9
FEATURE                Location/Qualifiers
REGION                 1..9
                       note = peptide
source                 1..9
                       mol_type = protein
                       organism = synthetic construct
SEQUENCE: 59
GMAVVFIEV                                                    9

SEQ ID NO: 60          moltype = AA  length = 9
FEATURE                Location/Qualifiers
REGION                 1..9
                       note = peptide
source                 1..9
                       mol_type = protein
                       organism = synthetic construct
SEQUENCE: 60
LLLTTLLAV                                                    9

SEQ ID NO: 61          moltype = AA  length = 9
FEATURE                Location/Qualifiers
REGION                 1..9
                       note = peptide
source                 1..9
                       mol_type = protein
                       organism = synthetic construct
SEQUENCE: 61
ALLTTLLLV                                                    9

SEQ ID NO: 62          moltype = AA  length = 9
```

-continued

```
FEATURE               Location/Qualifiers
REGION                1..9
                      note = peptide
source                1..9
                      mol_type = protein
                      organism = synthetic construct
SEQUENCE: 62
ALLTTLLGL                                                   9

SEQ ID NO: 63         moltype = AA  length = 9
FEATURE               Location/Qualifiers
REGION                1..9
                      note = peptide
source                1..9
                      mol_type = protein
                      organism = synthetic construct
SEQUENCE: 63
KIIGIILAV                                                   9

SEQ ID NO: 64         moltype = AA  length = 9
FEATURE               Location/Qualifiers
REGION                1..9
                      note = peptide
source                1..9
                      mol_type = protein
                      organism = synthetic construct
SEQUENCE: 64
YLVAILLLV                                                   9

SEQ ID NO: 65         moltype = AA  length = 9
FEATURE               Location/Qualifiers
REGION                1..9
                      note = peptide
source                1..9
                      mol_type = protein
                      organism = synthetic construct
SEQUENCE: 65
TLVAILLNV                                                   9

SEQ ID NO: 66         moltype = AA  length = 9
FEATURE               Location/Qualifiers
REGION                1..9
                      note = peptide
source                1..9
                      mol_type = protein
                      organism = synthetic construct
SEQUENCE: 66
MLVAILLAV                                                   9

SEQ ID NO: 67         moltype = AA  length = 9
FEATURE               Location/Qualifiers
REGION                1..9
                      note = peptide
source                1..9
                      mol_type = protein
                      organism = synthetic construct
SEQUENCE: 67
LLVAILLSV                                                   9

SEQ ID NO: 68         moltype = AA  length = 9
FEATURE               Location/Qualifiers
REGION                1..9
                      note = peptide
source                1..9
                      mol_type = protein
                      organism = synthetic construct
SEQUENCE: 68
FLVAILLNL                                                   9

SEQ ID NO: 69         moltype = AA  length = 9
FEATURE               Location/Qualifiers
REGION                1..9
                      note = peptide
source                1..9
                      mol_type = protein
                      organism = synthetic construct
SEQUENCE: 69
AMVAILLNI                                                   9
```

-continued

```
SEQ ID NO: 70           moltype = AA  length = 9
FEATURE                Location/Qualifiers
REGION                 1..9
                       note = peptide
source                 1..9
                       mol_type = protein
                       organism = synthetic construct
SEQUENCE: 70
ALVAILLAI                                                         9

SEQ ID NO: 71           moltype = AA  length = 9
FEATURE                Location/Qualifiers
REGION                 1..9
                       note = peptide
source                 1..9
                       mol_type = protein
                       organism = synthetic construct
SEQUENCE: 71
LLSDVGTLL                                                         9

SEQ ID NO: 72           moltype = AA  length = 9
FEATURE                Location/Qualifiers
REGION                 1..9
                       note = peptide
source                 1..9
                       mol_type = protein
                       organism = synthetic construct
SEQUENCE: 72
FLSTYLLPM                                                         9

SEQ ID NO: 73           moltype = AA  length = 9
FEATURE                Location/Qualifiers
REGION                 1..9
                       note = peptide
source                 1..9
                       mol_type = protein
                       organism = synthetic construct
SEQUENCE: 73
ALLEEYTGI                                                         9

SEQ ID NO: 74           moltype = AA  length = 9
FEATURE                Location/Qualifiers
REGION                 1..9
                       note = peptide
source                 1..9
                       mol_type = protein
                       organism = synthetic construct
SEQUENCE: 74
SLLCIVIGL                                                         9

SEQ ID NO: 75           moltype = AA  length = 9
FEATURE                Location/Qualifiers
REGION                 1..9
                       note = peptide
source                 1..9
                       mol_type = protein
                       organism = synthetic construct
SEQUENCE: 75
ILLCIVIGL                                                         9

SEQ ID NO: 76           moltype = AA  length = 9
FEATURE                Location/Qualifiers
REGION                 1..9
                       note = peptide
source                 1..9
                       mol_type = protein
                       organism = synthetic construct
SEQUENCE: 76
MLVTVVLTV                                                         9

SEQ ID NO: 77           moltype = AA  length = 9
FEATURE                Location/Qualifiers
REGION                 1..9
                       note = peptide
source                 1..9
                       mol_type = protein
                       organism = synthetic construct
SEQUENCE: 77
MLVTVVLLV                                                         9
```

```
SEQ ID NO: 78           moltype = AA  length = 9
FEATURE                 Location/Qualifiers
REGION                  1..9
                        note = peptide
source                  1..9
                        mol_type = protein
                        organism = synthetic construct
SEQUENCE: 78
LLVTVVLPV                                                          9

SEQ ID NO: 79           moltype = AA  length = 9
FEATURE                 Location/Qualifiers
REGION                  1..9
                        note = peptide
source                  1..9
                        mol_type = protein
                        organism = synthetic construct
SEQUENCE: 79
LLVTVVLAV                                                          9

SEQ ID NO: 80           moltype = AA  length = 9
FEATURE                 Location/Qualifiers
REGION                  1..9
                        note = peptide
source                  1..9
                        mol_type = protein
                        organism = synthetic construct
SEQUENCE: 80
KLVTVVLAV                                                          9

SEQ ID NO: 81           moltype = AA  length = 9
FEATURE                 Location/Qualifiers
REGION                  1..9
                        note = peptide
source                  1..9
                        mol_type = protein
                        organism = synthetic construct
SEQUENCE: 81
ILVTVVLGI                                                          9

SEQ ID NO: 82           moltype = AA  length = 9
FEATURE                 Location/Qualifiers
REGION                  1..9
                        note = peptide
source                  1..9
                        mol_type = protein
                        organism = synthetic construct
SEQUENCE: 82
LMALVLMLV                                                          9

SEQ ID NO: 83           moltype = AA  length = 9
FEATURE                 Location/Qualifiers
REGION                  1..9
                        note = peptide
source                  1..9
                        mol_type = protein
                        organism = synthetic construct
SEQUENCE: 83
GLTFWNPNV                                                          9

SEQ ID NO: 84           moltype = AA  length = 9
FEATURE                 Location/Qualifiers
REGION                  1..9
                        note = peptide
source                  1..9
                        mol_type = protein
                        organism = synthetic construct
SEQUENCE: 84
FMLLLSAAA                                                          9

SEQ ID NO: 85           moltype = AA  length = 9
FEATURE                 Location/Qualifiers
REGION                  1..9
                        note = peptide
source                  1..9
                        mol_type = protein
                        organism = synthetic construct
SEQUENCE: 85
```

-continued

```
FLLLLSAAL                                                    9

SEQ ID NO: 86          moltype = AA  length = 9
FEATURE                Location/Qualifiers
REGION                 1..9
                       note = peptide
source                 1..9
                       mol_type = protein
                       organism = synthetic construct
SEQUENCE: 86
YLLSAALTL                                                    9

SEQ ID NO: 87          moltype = AA  length = 9
FEATURE                Location/Qualifiers
REGION                 1..9
                       note = peptide
source                 1..9
                       mol_type = protein
                       organism = synthetic construct
SEQUENCE: 87
YLLSAALTI                                                    9

SEQ ID NO: 88          moltype = AA  length = 9
FEATURE                Location/Qualifiers
REGION                 1..9
                       note = peptide
source                 1..9
                       mol_type = protein
                       organism = synthetic construct
SEQUENCE: 88
VLLSAALLL                                                    9

SEQ ID NO: 89          moltype = AA  length = 9
FEATURE                Location/Qualifiers
REGION                 1..9
                       note = peptide
source                 1..9
                       mol_type = protein
                       organism = synthetic construct
SEQUENCE: 89
VLLSAALFL                                                    9

SEQ ID NO: 90          moltype = AA  length = 9
FEATURE                Location/Qualifiers
REGION                 1..9
                       note = peptide
source                 1..9
                       mol_type = protein
                       organism = synthetic construct
SEQUENCE: 90
SLLSAALTV                                                    9

SEQ ID NO: 91          moltype = AA  length = 9
FEATURE                Location/Qualifiers
REGION                 1..9
                       note = peptide
source                 1..9
                       mol_type = protein
                       organism = synthetic construct
SEQUENCE: 91
RLLSAALAL                                                    9

SEQ ID NO: 92          moltype = AA  length = 9
FEATURE                Location/Qualifiers
REGION                 1..9
                       note = peptide
source                 1..9
                       mol_type = protein
                       organism = synthetic construct
SEQUENCE: 92
LMLSAALLL                                                    9

SEQ ID NO: 93          moltype = AA  length = 9
FEATURE                Location/Qualifiers
REGION                 1..9
                       note = peptide
source                 1..9
                       mol_type = protein
                       organism = synthetic construct
```

```
SEQUENCE: 93
LMLSAALCV                                                          9

SEQ ID NO: 94          moltype = AA  length = 9
FEATURE                Location/Qualifiers
REGION                 1..9
                       note = peptide
source                 1..9
                       mol_type = protein
                       organism = synthetic construct
SEQUENCE: 94
LMLSAALAV                                                          9

SEQ ID NO: 95          moltype = AA  length = 9
FEATURE                Location/Qualifiers
REGION                 1..9
                       note = peptide
source                 1..9
                       mol_type = protein
                       organism = synthetic construct
SEQUENCE: 95
LLLSAALWV                                                          9

SEQ ID NO: 96          moltype = AA  length = 9
FEATURE                Location/Qualifiers
REGION                 1..9
                       note = peptide
source                 1..9
                       mol_type = protein
                       organism = synthetic construct
SEQUENCE: 96
LLLSAALTV                                                          9

SEQ ID NO: 97          moltype = AA  length = 9
FEATURE                Location/Qualifiers
REGION                 1..9
                       note = peptide
source                 1..9
                       mol_type = protein
                       organism = synthetic construct
SEQUENCE: 97
LLLSAALSV                                                          9

SEQ ID NO: 98          moltype = AA  length = 9
FEATURE                Location/Qualifiers
REGION                 1..9
                       note = peptide
source                 1..9
                       mol_type = protein
                       organism = synthetic construct
SEQUENCE: 98
LLLSAALMI                                                          9

SEQ ID NO: 99          moltype = AA  length = 9
FEATURE                Location/Qualifiers
REGION                 1..9
                       note = peptide
source                 1..9
                       mol_type = protein
                       organism = synthetic construct
SEQUENCE: 99
LLLSAALLL                                                          9

SEQ ID NO: 100         moltype = AA  length = 9
FEATURE                Location/Qualifiers
REGION                 1..9
                       note = peptide
source                 1..9
                       mol_type = protein
                       organism = synthetic construct
SEQUENCE: 100
LLLSAALCV                                                          9

SEQ ID NO: 101         moltype = AA  length = 9
FEATURE                Location/Qualifiers
REGION                 1..9
                       note = peptide
source                 1..9
                       mol_type = protein
```

```
                        organism = synthetic construct
SEQUENCE: 101
LLLSAALAL                                                    9

SEQ ID NO: 102          moltype = AA  length = 9
FEATURE                 Location/Qualifiers
REGION                  1..9
                        note = peptide
source                  1..9
                        mol_type = protein
                        organism = synthetic construct
SEQUENCE: 102
KLLSAALSV                                                    9

SEQ ID NO: 103          moltype = AA  length = 9
FEATURE                 Location/Qualifiers
REGION                  1..9
                        note = peptide
source                  1..9
                        mol_type = protein
                        organism = synthetic construct
SEQUENCE: 103
ILLSAALLL                                                    9

SEQ ID NO: 104          moltype = AA  length = 9
FEATURE                 Location/Qualifiers
REGION                  1..9
                        note = peptide
source                  1..9
                        mol_type = protein
                        organism = synthetic construct
SEQUENCE: 104
ILLSAALGI                                                    9

SEQ ID NO: 105          moltype = AA  length = 9
FEATURE                 Location/Qualifiers
REGION                  1..9
                        note = peptide
source                  1..9
                        mol_type = protein
                        organism = synthetic construct
SEQUENCE: 105
FLLSAALVV                                                    9

SEQ ID NO: 106          moltype = AA  length = 9
FEATURE                 Location/Qualifiers
REGION                  1..9
                        note = peptide
source                  1..9
                        mol_type = protein
                        organism = synthetic construct
SEQUENCE: 106
FLLSAALIL                                                    9

SEQ ID NO: 107          moltype = AA  length = 9
FEATURE                 Location/Qualifiers
REGION                  1..9
                        note = peptide
source                  1..9
                        mol_type = protein
                        organism = synthetic construct
SEQUENCE: 107
ALLSAALML                                                    9

SEQ ID NO: 108          moltype = AA  length = 9
FEATURE                 Location/Qualifiers
REGION                  1..9
                        note = peptide
source                  1..9
                        mol_type = protein
                        organism = synthetic construct
SEQUENCE: 108
ALLSAALLV                                                    9

SEQ ID NO: 109          moltype = AA  length = 9
FEATURE                 Location/Qualifiers
REGION                  1..9
                        note = peptide
source                  1..9
```

```
                       mol_type = protein
                       organism = synthetic construct
SEQUENCE: 109
ALLSAALLL                                                             9

SEQ ID NO: 110         moltype = AA  length = 9
FEATURE                Location/Qualifiers
REGION                 1..9
                       note = peptide
source                 1..9
                       mol_type = protein
                       organism = synthetic construct
SEQUENCE: 110
YMAGAMVQL                                                             9

SEQ ID NO: 111         moltype = AA  length = 9
FEATURE                Location/Qualifiers
REGION                 1..9
                       note = peptide
source                 1..9
                       mol_type = protein
                       organism = synthetic construct
SEQUENCE: 111
RMAGAMVPV                                                             9

SEQ ID NO: 112         moltype = AA  length = 9
FEATURE                Location/Qualifiers
REGION                 1..9
                       note = peptide
source                 1..9
                       mol_type = protein
                       organism = synthetic construct
SEQUENCE: 112
RLAGAMVDV                                                             9

SEQ ID NO: 113         moltype = AA  length = 9
FEATURE                Location/Qualifiers
REGION                 1..9
                       note = peptide
source                 1..9
                       mol_type = protein
                       organism = synthetic construct
SEQUENCE: 113
MMTGFVVLM                                                             9

SEQ ID NO: 114         moltype = AA  length = 9
FEATURE                Location/Qualifiers
REGION                 1..9
                       note = peptide
source                 1..9
                       mol_type = protein
                       organism = synthetic construct
SEQUENCE: 114
YLASSETHV                                                             9

SEQ ID NO: 115         moltype = AA  length = 9
FEATURE                Location/Qualifiers
REGION                 1..9
                       note = peptide
source                 1..9
                       mol_type = protein
                       organism = synthetic construct
SEQUENCE: 115
SMLSIGGYV                                                             9

SEQ ID NO: 116         moltype = AA  length = 9
FEATURE                Location/Qualifiers
REGION                 1..9
                       note = peptide
source                 1..9
                       mol_type = protein
                       organism = synthetic construct
SEQUENCE: 116
LLIYSFARV                                                             9

SEQ ID NO: 117         moltype = AA  length = 9
FEATURE                Location/Qualifiers
REGION                 1..9
                       note = peptide
```

-continued

```
source                  1..9
                        mol_type = protein
                        organism = synthetic construct
SEQUENCE: 117
KLIHELAEV                                                        9

SEQ ID NO: 118          moltype = AA  length = 9
FEATURE                 Location/Qualifiers
REGION                  1..9
                        note = peptide
source                  1..9
                        mol_type = protein
                        organism = synthetic construct
SEQUENCE: 118
ILIHELAHI                                                        9

SEQ ID NO: 119          moltype = AA  length = 9
FEATURE                 Location/Qualifiers
REGION                  1..9
                        note = peptide
source                  1..9
                        mol_type = protein
                        organism = synthetic construct
SEQUENCE: 119
HLWAGVVLV                                                        9

SEQ ID NO: 120          moltype = AA  length = 9
FEATURE                 Location/Qualifiers
REGION                  1..9
                        note = peptide
source                  1..9
                        mol_type = protein
                        organism = synthetic construct
SEQUENCE: 120
RLWDFTVGV                                                        9

SEQ ID NO: 121          moltype = AA  length = 9
FEATURE                 Location/Qualifiers
REGION                  1..9
                        note = peptide
source                  1..9
                        mol_type = protein
                        organism = synthetic construct
SEQUENCE: 121
VLASSILYI                                                        9

SEQ ID NO: 122          moltype = AA  length = 9
FEATURE                 Location/Qualifiers
REGION                  1..9
                        note = peptide
source                  1..9
                        mol_type = protein
                        organism = synthetic construct
SEQUENCE: 122
SLASSILQL                                                        9

SEQ ID NO: 123          moltype = AA  length = 9
FEATURE                 Location/Qualifiers
REGION                  1..9
                        note = peptide
source                  1..9
                        mol_type = protein
                        organism = synthetic construct
SEQUENCE: 123
ALASSILQL                                                        9

SEQ ID NO: 124          moltype = AA  length = 9
FEATURE                 Location/Qualifiers
REGION                  1..9
                        note = peptide
source                  1..9
                        mol_type = protein
                        organism = synthetic construct
SEQUENCE: 124
FLAVSLAPL                                                        9

SEQ ID NO: 125          moltype = AA  length = 9
FEATURE                 Location/Qualifiers
REGION                  1..9
```

```
                        note = peptide
source                  1..9
                        mol_type = protein
                        organism = synthetic construct
SEQUENCE: 125
ILVGLFVPV                                                          9

SEQ ID NO: 126          moltype = AA  length = 9
FEATURE                 Location/Qualifiers
REGION                  1..9
                        note = peptide
source                  1..9
                        mol_type = protein
                        organism = synthetic construct
SEQUENCE: 126
ILVGLFVAV                                                          9

SEQ ID NO: 127          moltype = AA  length = 9
FEATURE                 Location/Qualifiers
REGION                  1..9
                        note = peptide
source                  1..9
                        mol_type = protein
                        organism = synthetic construct
SEQUENCE: 127
YLFVLLAGI                                                          9

SEQ ID NO: 128          moltype = AA  length = 9
FEATURE                 Location/Qualifiers
REGION                  1..9
                        note = peptide
source                  1..9
                        mol_type = protein
                        organism = synthetic construct
SEQUENCE: 128
SLFVLLAAV                                                          9

SEQ ID NO: 129          moltype = AA  length = 9
FEATURE                 Location/Qualifiers
REGION                  1..9
                        note = peptide
source                  1..9
                        mol_type = protein
                        organism = synthetic construct
SEQUENCE: 129
KLFVLLALV                                                          9

SEQ ID NO: 130          moltype = AA  length = 9
FEATURE                 Location/Qualifiers
REGION                  1..9
                        note = peptide
source                  1..9
                        mol_type = protein
                        organism = synthetic construct
SEQUENCE: 130
GIYDFFVKV                                                          9

SEQ ID NO: 131          moltype = AA  length = 9
FEATURE                 Location/Qualifiers
REGION                  1..9
                        note = peptide
source                  1..9
                        mol_type = protein
                        organism = synthetic construct
SEQUENCE: 131
TIMGTLVSV                                                          9

SEQ ID NO: 132          moltype = AA  length = 9
FEATURE                 Location/Qualifiers
REGION                  1..9
                        note = peptide
source                  1..9
                        mol_type = protein
                        organism = synthetic construct
SEQUENCE: 132
RVMGTLVGI                                                          9

SEQ ID NO: 133          moltype = AA  length = 9
FEATURE                 Location/Qualifiers
```

```
REGION                  1..9
                        note = peptide
source                  1..9
                        mol_type = protein
                        organism = synthetic construct
SEQUENCE: 133
TLAEGLALA                                                                    9

SEQ ID NO: 134          moltype = AA  length = 9
FEATURE                 Location/Qualifiers
REGION                  1..9
                        note = peptide
source                  1..9
                        mol_type = protein
                        organism = synthetic construct
SEQUENCE: 134
FLAAGLGQV                                                                    9

SEQ ID NO: 135          moltype = AA  length = 9
FEATURE                 Location/Qualifiers
REGION                  1..9
                        note = peptide
source                  1..9
                        mol_type = protein
                        organism = synthetic construct
SEQUENCE: 135
VLESILHPV                                                                    9

SEQ ID NO: 136          moltype = AA  length = 9
FEATURE                 Location/Qualifiers
REGION                  1..9
                        note = peptide
source                  1..9
                        mol_type = protein
                        organism = synthetic construct
SEQUENCE: 136
RMESILHEV                                                                    9

SEQ ID NO: 137          moltype = AA  length = 9
FEATURE                 Location/Qualifiers
REGION                  1..9
                        note = peptide
source                  1..9
                        mol_type = protein
                        organism = synthetic construct
SEQUENCE: 137
ALLAALCYV                                                                    9

SEQ ID NO: 138          moltype = AA  length = 9
FEATURE                 Location/Qualifiers
REGION                  1..9
                        note = peptide
source                  1..9
                        mol_type = protein
                        organism = synthetic construct
SEQUENCE: 138
YLLALLAWL                                                                    9

SEQ ID NO: 139          moltype = AA  length = 9
FEATURE                 Location/Qualifiers
REGION                  1..9
                        note = peptide
source                  1..9
                        mol_type = protein
                        organism = synthetic construct
SEQUENCE: 139
VLLALLAEV                                                                    9

SEQ ID NO: 140          moltype = AA  length = 9
FEATURE                 Location/Qualifiers
REGION                  1..9
                        note = peptide
source                  1..9
                        mol_type = protein
                        organism = synthetic construct
SEQUENCE: 140
SLLALLAFV                                                                    9

SEQ ID NO: 141          moltype = AA  length = 9
```

-continued

```
FEATURE                 Location/Qualifiers
REGION                  1..9
                        note = peptide
source                  1..9
                        mol_type = protein
                        organism = synthetic construct
SEQUENCE: 141
RLLALLASV                                                                   9

SEQ ID NO: 142          moltype = AA  length = 9
FEATURE                 Location/Qualifiers
REGION                  1..9
                        note = peptide
source                  1..9
                        mol_type = protein
                        organism = synthetic construct
SEQUENCE: 142
RLLALLAAV                                                                   9

SEQ ID NO: 143          moltype = AA  length = 9
FEATURE                 Location/Qualifiers
REGION                  1..9
                        note = peptide
source                  1..9
                        mol_type = protein
                        organism = synthetic construct
SEQUENCE: 143
LLLALLAPV                                                                   9

SEQ ID NO: 144          moltype = AA  length = 9
FEATURE                 Location/Qualifiers
REGION                  1..9
                        note = peptide
source                  1..9
                        mol_type = protein
                        organism = synthetic construct
SEQUENCE: 144
ALLALLASV                                                                   9

SEQ ID NO: 145          moltype = AA  length = 9
FEATURE                 Location/Qualifiers
REGION                  1..9
                        note = peptide
source                  1..9
                        mol_type = protein
                        organism = synthetic construct
SEQUENCE: 145
ILDEAYVRV                                                                   9

SEQ ID NO: 146          moltype = AA  length = 9
FEATURE                 Location/Qualifiers
REGION                  1..9
                        note = peptide
source                  1..9
                        mol_type = protein
                        organism = synthetic construct
SEQUENCE: 146
ALLLLVVGV                                                                   9

SEQ ID NO: 147          moltype = AA  length = 9
FEATURE                 Location/Qualifiers
REGION                  1..9
                        note = peptide
source                  1..9
                        mol_type = protein
                        organism = synthetic construct
SEQUENCE: 147
GLGALLLLV                                                                   9

SEQ ID NO: 148          moltype = AA  length = 9
FEATURE                 Location/Qualifiers
REGION                  1..9
                        note = peptide
source                  1..9
                        mol_type = protein
                        organism = synthetic construct
SEQUENCE: 148
YMQEILHRL                                                                   9
```

```
SEQ ID NO: 149          moltype = AA  length = 9
FEATURE                 Location/Qualifiers
REGION                  1..9
                        note = peptide
source                  1..9
                        mol_type = protein
                        organism = synthetic construct
SEQUENCE: 149
TLAVVSLAV                                                         9

SEQ ID NO: 150          moltype = AA  length = 9
FEATURE                 Location/Qualifiers
REGION                  1..9
                        note = peptide
source                  1..9
                        mol_type = protein
                        organism = synthetic construct
SEQUENCE: 150
LLAVVSLFV                                                         9

SEQ ID NO: 151          moltype = AA  length = 9
FEATURE                 Location/Qualifiers
REGION                  1..9
                        note = peptide
source                  1..9
                        mol_type = protein
                        organism = synthetic construct
SEQUENCE: 151
YLVGILLVL                                                         9

SEQ ID NO: 152          moltype = AA  length = 9
FEATURE                 Location/Qualifiers
REGION                  1..9
                        note = peptide
source                  1..9
                        mol_type = protein
                        organism = synthetic construct
SEQUENCE: 152
KVVGILLPI                                                         9

SEQ ID NO: 153          moltype = AA  length = 9
FEATURE                 Location/Qualifiers
REGION                  1..9
                        note = peptide
source                  1..9
                        mol_type = protein
                        organism = synthetic construct
SEQUENCE: 153
ILVGILLVV                                                         9

SEQ ID NO: 154          moltype = AA  length = 9
FEATURE                 Location/Qualifiers
REGION                  1..9
                        note = peptide
source                  1..9
                        mol_type = protein
                        organism = synthetic construct
SEQUENCE: 154
FVVGILLQV                                                         9

SEQ ID NO: 155          moltype = AA  length = 9
FEATURE                 Location/Qualifiers
REGION                  1..9
                        note = peptide
source                  1..9
                        mol_type = protein
                        organism = synthetic construct
SEQUENCE: 155
ILDEAYVRV                                                         9

SEQ ID NO: 156          moltype = AA  length = 9
FEATURE                 Location/Qualifiers
REGION                  1..9
                        note = peptide
source                  1..9
                        mol_type = protein
                        organism = synthetic construct
SEQUENCE: 156
LLALLPPEV                                                         9
```

```
SEQ ID NO: 157          moltype = AA  length = 9
FEATURE                 Location/Qualifiers
REGION                  1..9
                        note = peptide
source                  1..9
                        mol_type = protein
                        organism = synthetic construct
SEQUENCE: 157
LLALLPPEL                                                         9

SEQ ID NO: 158          moltype = AA  length = 9
FEATURE                 Location/Qualifiers
REGION                  1..9
                        note = peptide
source                  1..9
                        mol_type = protein
                        organism = synthetic construct
SEQUENCE: 158
AMALLPPEV                                                         9

SEQ ID NO: 159          moltype = AA  length = 9
FEATURE                 Location/Qualifiers
REGION                  1..9
                        note = peptide
source                  1..9
                        mol_type = protein
                        organism = synthetic construct
SEQUENCE: 159
ALALLPPPV                                                         9

SEQ ID NO: 160          moltype = AA  length = 9
FEATURE                 Location/Qualifiers
REGION                  1..9
                        note = peptide
source                  1..9
                        mol_type = protein
                        organism = synthetic construct
SEQUENCE: 160
ILISAVVGL                                                         9

SEQ ID NO: 161          moltype = AA  length = 9
FEATURE                 Location/Qualifiers
REGION                  1..9
                        note = peptide
source                  1..9
                        mol_type = protein
                        organism = synthetic construct
SEQUENCE: 161
IVLGVVFGV                                                         9

SEQ ID NO: 162          moltype = AA  length = 9
FEATURE                 Location/Qualifiers
REGION                  1..9
                        note = peptide
source                  1..9
                        mol_type = protein
                        organism = synthetic construct
SEQUENCE: 162
IILGVVFGL                                                         9

SEQ ID NO: 163          moltype = AA  length = 9
FEATURE                 Location/Qualifiers
REGION                  1..9
                        note = peptide
source                  1..9
                        mol_type = protein
                        organism = synthetic construct
SEQUENCE: 163
YLLELLSAL                                                         9

SEQ ID NO: 164          moltype = AA  length = 9
FEATURE                 Location/Qualifiers
REGION                  1..9
                        note = peptide
source                  1..9
                        mol_type = protein
                        organism = synthetic construct
SEQUENCE: 164
```

```
IMWQFLLEL                                                      9

SEQ ID NO: 165          moltype = AA  length = 9
FEATURE                 Location/Qualifiers
REGION                  1..9
                        note = peptide
source                  1..9
                        mol_type = protein
                        organism = synthetic construct
SEQUENCE: 165
YLLDAEPQL                                                      9

SEQ ID NO: 166          moltype = AA  length = 9
FEATURE                 Location/Qualifiers
REGION                  1..9
                        note = peptide
source                  1..9
                        mol_type = protein
                        organism = synthetic construct
SEQUENCE: 166
KLTDTLIPL                                                      9

SEQ ID NO: 167          moltype = AA  length = 9
FEATURE                 Location/Qualifiers
REGION                  1..9
                        note = peptide
source                  1..9
                        mol_type = protein
                        organism = synthetic construct
SEQUENCE: 167
KLTDTLIEL                                                      9

SEQ ID NO: 168          moltype = AA  length = 9
FEATURE                 Location/Qualifiers
REGION                  1..9
                        note = peptide
source                  1..9
                        mol_type = protein
                        organism = synthetic construct
SEQUENCE: 168
YLLFAPNAV                                                      9

SEQ ID NO: 169          moltype = AA  length = 9
FEATURE                 Location/Qualifiers
REGION                  1..9
                        note = peptide
source                  1..9
                        mol_type = protein
                        organism = synthetic construct
SEQUENCE: 169
FLLFAPNSA                                                      9

SEQ ID NO: 170          moltype = AA  length = 9
FEATURE                 Location/Qualifiers
REGION                  1..9
                        note = peptide
source                  1..9
                        mol_type = protein
                        organism = synthetic construct
SEQUENCE: 170
YLDAEPPAV                                                      9

SEQ ID NO: 171          moltype = AA  length = 9
FEATURE                 Location/Qualifiers
REGION                  1..9
                        note = peptide
source                  1..9
                        mol_type = protein
                        organism = synthetic construct
SEQUENCE: 171
TLNSGVYLI                                                      9

SEQ ID NO: 172          moltype = AA  length = 9
FEATURE                 Location/Qualifiers
REGION                  1..9
                        note = peptide
source                  1..9
                        mol_type = protein
                        organism = synthetic construct
```

```
SEQUENCE: 172
KMNSGVYVI                                                   9

SEQ ID NO: 173          moltype = AA  length = 9
FEATURE                 Location/Qualifiers
REGION                  1..9
                        note = peptide
source                  1..9
                        mol_type = protein
                        organism = synthetic construct
SEQUENCE: 173
LLIGLVWSL                                                   9

SEQ ID NO: 174          moltype = AA  length = 9
FEATURE                 Location/Qualifiers
REGION                  1..9
                        note = peptide
source                  1..9
                        mol_type = protein
                        organism = synthetic construct
SEQUENCE: 174
YLYDLLLTV                                                   9

SEQ ID NO: 175          moltype = AA  length = 9
FEATURE                 Location/Qualifiers
REGION                  1..9
                        note = peptide
source                  1..9
                        mol_type = protein
                        organism = synthetic construct
SEQUENCE: 175
VLYDLLLEV                                                   9

SEQ ID NO: 176          moltype = AA  length = 9
FEATURE                 Location/Qualifiers
REGION                  1..9
                        note = peptide
source                  1..9
                        mol_type = protein
                        organism = synthetic construct
SEQUENCE: 176
TLYDLLLSL                                                   9

SEQ ID NO: 177          moltype = AA  length = 9
FEATURE                 Location/Qualifiers
REGION                  1..9
                        note = peptide
source                  1..9
                        mol_type = protein
                        organism = synthetic construct
SEQUENCE: 177
QLYDLLLVA                                                   9

SEQ ID NO: 178          moltype = AA  length = 9
FEATURE                 Location/Qualifiers
REGION                  1..9
                        note = peptide
source                  1..9
                        mol_type = protein
                        organism = synthetic construct
SEQUENCE: 178
QLYDLLLSL                                                   9

SEQ ID NO: 179          moltype = AA  length = 9
FEATURE                 Location/Qualifiers
REGION                  1..9
                        note = peptide
source                  1..9
                        mol_type = protein
                        organism = synthetic construct
SEQUENCE: 179
GLYDLLLRI                                                   9

SEQ ID NO: 180          moltype = AA  length = 9
FEATURE                 Location/Qualifiers
REGION                  1..9
                        note = peptide
source                  1..9
                        mol_type = protein
```

```
                        organism = synthetic construct
SEQUENCE: 180
AVYDLLLEV                                                            9

SEQ ID NO: 181          moltype = AA  length = 9
FEATURE                 Location/Qualifiers
REGION                  1..9
                        note = peptide
source                  1..9
                        mol_type = protein
                        organism = synthetic construct
SEQUENCE: 181
ALYDLLLEV                                                            9

SEQ ID NO: 182          moltype = AA  length = 9
FEATURE                 Location/Qualifiers
REGION                  1..9
                        note = peptide
source                  1..9
                        mol_type = protein
                        organism = synthetic construct
SEQUENCE: 182
VLLLILSGV                                                            9

SEQ ID NO: 183          moltype = AA  length = 9
FEATURE                 Location/Qualifiers
REGION                  1..9
                        note = peptide
source                  1..9
                        mol_type = protein
                        organism = synthetic construct
SEQUENCE: 183
VLLLILSEV                                                            9

SEQ ID NO: 184          moltype = AA  length = 9
FEATURE                 Location/Qualifiers
REGION                  1..9
                        note = peptide
source                  1..9
                        mol_type = protein
                        organism = synthetic construct
SEQUENCE: 184
SLLLILSFV                                                            9

SEQ ID NO: 185          moltype = AA  length = 9
FEATURE                 Location/Qualifiers
REGION                  1..9
                        note = peptide
source                  1..9
                        mol_type = protein
                        organism = synthetic construct
SEQUENCE: 185
MLLLILSYL                                                            9

SEQ ID NO: 186          moltype = AA  length = 9
FEATURE                 Location/Qualifiers
REGION                  1..9
                        note = peptide
source                  1..9
                        mol_type = protein
                        organism = synthetic construct
SEQUENCE: 186
ILLLILSGI                                                            9

SEQ ID NO: 187          moltype = AA  length = 9
FEATURE                 Location/Qualifiers
REGION                  1..9
                        note = peptide
source                  1..9
                        mol_type = protein
                        organism = synthetic construct
SEQUENCE: 187
FLLLILSLL                                                            9

SEQ ID NO: 188          moltype = AA  length = 9
FEATURE                 Location/Qualifiers
REGION                  1..9
                        note = peptide
source                  1..9
```

```
                        mol_type = protein
                        organism = synthetic construct
SEQUENCE: 188
FLLLILSFL                                                             9

SEQ ID NO: 189          moltype = AA  length = 9
FEATURE                 Location/Qualifiers
REGION                  1..9
                        note = peptide
source                  1..9
                        mol_type = protein
                        organism = synthetic construct
SEQUENCE: 189
SLAQLLLAI                                                             9

SEQ ID NO: 190          moltype = AA  length = 9
FEATURE                 Location/Qualifiers
REGION                  1..9
                        note = peptide
source                  1..9
                        mol_type = protein
                        organism = synthetic construct
SEQUENCE: 190
MLAQLLLTV                                                             9

SEQ ID NO: 191          moltype = AA  length = 9
FEATURE                 Location/Qualifiers
REGION                  1..9
                        note = peptide
source                  1..9
                        mol_type = protein
                        organism = synthetic construct
SEQUENCE: 191
KLIHLMAAV                                                             9

SEQ ID NO: 192          moltype = AA  length = 9
FEATURE                 Location/Qualifiers
REGION                  1..9
                        note = peptide
source                  1..9
                        mol_type = protein
                        organism = synthetic construct
SEQUENCE: 192
FLDKITDLV                                                             9

SEQ ID NO: 193          moltype = AA  length = 9
FEATURE                 Location/Qualifiers
REGION                  1..9
                        note = peptide
source                  1..9
                        mol_type = protein
                        organism = synthetic construct
SEQUENCE: 193
FLVEDETVI                                                             9

SEQ ID NO: 194          moltype = AA  length = 9
FEATURE                 Location/Qualifiers
REGION                  1..9
                        note = peptide
source                  1..9
                        mol_type = protein
                        organism = synthetic construct
SEQUENCE: 194
AVFRVLIPV                                                             9

SEQ ID NO: 195          moltype = AA  length = 9
FEATURE                 Location/Qualifiers
REGION                  1..9
                        note = peptide
source                  1..9
                        mol_type = protein
                        organism = synthetic construct
SEQUENCE: 195
LLSAVLALV                                                             9

SEQ ID NO: 196          moltype = AA  length = 9
FEATURE                 Location/Qualifiers
REGION                  1..9
                        note = peptide
```

```
source                1..9
                      mol_type = protein
                      organism = synthetic construct
SEQUENCE: 196
LLSAVLALA                                                         9

SEQ ID NO: 197        moltype = AA  length = 9
FEATURE               Location/Qualifiers
REGION                1..9
                      note = peptide
source                1..9
                      mol_type = protein
                      organism = synthetic construct
SEQUENCE: 197
GISAVLALV                                                         9

SEQ ID NO: 198        moltype = AA  length = 9
FEATURE               Location/Qualifiers
REGION                1..9
                      note = peptide
source                1..9
                      mol_type = protein
                      organism = synthetic construct
SEQUENCE: 198
NLWAGGFFL                                                         9

SEQ ID NO: 199        moltype = AA  length = 9
FEATURE               Location/Qualifiers
REGION                1..9
                      note = peptide
source                1..9
                      mol_type = protein
                      organism = synthetic construct
SEQUENCE: 199
YLALLVMLL                                                         9

SEQ ID NO: 200        moltype = AA  length = 9
FEATURE               Location/Qualifiers
REGION                1..9
                      note = peptide
source                1..9
                      mol_type = protein
                      organism = synthetic construct
SEQUENCE: 200
LLALLVMAV                                                         9

SEQ ID NO: 201        moltype = AA  length = 9
FEATURE               Location/Qualifiers
REGION                1..9
                      note = peptide
source                1..9
                      mol_type = protein
                      organism = synthetic construct
SEQUENCE: 201
ALALLVMAV                                                         9

SEQ ID NO: 202        moltype = AA  length = 9
FEATURE               Location/Qualifiers
REGION                1..9
                      note = peptide
source                1..9
                      mol_type = protein
                      organism = synthetic construct
SEQUENCE: 202
TMLSCLLHL                                                         9

SEQ ID NO: 203        moltype = AA  length = 9
FEATURE               Location/Qualifiers
REGION                1..9
                      note = peptide
source                1..9
                      mol_type = protein
                      organism = synthetic construct
SEQUENCE: 203
MLLSCLLFM                                                         9

SEQ ID NO: 204        moltype = AA  length = 9
FEATURE               Location/Qualifiers
REGION                1..9
```

```
                        note = peptide
source                  1..9
                        mol_type = protein
                        organism = synthetic construct
SEQUENCE: 204
LLLSCLLPL                                                          9

SEQ ID NO: 205          moltype = AA  length = 9
FEATURE                 Location/Qualifiers
REGION                  1..9
                        note = peptide
source                  1..9
                        mol_type = protein
                        organism = synthetic construct
SEQUENCE: 205
LLLSCLLHL                                                          9

SEQ ID NO: 206          moltype = AA  length = 9
FEATURE                 Location/Qualifiers
REGION                  1..9
                        note = peptide
source                  1..9
                        mol_type = protein
                        organism = synthetic construct
SEQUENCE: 206
ILLSCLLLL                                                          9

SEQ ID NO: 207          moltype = AA  length = 9
FEATURE                 Location/Qualifiers
REGION                  1..9
                        note = peptide
source                  1..9
                        mol_type = protein
                        organism = synthetic construct
SEQUENCE: 207
FLLSCLLCL                                                          9

SEQ ID NO: 208          moltype = AA  length = 9
FEATURE                 Location/Qualifiers
REGION                  1..9
                        note = peptide
source                  1..9
                        mol_type = protein
                        organism = synthetic construct
SEQUENCE: 208
ALLSCLLML                                                          9

SEQ ID NO: 209          moltype = AA  length = 9
FEATURE                 Location/Qualifiers
REGION                  1..9
                        note = peptide
source                  1..9
                        mol_type = protein
                        organism = synthetic construct
SEQUENCE: 209
YVAATLFAL                                                          9

SEQ ID NO: 210          moltype = AA  length = 9
FEATURE                 Location/Qualifiers
REGION                  1..9
                        note = peptide
source                  1..9
                        mol_type = protein
                        organism = synthetic construct
SEQUENCE: 210
YLYSEIPDI                                                          9

SEQ ID NO: 211          moltype = AA  length = 9
FEATURE                 Location/Qualifiers
REGION                  1..9
                        note = peptide
source                  1..9
                        mol_type = protein
                        organism = synthetic construct
SEQUENCE: 211
YMASTLVHL                                                          9

SEQ ID NO: 212          moltype = AA  length = 9
FEATURE                 Location/Qualifiers
```

```
REGION                  1..9
                        note = peptide
source                  1..9
                        mol_type = protein
                        organism = synthetic construct
SEQUENCE: 212
QMASTLVYL                                                            9

SEQ ID NO: 213          moltype = AA  length = 9
FEATURE                 Location/Qualifiers
REGION                  1..9
                        note = peptide
source                  1..9
                        mol_type = protein
                        organism = synthetic construct
SEQUENCE: 213
YQFDKIYSI                                                            9

SEQ ID NO: 214          moltype = AA  length = 9
FEATURE                 Location/Qualifiers
REGION                  1..9
                        note = peptide
source                  1..9
                        mol_type = protein
                        organism = synthetic construct
SEQUENCE: 214
MMFWLLLVV                                                            9

SEQ ID NO: 215          moltype = AA  length = 9
FEATURE                 Location/Qualifiers
REGION                  1..9
                        note = peptide
source                  1..9
                        mol_type = protein
                        organism = synthetic construct
SEQUENCE: 215
GMLWEIFGV                                                            9

SEQ ID NO: 216          moltype = AA  length = 9
FEATURE                 Location/Qualifiers
REGION                  1..9
                        note = peptide
source                  1..9
                        mol_type = protein
                        organism = synthetic construct
SEQUENCE: 216
AMKDGLPEV                                                            9

SEQ ID NO: 217          moltype = AA  length = 9
FEATURE                 Location/Qualifiers
REGION                  1..9
                        note = peptide
source                  1..9
                        mol_type = protein
                        organism = synthetic construct
SEQUENCE: 217
TLLDISFAA                                                            9

SEQ ID NO: 218          moltype = AA  length = 9
FEATURE                 Location/Qualifiers
REGION                  1..9
                        note = peptide
source                  1..9
                        mol_type = protein
                        organism = synthetic construct
SEQUENCE: 218
NMLDISFYL                                                            9

SEQ ID NO: 219          moltype = AA  length = 9
FEATURE                 Location/Qualifiers
REGION                  1..9
                        note = peptide
source                  1..9
                        mol_type = protein
                        organism = synthetic construct
SEQUENCE: 219
ILDISFPLV                                                            9

SEQ ID NO: 220          moltype = AA  length = 9
```

```
FEATURE                Location/Qualifiers
REGION                 1..9
                       note = peptide
source                 1..9
                       mol_type = protein
                       organism = synthetic construct
SEQUENCE: 220
LMDLSTTEV                                                        9

SEQ ID NO: 221         moltype = AA  length = 9
FEATURE                Location/Qualifiers
REGION                 1..9
                       note = peptide
source                 1..9
                       mol_type = protein
                       organism = synthetic construct
SEQUENCE: 221
RLSSYLVEI                                                        9

SEQ ID NO: 222         moltype = AA  length = 9
FEATURE                Location/Qualifiers
REGION                 1..9
                       note = peptide
source                 1..9
                       mol_type = protein
                       organism = synthetic construct
SEQUENCE: 222
MVSSYLVEV                                                        9

SEQ ID NO: 223         moltype = AA  length = 9
FEATURE                Location/Qualifiers
REGION                 1..9
                       note = peptide
source                 1..9
                       mol_type = protein
                       organism = synthetic construct
SEQUENCE: 223
KVSSYLVEV                                                        9

SEQ ID NO: 224         moltype = AA  length = 9
FEATURE                Location/Qualifiers
REGION                 1..9
                       note = peptide
source                 1..9
                       mol_type = protein
                       organism = synthetic construct
SEQUENCE: 224
ILSKILLFA                                                        9

SEQ ID NO: 225         moltype = AA  length = 9
FEATURE                Location/Qualifiers
REGION                 1..9
                       note = peptide
source                 1..9
                       mol_type = protein
                       organism = synthetic construct
SEQUENCE: 225
YQLSYSQMV                                                        9

SEQ ID NO: 226         moltype = AA  length = 9
FEATURE                Location/Qualifiers
REGION                 1..9
                       note = peptide
source                 1..9
                       mol_type = protein
                       organism = synthetic construct
SEQUENCE: 226
KLLSYSQEL                                                        9

SEQ ID NO: 227         moltype = AA  length = 9
FEATURE                Location/Qualifiers
REGION                 1..9
                       note = peptide
source                 1..9
                       mol_type = protein
                       organism = synthetic construct
SEQUENCE: 227
KIAELPFPL                                                        9
```

```
SEQ ID NO: 228          moltype = AA  length = 9
FEATURE                 Location/Qualifiers
REGION                  1..9
                        note = peptide
source                  1..9
                        mol_type = protein
                        organism = synthetic construct
SEQUENCE: 228
YLNESETVL                                                          9

SEQ ID NO: 229          moltype = AA  length = 9
FEATURE                 Location/Qualifiers
REGION                  1..9
                        note = peptide
source                  1..9
                        mol_type = protein
                        organism = synthetic construct
SEQUENCE: 229
MLVELLKKV                                                          9

SEQ ID NO: 230          moltype = AA  length = 9
FEATURE                 Location/Qualifiers
REGION                  1..9
                        note = peptide
source                  1..9
                        mol_type = protein
                        organism = synthetic construct
SEQUENCE: 230
KLVELLKLL                                                          9

SEQ ID NO: 231          moltype = AA  length = 9
FEATURE                 Location/Qualifiers
REGION                  1..9
                        note = peptide
source                  1..9
                        mol_type = protein
                        organism = synthetic construct
SEQUENCE: 231
ALVELLKPL                                                          9

SEQ ID NO: 232          moltype = AA  length = 9
FEATURE                 Location/Qualifiers
REGION                  1..9
                        note = peptide
source                  1..9
                        mol_type = protein
                        organism = synthetic construct
SEQUENCE: 232
FLASTTPTA                                                          9

SEQ ID NO: 233          moltype = AA  length = 9
FEATURE                 Location/Qualifiers
REGION                  1..9
                        note = peptide
source                  1..9
                        mol_type = protein
                        organism = synthetic construct
SEQUENCE: 233
SLAREVAAV                                                          9

SEQ ID NO: 234          moltype = AA  length = 9
FEATURE                 Location/Qualifiers
REGION                  1..9
                        note = peptide
source                  1..9
                        mol_type = protein
                        organism = synthetic construct
SEQUENCE: 234
GMAREVAAV                                                          9

SEQ ID NO: 235          moltype = AA  length = 9
FEATURE                 Location/Qualifiers
REGION                  1..9
                        note = peptide
source                  1..9
                        mol_type = protein
                        organism = synthetic construct
SEQUENCE: 235
WLLSLAFLL                                                          9
```

```
SEQ ID NO: 236          moltype = AA  length = 9
FEATURE                 Location/Qualifiers
REGION                  1..9
                        note = peptide
source                  1..9
                        mol_type = protein
                        organism = synthetic construct
SEQUENCE: 236
SLLSLAFSA                                                          9

SEQ ID NO: 237          moltype = AA  length = 9
FEATURE                 Location/Qualifiers
REGION                  1..9
                        note = peptide
source                  1..9
                        mol_type = protein
                        organism = synthetic construct
SEQUENCE: 237
LLLSLAFIL                                                          9

SEQ ID NO: 238          moltype = AA  length = 9
FEATURE                 Location/Qualifiers
REGION                  1..9
                        note = peptide
source                  1..9
                        mol_type = protein
                        organism = synthetic construct
SEQUENCE: 238
KLNPAQGYV                                                          9

SEQ ID NO: 239          moltype = AA  length = 9
FEATURE                 Location/Qualifiers
REGION                  1..9
                        note = peptide
source                  1..9
                        mol_type = protein
                        organism = synthetic construct
SEQUENCE: 239
KLWGLATLI                                                          9

SEQ ID NO: 240          moltype = AA  length = 9
FEATURE                 Location/Qualifiers
REGION                  1..9
                        note = peptide
source                  1..9
                        mol_type = protein
                        organism = synthetic construct
SEQUENCE: 240
VLALGLLAV                                                          9

SEQ ID NO: 241          moltype = AA  length = 9
FEATURE                 Location/Qualifiers
REGION                  1..9
                        note = peptide
source                  1..9
                        mol_type = protein
                        organism = synthetic construct
SEQUENCE: 241
SLALGLLQV                                                          9

SEQ ID NO: 242          moltype = AA  length = 9
FEATURE                 Location/Qualifiers
REGION                  1..9
                        note = peptide
source                  1..9
                        mol_type = protein
                        organism = synthetic construct
SEQUENCE: 242
SLALGLLLV                                                          9

SEQ ID NO: 243          moltype = AA  length = 9
FEATURE                 Location/Qualifiers
REGION                  1..9
                        note = peptide
source                  1..9
                        mol_type = protein
                        organism = synthetic construct
SEQUENCE: 243
```

```
MLALGLLEV                                                   9

SEQ ID NO: 244          moltype = AA  length = 9
FEATURE                 Location/Qualifiers
REGION                  1..9
                        note = peptide
source                  1..9
                        mol_type = protein
                        organism = synthetic construct
SEQUENCE: 244
GLALGLLFV                                                   9

SEQ ID NO: 245          moltype = AA  length = 9
FEATURE                 Location/Qualifiers
REGION                  1..9
                        note = peptide
source                  1..9
                        mol_type = protein
                        organism = synthetic construct
SEQUENCE: 245
GLALGLLAV                                                   9

SEQ ID NO: 246          moltype = AA  length = 9
FEATURE                 Location/Qualifiers
REGION                  1..9
                        note = peptide
source                  1..9
                        mol_type = protein
                        organism = synthetic construct
SEQUENCE: 246
FLALGLLFL                                                   9

SEQ ID NO: 247          moltype = AA  length = 9
FEATURE                 Location/Qualifiers
REGION                  1..9
                        note = peptide
source                  1..9
                        mol_type = protein
                        organism = synthetic construct
SEQUENCE: 247
ALALGLLMV                                                   9

SEQ ID NO: 248          moltype = AA  length = 9
FEATURE                 Location/Qualifiers
REGION                  1..9
                        note = peptide
source                  1..9
                        mol_type = protein
                        organism = synthetic construct
SEQUENCE: 248
VLLLAGAYV                                                   9

SEQ ID NO: 249          moltype = AA  length = 9
FEATURE                 Location/Qualifiers
REGION                  1..9
                        note = peptide
source                  1..9
                        mol_type = protein
                        organism = synthetic construct
SEQUENCE: 249
YLYTFLIVL                                                   9

SEQ ID NO: 250          moltype = AA  length = 9
FEATURE                 Location/Qualifiers
REGION                  1..9
                        note = peptide
source                  1..9
                        mol_type = protein
                        organism = synthetic construct
SEQUENCE: 250
GMYTFLIPM                                                   9

SEQ ID NO: 251          moltype = AA  length = 9
FEATURE                 Location/Qualifiers
REGION                  1..9
                        note = peptide
source                  1..9
                        mol_type = protein
                        organism = synthetic construct
```

-continued

```
SEQUENCE: 251
GLYTFLIPM                                                     9

SEQ ID NO: 252          moltype = AA  length = 9
FEATURE                 Location/Qualifiers
REGION                  1..9
                        note = peptide
source                  1..9
                        mol_type = protein
                        organism = synthetic construct
SEQUENCE: 252
FLISTTFAA                                                     9

SEQ ID NO: 253          moltype = AA  length = 9
FEATURE                 Location/Qualifiers
REGION                  1..9
                        note = peptide
source                  1..9
                        mol_type = protein
                        organism = synthetic construct
SEQUENCE: 253
ILLDTNYEI                                                     9

SEQ ID NO: 254          moltype = AA  length = 9
FEATURE                 Location/Qualifiers
REGION                  1..9
                        note = peptide
source                  1..9
                        mol_type = protein
                        organism = synthetic construct
SEQUENCE: 254
FLPFGFILV                                                     9

SEQ ID NO: 255          moltype = AA  length = 10
FEATURE                 Location/Qualifiers
REGION                  1..10
                        note = peptide
source                  1..10
                        mol_type = protein
                        organism = synthetic construct
SEQUENCE: 255
FLPFGFILPV                                                    10

SEQ ID NO: 256          moltype = AA  length = 9
FEATURE                 Location/Qualifiers
REGION                  1..9
                        note = peptide
source                  1..9
                        mol_type = protein
                        organism = synthetic construct
SEQUENCE: 256
MLYLLPLSL                                                     9

SEQ ID NO: 257          moltype = AA  length = 9
FEATURE                 Location/Qualifiers
REGION                  1..9
                        note = peptide
source                  1..9
                        mol_type = protein
                        organism = synthetic construct
SEQUENCE: 257
MLYLLPLAL                                                     9

SEQ ID NO: 258          moltype = AA  length = 9
FEATURE                 Location/Qualifiers
REGION                  1..9
                        note = peptide
source                  1..9
                        mol_type = protein
                        organism = synthetic construct
SEQUENCE: 258
LLYLLPLFL                                                     9

SEQ ID NO: 259          moltype = AA  length = 9
FEATURE                 Location/Qualifiers
REGION                  1..9
                        note = peptide
source                  1..9
                        mol_type = protein
```

-continued

```
                        organism = synthetic construct
SEQUENCE: 259
SMLYNLLAL                                                                    9

SEQ ID NO: 260          moltype = AA  length = 9
FEATURE                 Location/Qualifiers
REGION                  1..9
                        note = peptide
source                  1..9
                        mol_type = protein
                        organism = synthetic construct
SEQUENCE: 260
AMLYNLLAL                                                                    9

SEQ ID NO: 261          moltype = AA  length = 9
FEATURE                 Location/Qualifiers
REGION                  1..9
                        note = peptide
source                  1..9
                        mol_type = protein
                        organism = synthetic construct
SEQUENCE: 261
ALLYNLLAL                                                                    9

SEQ ID NO: 262          moltype = AA  length = 9
FEATURE                 Location/Qualifiers
REGION                  1..9
                        note = peptide
source                  1..9
                        mol_type = protein
                        organism = synthetic construct
SEQUENCE: 262
ILFLVLQRV                                                                    9

SEQ ID NO: 263          moltype = AA  length = 9
FEATURE                 Location/Qualifiers
REGION                  1..9
                        note = peptide
source                  1..9
                        mol_type = protein
                        organism = synthetic construct
SEQUENCE: 263
YLVAAVVLL                                                                    9

SEQ ID NO: 264          moltype = AA  length = 9
FEATURE                 Location/Qualifiers
REGION                  1..9
                        note = peptide
source                  1..9
                        mol_type = protein
                        organism = synthetic construct
SEQUENCE: 264
YLAERAGHV                                                                    9

SEQ ID NO: 265          moltype = AA  length = 9
FEATURE                 Location/Qualifiers
REGION                  1..9
                        note = peptide
source                  1..9
                        mol_type = protein
                        organism = synthetic construct
SEQUENCE: 265
ILVPLFFTL                                                                    9

SEQ ID NO: 266          moltype = AA  length = 9
FEATURE                 Location/Qualifiers
REGION                  1..9
                        note = peptide
source                  1..9
                        mol_type = protein
                        organism = synthetic construct
SEQUENCE: 266
GLVPLFFAL                                                                    9

SEQ ID NO: 267          moltype = AA  length = 9
FEATURE                 Location/Qualifiers
REGION                  1..9
                        note = peptide
source                  1..9
```

```
                        mol_type = protein
                        organism = synthetic construct
SEQUENCE: 267
FLVPLFFVV                                                   9

SEQ ID NO: 268          moltype = AA  length = 9
FEATURE                 Location/Qualifiers
REGION                  1..9
                        note = peptide
source                  1..9
                        mol_type = protein
                        organism = synthetic construct
SEQUENCE: 268
FLVPLFFLL                                                   9

SEQ ID NO: 269          moltype = AA  length = 9
FEATURE                 Location/Qualifiers
REGION                  1..9
                        note = peptide
source                  1..9
                        mol_type = protein
                        organism = synthetic construct
SEQUENCE: 269
ALVPLFFAL                                                   9

SEQ ID NO: 270          moltype = AA  length = 9
FEATURE                 Location/Qualifiers
REGION                  1..9
                        note = peptide
source                  1..9
                        mol_type = protein
                        organism = synthetic construct
SEQUENCE: 270
YMLPLLAGA                                                   9

SEQ ID NO: 271          moltype = AA  length = 9
FEATURE                 Location/Qualifiers
REGION                  1..9
                        note = peptide
source                  1..9
                        mol_type = protein
                        organism = synthetic construct
SEQUENCE: 271
YLLPLLALA                                                   9

SEQ ID NO: 272          moltype = AA  length = 9
FEATURE                 Location/Qualifiers
REGION                  1..9
                        note = peptide
source                  1..9
                        mol_type = protein
                        organism = synthetic construct
SEQUENCE: 272
WLLPLLAVV                                                   9

SEQ ID NO: 273          moltype = AA  length = 9
FEATURE                 Location/Qualifiers
REGION                  1..9
                        note = peptide
source                  1..9
                        mol_type = protein
                        organism = synthetic construct
SEQUENCE: 273
WLLPLLACL                                                   9

SEQ ID NO: 274          moltype = AA  length = 9
FEATURE                 Location/Qualifiers
REGION                  1..9
                        note = peptide
source                  1..9
                        mol_type = protein
                        organism = synthetic construct
SEQUENCE: 274
WLLPLLAAL                                                   9

SEQ ID NO: 275          moltype = AA  length = 9
FEATURE                 Location/Qualifiers
REGION                  1..9
                        note = peptide
```

```
source                  1..9
                        mol_type = protein
                        organism = synthetic construct
SEQUENCE: 275
TLLPLLAAV                                                          9

SEQ ID NO: 276          moltype = AA  length = 9
FEATURE                 Location/Qualifiers
REGION                  1..9
                        note = peptide
source                  1..9
                        mol_type = protein
                        organism = synthetic construct
SEQUENCE: 276
TLLPLLAAA                                                          9

SEQ ID NO: 277          moltype = AA  length = 9
FEATURE                 Location/Qualifiers
REGION                  1..9
                        note = peptide
source                  1..9
                        mol_type = protein
                        organism = synthetic construct
SEQUENCE: 277
SLLPLLAGV                                                          9

SEQ ID NO: 278          moltype = AA  length = 9
FEATURE                 Location/Qualifiers
REGION                  1..9
                        note = peptide
source                  1..9
                        mol_type = protein
                        organism = synthetic construct
SEQUENCE: 278
RLLPLLAVL                                                          9

SEQ ID NO: 279          moltype = AA  length = 9
FEATURE                 Location/Qualifiers
REGION                  1..9
                        note = peptide
source                  1..9
                        mol_type = protein
                        organism = synthetic construct
SEQUENCE: 279
RLLPLLAAI                                                          9

SEQ ID NO: 280          moltype = AA  length = 9
FEATURE                 Location/Qualifiers
REGION                  1..9
                        note = peptide
source                  1..9
                        mol_type = protein
                        organism = synthetic construct
SEQUENCE: 280
QLLPLLAYV                                                          9

SEQ ID NO: 281          moltype = AA  length = 9
FEATURE                 Location/Qualifiers
REGION                  1..9
                        note = peptide
source                  1..9
                        mol_type = protein
                        organism = synthetic construct
SEQUENCE: 281
LLLPLLAGL                                                          9

SEQ ID NO: 282          moltype = AA  length = 9
FEATURE                 Location/Qualifiers
REGION                  1..9
                        note = peptide
source                  1..9
                        mol_type = protein
                        organism = synthetic construct
SEQUENCE: 282
LLLPLLADL                                                          9

SEQ ID NO: 283          moltype = AA  length = 9
FEATURE                 Location/Qualifiers
REGION                  1..9
```

```
                        note = peptide
source                  1..9
                        mol_type = protein
                        organism = synthetic construct
SEQUENCE: 283
LLLPLLAAA                                                        9

SEQ ID NO: 284          moltype = AA  length = 9
FEATURE                 Location/Qualifiers
REGION                  1..9
                        note = peptide
source                  1..9
                        mol_type = protein
                        organism = synthetic construct
SEQUENCE: 284
HVLPLLATV                                                        9

SEQ ID NO: 285          moltype = AA  length = 9
FEATURE                 Location/Qualifiers
REGION                  1..9
                        note = peptide
source                  1..9
                        mol_type = protein
                        organism = synthetic construct
SEQUENCE: 285
HLLPLLAEV                                                        9

SEQ ID NO: 286          moltype = AA  length = 9
FEATURE                 Location/Qualifiers
REGION                  1..9
                        note = peptide
source                  1..9
                        mol_type = protein
                        organism = synthetic construct
SEQUENCE: 286
GLLPLLAKI                                                        9

SEQ ID NO: 287          moltype = AA  length = 9
FEATURE                 Location/Qualifiers
REGION                  1..9
                        note = peptide
source                  1..9
                        mol_type = protein
                        organism = synthetic construct
SEQUENCE: 287
GILPLLATV                                                        9

SEQ ID NO: 288          moltype = AA  length = 9
FEATURE                 Location/Qualifiers
REGION                  1..9
                        note = peptide
source                  1..9
                        mol_type = protein
                        organism = synthetic construct
SEQUENCE: 288
YLSDAVEAV                                                        9

SEQ ID NO: 289          moltype = AA  length = 9
FEATURE                 Location/Qualifiers
REGION                  1..9
                        note = peptide
source                  1..9
                        mol_type = protein
                        organism = synthetic construct
SEQUENCE: 289
ILREAAMPV                                                        9

SEQ ID NO: 290          moltype = AA  length = 9
FEATURE                 Location/Qualifiers
REGION                  1..9
                        note = peptide
source                  1..9
                        mol_type = protein
                        organism = synthetic construct
SEQUENCE: 290
FLIPAPESL                                                        9

SEQ ID NO: 291          moltype = AA  length = 9
FEATURE                 Location/Qualifiers
```

```
REGION                1..9
                      note = peptide
source                1..9
                      mol_type = protein
                      organism = synthetic construct
SEQUENCE: 291
FLLHGLNLM                                                           9

SEQ ID NO: 292        moltype = AA  length = 9
FEATURE               Location/Qualifiers
REGION                1..9
                      note = peptide
source                1..9
                      mol_type = protein
                      organism = synthetic construct
SEQUENCE: 292
YMSSLPQGL                                                           9

SEQ ID NO: 293        moltype = AA  length = 9
FEATURE               Location/Qualifiers
REGION                1..9
                      note = peptide
source                1..9
                      mol_type = protein
                      organism = synthetic construct
SEQUENCE: 293
YMILGVAMI                                                           9

SEQ ID NO: 294        moltype = AA  length = 9
FEATURE               Location/Qualifiers
REGION                1..9
                      note = peptide
source                1..9
                      mol_type = protein
                      organism = synthetic construct
SEQUENCE: 294
VLILGVAAV                                                           9

SEQ ID NO: 295        moltype = AA  length = 9
FEATURE               Location/Qualifiers
REGION                1..9
                      note = peptide
source                1..9
                      mol_type = protein
                      organism = synthetic construct
SEQUENCE: 295
SLILGVAAV                                                           9

SEQ ID NO: 296        moltype = AA  length = 9
FEATURE               Location/Qualifiers
REGION                1..9
                      note = peptide
source                1..9
                      mol_type = protein
                      organism = synthetic construct
SEQUENCE: 296
ILILGVAGI                                                           9

SEQ ID NO: 297        moltype = AA  length = 9
FEATURE               Location/Qualifiers
REGION                1..9
                      note = peptide
source                1..9
                      mol_type = protein
                      organism = synthetic construct
SEQUENCE: 297
LLDCIIAFL                                                           9

SEQ ID NO: 298        moltype = AA  length = 9
FEATURE               Location/Qualifiers
REGION                1..9
                      note = peptide
source                1..9
                      mol_type = protein
                      organism = synthetic construct
SEQUENCE: 298
LILGIFISV                                                           9

SEQ ID NO: 299        moltype = AA  length = 9
```

```
FEATURE                 Location/Qualifiers
REGION                  1..9
                        note = peptide
source                  1..9
                        mol_type = protein
                        organism = synthetic construct
SEQUENCE: 299
YLAVLGISL                                                                9

SEQ ID NO: 300          moltype = AA  length = 9
FEATURE                 Location/Qualifiers
REGION                  1..9
                        note = peptide
source                  1..9
                        mol_type = protein
                        organism = synthetic construct
SEQUENCE: 300
VLAAIVIGV                                                                9

SEQ ID NO: 301          moltype = AA  length = 9
FEATURE                 Location/Qualifiers
REGION                  1..9
                        note = peptide
source                  1..9
                        mol_type = protein
                        organism = synthetic construct
SEQUENCE: 301
LLACSLAML                                                                9

SEQ ID NO: 302          moltype = AA  length = 9
FEATURE                 Location/Qualifiers
REGION                  1..9
                        note = peptide
source                  1..9
                        mol_type = protein
                        organism = synthetic construct
SEQUENCE: 302
FVIGIVALV                                                                9

SEQ ID NO: 303          moltype = AA  length = 9
FEATURE                 Location/Qualifiers
REGION                  1..9
                        note = peptide
source                  1..9
                        mol_type = protein
                        organism = synthetic construct
SEQUENCE: 303
YVVAVPTPV                                                                9

SEQ ID NO: 304          moltype = AA  length = 9
FEATURE                 Location/Qualifiers
REGION                  1..9
                        note = peptide
source                  1..9
                        mol_type = protein
                        organism = synthetic construct
SEQUENCE: 304
YIVAVPTPV                                                                9

SEQ ID NO: 305          moltype = AA  length = 9
FEATURE                 Location/Qualifiers
REGION                  1..9
                        note = peptide
source                  1..9
                        mol_type = protein
                        organism = synthetic construct
SEQUENCE: 305
FIVAVPTPI                                                                9

SEQ ID NO: 306          moltype = AA  length = 9
FEATURE                 Location/Qualifiers
REGION                  1..9
                        note = peptide
source                  1..9
                        mol_type = protein
                        organism = synthetic construct
SEQUENCE: 306
MLKELSPEL                                                                9
```

```
SEQ ID NO: 307          moltype = AA  length = 9
FEATURE                 Location/Qualifiers
REGION                  1..9
                        note = peptide
source                  1..9
                        mol_type = protein
                        organism = synthetic construct
SEQUENCE: 307
FLKELSPGL                                                   9

SEQ ID NO: 308          moltype = AA  length = 9
FEATURE                 Location/Qualifiers
REGION                  1..9
                        note = peptide
source                  1..9
                        mol_type = protein
                        organism = synthetic construct
SEQUENCE: 308
FVADLVGHV                                                   9

SEQ ID NO: 309          moltype = AA  length = 9
FEATURE                 Location/Qualifiers
REGION                  1..9
                        note = peptide
source                  1..9
                        mol_type = protein
                        organism = synthetic construct
SEQUENCE: 309
SLLGTLEEL                                                   9

SEQ ID NO: 310          moltype = AA  length = 9
FEATURE                 Location/Qualifiers
REGION                  1..9
                        note = peptide
source                  1..9
                        mol_type = protein
                        organism = synthetic construct
SEQUENCE: 310
VMLSDVQSV                                                   9

SEQ ID NO: 311          moltype = AA  length = 9
FEATURE                 Location/Qualifiers
REGION                  1..9
                        note = peptide
source                  1..9
                        mol_type = protein
                        organism = synthetic construct
SEQUENCE: 311
RLLSDVQGL                                                   9

SEQ ID NO: 312          moltype = AA  length = 9
FEATURE                 Location/Qualifiers
REGION                  1..9
                        note = peptide
source                  1..9
                        mol_type = protein
                        organism = synthetic construct
SEQUENCE: 312
SLILILSSV                                                   9

SEQ ID NO: 313          moltype = AA  length = 9
FEATURE                 Location/Qualifiers
REGION                  1..9
                        note = peptide
source                  1..9
                        mol_type = protein
                        organism = synthetic construct
SEQUENCE: 313
KLILILSYL                                                   9

SEQ ID NO: 314          moltype = AA  length = 9
FEATURE                 Location/Qualifiers
REGION                  1..9
                        note = peptide
source                  1..9
                        mol_type = protein
                        organism = synthetic construct
SEQUENCE: 314
ALDAIFGGV                                                   9
```

```
SEQ ID NO: 315          moltype = AA  length = 9
FEATURE                 Location/Qualifiers
REGION                  1..9
                        note = peptide
source                  1..9
                        mol_type = protein
                        organism = synthetic construct
SEQUENCE: 315
FLITKAEEL                                                         9

SEQ ID NO: 316          moltype = AA  length = 9
FEATURE                 Location/Qualifiers
REGION                  1..9
                        note = peptide
source                  1..9
                        mol_type = protein
                        organism = synthetic construct
SEQUENCE: 316
SLLEELPAL                                                         9

SEQ ID NO: 317          moltype = AA  length = 9
FEATURE                 Location/Qualifiers
REGION                  1..9
                        note = peptide
source                  1..9
                        mol_type = protein
                        organism = synthetic construct
SEQUENCE: 317
MTLEELPFL                                                         9

SEQ ID NO: 318          moltype = AA  length = 9
FEATURE                 Location/Qualifiers
REGION                  1..9
                        note = peptide
source                  1..9
                        mol_type = protein
                        organism = synthetic construct
SEQUENCE: 318
IILEYIALL                                                         9

SEQ ID NO: 319          moltype = AA  length = 9
FEATURE                 Location/Qualifiers
REGION                  1..9
                        note = peptide
source                  1..9
                        mol_type = protein
                        organism = synthetic construct
SEQUENCE: 319
YMVFGIEGI                                                         9

SEQ ID NO: 320          moltype = AA  length = 9
FEATURE                 Location/Qualifiers
REGION                  1..9
                        note = peptide
source                  1..9
                        mol_type = protein
                        organism = synthetic construct
SEQUENCE: 320
SLSSSSPLV                                                         9

SEQ ID NO: 321          moltype = AA  length = 9
FEATURE                 Location/Qualifiers
REGION                  1..9
                        note = peptide
source                  1..9
                        mol_type = protein
                        organism = synthetic construct
SEQUENCE: 321
KLDELAHFL                                                         9

SEQ ID NO: 322          moltype = AA  length = 9
FEATURE                 Location/Qualifiers
REGION                  1..9
                        note = peptide
source                  1..9
                        mol_type = protein
                        organism = synthetic construct
SEQUENCE: 322
```

```
FVLEHVVPL                                                  9

SEQ ID NO: 323          moltype = AA  length = 9
FEATURE                 Location/Qualifiers
REGION                  1..9
                        note = peptide
source                  1..9
                        mol_type = protein
                        organism = synthetic construct
SEQUENCE: 323
YLLGVLLLL                                                  9

SEQ ID NO: 324          moltype = AA  length = 9
FEATURE                 Location/Qualifiers
REGION                  1..9
                        note = peptide
source                  1..9
                        mol_type = protein
                        organism = synthetic construct
SEQUENCE: 324
YILGVLLTA                                                  9

SEQ ID NO: 325          moltype = AA  length = 9
FEATURE                 Location/Qualifiers
REGION                  1..9
                        note = peptide
source                  1..9
                        mol_type = protein
                        organism = synthetic construct
SEQUENCE: 325
MLLGVLLLL                                                  9

SEQ ID NO: 326          moltype = AA  length = 9
FEATURE                 Location/Qualifiers
REGION                  1..9
                        note = peptide
source                  1..9
                        mol_type = protein
                        organism = synthetic construct
SEQUENCE: 326
MILGVLLFL                                                  9

SEQ ID NO: 327          moltype = AA  length = 9
FEATURE                 Location/Qualifiers
REGION                  1..9
                        note = peptide
source                  1..9
                        mol_type = protein
                        organism = synthetic construct
SEQUENCE: 327
LMLGVLLLA                                                  9

SEQ ID NO: 328          moltype = AA  length = 9
FEATURE                 Location/Qualifiers
REGION                  1..9
                        note = peptide
source                  1..9
                        mol_type = protein
                        organism = synthetic construct
SEQUENCE: 328
LLLGVLLLL                                                  9

SEQ ID NO: 329          moltype = AA  length = 9
FEATURE                 Location/Qualifiers
REGION                  1..9
                        note = peptide
source                  1..9
                        mol_type = protein
                        organism = synthetic construct
SEQUENCE: 329
KLLGVLLLV                                                  9

SEQ ID NO: 330          moltype = AA  length = 9
FEATURE                 Location/Qualifiers
REGION                  1..9
                        note = peptide
source                  1..9
                        mol_type = protein
                        organism = synthetic construct
```

-continued

```
SEQUENCE: 330
IILGVLLAV                                                    9

SEQ ID NO: 331          moltype = AA  length = 9
FEATURE                 Location/Qualifiers
REGION                  1..9
                        note = peptide
source                  1..9
                        mol_type = protein
                        organism = synthetic construct
SEQUENCE: 331
FILGVLLSL                                                    9

SEQ ID NO: 332          moltype = AA  length = 9
FEATURE                 Location/Qualifiers
REGION                  1..9
                        note = peptide
source                  1..9
                        mol_type = protein
                        organism = synthetic construct
SEQUENCE: 332
ALLGVLLLL                                                    9

SEQ ID NO: 333          moltype = AA  length = 9
FEATURE                 Location/Qualifiers
REGION                  1..9
                        note = peptide
source                  1..9
                        mol_type = protein
                        organism = synthetic construct
SEQUENCE: 333
ALLGVLLLA                                                    9

SEQ ID NO: 334          moltype = AA  length = 9
FEATURE                 Location/Qualifiers
REGION                  1..9
                        note = peptide
source                  1..9
                        mol_type = protein
                        organism = synthetic construct
SEQUENCE: 334
AILGVLLLV                                                    9

SEQ ID NO: 335          moltype = AA  length = 9
FEATURE                 Location/Qualifiers
REGION                  1..9
                        note = peptide
source                  1..9
                        mol_type = protein
                        organism = synthetic construct
SEQUENCE: 335
ILAAGVPEL                                                    9

SEQ ID NO: 336          moltype = AA  length = 9
FEATURE                 Location/Qualifiers
REGION                  1..9
                        note = peptide
source                  1..9
                        mol_type = protein
                        organism = synthetic construct
SEQUENCE: 336
YVSDILSYV                                                    9

SEQ ID NO: 337          moltype = AA  length = 9
FEATURE                 Location/Qualifiers
REGION                  1..9
                        note = peptide
source                  1..9
                        mol_type = protein
                        organism = synthetic construct
SEQUENCE: 337
YISDILSYV                                                    9

SEQ ID NO: 338          moltype = AA  length = 9
FEATURE                 Location/Qualifiers
REGION                  1..9
                        note = peptide
source                  1..9
                        mol_type = protein
```

```
                        organism = synthetic construct
SEQUENCE: 338
VISDILSFL                                                                9

SEQ ID NO: 339          moltype = AA  length = 9
FEATURE                 Location/Qualifiers
REGION                  1..9
                        note = peptide
source                  1..9
                        mol_type = protein
                        organism = synthetic construct
SEQUENCE: 339
SMSDILSRL                                                                9

SEQ ID NO: 340          moltype = AA  length = 9
FEATURE                 Location/Qualifiers
REGION                  1..9
                        note = peptide
source                  1..9
                        mol_type = protein
                        organism = synthetic construct
SEQUENCE: 340
FVSDILSAA                                                                9

SEQ ID NO: 341          moltype = AA  length = 9
FEATURE                 Location/Qualifiers
REGION                  1..9
                        note = peptide
source                  1..9
                        mol_type = protein
                        organism = synthetic construct
SEQUENCE: 341
WLLAASVTV                                                                9

SEQ ID NO: 342          moltype = AA  length = 9
FEATURE                 Location/Qualifiers
REGION                  1..9
                        note = peptide
source                  1..9
                        mol_type = protein
                        organism = synthetic construct
SEQUENCE: 342
ILLAASVLV                                                                9

SEQ ID NO: 343          moltype = AA  length = 9
FEATURE                 Location/Qualifiers
REGION                  1..9
                        note = peptide
source                  1..9
                        mol_type = protein
                        organism = synthetic construct
SEQUENCE: 343
FLLAASVMM                                                                9

SEQ ID NO: 344          moltype = AA  length = 9
FEATURE                 Location/Qualifiers
REGION                  1..9
                        note = peptide
source                  1..9
                        mol_type = protein
                        organism = synthetic construct
SEQUENCE: 344
ALLAASVLV                                                                9

SEQ ID NO: 345          moltype = AA  length = 9
FEATURE                 Location/Qualifiers
REGION                  1..9
                        note = peptide
source                  1..9
                        mol_type = protein
                        organism = synthetic construct
SEQUENCE: 345
LLAASVALL                                                                9

SEQ ID NO: 346          moltype = AA  length = 9
FEATURE                 Location/Qualifiers
REGION                  1..9
                        note = peptide
source                  1..9
```

```
                        mol_type = protein
                        organism = synthetic construct
SEQUENCE: 346
LLAASVAGV                                                             9

SEQ ID NO: 347          moltype = AA  length = 9
FEATURE                 Location/Qualifiers
REGION                  1..9
                        note = peptide
source                  1..9
                        mol_type = protein
                        organism = synthetic construct
SEQUENCE: 347
ILAASVAAV                                                             9

SEQ ID NO: 348          moltype = AA  length = 9
FEATURE                 Location/Qualifiers
REGION                  1..9
                        note = peptide
source                  1..9
                        mol_type = protein
                        organism = synthetic construct
SEQUENCE: 348
GLAASVAPV                                                             9

SEQ ID NO: 349          moltype = AA  length = 9
FEATURE                 Location/Qualifiers
REGION                  1..9
                        note = peptide
source                  1..9
                        mol_type = protein
                        organism = synthetic construct
SEQUENCE: 349
ALLRKVAEV                                                             9

SEQ ID NO: 350          moltype = AA  length = 9
FEATURE                 Location/Qualifiers
REGION                  1..9
                        note = peptide
source                  1..9
                        mol_type = protein
                        organism = synthetic construct
SEQUENCE: 350
SLPELYAWI                                                             9

SEQ ID NO: 351          moltype = AA  length = 9
FEATURE                 Location/Qualifiers
REGION                  1..9
                        note = peptide
source                  1..9
                        mol_type = protein
                        organism = synthetic construct
SEQUENCE: 351
ILYGKIKYL                                                             9

SEQ ID NO: 352          moltype = AA  length = 9
FEATURE                 Location/Qualifiers
REGION                  1..9
                        note = peptide
source                  1..9
                        mol_type = protein
                        organism = synthetic construct
SEQUENCE: 352
MLLGLAAFL                                                             9

SEQ ID NO: 353          moltype = AA  length = 9
FEATURE                 Location/Qualifiers
REGION                  1..9
                        note = peptide
source                  1..9
                        mol_type = protein
                        organism = synthetic construct
SEQUENCE: 353
GLLGLAAFL                                                             9

SEQ ID NO: 354          moltype = AA  length = 9
FEATURE                 Location/Qualifiers
REGION                  1..9
                        note = peptide
```

```
source                  1..9
                        mol_type = protein
                        organism = synthetic construct
SEQUENCE: 354
ALLGLAAFL                                                                     9

SEQ ID NO: 355          moltype = AA  length = 9
FEATURE                 Location/Qualifiers
REGION                  1..9
                        note = peptide
source                  1..9
                        mol_type = protein
                        organism = synthetic construct
SEQUENCE: 355
YLDEVKSLV                                                                     9

SEQ ID NO: 356          moltype = AA  length = 9
FEATURE                 Location/Qualifiers
REGION                  1..9
                        note = peptide
source                  1..9
                        mol_type = protein
                        organism = synthetic construct
SEQUENCE: 356
YLDEVKSLI                                                                     9

SEQ ID NO: 357          moltype = AA  length = 9
FEATURE                 Location/Qualifiers
REGION                  1..9
                        note = peptide
source                  1..9
                        mol_type = protein
                        organism = synthetic construct
SEQUENCE: 357
YLDEVKSIL                                                                     9

SEQ ID NO: 358          moltype = AA  length = 9
FEATURE                 Location/Qualifiers
REGION                  1..9
                        note = peptide
source                  1..9
                        mol_type = protein
                        organism = synthetic construct
SEQUENCE: 358
LLDEVKSLV                                                                     9

SEQ ID NO: 359          moltype = AA  length = 9
FEATURE                 Location/Qualifiers
REGION                  1..9
                        note = peptide
source                  1..9
                        mol_type = protein
                        organism = synthetic construct
SEQUENCE: 359
FILLSLSPV                                                                     9

SEQ ID NO: 360          moltype = AA  length = 9
FEATURE                 Location/Qualifiers
REGION                  1..9
                        note = peptide
source                  1..9
                        mol_type = protein
                        organism = synthetic construct
SEQUENCE: 360
RLFLFSVLV                                                                     9

SEQ ID NO: 361          moltype = AA  length = 9
FEATURE                 Location/Qualifiers
REGION                  1..9
                        note = peptide
source                  1..9
                        mol_type = protein
                        organism = synthetic construct
SEQUENCE: 361
ALTVYLVYL                                                                     9

SEQ ID NO: 362          moltype = AA  length = 9
FEATURE                 Location/Qualifiers
REGION                  1..9
```

```
                        note = peptide
source                  1..9
                        mol_type = protein
                        organism = synthetic construct
SEQUENCE: 362
RLLFVAVPI                                                         9

SEQ ID NO: 363          moltype = AA  length = 9
FEATURE                 Location/Qualifiers
REGION                  1..9
                        note = peptide
source                  1..9
                        mol_type = protein
                        organism = synthetic construct
SEQUENCE: 363
RLLFVAVGL                                                         9

SEQ ID NO: 364          moltype = AA  length = 9
FEATURE                 Location/Qualifiers
REGION                  1..9
                        note = peptide
source                  1..9
                        mol_type = protein
                        organism = synthetic construct
SEQUENCE: 364
FLLFVAVSV                                                         9

SEQ ID NO: 365          moltype = AA  length = 9
FEATURE                 Location/Qualifiers
REGION                  1..9
                        note = peptide
source                  1..9
                        mol_type = protein
                        organism = synthetic construct
SEQUENCE: 365
FISLFLFSV                                                         9

SEQ ID NO: 366          moltype = AA  length = 9
FEATURE                 Location/Qualifiers
REGION                  1..9
                        note = peptide
source                  1..9
                        mol_type = protein
                        organism = synthetic construct
SEQUENCE: 366
LIAGFVALV                                                         9

SEQ ID NO: 367          moltype = AA  length = 9
FEATURE                 Location/Qualifiers
REGION                  1..9
                        note = peptide
source                  1..9
                        mol_type = protein
                        organism = synthetic construct
SEQUENCE: 367
YLLVLMASI                                                         9

SEQ ID NO: 368          moltype = AA  length = 9
FEATURE                 Location/Qualifiers
REGION                  1..9
                        note = peptide
source                  1..9
                        mol_type = protein
                        organism = synthetic construct
SEQUENCE: 368
YLVGILLVL                                                         9

SEQ ID NO: 369          moltype = AA  length = 9
FEATURE                 Location/Qualifiers
REGION                  1..9
                        note = peptide
source                  1..9
                        mol_type = protein
                        organism = synthetic construct
SEQUENCE: 369
KIVGILLGI                                                         9

SEQ ID NO: 370          moltype = AA  length = 9
FEATURE                 Location/Qualifiers
```

```
REGION                 1..9
                       note = peptide
source                 1..9
                       mol_type = protein
                       organism = synthetic construct
SEQUENCE: 370
KIVGILLAV                                                            9

SEQ ID NO: 371         moltype = AA  length = 9
FEATURE                Location/Qualifiers
REGION                 1..9
                       note = peptide
source                 1..9
                       mol_type = protein
                       organism = synthetic construct
SEQUENCE: 371
ILVGILLVV                                                            9

SEQ ID NO: 372         moltype = AA  length = 9
FEATURE                Location/Qualifiers
REGION                 1..9
                       note = peptide
source                 1..9
                       mol_type = protein
                       organism = synthetic construct
SEQUENCE: 372
GIVGILLNV                                                            9

SEQ ID NO: 373         moltype = AA  length = 9
FEATURE                Location/Qualifiers
REGION                 1..9
                       note = peptide
source                 1..9
                       mol_type = protein
                       organism = synthetic construct
SEQUENCE: 373
GIVGILLAV                                                            9

SEQ ID NO: 374         moltype = AA  length = 9
FEATURE                Location/Qualifiers
REGION                 1..9
                       note = peptide
source                 1..9
                       mol_type = protein
                       organism = synthetic construct
SEQUENCE: 374
LLAVVLAFV                                                            9

SEQ ID NO: 375         moltype = AA  length = 9
FEATURE                Location/Qualifiers
REGION                 1..9
                       note = peptide
source                 1..9
                       mol_type = protein
                       organism = synthetic construct
SEQUENCE: 375
LLAVVLAAV                                                            9

SEQ ID NO: 376         moltype = AA  length = 9
FEATURE                Location/Qualifiers
REGION                 1..9
                       note = peptide
source                 1..9
                       mol_type = protein
                       organism = synthetic construct
SEQUENCE: 376
GVLDGTATV                                                            9

SEQ ID NO: 377         moltype = AA  length = 9
FEATURE                Location/Qualifiers
REGION                 1..9
                       note = peptide
source                 1..9
                       mol_type = protein
                       organism = synthetic construct
SEQUENCE: 377
ALADTNSYV                                                            9

SEQ ID NO: 378         moltype = AA  length = 9
```

```
FEATURE                 Location/Qualifiers
REGION                  1..9
                        note = peptide
source                  1..9
                        mol_type = protein
                        organism = synthetic construct
SEQUENCE: 378
ALADTNSYL                                                                     9

SEQ ID NO: 379          moltype = AA  length = 9
FEATURE                 Location/Qualifiers
REGION                  1..9
                        note = peptide
source                  1..9
                        mol_type = protein
                        organism = synthetic construct
SEQUENCE: 379
AMQAAIPML                                                                     9

SEQ ID NO: 380          moltype = AA  length = 9
FEATURE                 Location/Qualifiers
REGION                  1..9
                        note = peptide
source                  1..9
                        mol_type = protein
                        organism = synthetic construct
SEQUENCE: 380
IVLDGLDLV                                                                     9

SEQ ID NO: 381          moltype = AA  length = 9
FEATURE                 Location/Qualifiers
REGION                  1..9
                        note = peptide
source                  1..9
                        mol_type = protein
                        organism = synthetic construct
SEQUENCE: 381
AVLDGLDPV                                                                     9

SEQ ID NO: 382          moltype = AA  length = 9
FEATURE                 Location/Qualifiers
REGION                  1..9
                        note = peptide
source                  1..9
                        mol_type = protein
                        organism = synthetic construct
SEQUENCE: 382
YLLALLPLL                                                                     9

SEQ ID NO: 383          moltype = AA  length = 9
FEATURE                 Location/Qualifiers
REGION                  1..9
                        note = peptide
source                  1..9
                        mol_type = protein
                        organism = synthetic construct
SEQUENCE: 383
YLLALLPIL                                                                     9

SEQ ID NO: 384          moltype = AA  length = 9
FEATURE                 Location/Qualifiers
REGION                  1..9
                        note = peptide
source                  1..9
                        mol_type = protein
                        organism = synthetic construct
SEQUENCE: 384
QLLALLPGV                                                                     9

SEQ ID NO: 385          moltype = AA  length = 9
FEATURE                 Location/Qualifiers
REGION                  1..9
                        note = peptide
source                  1..9
                        mol_type = protein
                        organism = synthetic construct
SEQUENCE: 385
LLLALLPTV                                                                     9
```

-continued

```
SEQ ID NO: 386          moltype = AA  length = 9
FEATURE                 Location/Qualifiers
REGION                  1..9
                        note = peptide
source                  1..9
                        mol_type = protein
                        organism = synthetic construct
SEQUENCE: 386
FLRELLCQL                                                         9

SEQ ID NO: 387          moltype = AA  length = 9
FEATURE                 Location/Qualifiers
REGION                  1..9
                        note = peptide
source                  1..9
                        mol_type = protein
                        organism = synthetic construct
SEQUENCE: 387
LLYPVPLGV                                                         9

SEQ ID NO: 388          moltype = AA  length = 9
FEATURE                 Location/Qualifiers
REGION                  1..9
                        note = peptide
source                  1..9
                        mol_type = protein
                        organism = synthetic construct
SEQUENCE: 388
ALFLLSYTV                                                         9

SEQ ID NO: 389          moltype = AA  length = 9
FEATURE                 Location/Qualifiers
REGION                  1..9
                        note = peptide
source                  1..9
                        mol_type = protein
                        organism = synthetic construct
SEQUENCE: 389
YVLSLLLTL                                                         9

SEQ ID NO: 390          moltype = AA  length = 9
FEATURE                 Location/Qualifiers
REGION                  1..9
                        note = peptide
source                  1..9
                        mol_type = protein
                        organism = synthetic construct
SEQUENCE: 390
VLLSLLLIV                                                         9

SEQ ID NO: 391          moltype = AA  length = 9
FEATURE                 Location/Qualifiers
REGION                  1..9
                        note = peptide
source                  1..9
                        mol_type = protein
                        organism = synthetic construct
SEQUENCE: 391
SLLSLLLIL                                                         9

SEQ ID NO: 392          moltype = AA  length = 9
FEATURE                 Location/Qualifiers
REGION                  1..9
                        note = peptide
source                  1..9
                        mol_type = protein
                        organism = synthetic construct
SEQUENCE: 392
RLLSLLLVL                                                         9

SEQ ID NO: 393          moltype = AA  length = 9
FEATURE                 Location/Qualifiers
REGION                  1..9
                        note = peptide
source                  1..9
                        mol_type = protein
                        organism = synthetic construct
SEQUENCE: 393
LVLSLLLLV                                                         9
```

```
SEQ ID NO: 394          moltype = AA  length = 9
FEATURE                 Location/Qualifiers
REGION                  1..9
                        note = peptide
source                  1..9
                        mol_type = protein
                        organism = synthetic construct
SEQUENCE: 394
KLLSLLLVL                                                         9

SEQ ID NO: 395          moltype = AA  length = 9
FEATURE                 Location/Qualifiers
REGION                  1..9
                        note = peptide
source                  1..9
                        mol_type = protein
                        organism = synthetic construct
SEQUENCE: 395
ILLSLLLVL                                                         9

SEQ ID NO: 396          moltype = AA  length = 9
FEATURE                 Location/Qualifiers
REGION                  1..9
                        note = peptide
source                  1..9
                        mol_type = protein
                        organism = synthetic construct
SEQUENCE: 396
FTLSLLLTL                                                         9

SEQ ID NO: 397          moltype = AA  length = 9
FEATURE                 Location/Qualifiers
REGION                  1..9
                        note = peptide
source                  1..9
                        mol_type = protein
                        organism = synthetic construct
SEQUENCE: 397
ALLSLLLIL                                                         9

SEQ ID NO: 398          moltype = AA  length = 9
FEATURE                 Location/Qualifiers
REGION                  1..9
                        note = peptide
source                  1..9
                        mol_type = protein
                        organism = synthetic construct
SEQUENCE: 398
VLFVLSLFL                                                         9

SEQ ID NO: 399          moltype = AA  length = 9
FEATURE                 Location/Qualifiers
REGION                  1..9
                        note = peptide
source                  1..9
                        mol_type = protein
                        organism = synthetic construct
SEQUENCE: 399
ILFVLSLQL                                                         9

SEQ ID NO: 400          moltype = AA  length = 9
FEATURE                 Location/Qualifiers
REGION                  1..9
                        note = peptide
source                  1..9
                        mol_type = protein
                        organism = synthetic construct
SEQUENCE: 400
LLLEKQAEV                                                         9

SEQ ID NO: 401          moltype = AA  length = 9
FEATURE                 Location/Qualifiers
REGION                  1..9
                        note = peptide
source                  1..9
                        mol_type = protein
                        organism = synthetic construct
SEQUENCE: 401
```

```
VLSELKLAV                                                   9

SEQ ID NO: 402          moltype = AA  length = 9
FEATURE                 Location/Qualifiers
REGION                  1..9
                        note = peptide
source                  1..9
                        mol_type = protein
                        organism = synthetic construct
SEQUENCE: 402
RMIEHVLTV                                                   9

SEQ ID NO: 403          moltype = AA  length = 9
FEATURE                 Location/Qualifiers
REGION                  1..9
                        note = peptide
source                  1..9
                        mol_type = protein
                        organism = synthetic construct
SEQUENCE: 403
QIFDRLIPI                                                   9

SEQ ID NO: 404          moltype = AA  length = 9
FEATURE                 Location/Qualifiers
REGION                  1..9
                        note = peptide
source                  1..9
                        mol_type = protein
                        organism = synthetic construct
SEQUENCE: 404
GVFDRLIPI                                                   9

SEQ ID NO: 405          moltype = AA  length = 9
FEATURE                 Location/Qualifiers
REGION                  1..9
                        note = peptide
source                  1..9
                        mol_type = protein
                        organism = synthetic construct
SEQUENCE: 405
YLKEQFQTL                                                   9

SEQ ID NO: 406          moltype = AA  length = 9
FEATURE                 Location/Qualifiers
REGION                  1..9
                        note = peptide
source                  1..9
                        mol_type = protein
                        organism = synthetic construct
SEQUENCE: 406
SLLDSAFLL                                                   9

SEQ ID NO: 407          moltype = AA  length = 9
FEATURE                 Location/Qualifiers
REGION                  1..9
                        note = peptide
source                  1..9
                        mol_type = protein
                        organism = synthetic construct
SEQUENCE: 407
MLSLVFSLI                                                   9

SEQ ID NO: 408          moltype = AA  length = 9
FEATURE                 Location/Qualifiers
REGION                  1..9
                        note = peptide
source                  1..9
                        mol_type = protein
                        organism = synthetic construct
SEQUENCE: 408
LMSLVFSLV                                                   9

SEQ ID NO: 409          moltype = AA  length = 9
FEATURE                 Location/Qualifiers
REGION                  1..9
                        note = peptide
source                  1..9
                        mol_type = protein
                        organism = synthetic construct
```

```
SEQUENCE: 409
WMQILPYQV                                                    9

SEQ ID NO: 410          moltype = AA  length = 9
FEATURE                 Location/Qualifiers
REGION                  1..9
                        note = peptide
source                  1..9
                        mol_type = protein
                        organism = synthetic construct
SEQUENCE: 410
MMTGFTFGV                                                    9

SEQ ID NO: 411          moltype = AA  length = 9
FEATURE                 Location/Qualifiers
REGION                  1..9
                        note = peptide
source                  1..9
                        mol_type = protein
                        organism = synthetic construct
SEQUENCE: 411
MLLLLVNLV                                                    9

SEQ ID NO: 412          moltype = AA  length = 9
FEATURE                 Location/Qualifiers
REGION                  1..9
                        note = peptide
source                  1..9
                        mol_type = protein
                        organism = synthetic construct
SEQUENCE: 412
VLFGLLTFL                                                    9

SEQ ID NO: 413          moltype = AA  length = 9
FEATURE                 Location/Qualifiers
REGION                  1..9
                        note = peptide
source                  1..9
                        mol_type = protein
                        organism = synthetic construct
SEQUENCE: 413
QLFGLLTDV                                                    9

SEQ ID NO: 414          moltype = AA  length = 9
FEATURE                 Location/Qualifiers
REGION                  1..9
                        note = peptide
source                  1..9
                        mol_type = protein
                        organism = synthetic construct
SEQUENCE: 414
FLFGLLTMI                                                    9

SEQ ID NO: 415          moltype = AA  length = 9
FEATURE                 Location/Qualifiers
REGION                  1..9
                        note = peptide
source                  1..9
                        mol_type = protein
                        organism = synthetic construct
SEQUENCE: 415
FLFGLLTDA                                                    9

SEQ ID NO: 416          moltype = AA  length = 9
FEATURE                 Location/Qualifiers
REGION                  1..9
                        note = peptide
source                  1..9
                        mol_type = protein
                        organism = synthetic construct
SEQUENCE: 416
TLLLSLFLL                                                    9

SEQ ID NO: 417          moltype = AA  length = 9
FEATURE                 Location/Qualifiers
REGION                  1..9
                        note = peptide
source                  1..9
                        mol_type = protein
```

```
                        organism = synthetic construct
SEQUENCE: 417
FILLSLFML                                                                   9

SEQ ID NO: 418          moltype = AA  length = 9
FEATURE                 Location/Qualifiers
REGION                  1..9
                        note = peptide
source                  1..9
                        mol_type = protein
                        organism = synthetic construct
SEQUENCE: 418
ILLPPPPVV                                                                   9

SEQ ID NO: 419          moltype = AA  length = 9
FEATURE                 Location/Qualifiers
REGION                  1..9
                        note = peptide
source                  1..9
                        mol_type = protein
                        organism = synthetic construct
SEQUENCE: 419
VLLTLIFAL                                                                   9

SEQ ID NO: 420          moltype = AA  length = 9
FEATURE                 Location/Qualifiers
REGION                  1..9
                        note = peptide
source                  1..9
                        mol_type = protein
                        organism = synthetic construct
SEQUENCE: 420
RLLTLIFTL                                                                   9

SEQ ID NO: 421          moltype = AA  length = 9
FEATURE                 Location/Qualifiers
REGION                  1..9
                        note = peptide
source                  1..9
                        mol_type = protein
                        organism = synthetic construct
SEQUENCE: 421
QLLTLIFYL                                                                   9

SEQ ID NO: 422          moltype = AA  length = 9
FEATURE                 Location/Qualifiers
REGION                  1..9
                        note = peptide
source                  1..9
                        mol_type = protein
                        organism = synthetic construct
SEQUENCE: 422
LLLTLIFPI                                                                   9

SEQ ID NO: 423          moltype = AA  length = 9
FEATURE                 Location/Qualifiers
REGION                  1..9
                        note = peptide
source                  1..9
                        mol_type = protein
                        organism = synthetic construct
SEQUENCE: 423
FLLTLIFSL                                                                   9

SEQ ID NO: 424          moltype = AA  length = 9
FEATURE                 Location/Qualifiers
REGION                  1..9
                        note = peptide
source                  1..9
                        mol_type = protein
                        organism = synthetic construct
SEQUENCE: 424
VMVAIYFTL                                                                   9

SEQ ID NO: 425          moltype = AA  length = 9
FEATURE                 Location/Qualifiers
REGION                  1..9
                        note = peptide
source                  1..9
```

```
                        mol_type = protein
                        organism = synthetic construct
SEQUENCE: 425
LLGALLPAV                                                   9

SEQ ID NO: 426          moltype = AA  length = 9
FEATURE                 Location/Qualifiers
REGION                  1..9
                        note = peptide
source                  1..9
                        mol_type = protein
                        organism = synthetic construct
SEQUENCE: 426
ILGALLPLL                                                   9

SEQ ID NO: 427          moltype = AA  length = 9
FEATURE                 Location/Qualifiers
REGION                  1..9
                        note = peptide
source                  1..9
                        mol_type = protein
                        organism = synthetic construct
SEQUENCE: 427
SVAAFPVTV                                                   9

SEQ ID NO: 428          moltype = AA  length = 9
FEATURE                 Location/Qualifiers
REGION                  1..9
                        note = peptide
source                  1..9
                        mol_type = protein
                        organism = synthetic construct
SEQUENCE: 428
LLLSLFCLI                                                   9

SEQ ID NO: 429          moltype = AA  length = 9
FEATURE                 Location/Qualifiers
REGION                  1..9
                        note = peptide
source                  1..9
                        mol_type = protein
                        organism = synthetic construct
SEQUENCE: 429
KLLSLFCTL                                                   9

SEQ ID NO: 430          moltype = AA  length = 9
FEATURE                 Location/Qualifiers
REGION                  1..9
                        note = peptide
source                  1..9
                        mol_type = protein
                        organism = synthetic construct
SEQUENCE: 430
FLLSLFCIA                                                   9

SEQ ID NO: 431          moltype = AA  length = 9
FEATURE                 Location/Qualifiers
REGION                  1..9
                        note = peptide
source                  1..9
                        mol_type = protein
                        organism = synthetic construct
SEQUENCE: 431
ILLGVGFGI                                                   9

SEQ ID NO: 432          moltype = AA  length = 9
FEATURE                 Location/Qualifiers
REGION                  1..9
                        note = peptide
source                  1..9
                        mol_type = protein
                        organism = synthetic construct
SEQUENCE: 432
ALLGVGFGI                                                   9

SEQ ID NO: 433          moltype = AA  length = 9
FEATURE                 Location/Qualifiers
REGION                  1..9
                        note = peptide
```

```
source                  1..9
                        mol_type = protein
                        organism = synthetic construct
SEQUENCE: 433
RLIDEFQSV                                                      9

SEQ ID NO: 434          moltype = AA  length = 9
FEATURE                 Location/Qualifiers
REGION                  1..9
                        note = peptide
source                  1..9
                        mol_type = protein
                        organism = synthetic construct
SEQUENCE: 434
FLESVITTV                                                      9

SEQ ID NO: 435          moltype = AA  length = 9
FEATURE                 Location/Qualifiers
REGION                  1..9
                        note = peptide
source                  1..9
                        mol_type = protein
                        organism = synthetic construct
SEQUENCE: 435
GLFGVLIGV                                                      9

SEQ ID NO: 436          moltype = AA  length = 9
FEATURE                 Location/Qualifiers
REGION                  1..9
                        note = peptide
source                  1..9
                        mol_type = protein
                        organism = synthetic construct
SEQUENCE: 436
AMFGVLISV                                                      9

SEQ ID NO: 437          moltype = AA  length = 9
FEATURE                 Location/Qualifiers
REGION                  1..9
                        note = peptide
source                  1..9
                        mol_type = protein
                        organism = synthetic construct
SEQUENCE: 437
FIDFLLSEV                                                      9

SEQ ID NO: 438          moltype = AA  length = 9
FEATURE                 Location/Qualifiers
REGION                  1..9
                        note = peptide
source                  1..9
                        mol_type = protein
                        organism = synthetic construct
SEQUENCE: 438
GLFMVIAGV                                                      9

SEQ ID NO: 439          moltype = AA  length = 9
FEATURE                 Location/Qualifiers
REGION                  1..9
                        note = peptide
source                  1..9
                        mol_type = protein
                        organism = synthetic construct
SEQUENCE: 439
FLFMVIAFA                                                      9

SEQ ID NO: 440          moltype = AA  length = 9
FEATURE                 Location/Qualifiers
REGION                  1..9
                        note = peptide
source                  1..9
                        mol_type = protein
                        organism = synthetic construct
SEQUENCE: 440
HLPYLLFLL                                                      9

SEQ ID NO: 441          moltype = AA  length = 9
FEATURE                 Location/Qualifiers
REGION                  1..9
```

```
                        note = peptide
source                  1..9
                        mol_type = protein
                        organism = synthetic construct
SEQUENCE: 441
TLTACLVGV                                                                    9

SEQ ID NO: 442          moltype = AA  length = 9
FEATURE                 Location/Qualifiers
REGION                  1..9
                        note = peptide
source                  1..9
                        mol_type = protein
                        organism = synthetic construct
SEQUENCE: 442
MLSEKMVQL                                                                    9

SEQ ID NO: 443          moltype = AA  length = 9
FEATURE                 Location/Qualifiers
REGION                  1..9
                        note = peptide
source                  1..9
                        mol_type = protein
                        organism = synthetic construct
SEQUENCE: 443
NLFDLSLVA                                                                    9

SEQ ID NO: 444          moltype = AA  length = 9
FEATURE                 Location/Qualifiers
REGION                  1..9
                        note = peptide
source                  1..9
                        mol_type = protein
                        organism = synthetic construct
SEQUENCE: 444
GLFDLSLRV                                                                    9

SEQ ID NO: 445          moltype = AA  length = 9
FEATURE                 Location/Qualifiers
REGION                  1..9
                        note = peptide
source                  1..9
                        mol_type = protein
                        organism = synthetic construct
SEQUENCE: 445
ALFDLSLPI                                                                    9

SEQ ID NO: 446          moltype = AA  length = 9
FEATURE                 Location/Qualifiers
REGION                  1..9
                        note = peptide
source                  1..9
                        mol_type = protein
                        organism = synthetic construct
SEQUENCE: 446
TLPAVMAEV                                                                    9

SEQ ID NO: 447          moltype = AA  length = 9
FEATURE                 Location/Qualifiers
REGION                  1..9
                        note = peptide
source                  1..9
                        mol_type = protein
                        organism = synthetic construct
SEQUENCE: 447
LLAEPQASL                                                                    9

SEQ ID NO: 448          moltype = AA  length = 9
FEATURE                 Location/Qualifiers
REGION                  1..9
                        note = peptide
source                  1..9
                        mol_type = protein
                        organism = synthetic construct
SEQUENCE: 448
ILAEPQALV                                                                    9

SEQ ID NO: 449          moltype = AA  length = 9
FEATURE                 Location/Qualifiers
```

```
REGION                  1..9
                        note = peptide
source                  1..9
                        mol_type = protein
                        organism = synthetic construct
SEQUENCE: 449
FIAEPQAAL                                                                 9

SEQ ID NO: 450          moltype = AA  length = 9
FEATURE                 Location/Qualifiers
REGION                  1..9
                        note = peptide
source                  1..9
                        mol_type = protein
                        organism = synthetic construct
SEQUENCE: 450
LLFLLSALL                                                                 9

SEQ ID NO: 451          moltype = AA  length = 9
FEATURE                 Location/Qualifiers
REGION                  1..9
                        note = peptide
source                  1..9
                        mol_type = protein
                        organism = synthetic construct
SEQUENCE: 451
KMLTFLYTA                                                                 9

SEQ ID NO: 452          moltype = AA  length = 9
FEATURE                 Location/Qualifiers
REGION                  1..9
                        note = peptide
source                  1..9
                        mol_type = protein
                        organism = synthetic construct
SEQUENCE: 452
AVLHAIYGV                                                                 9

SEQ ID NO: 453          moltype = AA  length = 9
FEATURE                 Location/Qualifiers
REGION                  1..9
                        note = peptide
source                  1..9
                        mol_type = protein
                        organism = synthetic construct
SEQUENCE: 453
HLFAVLHAV                                                                 9

SEQ ID NO: 454          moltype = AA  length = 9
FEATURE                 Location/Qualifiers
REGION                  1..9
                        note = peptide
source                  1..9
                        mol_type = protein
                        organism = synthetic construct
SEQUENCE: 454
SVIAAIVLV                                                                 9

SEQ ID NO: 455          moltype = AA  length = 9
FEATURE                 Location/Qualifiers
REGION                  1..9
                        note = peptide
source                  1..9
                        mol_type = protein
                        organism = synthetic construct
SEQUENCE: 455
FVIAAIVCV                                                                 9

SEQ ID NO: 456          moltype = AA  length = 9
FEATURE                 Location/Qualifiers
REGION                  1..9
                        note = peptide
source                  1..9
                        mol_type = protein
                        organism = synthetic construct
SEQUENCE: 456
FIIAAIVAV                                                                 9

SEQ ID NO: 457          moltype = AA  length = 9
```

```
FEATURE                Location/Qualifiers
REGION                 1..9
                       note = peptide
source                 1..9
                       mol_type = protein
                       organism = synthetic construct
SEQUENCE: 457
AVIAAIVGV                                                           9

SEQ ID NO: 458         moltype = AA  length = 9
FEATURE                Location/Qualifiers
REGION                 1..9
                       note = peptide
source                 1..9
                       mol_type = protein
                       organism = synthetic construct
SEQUENCE: 458
YIAAIIAEA                                                           9

SEQ ID NO: 459         moltype = AA  length = 9
FEATURE                Location/Qualifiers
REGION                 1..9
                       note = peptide
source                 1..9
                       mol_type = protein
                       organism = synthetic construct
SEQUENCE: 459
FVAAIIASL                                                           9

SEQ ID NO: 460         moltype = AA  length = 9
FEATURE                Location/Qualifiers
REGION                 1..9
                       note = peptide
source                 1..9
                       mol_type = protein
                       organism = synthetic construct
SEQUENCE: 460
FIAAIIAPI                                                           9

SEQ ID NO: 461         moltype = AA  length = 9
FEATURE                Location/Qualifiers
REGION                 1..9
                       note = peptide
source                 1..9
                       mol_type = protein
                       organism = synthetic construct
SEQUENCE: 461
GLFKSILFL                                                           9

SEQ ID NO: 462         moltype = AA  length = 9
FEATURE                Location/Qualifiers
REGION                 1..9
                       note = peptide
source                 1..9
                       mol_type = protein
                       organism = synthetic construct
SEQUENCE: 462
MLLGTIHGV                                                           9

SEQ ID NO: 463         moltype = AA  length = 9
FEATURE                Location/Qualifiers
REGION                 1..9
                       note = peptide
source                 1..9
                       mol_type = protein
                       organism = synthetic construct
SEQUENCE: 463
LLSFFFAML                                                           9

SEQ ID NO: 464         moltype = AA  length = 9
FEATURE                Location/Qualifiers
REGION                 1..9
                       note = peptide
source                 1..9
                       mol_type = protein
                       organism = synthetic construct
SEQUENCE: 464
LLSFFFAAL                                                           9
```

```
SEQ ID NO: 465          moltype = AA  length = 9
FEATURE                 Location/Qualifiers
REGION                  1..9
                        note = peptide
source                  1..9
                        mol_type = protein
                        organism = synthetic construct
SEQUENCE: 465
FLSFFFAAM                                                         9

SEQ ID NO: 466          moltype = AA  length = 9
FEATURE                 Location/Qualifiers
REGION                  1..9
                        note = peptide
source                  1..9
                        mol_type = protein
                        organism = synthetic construct
SEQUENCE: 466
FLAVFLPVL                                                         9

SEQ ID NO: 467          moltype = AA  length = 9
FEATURE                 Location/Qualifiers
REGION                  1..9
                        note = peptide
source                  1..9
                        mol_type = protein
                        organism = synthetic construct
SEQUENCE: 467
SLLLGTILV                                                         9

SEQ ID NO: 468          moltype = AA  length = 9
FEATURE                 Location/Qualifiers
REGION                  1..9
                        note = peptide
source                  1..9
                        mol_type = protein
                        organism = synthetic construct
SEQUENCE: 468
ILLLGTILL                                                         9

SEQ ID NO: 469          moltype = AA  length = 9
FEATURE                 Location/Qualifiers
REGION                  1..9
                        note = peptide
source                  1..9
                        mol_type = protein
                        organism = synthetic construct
SEQUENCE: 469
RLSLIVALV                                                         9

SEQ ID NO: 470          moltype = AA  length = 9
FEATURE                 Location/Qualifiers
REGION                  1..9
                        note = peptide
source                  1..9
                        mol_type = protein
                        organism = synthetic construct
SEQUENCE: 470
RLSLIVAFV                                                         9

SEQ ID NO: 471          moltype = AA  length = 9
FEATURE                 Location/Qualifiers
REGION                  1..9
                        note = peptide
source                  1..9
                        mol_type = protein
                        organism = synthetic construct
SEQUENCE: 471
MISPNLFRV                                                         9

SEQ ID NO: 472          moltype = AA  length = 9
FEATURE                 Location/Qualifiers
REGION                  1..9
                        note = peptide
source                  1..9
                        mol_type = protein
                        organism = synthetic construct
SEQUENCE: 472
LLDHVLIAV                                                         9
```

```
SEQ ID NO: 473          moltype = AA  length = 9
FEATURE                 Location/Qualifiers
REGION                  1..9
                        note = peptide
source                  1..9
                        mol_type = protein
                        organism = synthetic construct
SEQUENCE: 473
RLIDEHLVV                                                          9

SEQ ID NO: 474          moltype = AA  length = 9
FEATURE                 Location/Qualifiers
REGION                  1..9
                        note = peptide
source                  1..9
                        mol_type = protein
                        organism = synthetic construct
SEQUENCE: 474
TLSEVLEYL                                                          9

SEQ ID NO: 475          moltype = AA  length = 9
FEATURE                 Location/Qualifiers
REGION                  1..9
                        note = peptide
source                  1..9
                        mol_type = protein
                        organism = synthetic construct
SEQUENCE: 475
FLLRPDTFL                                                          9

SEQ ID NO: 476          moltype = AA  length = 9
FEATURE                 Location/Qualifiers
REGION                  1..9
                        note = peptide
source                  1..9
                        mol_type = protein
                        organism = synthetic construct
SEQUENCE: 476
LMMTIINQV                                                          9

SEQ ID NO: 477          moltype = AA  length = 9
FEATURE                 Location/Qualifiers
REGION                  1..9
                        note = peptide
source                  1..9
                        mol_type = protein
                        organism = synthetic construct
SEQUENCE: 477
LLMTIINQV                                                          9

SEQ ID NO: 478          moltype = AA  length = 9
FEATURE                 Location/Qualifiers
REGION                  1..9
                        note = peptide
source                  1..9
                        mol_type = protein
                        organism = synthetic construct
SEQUENCE: 478
FLMTIINQV                                                          9

SEQ ID NO: 479          moltype = AA  length = 9
FEATURE                 Location/Qualifiers
REGION                  1..9
                        note = peptide
source                  1..9
                        mol_type = protein
                        organism = synthetic construct
SEQUENCE: 479
RLAGSVAGV                                                          9

SEQ ID NO: 480          moltype = AA  length = 9
FEATURE                 Location/Qualifiers
REGION                  1..9
                        note = peptide
source                  1..9
                        mol_type = protein
                        organism = synthetic construct
SEQUENCE: 480
```

```
KLAGSVAGV                                                        9

SEQ ID NO: 481          moltype = AA  length = 9
FEATURE                 Location/Qualifiers
REGION                  1..9
                        note = peptide
source                  1..9
                        mol_type = protein
                        organism = synthetic construct
SEQUENCE: 481
LLMMTIITV                                                        9

SEQ ID NO: 482          moltype = AA  length = 9
FEATURE                 Location/Qualifiers
REGION                  1..9
                        note = peptide
source                  1..9
                        mol_type = protein
                        organism = synthetic construct
SEQUENCE: 482
AMLSSLAGV                                                        9

SEQ ID NO: 483          moltype = AA  length = 9
FEATURE                 Location/Qualifiers
REGION                  1..9
                        note = peptide
source                  1..9
                        mol_type = protein
                        organism = synthetic construct
SEQUENCE: 483
YVFTMLSAV                                                        9

SEQ ID NO: 484          moltype = AA  length = 9
FEATURE                 Location/Qualifiers
REGION                  1..9
                        note = peptide
source                  1..9
                        mol_type = protein
                        organism = synthetic construct
SEQUENCE: 484
YLAGVIILI                                                        9

SEQ ID NO: 485          moltype = AA  length = 9
FEATURE                 Location/Qualifiers
REGION                  1..9
                        note = peptide
source                  1..9
                        mol_type = protein
                        organism = synthetic construct
SEQUENCE: 485
MLAGVIIYI                                                        9

SEQ ID NO: 486          moltype = AA  length = 9
FEATURE                 Location/Qualifiers
REGION                  1..9
                        note = peptide
source                  1..9
                        mol_type = protein
                        organism = synthetic construct
SEQUENCE: 486
MLAGVIIGI                                                        9

SEQ ID NO: 487          moltype = AA  length = 9
FEATURE                 Location/Qualifiers
REGION                  1..9
                        note = peptide
source                  1..9
                        mol_type = protein
                        organism = synthetic construct
SEQUENCE: 487
LLAGVIITI                                                        9

SEQ ID NO: 488          moltype = AA  length = 9
FEATURE                 Location/Qualifiers
REGION                  1..9
                        note = peptide
source                  1..9
                        mol_type = protein
                        organism = synthetic construct
```

```
SEQUENCE: 488
LLAGVIIGI                                                   9

SEQ ID NO: 489          moltype = AA  length = 9
FEATURE                 Location/Qualifiers
REGION                  1..9
                        note = peptide
source                  1..9
                        mol_type = protein
                        organism = synthetic construct
SEQUENCE: 489
GLAGVIITI                                                   9

SEQ ID NO: 490          moltype = AA  length = 9
FEATURE                 Location/Qualifiers
REGION                  1..9
                        note = peptide
source                  1..9
                        mol_type = protein
                        organism = synthetic construct
SEQUENCE: 490
GLAGVIIAV                                                   9

SEQ ID NO: 491          moltype = AA  length = 9
FEATURE                 Location/Qualifiers
REGION                  1..9
                        note = peptide
source                  1..9
                        mol_type = protein
                        organism = synthetic construct
SEQUENCE: 491
VMLFGVFMV                                                   9

SEQ ID NO: 492          moltype = AA  length = 9
FEATURE                 Location/Qualifiers
REGION                  1..9
                        note = peptide
source                  1..9
                        mol_type = protein
                        organism = synthetic construct
SEQUENCE: 492
VLLFGVFLV                                                   9

SEQ ID NO: 493          moltype = AA  length = 9
FEATURE                 Location/Qualifiers
REGION                  1..9
                        note = peptide
source                  1..9
                        mol_type = protein
                        organism = synthetic construct
SEQUENCE: 493
ILLFGVFMV                                                   9

SEQ ID NO: 494          moltype = AA  length = 9
FEATURE                 Location/Qualifiers
REGION                  1..9
                        note = peptide
source                  1..9
                        mol_type = protein
                        organism = synthetic construct
SEQUENCE: 494
FILFGVFML                                                   9

SEQ ID NO: 495          moltype = AA  length = 9
FEATURE                 Location/Qualifiers
REGION                  1..9
                        note = peptide
source                  1..9
                        mol_type = protein
                        organism = synthetic construct
SEQUENCE: 495
VLFGVFLGV                                                   9

SEQ ID NO: 496          moltype = AA  length = 9
FEATURE                 Location/Qualifiers
REGION                  1..9
                        note = peptide
source                  1..9
                        mol_type = protein
```

```
                        organism = synthetic construct
SEQUENCE: 496
GMFGVFLTL                                                                 9

SEQ ID NO: 497          moltype = AA  length = 9
FEATURE                 Location/Qualifiers
REGION                  1..9
                        note = peptide
source                  1..9
                        mol_type = protein
                        organism = synthetic construct
SEQUENCE: 497
FLFGVFLAM                                                                 9

SEQ ID NO: 498          moltype = AA  length = 9
FEATURE                 Location/Qualifiers
REGION                  1..9
                        note = peptide
source                  1..9
                        mol_type = protein
                        organism = synthetic construct
SEQUENCE: 498
VLDTAIIYI                                                                 9

SEQ ID NO: 499          moltype = AA  length = 9
FEATURE                 Location/Qualifiers
REGION                  1..9
                        note = peptide
source                  1..9
                        mol_type = protein
                        organism = synthetic construct
SEQUENCE: 499
KLDTAIIHV                                                                 9

SEQ ID NO: 500          moltype = AA  length = 9
FEATURE                 Location/Qualifiers
REGION                  1..9
                        note = peptide
source                  1..9
                        mol_type = protein
                        organism = synthetic construct
SEQUENCE: 500
LISSFAFLV                                                                 9

SEQ ID NO: 501          moltype = AA  length = 9
FEATURE                 Location/Qualifiers
REGION                  1..9
                        note = peptide
source                  1..9
                        mol_type = protein
                        organism = synthetic construct
SEQUENCE: 501
LISSFAFLL                                                                 9

SEQ ID NO: 502          moltype = AA  length = 9
FEATURE                 Location/Qualifiers
REGION                  1..9
                        note = peptide
source                  1..9
                        mol_type = protein
                        organism = synthetic construct
SEQUENCE: 502
FMLRLIINL                                                                 9

SEQ ID NO: 503          moltype = AA  length = 9
FEATURE                 Location/Qualifiers
REGION                  1..9
                        note = peptide
source                  1..9
                        mol_type = protein
                        organism = synthetic construct
SEQUENCE: 503
ALAIALFPV                                                                 9

SEQ ID NO: 504          moltype = AA  length = 9
FEATURE                 Location/Qualifiers
REGION                  1..9
                        note = peptide
source                  1..9
```

```
                        mol_type = protein
                        organism = synthetic construct
SEQUENCE: 504
ALWLHTSFA                                                               9

SEQ ID NO: 505          moltype = AA  length = 9
FEATURE                 Location/Qualifiers
REGION                  1..9
                        note = peptide
source                  1..9
                        mol_type = protein
                        organism = synthetic construct
SEQUENCE: 505
TMFGYTVFL                                                               9

SEQ ID NO: 506          moltype = AA  length = 9
FEATURE                 Location/Qualifiers
REGION                  1..9
                        note = peptide
source                  1..9
                        mol_type = protein
                        organism = synthetic construct
SEQUENCE: 506
YLAGIVFTL                                                               9

SEQ ID NO: 507          moltype = AA  length = 9
FEATURE                 Location/Qualifiers
REGION                  1..9
                        note = peptide
source                  1..9
                        mol_type = protein
                        organism = synthetic construct
SEQUENCE: 507
LMLLFAYYL                                                               9

SEQ ID NO: 508          moltype = AA  length = 9
FEATURE                 Location/Qualifiers
REGION                  1..9
                        note = peptide
source                  1..9
                        mol_type = protein
                        organism = synthetic construct
SEQUENCE: 508
YLFAYVLIV                                                               9

SEQ ID NO: 509          moltype = AA  length = 9
FEATURE                 Location/Qualifiers
REGION                  1..9
                        note = peptide
source                  1..9
                        mol_type = protein
                        organism = synthetic construct
SEQUENCE: 509
TLFAYVLGL                                                               9

SEQ ID NO: 510          moltype = AA  length = 9
FEATURE                 Location/Qualifiers
REGION                  1..9
                        note = peptide
source                  1..9
                        mol_type = protein
                        organism = synthetic construct
SEQUENCE: 510
GLLFAYVEV                                                               9

SEQ ID NO: 511          moltype = AA  length = 9
FEATURE                 Location/Qualifiers
REGION                  1..9
                        note = peptide
source                  1..9
                        mol_type = protein
                        organism = synthetic construct
SEQUENCE: 511
KILYSLVEV                                                               9

SEQ ID NO: 512          moltype = AA  length = 9
FEATURE                 Location/Qualifiers
REGION                  1..9
                        note = peptide
```

```
source                   1..9
                         mol_type = protein
                         organism = synthetic construct
SEQUENCE: 512
FLLLVNLLV                                                                    9

SEQ ID NO: 513           moltype = AA  length = 9
FEATURE                  Location/Qualifiers
REGION                   1..9
                         note = peptide
source                   1..9
                         mol_type = protein
                         organism = synthetic construct
SEQUENCE: 513
VIADVIALL                                                                    9

SEQ ID NO: 514           moltype = AA  length = 9
FEATURE                  Location/Qualifiers
REGION                   1..9
                         note = peptide
source                   1..9
                         mol_type = protein
                         organism = synthetic construct
SEQUENCE: 514
QIADVIAFL                                                                    9

SEQ ID NO: 515           moltype = AA  length = 9
FEATURE                  Location/Qualifiers
REGION                   1..9
                         note = peptide
source                   1..9
                         mol_type = protein
                         organism = synthetic construct
SEQUENCE: 515
LVADVIASV                                                                    9

SEQ ID NO: 516           moltype = AA  length = 9
FEATURE                  Location/Qualifiers
REGION                   1..9
                         note = peptide
source                   1..9
                         mol_type = protein
                         organism = synthetic construct
SEQUENCE: 516
LIADVIALL                                                                    9

SEQ ID NO: 517           moltype = AA  length = 9
FEATURE                  Location/Qualifiers
REGION                   1..9
                         note = peptide
source                   1..9
                         mol_type = protein
                         organism = synthetic construct
SEQUENCE: 517
LLYSLVFFL                                                                    9

SEQ ID NO: 518           moltype = AA  length = 9
FEATURE                  Location/Qualifiers
REGION                   1..9
                         note = peptide
source                   1..9
                         mol_type = protein
                         organism = synthetic construct
SEQUENCE: 518
FLVKINTNI                                                                    9

SEQ ID NO: 519           moltype = AA  length = 9
FEATURE                  Location/Qualifiers
REGION                   1..9
                         note = peptide
source                   1..9
                         mol_type = protein
                         organism = synthetic construct
SEQUENCE: 519
KLDSLGFTL                                                                    9

SEQ ID NO: 520           moltype = AA  length = 9
FEATURE                  Location/Qualifiers
REGION                   1..9
```

```
                        note = peptide
source                  1..9
                        mol_type = protein
                        organism = synthetic construct
SEQUENCE: 520
KLDSLGFSL                                                                  9

SEQ ID NO: 521          moltype = AA  length = 9
FEATURE                 Location/Qualifiers
REGION                  1..9
                        note = peptide
source                  1..9
                        mol_type = protein
                        organism = synthetic construct
SEQUENCE: 521
FLDSLGFSL                                                                  9

SEQ ID NO: 522          moltype = AA  length = 9
FEATURE                 Location/Qualifiers
REGION                  1..9
                        note = peptide
source                  1..9
                        mol_type = protein
                        organism = synthetic construct
SEQUENCE: 522
FMRDEFPDV                                                                  9

SEQ ID NO: 523          moltype = AA  length = 9
FEATURE                 Location/Qualifiers
REGION                  1..9
                        note = peptide
source                  1..9
                        mol_type = protein
                        organism = synthetic construct
SEQUENCE: 523
FLRDEFPEA                                                                  9

SEQ ID NO: 524          moltype = AA  length = 9
FEATURE                 Location/Qualifiers
REGION                  1..9
                        note = peptide
source                  1..9
                        mol_type = protein
                        organism = synthetic construct
SEQUENCE: 524
SMEELLWFV                                                                  9

SEQ ID NO: 525          moltype = AA  length = 9
FEATURE                 Location/Qualifiers
REGION                  1..9
                        note = peptide
source                  1..9
                        mol_type = protein
                        organism = synthetic construct
SEQUENCE: 525
YLLAGLVLL                                                                  9

SEQ ID NO: 526          moltype = AA  length = 9
FEATURE                 Location/Qualifiers
REGION                  1..9
                        note = peptide
source                  1..9
                        mol_type = protein
                        organism = synthetic construct
SEQUENCE: 526
YLLAGLVLI                                                                  9

SEQ ID NO: 527          moltype = AA  length = 9
FEATURE                 Location/Qualifiers
REGION                  1..9
                        note = peptide
source                  1..9
                        mol_type = protein
                        organism = synthetic construct
SEQUENCE: 527
WLVGAVLTL                                                                  9

SEQ ID NO: 528          moltype = AA  length = 9
FEATURE                 Location/Qualifiers
```

```
REGION                1..9
                      note = peptide
source                1..9
                      mol_type = protein
                      organism = synthetic construct
SEQUENCE: 528
LLVGAVLTV                                                      9

SEQ ID NO: 529        moltype = AA  length = 9
FEATURE               Location/Qualifiers
REGION                1..9
                      note = peptide
source                1..9
                      mol_type = protein
                      organism = synthetic construct
SEQUENCE: 529
ALVGAVLTV                                                      9

SEQ ID NO: 530        moltype = AA  length = 9
FEATURE               Location/Qualifiers
REGION                1..9
                      note = peptide
source                1..9
                      mol_type = protein
                      organism = synthetic construct
SEQUENCE: 530
ALVGAVLLV                                                      9

SEQ ID NO: 531        moltype = AA  length = 9
FEATURE               Location/Qualifiers
REGION                1..9
                      note = peptide
source                1..9
                      mol_type = protein
                      organism = synthetic construct
SEQUENCE: 531
CLSDYVIPV                                                      9

SEQ ID NO: 532        moltype = AA  length = 9
FEATURE               Location/Qualifiers
REGION                1..9
                      note = peptide
source                1..9
                      mol_type = protein
                      organism = synthetic construct
SEQUENCE: 532
KLAGLVSSV                                                      9

SEQ ID NO: 533        moltype = AA  length = 9
FEATURE               Location/Qualifiers
REGION                1..9
                      note = peptide
source                1..9
                      mol_type = protein
                      organism = synthetic construct
SEQUENCE: 533
GMSPASFFA                                                      9

SEQ ID NO: 534        moltype = AA  length = 9
FEATURE               Location/Qualifiers
REGION                1..9
                      note = peptide
source                1..9
                      mol_type = protein
                      organism = synthetic construct
SEQUENCE: 534
ALGAVLTAV                                                      9

SEQ ID NO: 535        moltype = AA  length = 9
FEATURE               Location/Qualifiers
REGION                1..9
                      note = peptide
source                1..9
                      mol_type = protein
                      organism = synthetic construct
SEQUENCE: 535
YLTALLAEM                                                      9

SEQ ID NO: 536        moltype = AA  length = 9
```

```
FEATURE                 Location/Qualifiers
REGION                  1..9
                        note = peptide
source                  1..9
                        mol_type = protein
                        organism = synthetic construct
SEQUENCE: 536
VLTALLAAV                                                                9

SEQ ID NO: 537          moltype = AA  length = 9
FEATURE                 Location/Qualifiers
REGION                  1..9
                        note = peptide
source                  1..9
                        mol_type = protein
                        organism = synthetic construct
SEQUENCE: 537
RLTALLAAV                                                                9

SEQ ID NO: 538          moltype = AA  length = 9
FEATURE                 Location/Qualifiers
REGION                  1..9
                        note = peptide
source                  1..9
                        mol_type = protein
                        organism = synthetic construct
SEQUENCE: 538
GLTALLAPV                                                                9

SEQ ID NO: 539          moltype = AA  length = 9
FEATURE                 Location/Qualifiers
REGION                  1..9
                        note = peptide
source                  1..9
                        mol_type = protein
                        organism = synthetic construct
SEQUENCE: 539
FLTALLATV                                                                9

SEQ ID NO: 540          moltype = AA  length = 9
FEATURE                 Location/Qualifiers
REGION                  1..9
                        note = peptide
source                  1..9
                        mol_type = protein
                        organism = synthetic construct
SEQUENCE: 540
TLTESLLYL                                                                9

SEQ ID NO: 541          moltype = AA  length = 9
FEATURE                 Location/Qualifiers
REGION                  1..9
                        note = peptide
source                  1..9
                        mol_type = protein
                        organism = synthetic construct
SEQUENCE: 541
KLTESLLTI                                                                9

SEQ ID NO: 542          moltype = AA  length = 9
FEATURE                 Location/Qualifiers
REGION                  1..9
                        note = peptide
source                  1..9
                        mol_type = protein
                        organism = synthetic construct
SEQUENCE: 542
ILTESLLFL                                                                9

SEQ ID NO: 543          moltype = AA  length = 9
FEATURE                 Location/Qualifiers
REGION                  1..9
                        note = peptide
source                  1..9
                        mol_type = protein
                        organism = synthetic construct
SEQUENCE: 543
RLALLSPYI                                                                9
```

```
SEQ ID NO: 544          moltype = AA  length = 9
FEATURE                 Location/Qualifiers
REGION                  1..9
                        note = peptide
source                  1..9
                        mol_type = protein
                        organism = synthetic construct
SEQUENCE: 544
SILGFIIAA                                                       9

SEQ ID NO: 545          moltype = AA  length = 9
FEATURE                 Location/Qualifiers
REGION                  1..9
                        note = peptide
source                  1..9
                        mol_type = protein
                        organism = synthetic construct
SEQUENCE: 545
LILGFIIAV                                                       9

SEQ ID NO: 546          moltype = AA  length = 9
FEATURE                 Location/Qualifiers
REGION                  1..9
                        note = peptide
source                  1..9
                        mol_type = protein
                        organism = synthetic construct
SEQUENCE: 546
FVLGFIITI                                                       9

SEQ ID NO: 547          moltype = AA  length = 9
FEATURE                 Location/Qualifiers
REGION                  1..9
                        note = peptide
source                  1..9
                        mol_type = protein
                        organism = synthetic construct
SEQUENCE: 547
FILGFIITI                                                       9

SEQ ID NO: 548          moltype = AA  length = 9
FEATURE                 Location/Qualifiers
REGION                  1..9
                        note = peptide
source                  1..9
                        mol_type = protein
                        organism = synthetic construct
SEQUENCE: 548
SLSGLLSGV                                                       9

SEQ ID NO: 549          moltype = AA  length = 9
FEATURE                 Location/Qualifiers
REGION                  1..9
                        note = peptide
source                  1..9
                        mol_type = protein
                        organism = synthetic construct
SEQUENCE: 549
FLSGLLSAL                                                       9

SEQ ID NO: 550          moltype = AA  length = 9
FEATURE                 Location/Qualifiers
REGION                  1..9
                        note = peptide
source                  1..9
                        mol_type = protein
                        organism = synthetic construct
SEQUENCE: 550
ILPLILITV                                                       9

SEQ ID NO: 551          moltype = AA  length = 9
FEATURE                 Location/Qualifiers
REGION                  1..9
                        note = peptide
source                  1..9
                        mol_type = protein
                        organism = synthetic construct
SEQUENCE: 551
MLGFIIAFL                                                       9
```

```
SEQ ID NO: 552          moltype = AA  length = 9
FEATURE                 Location/Qualifiers
REGION                  1..9
                        note = peptide
source                  1..9
                        mol_type = protein
                        organism = synthetic construct
SEQUENCE: 552
LLGFIIAEV                                                           9

SEQ ID NO: 553          moltype = AA  length = 9
FEATURE                 Location/Qualifiers
REGION                  1..9
                        note = peptide
source                  1..9
                        mol_type = protein
                        organism = synthetic construct
SEQUENCE: 553
ILGFIIAAV                                                           9

SEQ ID NO: 554          moltype = AA  length = 9
FEATURE                 Location/Qualifiers
REGION                  1..9
                        note = peptide
source                  1..9
                        mol_type = protein
                        organism = synthetic construct
SEQUENCE: 554
FLGFIIADV                                                           9

SEQ ID NO: 555          moltype = AA  length = 9
FEATURE                 Location/Qualifiers
REGION                  1..9
                        note = peptide
source                  1..9
                        mol_type = protein
                        organism = synthetic construct
SEQUENCE: 555
MIITVLLLV                                                           9

SEQ ID NO: 556          moltype = AA  length = 9
FEATURE                 Location/Qualifiers
REGION                  1..9
                        note = peptide
source                  1..9
                        mol_type = protein
                        organism = synthetic construct
SEQUENCE: 556
FIITVLLGL                                                           9

SEQ ID NO: 557          moltype = AA  length = 9
FEATURE                 Location/Qualifiers
REGION                  1..9
                        note = peptide
source                  1..9
                        mol_type = protein
                        organism = synthetic construct
SEQUENCE: 557
YQIGDSVLL                                                           9

SEQ ID NO: 558          moltype = AA  length = 9
FEATURE                 Location/Qualifiers
REGION                  1..9
                        note = peptide
source                  1..9
                        mol_type = protein
                        organism = synthetic construct
SEQUENCE: 558
MLSSLIIPL                                                           9

SEQ ID NO: 559          moltype = AA  length = 9
FEATURE                 Location/Qualifiers
REGION                  1..9
                        note = peptide
source                  1..9
                        mol_type = protein
                        organism = synthetic construct
SEQUENCE: 559
```

```
ILIDGAYTV                                                9

SEQ ID NO: 560          moltype = AA  length = 9
FEATURE                 Location/Qualifiers
REGION                  1..9
                        note = peptide
source                  1..9
                        mol_type = protein
                        organism = synthetic construct
SEQUENCE: 560
YLLEEGSSV                                                9

SEQ ID NO: 561          moltype = AA  length = 9
FEATURE                 Location/Qualifiers
REGION                  1..9
                        note = peptide
source                  1..9
                        mol_type = protein
                        organism = synthetic construct
SEQUENCE: 561
YMFGFTLTM                                                9

SEQ ID NO: 562          moltype = AA  length = 9
FEATURE                 Location/Qualifiers
REGION                  1..9
                        note = peptide
source                  1..9
                        mol_type = protein
                        organism = synthetic construct
SEQUENCE: 562
YLFGFTLGM                                                9

SEQ ID NO: 563          moltype = AA  length = 9
FEATURE                 Location/Qualifiers
REGION                  1..9
                        note = peptide
source                  1..9
                        mol_type = protein
                        organism = synthetic construct
SEQUENCE: 563
VLFGFTLSI                                                9

SEQ ID NO: 564          moltype = AA  length = 9
FEATURE                 Location/Qualifiers
REGION                  1..9
                        note = peptide
source                  1..9
                        mol_type = protein
                        organism = synthetic construct
SEQUENCE: 564
RMFGFTLML                                                9

SEQ ID NO: 565          moltype = AA  length = 9
FEATURE                 Location/Qualifiers
REGION                  1..9
                        note = peptide
source                  1..9
                        mol_type = protein
                        organism = synthetic construct
SEQUENCE: 565
LMFGFTLRT                                                9

SEQ ID NO: 566          moltype = AA  length = 9
FEATURE                 Location/Qualifiers
REGION                  1..9
                        note = peptide
source                  1..9
                        mol_type = protein
                        organism = synthetic construct
SEQUENCE: 566
YLLFGFTRV                                                9

SEQ ID NO: 567          moltype = AA  length = 9
FEATURE                 Location/Qualifiers
REGION                  1..9
                        note = peptide
source                  1..9
                        mol_type = protein
                        organism = synthetic construct
```

```
SEQUENCE: 567
VLGPLAALV                                                   9

SEQ ID NO: 568          moltype = AA  length = 9
FEATURE                 Location/Qualifiers
REGION                  1..9
                        note = peptide
source                  1..9
                        mol_type = protein
                        organism = synthetic construct
SEQUENCE: 568
ILGPLAAWL                                                   9

SEQ ID NO: 569          moltype = AA  length = 9
FEATURE                 Location/Qualifiers
REGION                  1..9
                        note = peptide
source                  1..9
                        mol_type = protein
                        organism = synthetic construct
SEQUENCE: 569
SLNALLPYV                                                   9

SEQ ID NO: 570          moltype = AA  length = 9
FEATURE                 Location/Qualifiers
REGION                  1..9
                        note = peptide
source                  1..9
                        mol_type = protein
                        organism = synthetic construct
SEQUENCE: 570
MMIPQVATL                                                   9

SEQ ID NO: 571          moltype = AA  length = 9
FEATURE                 Location/Qualifiers
REGION                  1..9
                        note = peptide
source                  1..9
                        mol_type = protein
                        organism = synthetic construct
SEQUENCE: 571
MMIPQVATI                                                   9

SEQ ID NO: 572          moltype = AA  length = 9
FEATURE                 Location/Qualifiers
REGION                  1..9
                        note = peptide
source                  1..9
                        mol_type = protein
                        organism = synthetic construct
SEQUENCE: 572
YLSDIQNAI                                                   9

SEQ ID NO: 573          moltype = AA  length = 9
FEATURE                 Location/Qualifiers
REGION                  1..9
                        note = peptide
source                  1..9
                        mol_type = protein
                        organism = synthetic construct
SEQUENCE: 573
VMSDIQNRV                                                   9

SEQ ID NO: 574          moltype = AA  length = 9
FEATURE                 Location/Qualifiers
REGION                  1..9
                        note = peptide
source                  1..9
                        mol_type = protein
                        organism = synthetic construct
SEQUENCE: 574
YQAVVLPGL                                                   9

SEQ ID NO: 575          moltype = AA  length = 9
FEATURE                 Location/Qualifiers
REGION                  1..9
                        note = peptide
source                  1..9
                        mol_type = protein
```

```
                        organism = synthetic construct
SEQUENCE: 575
LLLEQFLSV                                                                     9

SEQ ID NO: 576          moltype = AA  length = 9
FEATURE                 Location/Qualifiers
REGION                  1..9
                        note = peptide
source                  1..9
                        mol_type = protein
                        organism = synthetic construct
SEQUENCE: 576
LLLEQFLAI                                                                     9

SEQ ID NO: 577          moltype = AA  length = 9
FEATURE                 Location/Qualifiers
REGION                  1..9
                        note = peptide
source                  1..9
                        mol_type = protein
                        organism = synthetic construct
SEQUENCE: 577
ALLEQFLTA                                                                     9

SEQ ID NO: 578          moltype = AA  length = 9
FEATURE                 Location/Qualifiers
REGION                  1..9
                        note = peptide
source                  1..9
                        mol_type = protein
                        organism = synthetic construct
SEQUENCE: 578
GVSGYISPV                                                                     9

SEQ ID NO: 579          moltype = AA  length = 9
FEATURE                 Location/Qualifiers
REGION                  1..9
                        note = peptide
source                  1..9
                        mol_type = protein
                        organism = synthetic construct
SEQUENCE: 579
KLTDISSLV                                                                     9

SEQ ID NO: 580          moltype = AA  length = 9
FEATURE                 Location/Qualifiers
REGION                  1..9
                        note = peptide
source                  1..9
                        mol_type = protein
                        organism = synthetic construct
SEQUENCE: 580
YLLSNFYTV                                                                     9

SEQ ID NO: 581          moltype = AA  length = 9
FEATURE                 Location/Qualifiers
source                  1..9
                        mol_type = protein
                        organism = Homo sapiens
SEQUENCE: 581
FLFLLFFWL                                                                     9

SEQ ID NO: 582          moltype = AA  length = 9
FEATURE                 Location/Qualifiers
source                  1..9
                        mol_type = protein
                        organism = Homo sapiens
SEQUENCE: 582
SLSLGFLFL                                                                     9

SEQ ID NO: 583          moltype = AA  length = 9
FEATURE                 Location/Qualifiers
source                  1..9
                        mol_type = protein
                        organism = Homo sapiens
SEQUENCE: 583
LSLGFLFLL                                                                     9

SEQ ID NO: 584          moltype = AA  length = 9
```

```
FEATURE                Location/Qualifiers
source                 1..9
                       mol_type = protein
                       organism = Homo sapiens
SEQUENCE: 584
YTSNDSYIV                                                          9

SEQ ID NO: 585         moltype = AA  length = 9
FEATURE                Location/Qualifiers
source                 1..9
                       mol_type = protein
                       organism = Homo sapiens
SEQUENCE: 585
ILIDSGADI                                                          9

SEQ ID NO: 586         moltype = AA  length = 9
FEATURE                Location/Qualifiers
source                 1..9
                       mol_type = protein
                       organism = Homo sapiens
SEQUENCE: 586
SLFESSAKI                                                          9

SEQ ID NO: 587         moltype = AA  length = 9
FEATURE                Location/Qualifiers
source                 1..9
                       mol_type = protein
                       organism = Homo sapiens
SEQUENCE: 587
SLTPLLLSI                                                          9

SEQ ID NO: 588         moltype = AA  length = 9
FEATURE                Location/Qualifiers
source                 1..9
                       mol_type = protein
                       organism = Homo sapiens
SEQUENCE: 588
MSAVILTAV                                                          9

SEQ ID NO: 589         moltype = AA  length = 9
FEATURE                Location/Qualifiers
source                 1..9
                       mol_type = protein
                       organism = Homo sapiens
SEQUENCE: 589
ALAAIAAFM                                                          9

SEQ ID NO: 590         moltype = AA  length = 9
FEATURE                Location/Qualifiers
source                 1..9
                       mol_type = protein
                       organism = Homo sapiens
SEQUENCE: 590
VSAAFQAGV                                                          9

SEQ ID NO: 591         moltype = AA  length = 9
FEATURE                Location/Qualifiers
source                 1..9
                       mol_type = protein
                       organism = Homo sapiens
SEQUENCE: 591
KLVNLGFQA                                                          9

SEQ ID NO: 592         moltype = AA  length = 9
FEATURE                Location/Qualifiers
source                 1..9
                       mol_type = protein
                       organism = Homo sapiens
SEQUENCE: 592
ELLDFSSWL                                                          9

SEQ ID NO: 593         moltype = AA  length = 9
FEATURE                Location/Qualifiers
source                 1..9
                       mol_type = protein
                       organism = Homo sapiens
SEQUENCE: 593
LTLGEFLKL                                                          9
```

```
SEQ ID NO: 594          moltype = AA  length = 9
FEATURE                 Location/Qualifiers
source                  1..9
                        mol_type = protein
                        organism = Homo sapiens
SEQUENCE: 594
AAGDILALV                                                             9

SEQ ID NO: 595          moltype = AA  length = 9
FEATURE                 Location/Qualifiers
source                  1..9
                        mol_type = protein
                        organism = Homo sapiens
SEQUENCE: 595
ALVFGLLFA                                                             9

SEQ ID NO: 596          moltype = AA  length = 9
FEATURE                 Location/Qualifiers
source                  1..9
                        mol_type = protein
                        organism = Homo sapiens
SEQUENCE: 596
FQYEGSLTT                                                             9

SEQ ID NO: 597          moltype = AA  length = 9
FEATURE                 Location/Qualifiers
source                  1..9
                        mol_type = protein
                        organism = Homo sapiens
SEQUENCE: 597
HLSTAFARV                                                             9

SEQ ID NO: 598          moltype = AA  length = 9
FEATURE                 Location/Qualifiers
source                  1..9
                        mol_type = protein
                        organism = Homo sapiens
SEQUENCE: 598
LSLLLLVPV                                                             9

SEQ ID NO: 599          moltype = AA  length = 9
FEATURE                 Location/Qualifiers
source                  1..9
                        mol_type = protein
                        organism = Homo sapiens
SEQUENCE: 599
QLLLSLLLL                                                             9

SEQ ID NO: 600          moltype = AA  length = 9
FEATURE                 Location/Qualifiers
source                  1..9
                        mol_type = protein
                        organism = Homo sapiens
SEQUENCE: 600
VQLLLSLLL                                                             9

SEQ ID NO: 601          moltype = AA  length = 9
FEATURE                 Location/Qualifiers
source                  1..9
                        mol_type = protein
                        organism = Homo sapiens
SEQUENCE: 601
NLAKYVAEL                                                             9

SEQ ID NO: 602          moltype = AA  length = 9
FEATURE                 Location/Qualifiers
source                  1..9
                        mol_type = protein
                        organism = Homo sapiens
SEQUENCE: 602
LIAAAAFCL                                                             9

SEQ ID NO: 603          moltype = AA  length = 9
FEATURE                 Location/Qualifiers
source                  1..9
                        mol_type = protein
                        organism = Homo sapiens
SEQUENCE: 603
LLNDRVLRA                                                             9
```

```
SEQ ID NO: 604          moltype = AA  length = 9
FEATURE                 Location/Qualifiers
source                  1..9
                        mol_type = protein
                        organism = Homo sapiens
SEQUENCE: 604
GILLTTLLV                                                              9

SEQ ID NO: 605          moltype = AA  length = 9
FEATURE                 Location/Qualifiers
source                  1..9
                        mol_type = protein
                        organism = Homo sapiens
SEQUENCE: 605
ILAVVFIRI                                                              9

SEQ ID NO: 606          moltype = AA  length = 9
FEATURE                 Location/Qualifiers
source                  1..9
                        mol_type = protein
                        organism = Homo sapiens
SEQUENCE: 606
ILLTTLLVI                                                              9

SEQ ID NO: 607          moltype = AA  length = 9
FEATURE                 Location/Qualifiers
source                  1..9
                        mol_type = protein
                        organism = Homo sapiens
SEQUENCE: 607
LVIGIILAV                                                              9

SEQ ID NO: 608          moltype = AA  length = 9
FEATURE                 Location/Qualifiers
source                  1..9
                        mol_type = protein
                        organism = Homo sapiens
SEQUENCE: 608
ALVAILLCI                                                              9

SEQ ID NO: 609          moltype = AA  length = 9
FEATURE                 Location/Qualifiers
source                  1..9
                        mol_type = protein
                        organism = Homo sapiens
SEQUENCE: 609
EMSDVGTFV                                                              9

SEQ ID NO: 610          moltype = AA  length = 9
FEATURE                 Location/Qualifiers
source                  1..9
                        mol_type = protein
                        organism = Homo sapiens
SEQUENCE: 610
EMSTYLLPV                                                              9

SEQ ID NO: 611          moltype = AA  length = 9
FEATURE                 Location/Qualifiers
source                  1..9
                        mol_type = protein
                        organism = Homo sapiens
SEQUENCE: 611
FLLEEYTGS                                                              9

SEQ ID NO: 612          moltype = AA  length = 9
FEATURE                 Location/Qualifiers
source                  1..9
                        mol_type = protein
                        organism = Homo sapiens
SEQUENCE: 612
ILLCIVILL                                                              9

SEQ ID NO: 613          moltype = AA  length = 9
FEATURE                 Location/Qualifiers
source                  1..9
                        mol_type = protein
                        organism = Homo sapiens
SEQUENCE: 613
```

```
LLVTVVLFA                                                        9

SEQ ID NO: 614          moltype = AA  length = 9
FEATURE                 Location/Qualifiers
source                  1..9
                        mol_type = protein
                        organism = Homo sapiens
SEQUENCE: 614
AVALVLMLL                                                        9

SEQ ID NO: 615          moltype = AA  length = 9
FEATURE                 Location/Qualifiers
source                  1..9
                        mol_type = protein
                        organism = Homo sapiens
SEQUENCE: 615
LLTFWNPPT                                                        9

SEQ ID NO: 616          moltype = AA  length = 9
FEATURE                 Location/Qualifiers
source                  1..9
                        mol_type = protein
                        organism = Homo sapiens
SEQUENCE: 616
KQLLLSAAL                                                        9

SEQ ID NO: 617          moltype = AA  length = 9
FEATURE                 Location/Qualifiers
source                  1..9
                        mol_type = protein
                        organism = Homo sapiens
SEQUENCE: 617
LLLSAALSA                                                        9

SEQ ID NO: 618          moltype = AA  length = 9
FEATURE                 Location/Qualifiers
source                  1..9
                        mol_type = protein
                        organism = Homo sapiens
SEQUENCE: 618
QLAGAMVWA                                                        9

SEQ ID NO: 619          moltype = AA  length = 9
FEATURE                 Location/Qualifiers
source                  1..9
                        mol_type = protein
                        organism = Homo sapiens
SEQUENCE: 619
SQTGFVVLV                                                        9

SEQ ID NO: 620          moltype = AA  length = 9
FEATURE                 Location/Qualifiers
source                  1..9
                        mol_type = protein
                        organism = Homo sapiens
SEQUENCE: 620
TLASSETGV                                                        9

SEQ ID NO: 621          moltype = AA  length = 9
FEATURE                 Location/Qualifiers
source                  1..9
                        mol_type = protein
                        organism = Homo sapiens
SEQUENCE: 621
ILLSIGGYL                                                        9

SEQ ID NO: 622          moltype = AA  length = 9
FEATURE                 Location/Qualifiers
source                  1..9
                        mol_type = protein
                        organism = Homo sapiens
SEQUENCE: 622
HLIYSFASI                                                        9

SEQ ID NO: 623          moltype = AA  length = 9
FEATURE                 Location/Qualifiers
source                  1..9
                        mol_type = protein
                        organism = Homo sapiens
```

```
SEQUENCE: 623
VLIHELAEA                                                          9

SEQ ID NO: 624          moltype = AA  length = 9
FEATURE                 Location/Qualifiers
source                  1..9
                        mol_type = protein
                        organism = Homo sapiens
SEQUENCE: 624
SLWAGVVVL                                                          9

SEQ ID NO: 625          moltype = AA  length = 9
FEATURE                 Location/Qualifiers
source                  1..9
                        mol_type = protein
                        organism = Homo sapiens
SEQUENCE: 625
WLWDFTVTT                                                          9

SEQ ID NO: 626          moltype = AA  length = 9
FEATURE                 Location/Qualifiers
source                  1..9
                        mol_type = protein
                        organism = Homo sapiens
SEQUENCE: 626
LLASSILCA                                                          9

SEQ ID NO: 627          moltype = AA  length = 9
FEATURE                 Location/Qualifiers
source                  1..9
                        mol_type = protein
                        organism = Homo sapiens
SEQUENCE: 627
KLAVSLAET                                                          9

SEQ ID NO: 628          moltype = AA  length = 9
FEATURE                 Location/Qualifiers
source                  1..9
                        mol_type = protein
                        organism = Homo sapiens
SEQUENCE: 628
ALVGLFVLL                                                          9

SEQ ID NO: 629          moltype = AA  length = 9
FEATURE                 Location/Qualifiers
source                  1..9
                        mol_type = protein
                        organism = Homo sapiens
SEQUENCE: 629
GLFVLLAFL                                                          9

SEQ ID NO: 630          moltype = AA  length = 9
FEATURE                 Location/Qualifiers
source                  1..9
                        mol_type = protein
                        organism = Homo sapiens
SEQUENCE: 630
SVYDFFVWL                                                          9

SEQ ID NO: 631          moltype = AA  length = 9
FEATURE                 Location/Qualifiers
source                  1..9
                        mol_type = protein
                        organism = Homo sapiens
SEQUENCE: 631
VVMGTLVAL                                                          9

SEQ ID NO: 632          moltype = AA  length = 9
FEATURE                 Location/Qualifiers
source                  1..9
                        mol_type = protein
                        organism = Homo sapiens
SEQUENCE: 632
GTAEGLALA                                                          9

SEQ ID NO: 633          moltype = AA  length = 9
FEATURE                 Location/Qualifiers
source                  1..9
                        mol_type = protein
```

```
                       organism = Homo sapiens
SEQUENCE: 633
GLAAGLGPA                                                          9

SEQ ID NO: 634         moltype = AA  length = 9
FEATURE                Location/Qualifiers
source                 1..9
                       mol_type = protein
                       organism = Homo sapiens
SEQUENCE: 634
ALESILHRI                                                          9

SEQ ID NO: 635         moltype = AA  length = 9
FEATURE                Location/Qualifiers
source                 1..9
                       mol_type = protein
                       organism = Homo sapiens
SEQUENCE: 635
ALLAALCPA                                                          9

SEQ ID NO: 636         moltype = AA  length = 9
FEATURE                Location/Qualifiers
source                 1..9
                       mol_type = protein
                       organism = Homo sapiens
SEQUENCE: 636
ALLALLAAL                                                          9

SEQ ID NO: 637         moltype = AA  length = 9
FEATURE                Location/Qualifiers
source                 1..9
                       mol_type = protein
                       organism = Homo sapiens
SEQUENCE: 637
ILDEAYVMA                                                          9

SEQ ID NO: 638         moltype = AA  length = 9
FEATURE                Location/Qualifiers
source                 1..9
                       mol_type = protein
                       organism = Homo sapiens
SEQUENCE: 638
LLLLLVVAL                                                          9

SEQ ID NO: 639         moltype = AA  length = 9
FEATURE                Location/Qualifiers
source                 1..9
                       mol_type = protein
                       organism = Homo sapiens
SEQUENCE: 639
MVGALLLLL                                                          9

SEQ ID NO: 640         moltype = AA  length = 9
FEATURE                Location/Qualifiers
source                 1..9
                       mol_type = protein
                       organism = Homo sapiens
SEQUENCE: 640
NLQEILHGA                                                          9

SEQ ID NO: 641         moltype = AA  length = 9
FEATURE                Location/Qualifiers
source                 1..9
                       mol_type = protein
                       organism = Homo sapiens
SEQUENCE: 641
SLAVVSLNI                                                          9

SEQ ID NO: 642         moltype = AA  length = 9
FEATURE                Location/Qualifiers
source                 1..9
                       mol_type = protein
                       organism = Homo sapiens
SEQUENCE: 642
AVVGILLVV                                                          9

SEQ ID NO: 643         moltype = AA  length = 9
FEATURE                Location/Qualifiers
source                 1..9
```

```
                        mol_type = protein
                        organism = Homo sapiens
SEQUENCE: 643
ILDEAYVMA                                                         9

SEQ ID NO: 644          moltype = AA  length = 9
FEATURE                 Location/Qualifiers
source                  1..9
                        mol_type = protein
                        organism = Homo sapiens
SEQUENCE: 644
LLALLPPGA                                                         9

SEQ ID NO: 645          moltype = AA  length = 9
FEATURE                 Location/Qualifiers
source                  1..9
                        mol_type = protein
                        organism = Homo sapiens
SEQUENCE: 645
SIISAVVGI                                                         9

SEQ ID NO: 646          moltype = AA  length = 9
FEATURE                 Location/Qualifiers
source                  1..9
                        mol_type = protein
                        organism = Homo sapiens
SEQUENCE: 646
VVLGVVFGI                                                         9

SEQ ID NO: 647          moltype = AA  length = 9
FEATURE                 Location/Qualifiers
source                  1..9
                        mol_type = protein
                        organism = Homo sapiens
SEQUENCE: 647
FLLELLSDS                                                         9

SEQ ID NO: 648          moltype = AA  length = 9
FEATURE                 Location/Qualifiers
source                  1..9
                        mol_type = protein
                        organism = Homo sapiens
SEQUENCE: 648
ALLDAEPPI                                                         9

SEQ ID NO: 649          moltype = AA  length = 9
FEATURE                 Location/Qualifiers
source                  1..9
                        mol_type = protein
                        organism = Homo sapiens
SEQUENCE: 649
KITDTLIHL                                                         9

SEQ ID NO: 650          moltype = AA  length = 9
FEATURE                 Location/Qualifiers
source                  1..9
                        mol_type = protein
                        organism = Homo sapiens
SEQUENCE: 650
KLLFAPNLL                                                         9

SEQ ID NO: 651          moltype = AA  length = 9
FEATURE                 Location/Qualifiers
source                  1..9
                        mol_type = protein
                        organism = Homo sapiens
SEQUENCE: 651
LLDAEPPIL                                                         9

SEQ ID NO: 652          moltype = AA  length = 9
FEATURE                 Location/Qualifiers
source                  1..9
                        mol_type = protein
                        organism = Homo sapiens
SEQUENCE: 652
LLNSGVYTF                                                         9

SEQ ID NO: 653          moltype = AA  length = 9
FEATURE                 Location/Qualifiers
```

```
source                1..9
                      mol_type = protein
                      organism = Homo sapiens
SEQUENCE: 653
LMIGLVWRS                                                          9

SEQ ID NO: 654        moltype = AA  length = 9
FEATURE               Location/Qualifiers
source                1..9
                      mol_type = protein
                      organism = Homo sapiens
SEQUENCE: 654
PLYDLLLEM                                                          9

SEQ ID NO: 655        moltype = AA  length = 9
FEATURE               Location/Qualifiers
source                1..9
                      mol_type = protein
                      organism = Homo sapiens
SEQUENCE: 655
QLLLILSHI                                                          9

SEQ ID NO: 656        moltype = AA  length = 9
FEATURE               Location/Qualifiers
source                1..9
                      mol_type = protein
                      organism = Homo sapiens
SEQUENCE: 656
RLAQLLLIL                                                          9

SEQ ID NO: 657        moltype = AA  length = 9
FEATURE               Location/Qualifiers
source                1..9
                      mol_type = protein
                      organism = Homo sapiens
SEQUENCE: 657
TLIHLMAKA                                                          9

SEQ ID NO: 658        moltype = AA  length = 9
FEATURE               Location/Qualifiers
source                1..9
                      mol_type = protein
                      organism = Homo sapiens
SEQUENCE: 658
VLDKITDTL                                                          9

SEQ ID NO: 659        moltype = AA  length = 9
FEATURE               Location/Qualifiers
source                1..9
                      mol_type = protein
                      organism = Homo sapiens
SEQUENCE: 659
FMVEDETVL                                                          9

SEQ ID NO: 660        moltype = AA  length = 9
FEATURE               Location/Qualifiers
source                1..9
                      mol_type = protein
                      organism = Homo sapiens
SEQUENCE: 660
SMFRVLIGT                                                          9

SEQ ID NO: 661        moltype = AA  length = 9
FEATURE               Location/Qualifiers
source                1..9
                      mol_type = protein
                      organism = Homo sapiens
SEQUENCE: 661
ATSAVLALL                                                          9

SEQ ID NO: 662        moltype = AA  length = 9
FEATURE               Location/Qualifiers
source                1..9
                      mol_type = protein
                      organism = Homo sapiens
SEQUENCE: 662
TGWAGGFFV                                                          9

SEQ ID NO: 663        moltype = AA  length = 9
```

```
FEATURE                 Location/Qualifiers
source                  1..9
                        mol_type = protein
                        organism = Homo sapiens
SEQUENCE: 663
VLALLVMCI                                                                   9

SEQ ID NO: 664          moltype = AA  length = 9
FEATURE                 Location/Qualifiers
source                  1..9
                        mol_type = protein
                        organism = Homo sapiens
SEQUENCE: 664
ALLSCLLLT                                                                   9

SEQ ID NO: 665          moltype = AA  length = 9
FEATURE                 Location/Qualifiers
source                  1..9
                        mol_type = protein
                        organism = Homo sapiens
SEQUENCE: 665
CVAATLFWL                                                                   9

SEQ ID NO: 666          moltype = AA  length = 9
FEATURE                 Location/Qualifiers
source                  1..9
                        mol_type = protein
                        organism = Homo sapiens
SEQUENCE: 666
EMYSEIPEI                                                                   9

SEQ ID NO: 667          moltype = AA  length = 9
FEATURE                 Location/Qualifiers
source                  1..9
                        mol_type = protein
                        organism = Homo sapiens
SEQUENCE: 667
KMASTLVVA                                                                   9

SEQ ID NO: 668          moltype = AA  length = 9
FEATURE                 Location/Qualifiers
source                  1..9
                        mol_type = protein
                        organism = Homo sapiens
SEQUENCE: 668
SIFDKIYST                                                                   9

SEQ ID NO: 669          moltype = AA  length = 9
FEATURE                 Location/Qualifiers
source                  1..9
                        mol_type = protein
                        organism = Homo sapiens
SEQUENCE: 669
TLFWLLLTL                                                                   9

SEQ ID NO: 670          moltype = AA  length = 9
FEATURE                 Location/Qualifiers
source                  1..9
                        mol_type = protein
                        organism = Homo sapiens
SEQUENCE: 670
VLLWEIFSL                                                                   9

SEQ ID NO: 671          moltype = AA  length = 9
FEATURE                 Location/Qualifiers
source                  1..9
                        mol_type = protein
                        organism = Homo sapiens
SEQUENCE: 671
WLKDGLPAT                                                                   9

SEQ ID NO: 672          moltype = AA  length = 9
FEATURE                 Location/Qualifiers
source                  1..9
                        mol_type = protein
                        organism = Homo sapiens
SEQUENCE: 672
ILLDISFPG                                                                   9
```

```
SEQ ID NO: 673          moltype = AA  length = 9
FEATURE                 Location/Qualifiers
source                  1..9
                        mol_type = protein
                        organism = Homo sapiens
SEQUENCE: 673
LLDISFPGL                                                          9

SEQ ID NO: 674          moltype = AA  length = 9
FEATURE                 Location/Qualifiers
source                  1..9
                        mol_type = protein
                        organism = Homo sapiens
SEQUENCE: 674
LMDLSTTPL                                                          9

SEQ ID NO: 675          moltype = AA  length = 9
FEATURE                 Location/Qualifiers
source                  1..9
                        mol_type = protein
                        organism = Homo sapiens
SEQUENCE: 675
RVSSYLVPI                                                          9

SEQ ID NO: 676          moltype = AA  length = 9
FEATURE                 Location/Qualifiers
source                  1..9
                        mol_type = protein
                        organism = Homo sapiens
SEQUENCE: 676
SLSKILLDI                                                          9

SEQ ID NO: 677          moltype = AA  length = 9
FEATURE                 Location/Qualifiers
source                  1..9
                        mol_type = protein
                        organism = Homo sapiens
SEQUENCE: 677
SQLSYSQEV                                                          9

SEQ ID NO: 678          moltype = AA  length = 9
FEATURE                 Location/Qualifiers
source                  1..9
                        mol_type = protein
                        organism = Homo sapiens
SEQUENCE: 678
WAAELPFPA                                                          9

SEQ ID NO: 679          moltype = AA  length = 9
FEATURE                 Location/Qualifiers
source                  1..9
                        mol_type = protein
                        organism = Homo sapiens
SEQUENCE: 679
LLNESETKV                                                          9

SEQ ID NO: 680          moltype = AA  length = 9
FEATURE                 Location/Qualifiers
source                  1..9
                        mol_type = protein
                        organism = Homo sapiens
SEQUENCE: 680
RLVELLKDL                                                          9

SEQ ID NO: 681          moltype = AA  length = 9
FEATURE                 Location/Qualifiers
source                  1..9
                        mol_type = protein
                        organism = Homo sapiens
SEQUENCE: 681
GLASTTPEA                                                          9

SEQ ID NO: 682          moltype = AA  length = 9
FEATURE                 Location/Qualifiers
source                  1..9
                        mol_type = protein
                        organism = Homo sapiens
SEQUENCE: 682
RMAREVAAL                                                          9
```

```
SEQ ID NO: 683          moltype = AA  length = 9
FEATURE                 Location/Qualifiers
source                  1..9
                        mol_type = protein
                        organism = Homo sapiens
SEQUENCE: 683
FLLSLAFYG                                                                9

SEQ ID NO: 684          moltype = AA  length = 9
FEATURE                 Location/Qualifiers
source                  1..9
                        mol_type = protein
                        organism = Homo sapiens
SEQUENCE: 684
ILNPAQGFL                                                                9

SEQ ID NO: 685          moltype = AA  length = 9
FEATURE                 Location/Qualifiers
source                  1..9
                        mol_type = protein
                        organism = Homo sapiens
SEQUENCE: 685
MAWGLATLL                                                                9

SEQ ID NO: 686          moltype = AA  length = 9
FEATURE                 Location/Qualifiers
source                  1..9
                        mol_type = protein
                        organism = Homo sapiens
SEQUENCE: 686
RLALGLLQL                                                                9

SEQ ID NO: 687          moltype = AA  length = 9
FEATURE                 Location/Qualifiers
source                  1..9
                        mol_type = protein
                        organism = Homo sapiens
SEQUENCE: 687
RLLLAGAEV                                                                9

SEQ ID NO: 688          moltype = AA  length = 9
FEATURE                 Location/Qualifiers
source                  1..9
                        mol_type = protein
                        organism = Homo sapiens
SEQUENCE: 688
CLYTFLIST                                                                9

SEQ ID NO: 689          moltype = AA  length = 9
FEATURE                 Location/Qualifiers
source                  1..9
                        mol_type = protein
                        organism = Homo sapiens
SEQUENCE: 689
FLISTTFGC                                                                9

SEQ ID NO: 690          moltype = AA  length = 9
FEATURE                 Location/Qualifiers
source                  1..9
                        mol_type = protein
                        organism = Homo sapiens
SEQUENCE: 690
VLLDTNYNL                                                                9

SEQ ID NO: 691          moltype = AA  length = 9
FEATURE                 Location/Qualifiers
source                  1..9
                        mol_type = protein
                        organism = Homo sapiens
SEQUENCE: 691
WLPFGFILI                                                                9

SEQ ID NO: 692          moltype = AA  length = 10
FEATURE                 Location/Qualifiers
source                  1..10
                        mol_type = protein
                        organism = Homo sapiens
SEQUENCE: 692
```

```
WLPFGFILIL                                                10

SEQ ID NO: 693          moltype = AA  length = 9
FEATURE                 Location/Qualifiers
source                  1..9
                        mol_type = protein
                        organism = Homo sapiens
SEQUENCE: 693
ALYLLPLLA                                                 9

SEQ ID NO: 694          moltype = AA  length = 9
FEATURE                 Location/Qualifiers
source                  1..9
                        mol_type = protein
                        organism = Homo sapiens
SEQUENCE: 694
FALYNLLAL                                                 9

SEQ ID NO: 695          moltype = AA  length = 9
FEATURE                 Location/Qualifiers
source                  1..9
                        mol_type = protein
                        organism = Homo sapiens
SEQUENCE: 695
QLFLVLQAL                                                 9

SEQ ID NO: 696          moltype = AA  length = 9
FEATURE                 Location/Qualifiers
source                  1..9
                        mol_type = protein
                        organism = Homo sapiens
SEQUENCE: 696
RLVAAVVLL                                                 9

SEQ ID NO: 697          moltype = AA  length = 9
FEATURE                 Location/Qualifiers
source                  1..9
                        mol_type = protein
                        organism = Homo sapiens
SEQUENCE: 697
VLAERAGAV                                                 9

SEQ ID NO: 698          moltype = AA  length = 9
FEATURE                 Location/Qualifiers
source                  1..9
                        mol_type = protein
                        organism = Homo sapiens
SEQUENCE: 698
WLVPLFFAA                                                 9

SEQ ID NO: 699          moltype = AA  length = 9
FEATURE                 Location/Qualifiers
source                  1..9
                        mol_type = protein
                        organism = Homo sapiens
SEQUENCE: 699
YLLPLLATC                                                 9

SEQ ID NO: 700          moltype = AA  length = 9
FEATURE                 Location/Qualifiers
source                  1..9
                        mol_type = protein
                        organism = Homo sapiens
SEQUENCE: 700
GLSDAVEAL                                                 9

SEQ ID NO: 701          moltype = AA  length = 9
FEATURE                 Location/Qualifiers
source                  1..9
                        mol_type = protein
                        organism = Homo sapiens
SEQUENCE: 701
MLREAAMGI                                                 9

SEQ ID NO: 702          moltype = AA  length = 9
FEATURE                 Location/Qualifiers
source                  1..9
                        mol_type = protein
                        organism = Homo sapiens
```

-continued

```
SEQUENCE: 702
ALIPAPELV                                                   9

SEQ ID NO: 703          moltype = AA  length = 9
FEATURE                 Location/Qualifiers
source                  1..9
                        mol_type = protein
                        organism = Homo sapiens
SEQUENCE: 703
NLLHGLNLL                                                   9

SEQ ID NO: 704          moltype = AA  length = 9
FEATURE                 Location/Qualifiers
source                  1..9
                        mol_type = protein
                        organism = Homo sapiens
SEQUENCE: 704
YVSSLPQPL                                                   9

SEQ ID NO: 705          moltype = AA  length = 9
FEATURE                 Location/Qualifiers
source                  1..9
                        mol_type = protein
                        organism = Homo sapiens
SEQUENCE: 705
YLILGVAGS                                                   9

SEQ ID NO: 706          moltype = AA  length = 9
FEATURE                 Location/Qualifiers
source                  1..9
                        mol_type = protein
                        organism = Homo sapiens
SEQUENCE: 706
NMDCIIAEI                                                   9

SEQ ID NO: 707          moltype = AA  length = 9
FEATURE                 Location/Qualifiers
source                  1..9
                        mol_type = protein
                        organism = Homo sapiens
SEQUENCE: 707
AVLGIFIIV                                                   9

SEQ ID NO: 708          moltype = AA  length = 9
FEATURE                 Location/Qualifiers
source                  1..9
                        mol_type = protein
                        organism = Homo sapiens
SEQUENCE: 708
KLAVLGIFI                                                   9

SEQ ID NO: 709          moltype = AA  length = 9
FEATURE                 Location/Qualifiers
source                  1..9
                        mol_type = protein
                        organism = Homo sapiens
SEQUENCE: 709
AIAAIVIGI                                                   9

SEQ ID NO: 710          moltype = AA  length = 9
FEATURE                 Location/Qualifiers
source                  1..9
                        mol_type = protein
                        organism = Homo sapiens
SEQUENCE: 710
ALACSLAAC                                                   9

SEQ ID NO: 711          moltype = AA  length = 9
FEATURE                 Location/Qualifiers
source                  1..9
                        mol_type = protein
                        organism = Homo sapiens
SEQUENCE: 711
IVIGIVALA                                                   9

SEQ ID NO: 712          moltype = AA  length = 9
FEATURE                 Location/Qualifiers
source                  1..9
                        mol_type = protein
```

```
                        organism = Homo sapiens
SEQUENCE: 712
RIVAVPTPL                                                   9

SEQ ID NO: 713          moltype = AA  length = 9
FEATURE                 Location/Qualifiers
source                  1..9
                        mol_type = protein
                        organism = Homo sapiens
SEQUENCE: 713
SLKELSPGI                                                   9

SEQ ID NO: 714          moltype = AA  length = 9
FEATURE                 Location/Qualifiers
source                  1..9
                        mol_type = protein
                        organism = Homo sapiens
SEQUENCE: 714
KVADLVGFL                                                   9

SEQ ID NO: 715          moltype = AA  length = 9
FEATURE                 Location/Qualifiers
source                  1..9
                        mol_type = protein
                        organism = Homo sapiens
SEQUENCE: 715
GMLSDVQSM                                                   9

SEQ ID NO: 716          moltype = AA  length = 9
FEATURE                 Location/Qualifiers
source                  1..9
                        mol_type = protein
                        organism = Homo sapiens
SEQUENCE: 716
ILILILSIV                                                   9

SEQ ID NO: 717          moltype = AA  length = 9
FEATURE                 Location/Qualifiers
source                  1..9
                        mol_type = protein
                        organism = Homo sapiens
SEQUENCE: 717
AMDAIFGSL                                                   9

SEQ ID NO: 718          moltype = AA  length = 9
FEATURE                 Location/Qualifiers
source                  1..9
                        mol_type = protein
                        organism = Homo sapiens
SEQUENCE: 718
GLITKAEML                                                   9

SEQ ID NO: 719          moltype = AA  length = 9
FEATURE                 Location/Qualifiers
source                  1..9
                        mol_type = protein
                        organism = Homo sapiens
SEQUENCE: 719
GTLEELPAA                                                   9

SEQ ID NO: 720          moltype = AA  length = 9
FEATURE                 Location/Qualifiers
source                  1..9
                        mol_type = protein
                        organism = Homo sapiens
SEQUENCE: 720
KVLEYIANA                                                   9

SEQ ID NO: 721          moltype = AA  length = 9
FEATURE                 Location/Qualifiers
source                  1..9
                        mol_type = protein
                        organism = Homo sapiens
SEQUENCE: 721
QLVFGIEVV                                                   9

SEQ ID NO: 722          moltype = AA  length = 9
FEATURE                 Location/Qualifiers
source                  1..9
```

```
                        mol_type = protein
                        organism = Homo sapiens
SEQUENCE: 722
AVSSSSPLV                                                     9

SEQ ID NO: 723          moltype = AA  length = 9
FEATURE                 Location/Qualifiers
source                  1..9
                        mol_type = protein
                        organism = Homo sapiens
SEQUENCE: 723
KVDELAHFL                                                     9

SEQ ID NO: 724          moltype = AA  length = 9
FEATURE                 Location/Qualifiers
source                  1..9
                        mol_type = protein
                        organism = Homo sapiens
SEQUENCE: 724
KVLEHVVRV                                                     9

SEQ ID NO: 725          moltype = AA  length = 9
FEATURE                 Location/Qualifiers
source                  1..9
                        mol_type = protein
                        organism = Homo sapiens
SEQUENCE: 725
VILGVLLLI                                                     9

SEQ ID NO: 726          moltype = AA  length = 9
FEATURE                 Location/Qualifiers
source                  1..9
                        mol_type = protein
                        organism = Homo sapiens
SEQUENCE: 726
MTAAGVPQL                                                     9

SEQ ID NO: 727          moltype = AA  length = 9
FEATURE                 Location/Qualifiers
source                  1..9
                        mol_type = protein
                        organism = Homo sapiens
SEQUENCE: 727
SVSDILSPL                                                     9

SEQ ID NO: 728          moltype = AA  length = 9
FEATURE                 Location/Qualifiers
source                  1..9
                        mol_type = protein
                        organism = Homo sapiens
SEQUENCE: 728
ALLAASVAL                                                     9

SEQ ID NO: 729          moltype = AA  length = 9
FEATURE                 Location/Qualifiers
source                  1..9
                        mol_type = protein
                        organism = Homo sapiens
SEQUENCE: 729
LLAASVALA                                                     9

SEQ ID NO: 730          moltype = AA  length = 9
FEATURE                 Location/Qualifiers
source                  1..9
                        mol_type = protein
                        organism = Homo sapiens
SEQUENCE: 730
QLLRKVAEL                                                     9

SEQ ID NO: 731          moltype = AA  length = 9
FEATURE                 Location/Qualifiers
source                  1..9
                        mol_type = protein
                        organism = Homo sapiens
SEQUENCE: 731
TLPELYAFT                                                     9

SEQ ID NO: 732          moltype = AA  length = 9
FEATURE                 Location/Qualifiers
```

-continued

```
source                  1..9
                        mol_type = protein
                        organism = Homo sapiens
SEQUENCE: 732
YLYGKIKKT                                                          9

SEQ ID NO: 733          moltype = AA  length = 9
FEATURE                 Location/Qualifiers
source                  1..9
                        mol_type = protein
                        organism = Homo sapiens
SEQUENCE: 733
QVLGLAAYL                                                          9

SEQ ID NO: 734          moltype = AA  length = 9
FEATURE                 Location/Qualifiers
source                  1..9
                        mol_type = protein
                        organism = Homo sapiens
SEQUENCE: 734
GLDEVKSSL                                                          9

SEQ ID NO: 735          moltype = AA  length = 9
FEATURE                 Location/Qualifiers
source                  1..9
                        mol_type = protein
                        organism = Homo sapiens
SEQUENCE: 735
FVLLSLSGA                                                          9

SEQ ID NO: 736          moltype = AA  length = 9
FEATURE                 Location/Qualifiers
source                  1..9
                        mol_type = protein
                        organism = Homo sapiens
SEQUENCE: 736
SLFLFSVLL                                                          9

SEQ ID NO: 737          moltype = AA  length = 9
FEATURE                 Location/Qualifiers
source                  1..9
                        mol_type = protein
                        organism = Homo sapiens
SEQUENCE: 737
SLTVYLVVA                                                          9

SEQ ID NO: 738          moltype = AA  length = 9
FEATURE                 Location/Qualifiers
source                  1..9
                        mol_type = protein
                        organism = Homo sapiens
SEQUENCE: 738
VLLFVAVRL                                                          9

SEQ ID NO: 739          moltype = AA  length = 9
FEATURE                 Location/Qualifiers
source                  1..9
                        mol_type = protein
                        organism = Homo sapiens
SEQUENCE: 739
VSSLFLFSV                                                          9

SEQ ID NO: 740          moltype = AA  length = 9
FEATURE                 Location/Qualifiers
source                  1..9
                        mol_type = protein
                        organism = Homo sapiens
SEQUENCE: 740
SIAGFVASI                                                          9

SEQ ID NO: 741          moltype = AA  length = 9
FEATURE                 Location/Qualifiers
source                  1..9
                        mol_type = protein
                        organism = Homo sapiens
SEQUENCE: 741
ILLVLMAVV                                                          9

SEQ ID NO: 742          moltype = AA  length = 9
```

```
FEATURE                Location/Qualifiers
source                 1..9
                       mol_type = protein
                       organism = Homo sapiens
SEQUENCE: 742
LIVGILLVL                                                                     9

SEQ ID NO: 743         moltype = AA  length = 9
FEATURE                Location/Qualifiers
source                 1..9
                       mol_type = protein
                       organism = Homo sapiens
SEQUENCE: 743
LMAVVLASL                                                                     9

SEQ ID NO: 744         moltype = AA  length = 9
FEATURE                Location/Qualifiers
source                 1..9
                       mol_type = protein
                       organism = Homo sapiens
SEQUENCE: 744
PLLDGTATL                                                                     9

SEQ ID NO: 745         moltype = AA  length = 9
FEATURE                Location/Qualifiers
source                 1..9
                       mol_type = protein
                       organism = Homo sapiens
SEQUENCE: 745
SLADTNSLA                                                                     9

SEQ ID NO: 746         moltype = AA  length = 9
FEATURE                Location/Qualifiers
source                 1..9
                       mol_type = protein
                       organism = Homo sapiens
SEQUENCE: 746
VLQAAIPLT                                                                     9

SEQ ID NO: 747         moltype = AA  length = 9
FEATURE                Location/Qualifiers
source                 1..9
                       mol_type = protein
                       organism = Homo sapiens
SEQUENCE: 747
AVLDGLDVL                                                                     9

SEQ ID NO: 748         moltype = AA  length = 9
FEATURE                Location/Qualifiers
source                 1..9
                       mol_type = protein
                       organism = Homo sapiens
SEQUENCE: 748
QLLALLPSL                                                                     9

SEQ ID NO: 749         moltype = AA  length = 9
FEATURE                Location/Qualifiers
source                 1..9
                       mol_type = protein
                       organism = Homo sapiens
SEQUENCE: 749
RLRELLCEL                                                                     9

SEQ ID NO: 750         moltype = AA  length = 9
FEATURE                Location/Qualifiers
source                 1..9
                       mol_type = protein
                       organism = Homo sapiens
SEQUENCE: 750
VLYPVPLES                                                                     9

SEQ ID NO: 751         moltype = AA  length = 9
FEATURE                Location/Qualifiers
source                 1..9
                       mol_type = protein
                       organism = Homo sapiens
SEQUENCE: 751
AVFLLSYAV                                                                     9
```

```
SEQ ID NO: 752          moltype = AA  length = 9
FEATURE                 Location/Qualifiers
source                  1..9
                        mol_type = protein
                        organism = Homo sapiens
SEQUENCE: 752
FVLSLLLIL                                                           9

SEQ ID NO: 753          moltype = AA  length = 9
FEATURE                 Location/Qualifiers
source                  1..9
                        mol_type = protein
                        organism = Homo sapiens
SEQUENCE: 753
IIFVLSLLL                                                           9

SEQ ID NO: 754          moltype = AA  length = 9
FEATURE                 Location/Qualifiers
source                  1..9
                        mol_type = protein
                        organism = Homo sapiens
SEQUENCE: 754
LILEKQAAV                                                           9

SEQ ID NO: 755          moltype = AA  length = 9
FEATURE                 Location/Qualifiers
source                  1..9
                        mol_type = protein
                        organism = Homo sapiens
SEQUENCE: 755
LISELKLAV                                                           9

SEQ ID NO: 756          moltype = AA  length = 9
FEATURE                 Location/Qualifiers
source                  1..9
                        mol_type = protein
                        organism = Homo sapiens
SEQUENCE: 756
RAIEHVLQV                                                           9

SEQ ID NO: 757          moltype = AA  length = 9
FEATURE                 Location/Qualifiers
source                  1..9
                        mol_type = protein
                        organism = Homo sapiens
SEQUENCE: 757
SSFDRLIPL                                                           9

SEQ ID NO: 758          moltype = AA  length = 9
FEATURE                 Location/Qualifiers
source                  1..9
                        mol_type = protein
                        organism = Homo sapiens
SEQUENCE: 758
TLKEQFQFV                                                           9

SEQ ID NO: 759          moltype = AA  length = 9
FEATURE                 Location/Qualifiers
source                  1..9
                        mol_type = protein
                        organism = Homo sapiens
SEQUENCE: 759
AILDSAFLL                                                           9

SEQ ID NO: 760          moltype = AA  length = 9
FEATURE                 Location/Qualifiers
source                  1..9
                        mol_type = protein
                        organism = Homo sapiens
SEQUENCE: 760
AISLVFSLV                                                           9

SEQ ID NO: 761          moltype = AA  length = 9
FEATURE                 Location/Qualifiers
source                  1..9
                        mol_type = protein
                        organism = Homo sapiens
SEQUENCE: 761
ALQILPYTL                                                           9
```

```
SEQ ID NO: 762          moltype = AA  length = 9
FEATURE                 Location/Qualifiers
source                  1..9
                        mol_type = protein
                        organism = Homo sapiens
SEQUENCE: 762
ALTGFTFSA                                                            9

SEQ ID NO: 763          moltype = AA  length = 9
FEATURE                 Location/Qualifiers
source                  1..9
                        mol_type = protein
                        organism = Homo sapiens
SEQUENCE: 763
AQLLLVNLL                                                            9

SEQ ID NO: 764          moltype = AA  length = 9
FEATURE                 Location/Qualifiers
source                  1..9
                        mol_type = protein
                        organism = Homo sapiens
SEQUENCE: 764
CLFGLLTLI                                                            9

SEQ ID NO: 765          moltype = AA  length = 9
FEATURE                 Location/Qualifiers
source                  1..9
                        mol_type = protein
                        organism = Homo sapiens
SEQUENCE: 765
GILLSLFLI                                                            9

SEQ ID NO: 766          moltype = AA  length = 9
FEATURE                 Location/Qualifiers
source                  1..9
                        mol_type = protein
                        organism = Homo sapiens
SEQUENCE: 766
GLLPPPPAL                                                            9

SEQ ID NO: 767          moltype = AA  length = 9
FEATURE                 Location/Qualifiers
source                  1..9
                        mol_type = protein
                        organism = Homo sapiens
SEQUENCE: 767
GLLTLIFLT                                                            9

SEQ ID NO: 768          moltype = AA  length = 9
FEATURE                 Location/Qualifiers
source                  1..9
                        mol_type = protein
                        organism = Homo sapiens
SEQUENCE: 768
GLVAIYFAT                                                            9

SEQ ID NO: 769          moltype = AA  length = 9
FEATURE                 Location/Qualifiers
source                  1..9
                        mol_type = protein
                        organism = Homo sapiens
SEQUENCE: 769
NLGALLPRL                                                            9

SEQ ID NO: 770          moltype = AA  length = 9
FEATURE                 Location/Qualifiers
source                  1..9
                        mol_type = protein
                        organism = Homo sapiens
SEQUENCE: 770
SVAAFPVAA                                                            9

SEQ ID NO: 771          moltype = AA  length = 9
FEATURE                 Location/Qualifiers
source                  1..9
                        mol_type = protein
                        organism = Homo sapiens
SEQUENCE: 771
```

```
FLLSLFCVT                                                   9

SEQ ID NO: 772          moltype = AA  length = 9
FEATURE                 Location/Qualifiers
source                  1..9
                        mol_type = protein
                        organism = Homo sapiens
SEQUENCE: 772
FSLGVGFGV                                                   9

SEQ ID NO: 773          moltype = AA  length = 9
FEATURE                 Location/Qualifiers
source                  1..9
                        mol_type = protein
                        organism = Homo sapiens
SEQUENCE: 773
GLIDEFQLL                                                   9

SEQ ID NO: 774          moltype = AA  length = 9
FEATURE                 Location/Qualifiers
source                  1..9
                        mol_type = protein
                        organism = Homo sapiens
SEQUENCE: 774
GMESVITGL                                                   9

SEQ ID NO: 775          moltype = AA  length = 9
FEATURE                 Location/Qualifiers
source                  1..9
                        mol_type = protein
                        organism = Homo sapiens
SEQUENCE: 775
ILFGVLIEA                                                   9

SEQ ID NO: 776          moltype = AA  length = 9
FEATURE                 Location/Qualifiers
source                  1..9
                        mol_type = protein
                        organism = Homo sapiens
SEQUENCE: 776
KIDFLLSVI                                                   9

SEQ ID NO: 777          moltype = AA  length = 9
FEATURE                 Location/Qualifiers
source                  1..9
                        mol_type = protein
                        organism = Homo sapiens
SEQUENCE: 777
LLFMVIAGM                                                   9

SEQ ID NO: 778          moltype = AA  length = 9
FEATURE                 Location/Qualifiers
source                  1..9
                        mol_type = protein
                        organism = Homo sapiens
SEQUENCE: 778
LVPYLLFMV                                                   9

SEQ ID NO: 779          moltype = AA  length = 9
FEATURE                 Location/Qualifiers
source                  1..9
                        mol_type = protein
                        organism = Homo sapiens
SEQUENCE: 779
QLTACLVLV                                                   9

SEQ ID NO: 780          moltype = AA  length = 9
FEATURE                 Location/Qualifiers
source                  1..9
                        mol_type = protein
                        organism = Homo sapiens
SEQUENCE: 780
MISEKMVKL                                                   9

SEQ ID NO: 781          moltype = AA  length = 9
FEATURE                 Location/Qualifiers
source                  1..9
                        mol_type = protein
                        organism = Homo sapiens
```

```
SEQUENCE: 781
LMFDLSLNF                                                     9

SEQ ID NO: 782          moltype = AA  length = 9
FEATURE                 Location/Qualifiers
source                  1..9
                        mol_type = protein
                        organism = Homo sapiens
SEQUENCE: 782
ALPAVMAGL                                                     9

SEQ ID NO: 783          moltype = AA  length = 9
FEATURE                 Location/Qualifiers
source                  1..9
                        mol_type = protein
                        organism = Homo sapiens
SEQUENCE: 783
GLAEPQAAA                                                     9

SEQ ID NO: 784          moltype = AA  length = 9
FEATURE                 Location/Qualifiers
source                  1..9
                        mol_type = protein
                        organism = Homo sapiens
SEQUENCE: 784
GIFLLSALA                                                     9

SEQ ID NO: 785          moltype = AA  length = 9
FEATURE                 Location/Qualifiers
source                  1..9
                        mol_type = protein
                        organism = Homo sapiens
SEQUENCE: 785
ASLTFLYTL                                                     9

SEQ ID NO: 786          moltype = AA  length = 9
FEATURE                 Location/Qualifiers
source                  1..9
                        mol_type = protein
                        organism = Homo sapiens
SEQUENCE: 786
AVLHAIYSL                                                     9

SEQ ID NO: 787          moltype = AA  length = 9
FEATURE                 Location/Qualifiers
source                  1..9
                        mol_type = protein
                        organism = Homo sapiens
SEQUENCE: 787
FFFAVLHAI                                                     9

SEQ ID NO: 788          moltype = AA  length = 9
FEATURE                 Location/Qualifiers
source                  1..9
                        mol_type = protein
                        organism = Homo sapiens
SEQUENCE: 788
GVIAAIVQL                                                     9

SEQ ID NO: 789          moltype = AA  length = 9
FEATURE                 Location/Qualifiers
source                  1..9
                        mol_type = protein
                        organism = Homo sapiens
SEQUENCE: 789
KIAAIIASL                                                     9

SEQ ID NO: 790          moltype = AA  length = 9
FEATURE                 Location/Qualifiers
source                  1..9
                        mol_type = protein
                        organism = Homo sapiens
SEQUENCE: 790
LIFKSILFL                                                     9

SEQ ID NO: 791          moltype = AA  length = 9
FEATURE                 Location/Qualifiers
source                  1..9
                        mol_type = protein
```

```
                        organism = Homo sapiens
SEQUENCE: 791
LLLGTIHAL                                                       9

SEQ ID NO: 792          moltype = AA  length = 9
FEATURE                 Location/Qualifiers
source                  1..9
                        mol_type = protein
                        organism = Homo sapiens
SEQUENCE: 792
LLSFFFAVL                                                       9

SEQ ID NO: 793          moltype = AA  length = 9
FEATURE                 Location/Qualifiers
source                  1..9
                        mol_type = protein
                        organism = Homo sapiens
SEQUENCE: 793
MIAVFLPIV                                                       9

SEQ ID NO: 794          moltype = AA  length = 9
FEATURE                 Location/Qualifiers
source                  1..9
                        mol_type = protein
                        organism = Homo sapiens
SEQUENCE: 794
SLLLGTIHA                                                       9

SEQ ID NO: 795          moltype = AA  length = 9
FEATURE                 Location/Qualifiers
source                  1..9
                        mol_type = protein
                        organism = Homo sapiens
SEQUENCE: 795
SLSLIVAVI                                                       9

SEQ ID NO: 796          moltype = AA  length = 9
FEATURE                 Location/Qualifiers
source                  1..9
                        mol_type = protein
                        organism = Homo sapiens
SEQUENCE: 796
IISPNLFYA                                                       9

SEQ ID NO: 797          moltype = AA  length = 9
FEATURE                 Location/Qualifiers
source                  1..9
                        mol_type = protein
                        organism = Homo sapiens
SEQUENCE: 797
LLDHVLIEM                                                       9

SEQ ID NO: 798          moltype = AA  length = 9
FEATURE                 Location/Qualifiers
source                  1..9
                        mol_type = protein
                        organism = Homo sapiens
SEQUENCE: 798
VLIDEHLVL                                                       9

SEQ ID NO: 799          moltype = AA  length = 9
FEATURE                 Location/Qualifiers
source                  1..9
                        mol_type = protein
                        organism = Homo sapiens
SEQUENCE: 799
YSSEVLEYM                                                       9

SEQ ID NO: 800          moltype = AA  length = 9
FEATURE                 Location/Qualifiers
source                  1..9
                        mol_type = protein
                        organism = Homo sapiens
SEQUENCE: 800
ILLRPDTYI                                                       9

SEQ ID NO: 801          moltype = AA  length = 9
FEATURE                 Location/Qualifiers
source                  1..9
```

```
                        mol_type = protein
                        organism = Homo sapiens
SEQUENCE: 801
LMMTIINLA                                                          9

SEQ ID NO: 802          moltype = AA  length = 9
FEATURE                 Location/Qualifiers
source                  1..9
                        mol_type = protein
                        organism = Homo sapiens
SEQUENCE: 802
QLAGSVAEM                                                          9

SEQ ID NO: 803          moltype = AA  length = 9
FEATURE                 Location/Qualifiers
source                  1..9
                        mol_type = protein
                        organism = Homo sapiens
SEQUENCE: 803
SLMMTIINL                                                          9

SEQ ID NO: 804          moltype = AA  length = 9
FEATURE                 Location/Qualifiers
source                  1..9
                        mol_type = protein
                        organism = Homo sapiens
SEQUENCE: 804
TMLSSLARL                                                          9

SEQ ID NO: 805          moltype = AA  length = 9
FEATURE                 Location/Qualifiers
source                  1..9
                        mol_type = protein
                        organism = Homo sapiens
SEQUENCE: 805
YIFTMLSSL                                                          9

SEQ ID NO: 806          moltype = AA  length = 9
FEATURE                 Location/Qualifiers
source                  1..9
                        mol_type = protein
                        organism = Homo sapiens
SEQUENCE: 806
DLAGVIIEL                                                          9

SEQ ID NO: 807          moltype = AA  length = 9
FEATURE                 Location/Qualifiers
source                  1..9
                        mol_type = protein
                        organism = Homo sapiens
SEQUENCE: 807
FGLFGVFLV                                                          9

SEQ ID NO: 808          moltype = AA  length = 9
FEATURE                 Location/Qualifiers
source                  1..9
                        mol_type = protein
                        organism = Homo sapiens
SEQUENCE: 808
GLFGVFLVL                                                          9

SEQ ID NO: 809          moltype = AA  length = 9
FEATURE                 Location/Qualifiers
source                  1..9
                        mol_type = protein
                        organism = Homo sapiens
SEQUENCE: 809
ILDTAIIVI                                                          9

SEQ ID NO: 810          moltype = AA  length = 9
FEATURE                 Location/Qualifiers
source                  1..9
                        mol_type = protein
                        organism = Homo sapiens
SEQUENCE: 810
IVSSFAFGL                                                          9

SEQ ID NO: 811          moltype = AA  length = 9
FEATURE                 Location/Qualifiers
```

```
source                  1..9
                        mol_type = protein
                        organism = Homo sapiens
SEQUENCE: 811
RLLRLIILL                                                         9

SEQ ID NO: 812          moltype = AA  length = 9
FEATURE                 Location/Qualifiers
source                  1..9
                        mol_type = protein
                        organism = Homo sapiens
SEQUENCE: 812
SLAIALFFL                                                         9

SEQ ID NO: 813          moltype = AA  length = 9
FEATURE                 Location/Qualifiers
source                  1..9
                        mol_type = protein
                        organism = Homo sapiens
SEQUENCE: 813
YFWLHTSFI                                                         9

SEQ ID NO: 814          moltype = AA  length = 9
FEATURE                 Location/Qualifiers
source                  1..9
                        mol_type = protein
                        organism = Homo sapiens
SEQUENCE: 814
AMFGYTVGT                                                         9

SEQ ID NO: 815          moltype = AA  length = 9
FEATURE                 Location/Qualifiers
source                  1..9
                        mol_type = protein
                        organism = Homo sapiens
SEQUENCE: 815
FIAGIVFRL                                                         9

SEQ ID NO: 816          moltype = AA  length = 9
FEATURE                 Location/Qualifiers
source                  1..9
                        mol_type = protein
                        organism = Homo sapiens
SEQUENCE: 816
FLLLFAYVL                                                         9

SEQ ID NO: 817          moltype = AA  length = 9
FEATURE                 Location/Qualifiers
source                  1..9
                        mol_type = protein
                        organism = Homo sapiens
SEQUENCE: 817
LLFAYVLLM                                                         9

SEQ ID NO: 818          moltype = AA  length = 9
FEATURE                 Location/Qualifiers
source                  1..9
                        mol_type = protein
                        organism = Homo sapiens
SEQUENCE: 818
LLLFAYVLL                                                         9

SEQ ID NO: 819          moltype = AA  length = 9
FEATURE                 Location/Qualifiers
source                  1..9
                        mol_type = protein
                        organism = Homo sapiens
SEQUENCE: 819
LVLYSLVFV                                                         9

SEQ ID NO: 820          moltype = AA  length = 9
FEATURE                 Location/Qualifiers
source                  1..9
                        mol_type = protein
                        organism = Homo sapiens
SEQUENCE: 820
NILLVNLLV                                                         9

SEQ ID NO: 821          moltype = AA  length = 9
```

-continued

```
FEATURE                Location/Qualifiers
source                 1..9
                       mol_type = protein
                       organism = Homo sapiens
SEQUENCE: 821
QIADVIASL                                                     9

SEQ ID NO: 822         moltype = AA  length = 9
FEATURE                Location/Qualifiers
source                 1..9
                       mol_type = protein
                       organism = Homo sapiens
SEQUENCE: 822
VLYSLVFVL                                                     9

SEQ ID NO: 823         moltype = AA  length = 9
FEATURE                Location/Qualifiers
source                 1..9
                       mol_type = protein
                       organism = Homo sapiens
SEQUENCE: 823
YLVKINTKA                                                     9

SEQ ID NO: 824         moltype = AA  length = 9
FEATURE                Location/Qualifiers
source                 1..9
                       mol_type = protein
                       organism = Homo sapiens
SEQUENCE: 824
FLDSLGFST                                                     9

SEQ ID NO: 825         moltype = AA  length = 9
FEATURE                Location/Qualifiers
source                 1..9
                       mol_type = protein
                       organism = Homo sapiens
SEQUENCE: 825
SLRDEFPLL                                                     9

SEQ ID NO: 826         moltype = AA  length = 9
FEATURE                Location/Qualifiers
source                 1..9
                       mol_type = protein
                       organism = Homo sapiens
SEQUENCE: 826
VLEELLWFI                                                     9

SEQ ID NO: 827         moltype = AA  length = 9
FEATURE                Location/Qualifiers
source                 1..9
                       mol_type = protein
                       organism = Homo sapiens
SEQUENCE: 827
ALLAGLVSL                                                     9

SEQ ID NO: 828         moltype = AA  length = 9
FEATURE                Location/Qualifiers
source                 1..9
                       mol_type = protein
                       organism = Homo sapiens
SEQUENCE: 828
AMVGAVLTA                                                     9

SEQ ID NO: 829         moltype = AA  length = 9
FEATURE                Location/Qualifiers
source                 1..9
                       mol_type = protein
                       organism = Homo sapiens
SEQUENCE: 829
ISSDYVIPI                                                     9

SEQ ID NO: 830         moltype = AA  length = 9
FEATURE                Location/Qualifiers
source                 1..9
                       mol_type = protein
                       organism = Homo sapiens
SEQUENCE: 830
LLAGLVSLL                                                     9
```

```
SEQ ID NO: 831          moltype = AA  length = 9
FEATURE                 Location/Qualifiers
source                  1..9
                        mol_type = protein
                        organism = Homo sapiens
SEQUENCE: 831
LLSPASFFS                                                          9

SEQ ID NO: 832          moltype = AA  length = 9
FEATURE                 Location/Qualifiers
source                  1..9
                        mol_type = protein
                        organism = Homo sapiens
SEQUENCE: 832
MVGAVLTAL                                                          9

SEQ ID NO: 833          moltype = AA  length = 9
FEATURE                 Location/Qualifiers
source                  1..9
                        mol_type = protein
                        organism = Homo sapiens
SEQUENCE: 833
VLTALLAGL                                                          9

SEQ ID NO: 834          moltype = AA  length = 9
FEATURE                 Location/Qualifiers
source                  1..9
                        mol_type = protein
                        organism = Homo sapiens
SEQUENCE: 834
ALTESLLVA                                                          9

SEQ ID NO: 835          moltype = AA  length = 9
FEATURE                 Location/Qualifiers
source                  1..9
                        mol_type = protein
                        organism = Homo sapiens
SEQUENCE: 835
LLALLSPGA                                                          9

SEQ ID NO: 836          moltype = AA  length = 9
FEATURE                 Location/Qualifiers
source                  1..9
                        mol_type = protein
                        organism = Homo sapiens
SEQUENCE: 836
LVLGFIIAL                                                          9

SEQ ID NO: 837          moltype = AA  length = 9
FEATURE                 Location/Qualifiers
source                  1..9
                        mol_type = protein
                        organism = Homo sapiens
SEQUENCE: 837
SLSGLLSPA                                                          9

SEQ ID NO: 838          moltype = AA  length = 9
FEATURE                 Location/Qualifiers
source                  1..9
                        mol_type = protein
                        organism = Homo sapiens
SEQUENCE: 838
TLPLILILL                                                          9

SEQ ID NO: 839          moltype = AA  length = 9
FEATURE                 Location/Qualifiers
source                  1..9
                        mol_type = protein
                        organism = Homo sapiens
SEQUENCE: 839
VLGFIIALA                                                          9

SEQ ID NO: 840          moltype = AA  length = 9
FEATURE                 Location/Qualifiers
source                  1..9
                        mol_type = protein
                        organism = Homo sapiens
SEQUENCE: 840
VVITVLLSV                                                          9
```

```
SEQ ID NO: 841          moltype = AA  length = 9
FEATURE                 Location/Qualifiers
source                  1..9
                        mol_type = protein
                        organism = Homo sapiens
SEQUENCE: 841
AQIGDSVML                                                     9

SEQ ID NO: 842          moltype = AA  length = 9
FEATURE                 Location/Qualifiers
source                  1..9
                        mol_type = protein
                        organism = Homo sapiens
SEQUENCE: 842
FASSLIIPA                                                     9

SEQ ID NO: 843          moltype = AA  length = 9
FEATURE                 Location/Qualifiers
source                  1..9
                        mol_type = protein
                        organism = Homo sapiens
SEQUENCE: 843
KSIDGAYTI                                                     9

SEQ ID NO: 844          moltype = AA  length = 9
FEATURE                 Location/Qualifiers
source                  1..9
                        mol_type = protein
                        organism = Homo sapiens
SEQUENCE: 844
SILEEGSSV                                                     9

SEQ ID NO: 845          moltype = AA  length = 9
FEATURE                 Location/Qualifiers
source                  1..9
                        mol_type = protein
                        organism = Homo sapiens
SEQUENCE: 845
LLFGFTLVS                                                     9

SEQ ID NO: 846          moltype = AA  length = 9
FEATURE                 Location/Qualifiers
source                  1..9
                        mol_type = protein
                        organism = Homo sapiens
SEQUENCE: 846
LLLFGFTLV                                                     9

SEQ ID NO: 847          moltype = AA  length = 9
FEATURE                 Location/Qualifiers
source                  1..9
                        mol_type = protein
                        organism = Homo sapiens
SEQUENCE: 847
RLGPLAAAL                                                     9

SEQ ID NO: 848          moltype = AA  length = 9
FEATURE                 Location/Qualifiers
source                  1..9
                        mol_type = protein
                        organism = Homo sapiens
SEQUENCE: 848
DLNALLPAV                                                     9

SEQ ID NO: 849          moltype = AA  length = 9
FEATURE                 Location/Qualifiers
source                  1..9
                        mol_type = protein
                        organism = Homo sapiens
SEQUENCE: 849
ILIPQVAYT                                                     9

SEQ ID NO: 850          moltype = AA  length = 9
FEATURE                 Location/Qualifiers
source                  1..9
                        mol_type = protein
                        organism = Homo sapiens
SEQUENCE: 850
```

NLSDIQNVL 9

SEQ ID NO: 851 moltype = AA length = 9
FEATURE Location/Qualifiers
source 1..9
mol_type = protein
organism = Homo sapiens
SEQUENCE: 851
VQAVVLPTV 9

SEQ ID NO: 852 moltype = AA length = 9
FEATURE Location/Qualifiers
source 1..9
mol_type = protein
organism = Homo sapiens
SEQUENCE: 852
LVLEQFLTI 9

SEQ ID NO: 853 moltype = AA length = 9
FEATURE Location/Qualifiers
source 1..9
mol_type = protein
organism = Homo sapiens
SEQUENCE: 853
RISGYISEA 9

SEQ ID NO: 854 moltype = AA length = 9
FEATURE Location/Qualifiers
source 1..9
mol_type = protein
organism = Homo sapiens
SEQUENCE: 854
AMTDISSLA 9

SEQ ID NO: 855 moltype = AA length = 9
FEATURE Location/Qualifiers
source 1..9
mol_type = protein
organism = Homo sapiens
SEQUENCE: 855
VLLSNFYYG 9

SEQ ID NO: 856 moltype = AA length = 20
FEATURE Location/Qualifiers
REGION 1..20
note = peptide
source 1..20
mol_type = protein
organism = synthetic construct
SEQUENCE: 856
MAKTIAYDEE ARRGLERGLN 20

SEQ ID NO: 857 moltype = AA length = 9
FEATURE Location/Qualifiers
source 1..9
mol_type = protein
organism = Homo sapiens
SEQUENCE: 857
QLWQFLLEL 9

SEQ ID NO: 858 moltype = AA length = 9
FEATURE Location/Qualifiers
source 1..9
mol_type = protein
organism = Homo sapiens
SEQUENCE: 858
LVLGTLEEV 9

SEQ ID NO: 859 moltype = AA length = 15
FEATURE Location/Qualifiers
REGION 1..15
note = peptide
source 1..15
mol_type = protein
organism = synthetic construct
SEQUENCE: 859
KSVWSKLQSI GIRQH 15

SEQ ID NO: 860 moltype = AA length = 13

```
FEATURE                 Location/Qualifiers
REGION                  1..13
                        note = peptide
source                  1..13
                        mol_type = protein
                        organism = synthetic construct
SEQUENCE: 860
TPPAYRPPNA PIL                                                            13

SEQ ID NO: 861          moltype = AA  length = 9
FEATURE                 Location/Qualifiers
REGION                  1..9
                        note = peptide
source                  1..9
                        mol_type = protein
                        organism = synthetic construct
SEQUENCE: 861
WLLDISFPL                                                                 9

SEQ ID NO: 862          moltype = AA  length = 9
FEATURE                 Location/Qualifiers
REGION                  1..9
                        note = peptide
source                  1..9
                        mol_type = protein
                        organism = synthetic construct
SEQUENCE: 862
HLLDISFPA                                                                 9

SEQ ID NO: 863          moltype = AA  length = 9
FEATURE                 Location/Qualifiers
REGION                  1..9
                        note = peptide
source                  1..9
                        mol_type = protein
                        organism = synthetic construct
SEQUENCE: 863
ELLDISFPA                                                                 9

SEQ ID NO: 864          moltype = AA  length = 9
FEATURE                 Location/Qualifiers
REGION                  1..9
                        note = peptide
source                  1..9
                        mol_type = protein
                        organism = synthetic construct
SEQUENCE: 864
VLLDISFEL                                                                 9

SEQ ID NO: 865          moltype = AA  length = 9
FEATURE                 Location/Qualifiers
REGION                  1..9
                        note = peptide
source                  1..9
                        mol_type = protein
                        organism = synthetic construct
SEQUENCE: 865
VLLDISFKV                                                                 9

SEQ ID NO: 866          moltype = AA  length = 9
FEATURE                 Location/Qualifiers
REGION                  1..9
                        note = peptide
source                  1..9
                        mol_type = protein
                        organism = synthetic construct
SEQUENCE: 866
IMLDISFLL                                                                 9

SEQ ID NO: 867          moltype = AA  length = 9
FEATURE                 Location/Qualifiers
REGION                  1..9
                        note = peptide
source                  1..9
                        mol_type = protein
                        organism = synthetic construct
SEQUENCE: 867
LLDISFPSL                                                                 9
```

```
SEQ ID NO: 868          moltype = AA  length = 9
FEATURE                 Location/Qualifiers
REGION                  1..9
                        note = peptide
source                  1..9
                        mol_type = protein
                        organism = synthetic construct
SEQUENCE: 868
LMDLSTTNV                                                                  9

SEQ ID NO: 869          moltype = AA  length = 9
FEATURE                 Location/Qualifiers
REGION                  1..9
                        note = peptide
source                  1..9
                        mol_type = protein
                        organism = synthetic construct
SEQUENCE: 869
MLSSYLVPI                                                                  9

SEQ ID NO: 870          moltype = AA  length = 9
FEATURE                 Location/Qualifiers
REGION                  1..9
                        note = peptide
source                  1..9
                        mol_type = protein
                        organism = synthetic construct
SEQUENCE: 870
LLSSYLVPI                                                                  9

SEQ ID NO: 871          moltype = AA  length = 9
FEATURE                 Location/Qualifiers
REGION                  1..9
                        note = peptide
source                  1..9
                        mol_type = protein
                        organism = synthetic construct
SEQUENCE: 871
FVSSYLVPT                                                                  9

SEQ ID NO: 872          moltype = AA  length = 9
FEATURE                 Location/Qualifiers
REGION                  1..9
                        note = peptide
source                  1..9
                        mol_type = protein
                        organism = synthetic construct
SEQUENCE: 872
SLSLHDMFL                                                                  9

SEQ ID NO: 873          moltype = AA  length = 9
FEATURE                 Location/Qualifiers
REGION                  1..9
                        note = peptide
source                  1..9
                        mol_type = protein
                        organism = synthetic construct
SEQUENCE: 873
KLKPLLPWI                                                                  9

SEQ ID NO: 874          moltype = AA  length = 9
FEATURE                 Location/Qualifiers
REGION                  1..9
                        note = peptide
source                  1..9
                        mol_type = protein
                        organism = synthetic construct
SEQUENCE: 874
KLKPLLPFL                                                                  9

SEQ ID NO: 875          moltype = AA  length = 9
FEATURE                 Location/Qualifiers
REGION                  1..9
                        note = peptide
source                  1..9
                        mol_type = protein
                        organism = synthetic construct
SEQUENCE: 875
KVVPIQFPV                                                                  9
```

```
SEQ ID NO: 876          moltype = AA  length = 9
FEATURE                 Location/Qualifiers
REGION                  1..9
                        note = peptide
source                  1..9
                        mol_type = protein
                        organism = synthetic construct
SEQUENCE: 876
KIVPIQFPI                                                         9

SEQ ID NO: 877          moltype = AA  length = 9
FEATURE                 Location/Qualifiers
REGION                  1..9
                        note = peptide
source                  1..9
                        mol_type = protein
                        organism = synthetic construct
SEQUENCE: 877
YQAMIQFLI                                                         9

SEQ ID NO: 878          moltype = AA  length = 10
FEATURE                 Location/Qualifiers
REGION                  1..10
                        note = peptide
source                  1..10
                        mol_type = protein
                        organism = synthetic construct
SEQUENCE: 878
FMPFGFILPI                                                        10

SEQ ID NO: 879          moltype = AA  length = 10
FEATURE                 Location/Qualifiers
REGION                  1..10
                        note = peptide
source                  1..10
                        mol_type = protein
                        organism = synthetic construct
SEQUENCE: 879
FMPFGFILGV                                                        10

SEQ ID NO: 880          moltype = AA  length = 10
FEATURE                 Location/Qualifiers
REGION                  1..10
                        note = peptide
source                  1..10
                        mol_type = protein
                        organism = synthetic construct
SEQUENCE: 880
FLISTTFTIN                                                        10

SEQ ID NO: 881          moltype = AA  length = 10
FEATURE                 Location/Qualifiers
REGION                  1..10
                        note = peptide
source                  1..10
                        mol_type = protein
                        organism = synthetic construct
SEQUENCE: 881
FMISTTFMRL                                                        10

SEQ ID NO: 882          moltype = AA  length = 10
FEATURE                 Location/Qualifiers
REGION                  1..10
                        note = peptide
source                  1..10
                        mol_type = protein
                        organism = synthetic construct
SEQUENCE: 882
QMISTTFGNV                                                        10

SEQ ID NO: 883          moltype = AA  length = 10
FEATURE                 Location/Qualifiers
REGION                  1..10
                        note = peptide
source                  1..10
                        mol_type = protein
                        organism = synthetic construct
SEQUENCE: 883
```

```
WLYLQWQPSV                                                  10

SEQ ID NO: 884          moltype = AA  length = 10
FEATURE                 Location/Qualifiers
REGION                  1..10
                        note = peptide
source                  1..10
                        mol_type = protein
                        organism = synthetic construct
SEQUENCE: 884
FVLLDTNYEI                                                  10

SEQ ID NO: 885          moltype = AA  length = 10
FEATURE                 Location/Qualifiers
REGION                  1..10
                        note = peptide
source                  1..10
                        mol_type = protein
                        organism = synthetic construct
SEQUENCE: 885
FILLDTNYEI                                                  10

SEQ ID NO: 886          moltype = AA  length = 10
FEATURE                 Location/Qualifiers
REGION                  1..10
                        note = peptide
source                  1..10
                        mol_type = protein
                        organism = synthetic construct
SEQUENCE: 886
YELQNIVLPI                                                  10

SEQ ID NO: 887          moltype = AA  length = 10
FEATURE                 Location/Qualifiers
REGION                  1..10
                        note = peptide
source                  1..10
                        mol_type = protein
                        organism = synthetic construct
SEQUENCE: 887
FMLQNIVKNL                                                  10

SEQ ID NO: 888          moltype = AA  length = 9
FEATURE                 Location/Qualifiers
source                  1..9
                        mol_type = protein
                        organism = Homo sapiens
SEQUENCE: 888
NLSLHDMFV                                                   9

SEQ ID NO: 889          moltype = AA  length = 9
FEATURE                 Location/Qualifiers
source                  1..9
                        mol_type = protein
                        organism = Homo sapiens
SEQUENCE: 889
KMKPLLPRV                                                   9

SEQ ID NO: 890          moltype = AA  length = 9
FEATURE                 Location/Qualifiers
source                  1..9
                        mol_type = protein
                        organism = Homo sapiens
SEQUENCE: 890
YLVPIQFPV                                                   9

SEQ ID NO: 891          moltype = AA  length = 9
FEATURE                 Location/Qualifiers
source                  1..9
                        mol_type = protein
                        organism = Homo sapiens
SEQUENCE: 891
YMAMIQFAI                                                   9

SEQ ID NO: 892          moltype = AA  length = 10
FEATURE                 Location/Qualifiers
source                  1..10
                        mol_type = protein
                        organism = Homo sapiens
```

-continued

```
SEQUENCE: 892
FLISTTFGCT                                                        10

SEQ ID NO: 893          moltype = AA  length = 10
FEATURE                 Location/Qualifiers
source                  1..10
                        mol_type = protein
                        organism = Homo sapiens
SEQUENCE: 893
YLYLQWQPPL                                                        10

SEQ ID NO: 894          moltype = AA  length = 10
FEATURE                 Location/Qualifiers
source                  1..10
                        mol_type = protein
                        organism = Homo sapiens
SEQUENCE: 894
GVLLDTNYNL                                                        10

SEQ ID NO: 895          moltype = AA  length = 10
FEATURE                 Location/Qualifiers
source                  1..10
                        mol_type = protein
                        organism = Homo sapiens
SEQUENCE: 895
FQLQNIVKPL                                                        10

SEQ ID NO: 896          moltype = AA  length = 9
FEATURE                 Location/Qualifiers
REGION                  1..9
                        note = comparative peptide
source                  1..9
                        mol_type = protein
                        organism = synthetic construct
SEQUENCE: 896
ALPFGFILV                                                         9

SEQ ID NO: 897          moltype = AA  length = 9
FEATURE                 Location/Qualifiers
REGION                  1..9
                        note = comparative peptide
source                  1..9
                        mol_type = protein
                        organism = synthetic construct
SEQUENCE: 897
ILPFGFILA                                                         9

SEQ ID NO: 898          moltype = AA  length = 9
FEATURE                 Location/Qualifiers
REGION                  1..9
                        note = comparative peptide
source                  1..9
                        mol_type = protein
                        organism = synthetic construct
SEQUENCE: 898
FLPFGFILM                                                         9

SEQ ID NO: 899          moltype = AA  length = 9
FEATURE                 Location/Qualifiers
REGION                  1..9
                        note = comparative peptide
source                  1..9
                        mol_type = protein
                        organism = synthetic construct
SEQUENCE: 899
LMLGEFLKL                                                         9
```

What is claimed is:

1. A combination comprising:

(i1) an antigenic peptide (a) having an amino acid sequence comprising or consisting of SEQ ID NO: 32, an antigenic peptide (b) having an amino acid sequence comprising or consisting of SEQ ID NO: 220, and a helper peptide having an amino acid sequence comprising or consisting of SEQ ID NO: 859, (ii1) an immunogenic compound comprising the antigenic peptide (a) of (i1) an immunogenic compound comprising the antigenic peptide (b) of (i1), and a compound comprising the helper peptide of (i1), (iii1) a nanoparticle loaded with the antigenic peptide (a) of (i1) or the immunogenic compound comprising the antigenic peptide (a) of (ii1), a nanoparticle loaded with the antigenic peptide (b) of (i1) or the immunogenic compound comprising the antigenic peptide (b) of (ii1), and a nanoparticle loaded with the helper peptide of (i1) or the compound comprising the helper peptide of (ii1), (iv1) an isolated cell loaded with the antigenic peptide (a) of (i1) or the immunogenic compound comprising the antigenic peptide (a) of (ii1), an isolated cell loaded with the antigenic peptide (b) of (i1) or the immunogenic compound comprising the antigenic peptide (b) of (ii1), and an isolated cell loaded with the helper peptide of (i) or the compound comprising the helper peptide of (ii1), (v1) a nucleic acid encoding the antigenic peptide (a) of (i1) or the immunogenic compound comprising the antigenic peptide (a) of (ii1), a nucleic acid encoding the antigenic peptide (b) of (i1) or the immunogenic compound comprising the antigenic peptide (b) of (ii), and a nucleic acid encoding the helper peptide of (i1) or the compound comprising the helper peptide of (ii1), wherein the immunogenic compounds and the compound comprising the helper peptide are peptides or proteins, or (vi1) an isolated host cell comprising a nucleic acid encoding the antigenic peptide (a) of (i1) or the immunogenic compound comprising the antigenic peptide (a) of (ii1), an isolated host cell comprising a nucleic acid encoding the antigenic peptide (b) of (i1) or the immunogenic compound comprising the antigenic peptide (b) of (ii1), and an isolated host cell comprising nucleic acid encoding the helper peptide of (i1) or the compound comprising the helper peptide of (ii1).

2. The combination of claim 1, further comprising:

(i2) an antigenic peptide having an amino acid sequence comprising or consisting of SEQ ID NO: 255, (ii2) an immunogenic compound comprising the antigenic peptide of (i2), (iii2) a nanoparticle loaded with the antigenic peptide of (i2) or the immunogenic compound of (ii2), (iv2) an isolated cell loaded with the antigenic peptide of (i2) or the immunogenic compound of (ii2), (v2) a nucleic acid encoding the antigenic peptide of (i2) or the immunogenic compound of (ii2), wherein the immunogenic compound is a peptide or a protein, and/or (vi2) an isolated host cell comprising the nucleic acid of (v2).

3. A pharmaceutical composition comprising:

(i1) an antigenic peptide (a) having an amino acid sequence comprising or consisting of SEQ ID NO: 32, an antigenic peptide (b) having an amino acid sequence comprising or consisting of SEQ ID NO: 220, and a helper peptide having an amino acid sequence comprising or consisting of SEQ ID NO: 859, (ii1) an immunogenic compound comprising the antigenic peptide (a) of (i1) an immunogenic compound comprising the antigenic peptide (b) of (i1), and a compound comprising the helper peptide of (i1), (iii1) a nanoparticle loaded with the antigenic peptide (a) of (i1) or the immunogenic compound comprising the antigenic peptide (a) of (ii1), a nanoparticle loaded with the antigenic peptide (b) of (i1) or the immunogenic compound comprising the antigenic peptide (b) of (ii1), and a nanoparticle loaded with the helper peptide of (i1) or the compound comprising the helper peptide of (ii1), (iv1) a nanoparticle loaded with the antigenic peptide (a) of (i1) or the immunogenic compound comprising the antigenic peptide (a) of (ii1), with the antigenic peptide (b) of (i1) or the immunogenic compound comprising the antigenic peptide (b) of (ii1), and with the helper peptide of (i1) or the compound comprising the helper peptide of (ii1), (v1) an isolated cell loaded with the antigenic peptide (a) of (i1) or the immunogenic compound comprising the antigenic peptide (a) of (ii1), an isolated cell loaded with the antigenic peptide (b) of (i1) or the immunogenic compound comprising the antigenic peptide (b) of (ii1), and an isolated cell loaded with the helper peptide of (i1) or the compound comprising the helper peptide of (ii1), (vi1) an isolated cell loaded with the antigenic peptide (a) of (i1) or the immunogenic compound comprising the antigenic peptide (a) of (ii1), with the antigenic peptide (b) of (i1) or the immunogenic compound comprising the antigenic peptide (b) of (ii1), and with the helper peptide of (i1) or the compound comprising the helper peptide of (ii1), (vii1) a nucleic acid encoding the antigenic peptide (a) of (i1) or the immunogenic compound comprising the antigenic peptide (a) of (ii1), a nucleic acid encoding the antigenic peptide (b) of (i1) or the immunogenic compound comprising the antigenic peptide (b) of (ii1), and a nucleic acid encoding the helper peptide of (i1) or the compound comprising the helper peptide of (ii1), wherein the immunogenic compounds and the compound comprising the helper peptide are peptides or proteins, (viii1) an isolated host cell comprising a nucleic acid encoding the antigenic peptide (a) of (i1) or the immunogenic compound comprising the antigenic peptide (a) of (ii1), an isolated host cell comprising a nucleic acid encoding the antigenic peptide (b) of (i1) or the immunogenic compound comprising the antigenic peptide (b) of (ii1), and an isolated host cell comprising nucleic acid encoding the helper peptide of (i1) or the compound comprising the helper peptide of (ii1), or (ix1) an isolated host cell comprising a nucleic acid encoding the antigenic peptide (a) of (i1) or the immunogenic compound comprising the antigenic peptide (a) of (ii1), a nucleic acid encoding the antigenic peptide (b) of (i1) or the immunogenic compound comprising the antigenic peptide (b) of (ii1), and a nucleic acid encoding the helper peptide of (i1) or the compound comprising the helper peptide of (ii1), and, optionally, one or more pharmaceutically acceptable excipients or carriers.

4. The pharmaceutical composition of claim 3, further comprising:

(i2) an antigenic peptide having an amino acid sequence comprising or consisting of SEQ ID NO: 255, (ii2) an immunogenic compound comprising the antigenic peptide of (i2), (iii2) a nanoparticle loaded with the antigenic peptide of (i2) or the immunogenic compound of (ii2), (iv2) an isolated cell loaded with the antigenic peptide of (i2) or the immunogenic compound of (ii2), (v2) a nucleic acid encoding the antigenic peptide of (i2) or the immunogenic compound of (ii2), wherein the immunogenic compound is a peptide or a protein, and/or (vi2) an isolated host cell comprising the nucleic acid of (v2).

5. A method for treating a cancer or initiating, enhancing or prolonging an anti-tumor-response in a subject in need thereof, the method comprising administering to the subject the combination of claim 1.

6. The method of claim 5, wherein the combination as defined in claim 1 further comprises:

(i2) an antigenic peptide having an amino acid sequence comprising or consisting of SEQ ID NO: 255, (ii2) an immunogenic compound comprising the antigenic peptide of (i2), (iii2) a nanoparticle loaded with the antigenic peptide of (i2) or the immunogenic compound of (ii2), (iv2) an isolated cell loaded with the antigenic peptide of (i2) or the immunogenic compound of (ii2), (v2) a nucleic acid encoding the antigenic peptide of (i2) or the immunogenic compound of (ii2), wherein the immunogenic compound is a peptide or a protein, and/or (vi2) an isolated host cell comprising the nucleic acid of (v2).

7. The method of claim 5, wherein the cancer is selected from glioma, kidney cancer, skin cancer, lung cancer, ovarian cancer, breast cancer, colorectal cancer, liver cancer, pancreatic cancer, head and neck cancer, urothelial cancer, and prostate cancer.

8. A method for treating a cancer or initiating, enhancing or prolonging an anti-tumor-response in a subject in need thereof, the method comprising administering to the subject the pharmaceutical composition of claim 3.

9. The method of claim 8, wherein the pharmaceutical composition further comprises:

(i2) an antigenic peptide having an amino acid sequence comprising or consisting of SEQ ID NO: 255, (ii2) an immunogenic compound comprising the antigenic peptide of (i2), (iii2) a nanoparticle loaded with the antigenic peptide of (i2) or the immunogenic compound of (ii2), (iv2) an isolated cell loaded with the antigenic peptide of (i2) or the immunogenic compound of (ii2), (v2) a nucleic acid encoding the antigenic peptide of (i2) or the immunogenic compound of (ii2), wherein the immunogenic compound is a peptide or a protein, and/or (vi2) an isolated host cell comprising the nucleic acid of (v2).

10. The method of claim 8, wherein the cancer is selected from glioma, kidney cancer, skin cancer, lung cancer, ovarian cancer, breast cancer, colorectal cancer, liver cancer, pancreatic cancer, head and neck cancer, urothelial cancer, and prostate cancer.

11. A kit comprising a peptide-MHC (pMHC) multimer comprising an antigenic peptide (a) having an amino acid sequence comprising or consisting of SEQ ID NO: 32 and a peptide-MHC (pMHC) multimer comprising an antigenic peptide (b) having an amino acid sequence comprising or consisting of SEQ ID NO: 220.

12. The kit of claim 11, further comprising a peptide-MHC (pMHC) multimer comprising an antigenic peptide having an amino acid sequence comprising or consisting of SEQ ID NO: 255.

* * * * *